US006461863B1

(12) United States Patent
Jarvis

(10) Patent No.: US 6,461,863 B1
(45) Date of Patent: Oct. 8, 2002

(54) MODIFYING INSECT CELL GYLCOSYLATION PATHWAYS WITH BACULOVIRUS EXPRESSION VECTORS

(75) Inventor: Donald L. Jarvis, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 09/242,435

(22) PCT Filed: Aug. 15, 1997

(86) PCT No.: PCT/US97/14428

§ 371 (c)(1),
(2), (4) Date: Nov. 29, 1999

(87) PCT Pub. No.: WO98/06835

PCT Pub. Date: Feb. 19, 1998

Related U.S. Application Data
(60) Provisional application No. 60/024,078, filed on Aug. 16, 1996.

(51) Int. Cl.$^7$ .......................... C12P 21/06; C12P 21/04; C12N 5/00; C12N 5/06; C12N 15/00
(52) U.S. Cl. .................. 435/320.1; 435/69.1; 435/70.1; 435/325; 435/348
(58) Field of Search .............................. 435/320.1, 348, 435/325, 70.1, 69.1; 424/93.2; 536/23.1, 23.5, 24.1, 320.1

(56) References Cited

U.S. PATENT DOCUMENTS

| 5,047,335 A | * | 9/1991 | Paulson et al. ............. 435/69.1 |
| 5,077,214 A | | 12/1991 | Guarino et al. ........... 435/240.2 |
| 5,162,222 A | | 11/1992 | Guarino et al. ........... 435/240.2 |

FOREIGN PATENT DOCUMENTS

| WO | WO 92/05265 | 4/1992 |

OTHER PUBLICATIONS

Joziasse et al., Eur. J. Biochem., 191(1):75–83, Jul. 1990.*
Sarkar et al., Glycoconj. J., 11(3):204–209, Jun. 1994.*
Voss et al.; Expression of human interferon ?1 in sf9 cells, 1993, Eur. J. Biochem. 217: 913–919.*
Ackermann et al., "Pilot–scale production of glycoproteins with recombinant baculoviruses Evaluation of different host cell lines with respect to productivity, protein integrity and glycosylation," Expr. Conf. Abstr., ST13, 1995.
Adams and McClintock, In: Atlas of Invertebrate Viruses, Adams J.R. and Bonami, J.R., eds., CRC Press, Inc., Boca Raton, Florida, 87–226, 1991.
Altmann et al., "Processing of asparagine–linked oligosaccharides in insect cells. N–Acetylglocusaminyltransferase I and II activities in cultured lepidopteran cells," Glycobiology, 3:619–625, 1993.
Blissard and Rohrmann, "Baculovirus diversity and molecular biology," Annu. Rev. Entomol., 35:127–155, 1990.

Davidson and Castellino, "Asparagine–linked oligosaccharide processing in lepitopteran insect cells. Temporal dependence of the nature of the oligosaccharides assembled on asparagine–289 of recombinant human plasminogen produced in baculovirus vector infected spodoptera frugiperda (IPLB–SF–21AE) cells," Biochemistry, 30:6167–6174, 1991.
Davidson et al., "Oligosaccharide processing in the insect expression of human plasminogen cDNA by lepidopteran insect (spodoptera frugiperda) cells," Biochemistry, 29:5584–5590, 1990.
Grabenhorst et al., "Construction of stable BHK–21 cells coexpressing human secretory glycoproteins and human Gal(β1–4)GlcNAc–R α2,6–sialyltransferase. β2,6–linked NeuAc is preferentially attached to the Gal(β1–4)GlcNAc(β1–2) Man(α1–3)–branch of diantennary oligosaccharides from secreted recombinant β–trace protein," Eur. J. Biochem., 232:718–725, 1995.
Harduin–Lepers et al., "Characterization of two cis–regulatory regions in the murine β1–4–galactosyltransferase gene," J.Biol. Chem., 268:14348–14359, 1993.
Huh and Weaver, "Identifying the RNA polymerases that synthesize specific transcripts of the Autographa californica nuclear polyhedrosis virus," J. Gen. Virol., 71:195–202, 1990.
Jarvis and Summers, "Baculovirus expression vectors," In: Recombinant DNA Vaccines: Rationale and Strategies, R.E. Isaacson (ed.), Marcel Dekker, Inc., New York, Ch. 11:265–291, 1992.
Jarvis and Summers, "Glycosylation and secretion of human tissue plasminogen activator in recombinant baculovirus–infected insect cells," Mol. Cell. Biol., 9:214–223, 1989.
Jarvis, "Foreign gene expression in insect cells," In: Insect Cell Culture Engineering, M.F.A Goosen, A. Daugulis, and P.Faulkner (eds.), Marcel Dekker, Inc., New York, Ch. 8:193–217, 1993.
Jarvis et al., "Use of early baculovirus promoters for continuous expression and efficent processing of foreign gene products in stably transformed lepidopteran cells," Bio/Technology, 8:950–955, 1990.
Jarvis and Finn, "Modifying the insect cell N–glycosylation pathway with immediate early baculovirus expression vectors," Nature Biotechnology, 14:1288–1292, 1996.
Jarvis et al., "Construction and characterization of immediate early baculovirus pesticides," Biological Control, 7:228–235, 1996.

(List continued on next page.)

Primary Examiner—Deborah Crouch
Assistant Examiner—Joseph T. Woitach
(74) Attorney, Agent, or Firm—Fulbright & Jaworski L.L.P.

(57) ABSTRACT

Disclosed are a variety of recombinant baculovirus vectors, and host insect cells, which comprise at least one oligosaccharide processing enzyme gene. The vectors and cells may optionally comprise other heterologous structural genes, including further protein processing enzymes. Methods of making and using the recombinant baculoviruses and vectors are provided, including their uses in recombiant protein production and as insecticides.

46 Claims, 23 Drawing Sheets

OTHER PUBLICATIONS

Jarvis and Finn, "Biochemical analysis of the N-glycosylation pathway in baculovirus-infected lepidopteran insect cells," *Virology*, 212:500–511, 1995.

Kalsner et al., "Insertion into *aspergillus nidulans* of functional UDP–GlcNAc: β3–D–mannoside β–1,2–N–acetylglucosaminyltransferase I, the enzyme catalysing the first committed step from oligomannose to hybrid and complex N–glycans," *Glycoconjugate J.*, 12:360–370, 1995.

King and Possee, "The baculovirus expression system: a laboratory guide," Chapman and Hall, London, 1992.

Kubelka et al., "Structures of the N–linked oligosaccarides of the membrane glycoproteins from three lepidopteran cell lines (Sf–21, IZD–Mb–0503, Bm–N)[1]," *Arch. Bioch. Biophys.*, 308:148–157, 1994.

Lee et al., "Alteration of terminal glycosylation sequences on N–linked oligosaccharides of Chinese hamster ovary cells by expression of β–galactoside α2,6–Sialytransferase," *J. Biol. Chem.*, 264:13848–13855, 1989.

Licari and Bailey, "Expression of cloned β–galactoside α2,6–sialyltransferase alters terminal glycosylation in baculovirus–infested insect cells in spite of endogenous sialidase activity," ABSTRACT P416, *J. Cell. Biochem.*, Supp. 16A:173, 1992.

Lu and Miller, "The roles of eighteen baclovirus late expression factor genes in transcription and DNA replication," *J. Virol.*, 69:975–982, 1995.

Luckow and Summers, "Trends in the development of baculovirus expression vectors," *Bio/Technology*, 6:47–55, 1988.

Luckow, In: Recombinant DNA technology and applications, (A. Prokop, R. K. Bajpai and C. S. Ho, eds.), McGraw–Hill, Inc., New York, pp. 97–152, 1991.

Maeda, "Expression of foreign genes in insects using baculovirus vectors," *Ann. Rev. Entomol.*, 34:351–372, 1989.

McLachlin and Miller, "Identification of characterization of vlf–1, a baculovirus gene involved in a very late gene expression," *J. Virol.*, 68:7746–7756, 1994.

Miller, "Baculoviruses as gene expression vectors," *Ann. Rev. Microbiol.*, 42:177–199, 1988.

Minch et al., "Tissue plasminogen activator coexpressed in chinese hamster ovary cells with a(2,6)–sialytransferase contains neuaca (2,6) galb(1,4)Glc–n–acr linkages," *Biotechnol. Prog.*, 11:348–351, 1995.

Montreuil et al., In: New Comprehensive Biochemistry, (A. Neuberger and L. L. M. Van Deenen, series eds.), Elsevier, Amsterdam, 1995.

Murphy et al., "Temporal expression of HIV–1 envelope proteins in baculovirus–infected insect cells: Implications for glycosylation and CD4 binding," *Gen. Anal. Tech. Appl.*, 7:160–171, 1990.

O'Reilly et al., In Baculovirus expression vectors, W.H. Freeman and Company, N.Y, 1992.

Ogonah et al., "Isolation and characterization of an insect cell line able to perform complex N–linked glycosylation on recombinant proteins," *Bio/Technology*, 14:197–202, 1996.

Passarelli and Miller, "Three baculovirus genes involved in late and very late gene expression: ie–1, ie–n, and lef–2," *J. Virol.*, 67:2149–2158, 1993.

Pennock et al., "Strong regulated expression of *escherichia coli* β–galactosidase in insect cells with a baculovirus vector," *Mol. Cell. Biol.*, 4:399–406, 1984.

Richardson, editor, "Baculovirus expression protocols," vol. 39 In: Methods in Molecular Biology, (J. M. Walker, series ed.), Humana Press, Totowa, New Jersey, 1995.

Russo et al., "β1,4–galactosyltransferase: a short NH2–terminal fragment that includes the cytoplasmic and transmembrane domain is sufficient for golgi retention," *J. Biol. Chem.*, 267:9241–9247, 1992.

Staudacher et al., "Distinct N–glycan fucosylation potentials of three lepidopteran cell lines," *Eur. J. Biochem.*, 207:987–993, 1992.

Todd et al., "Eighteen baculovirus genes, including lef–11, p35, 39K, and p47, support late gene expression," *J. Virol.*, 69:968–974, 1995.

Velardo et al., "The presence of UDP–N–acetylglucosamine:α–3–mannosideβ1, 2–N–acetylglucosaminyltransferase I activity inn *spodoptera frugiperda* cells (IPLB–SF–21AE) and its enhancement as a result of baculovirus infection," *J. Biol. Chem.* 268:17902–17907, 1993.

Wagner et al., "Elongation of the N–glycans of fowl plague virus hemagglutinin expressed in *Spodoptera frugiperda* (Sf9) cells by coexpression of human β1, 2–N–acetylglucosaminyltransferase I," *Glycobiology*, 62(2):165–175, 1996.

Xu et al., "Differential transcription of baculovirus late and very late promoters: Fractional of nuclear extracts by phosphocellulose chromatography," *J. Virol.*, 69, 2912–2917, 1995.

Angata and Varki, "Cloning, characterization, and phylogenetic analysis of Siglec–9, a new member of the CD33–related group of Siglecs," *J. Bio. Chem.*, 275(29):22127–22135, 2000.

Breitbach and Jarvis, "Improved glycosylation of a foreign protein by Tn–5B1–4 cells engineered to express mammalian glycosyltransferases," *Biotech. & Bioengin.*, 74(3):230–239, 2001.

Hollister and Jarvis, "Engineering lepidopteran insect cells for sialoglycoprotein production by genetic transformation with mammalian β1, 4–galactosyltransferase and α2,6–sialytransferase genes," *Glycobiology*, 11(1):1–9, 2001.

Hooker et al., "Constraints on the transport and glycosylation of recombinant IFN–γ in Chinese hamster ovary and insect cells," *Biotech. & Bioeng.*, 63(5):559–572, 1999.

Jarvis et al., "Novel baculovirus expression vectors that provide sialylation of recombinant glycoproteins in lepidopteran insect cells," *J. of Virology*, 75(13):6223–6227, 2001.

Voss et al., "Expression of human interferon ω1 in Sf9 cells," *Eur. J. Biochem.*, 217:913–919, 1993.

\* cited by examiner

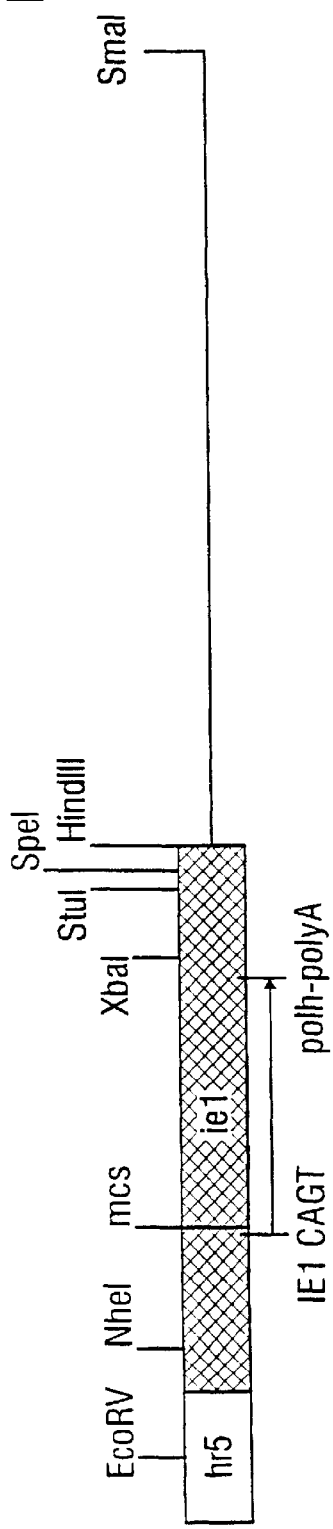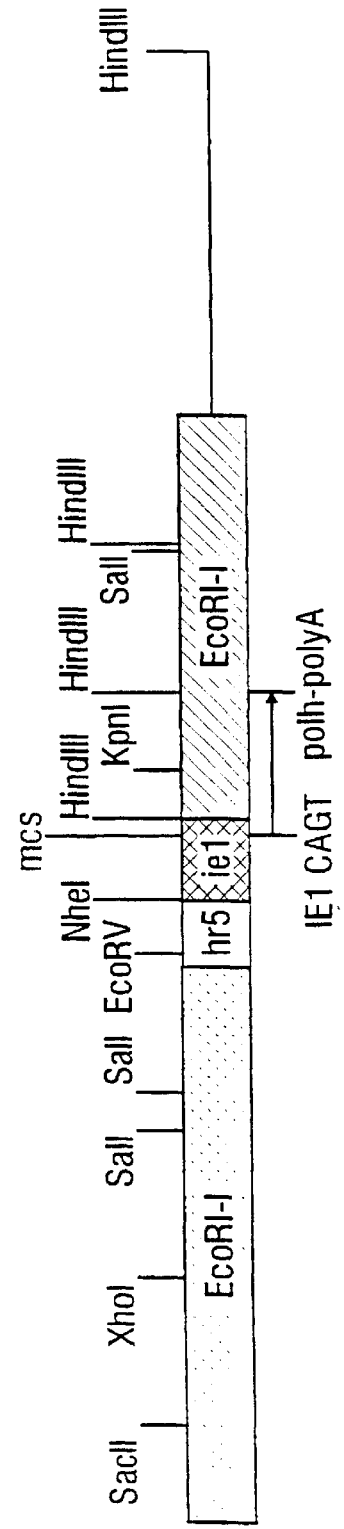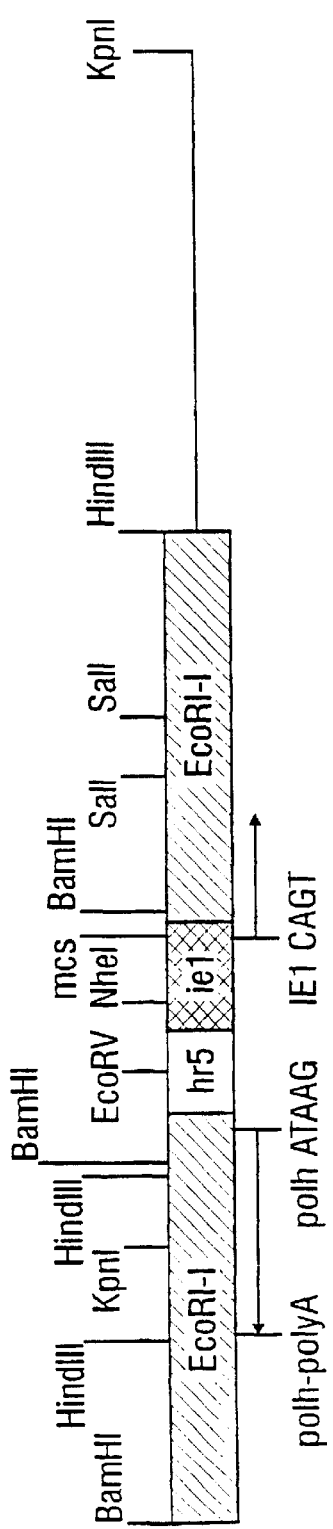

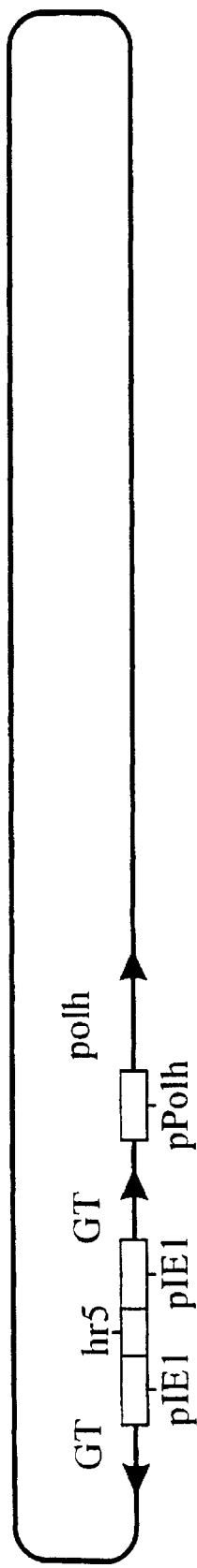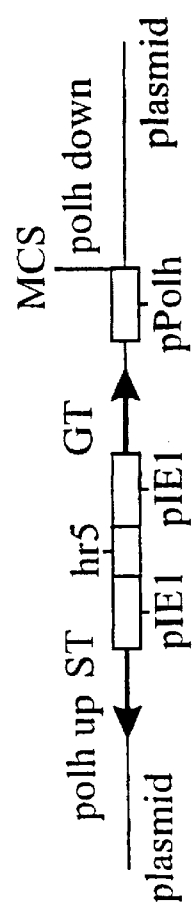
FIG. 20A
FIG. 20B

SEQUENCE LISTING

```
<160> NUMBER OF SEQ ID NOS: 30

<210> SEQ ID NO 1
<211> LENGTH: 2167
<212> TYPE: DNA
<213> ORGANISM: Artificial Sequence
<220> FEATURE:
<221> NAME/KEY: CDS
<222> LOCATION: (46)..(2010)
<223> OTHER INFORMATION: Description of Artificial Sequence:   Synthetic
      Primer

<400> SEQUENCE: 1
ctatttattt agatttttaa gtgtaggttc tgtgtttacg taaac atg acg ggg att     57
                                                  Met Thr Gly Ile
                                                    1 tta cct acc tac cag cga ttt gta aat gga gtt cct gta ccg tcc att    105
Leu Pro Thr Tyr Gln Arg Phe Val Asn Gly Val Pro Val Pro Ser Ile
  5                  10                  15                  20 tct cga cgt tcg ttc cgt cta cgg gag aaa tat ttg att gtt tct gta    153
Ser Arg Arg Ser Phe Arg Leu Arg Glu Lys Tyr Leu Ile Val Ser Val
```

-continued

| | | | | | | | | | | | | | | | | |
|---|---|---|---|---|---|---|---|---|---|---|---|---|---|---|---|---|
| | | | | 25 | | | | | 30 | | | | | 35 | | |
| ctt | ttg | aca | ttc | ggg | atc | gtg | tgg | tta | gga | gca | tta | ttc | tac | ttg | cca | 201 |
| Leu | Leu | Thr | Phe | Gly | Ile | Val | Trp | Leu | Gly | Ala | Leu | Phe | Tyr | Leu | Pro | |
| | | | 40 | | | | | 45 | | | | | 50 | | | |
| gag | ttt | aaa | agt | tca | aat | agt | gtg | aac | gat | agt | gtt | tac | aat | gta | tac | 249 |
| Glu | Phe | Lys | Ser | Ser | Asn | Ser | Val | Asn | Asp | Ser | Val | Tyr | Asn | Val | Tyr | |
| | | 55 | | | | | 60 | | | | | 65 | | | | |
| aaa | aga | atc | cag | aaa | gct | ggc | cca | gag | ctg | ctc | atg | ccg | cct | cct | ctg | 297 |
| Lys | Arg | Ile | Gln | Lys | Ala | Gly | Pro | Glu | Leu | Leu | Met | Pro | Pro | Pro | Leu | |
| 70 | | | | | 75 | | | | | 80 | | | | | | |
| gca | caa | aac | gat | gtc | ggt | gac | ttt | cct | gtg | att | ggg | atc | gct | cac | cat | 345 |
| Ala | Gln | Asn | Asp | Val | Gly | Asp | Phe | Pro | Val | Ile | Gly | Ile | Ala | His | His | |
| 85 | | | | | 90 | | | | | 95 | | | | | 100 | |
| ggt | gaa | ggg | ggt | gat | gat | cct | cac | gta | att | gag | gac | agg | aac | cgg | cta | 393 |
| Gly | Glu | Gly | Gly | Asp | Asp | Pro | His | Val | Ile | Glu | Asp | Arg | Asn | Arg | Leu | |
| | | | | 105 | | | | | 110 | | | | | 115 | | |
| cga | gct | aag | ata | gag | gag | gat | atg | gga | atg | aaa | gtg | ttg | gag | agg | cct | 441 |
| Arg | Ala | Lys | Ile | Glu | Glu | Asp | Met | Gly | Met | Lys | Val | Leu | Glu | Arg | Pro | |
| | | | 120 | | | | | 125 | | | | | 130 | | | |
| cag | ttt | gac | gta | gca | cct | tcc | gtg | tcg | tct | tcg | cga | ggg | ccc | agc | aag | 489 |
| Gln | Phe | Asp | Val | Ala | Pro | Ser | Val | Ser | Ser | Ser | Arg | Gly | Pro | Ser | Lys | |
| | | 135 | | | | | 140 | | | | | 145 | | | | |
| ccg | cca | gtc | gat | gcg | att | gag | gag | ccc | gcg | gta | ggg | aac | aat | gca | gct | 537 |
| Pro | Pro | Val | Asp | Ala | Ile | Glu | Glu | Pro | Ala | Val | Gly | Asn | Asn | Ala | Ala | |
| 150 | | | | | 155 | | | | | 160 | | | | | | |
| aac | aaa | gac | gtg | tcg | ccg | tca | ggc | ccg | aag | gct | gag | agc | tcg | gac | aag | 585 |
| Asn | Lys | Asp | Val | Ser | Pro | Ser | Gly | Pro | Lys | Ala | Glu | Ser | Ser | Asp | Lys | |
| 165 | | | | | 170 | | | | | 175 | | | | | 180 | |
| ttt | gtg | gct | gtg | gcc | ctg | gca | cca | gga | gct | gac | cct | gag | atc | aag | cac | 633 |
| Phe | Val | Ala | Val | Ala | Leu | Ala | Pro | Gly | Ala | Asp | Pro | Glu | Ile | Lys | His | |
| | | | | 185 | | | | | 190 | | | | | 195 | | |
| aag | ctg | gag | act | gtc | aaa | aag | atg | atg | ctg | cac | gcg | tgg | tac | aac | tac | 681 |
| Lys | Leu | Glu | Thr | Val | Lys | Lys | Met | Met | Leu | His | Ala | Trp | Tyr | Asn | Tyr | |
| | | | 200 | | | | | 205 | | | | | 210 | | | |
| aag | ctg | tat | gct | tgg | ggc | aag | aat | gag | ctg | aag | ccg | atg | tcg | aag | cga | 729 |
| Lys | Leu | Tyr | Ala | Trp | Gly | Lys | Asn | Glu | Leu | Lys | Pro | Met | Ser | Lys | Arg | |
| | | 215 | | | | | 220 | | | | | 225 | | | | |
| gct | cac | ttg | tcc | agc | gtg | ttc | ggc | gcg | ggc | gaa | ctt | ggc | gcc | acc | atc | 777 |
| Ala | His | Leu | Ser | Ser | Val | Phe | Gly | Ala | Gly | Glu | Leu | Gly | Ala | Thr | Ile | |
| 230 | | | | | 235 | | | | | 240 | | | | | | |
| gtc | gat | ggt | ctc | gac | acc | ctc | tac | ctc | atg | gga | ctc | aac | gac | gaa | ttc | 825 |
| Val | Asp | Gly | Leu | Asp | Thr | Leu | Tyr | Leu | Met | Gly | Leu | Asn | Asp | Glu | Phe | |
| 245 | | | | | 250 | | | | | 255 | | | | | 260 | |
| cga | gag | ggc | cgc | gac | tgg | gtc | gct | gaa | cat | ttg | cat | att | aat | gaa | atc | 873 |
| Arg | Glu | Gly | Arg | Asp | Trp | Val | Ala | Glu | His | Leu | His | Ile | Asn | Glu | Ile | |
| | | | | 265 | | | | | 270 | | | | | 275 | | |
| gat | tcc | gac | tta | tct | gtg | ttc | gag | acg | acg | atc | cgg | ttt | gtc | gga | ggt | 921 |
| Asp | Ser | Asp | Leu | Ser | Val | Phe | Glu | Thr | Thr | Ile | Arg | Phe | Val | Gly | Gly | |
| | | | 280 | | | | | 285 | | | | | 290 | | | |
| ctc | ctg | tca | tgt | tac | gcg | ctg | acc | ggc | gac | acg | atg | ttc | cga | gac | aag | 969 |
| Leu | Leu | Ser | Cys | Tyr | Ala | Leu | Thr | Gly | Asp | Thr | Met | Phe | Arg | Asp | Lys | |
| | | 295 | | | | | 300 | | | | | 305 | | | | |
| gcg | gcg | gaa | gta | ggc | gac | gct | ttg | ctg | cca | gca | ttc | gac | aca | ccc | acc | 1017 |
| Ala | Ala | Glu | Val | Gly | Asp | Ala | Leu | Leu | Pro | Ala | Phe | Asp | Thr | Pro | Thr | |
| 310 | | | | | 315 | | | | | 320 | | | | | | |
| ggg | ttg | cca | tat | gct | ctc | atc | aac | ccg | tcc | acc | aag | gca | agc | cgt | cag | 1065 |
| Gly | Leu | Pro | Tyr | Ala | Leu | Ile | Asn | Pro | Ser | Thr | Lys | Ala | Ser | Arg | Gln | |
| 325 | | | | | 330 | | | | | 335 | | | | | 340 | |
| tac | cac | tgg | gcg | ggt | ccg | aac | agc | atc | cta | tcg | gag | ctg | gga | acg | ctc | 1113 |

-continued

```
Tyr His Trp Ala Gly Pro Asn Ser Ile Leu Ser Glu Leu Gly Thr Leu
            345                 350                 355 cac ctc gag ttc acg tac ctc agt gac gtc acg ggc cgt gat att tac      1161
His Leu Glu Phe Thr Tyr Leu Ser Asp Val Thr Gly Arg Asp Ile Tyr
        360                 365                 370 aga caa aaa gtg agc cgc atc cgt gag gtt ttg gat cag atc gac aaa      1209
Arg Gln Lys Val Ser Arg Ile Arg Glu Val Leu Asp Gln Ile Asp Lys
    375                 380                 385 cct ggc gac ttg tac ccc aac ttc atc aac cca cgc act gga caa tgg      1257
Pro Gly Asp Leu Tyr Pro Asn Phe Ile Asn Pro Arg Thr Gly Gln Trp
390                 395                 400 gga caa agg cac atg tct ctg ggc gct ctc ggc gac tcg ttc tac gag      1305
Gly Gln Arg His Met Ser Leu Gly Ala Leu Gly Asp Ser Phe Tyr Glu
405                 410                 415                 420 tac tta ctg aag gcg tgg ctg atg tct ggc ggc gct gac gag cag gct      1353
Tyr Leu Leu Lys Ala Trp Leu Met Ser Gly Gly Ala Asp Glu Gln Ala
                425                 430                 435 cgc atc atg ttc gac acg gcc atg cag gcg gcg ctc gac aaa atg ctg      1401
Arg Ile Met Phe Asp Thr Ala Met Gln Ala Ala Leu Asp Lys Met Leu
                440                 445                 450 cgt gtc tcg ccc tcc ggc ctc gct tac ctc gcc gag ctc aag tac gga      1449
Arg Val Ser Pro Ser Gly Leu Ala Tyr Leu Ala Glu Leu Lys Tyr Gly
            455                 460                 465 cgt atc att gaa gag aag atg gac cac ctt tcg tgc ttc gct ggc ggt      1497
Arg Ile Ile Glu Glu Lys Met Asp His Leu Ser Cys Phe Ala Gly Gly
470                 475                 480 atg ttc gca ctg gcg tcg act acc ctg gac aac tcg atg tcg gag cgc      1545
Met Phe Ala Leu Ala Ser Thr Thr Leu Asp Asn Ser Met Ser Glu Arg
485                 490                 495                 500 tac atg gac gtg gcc aag aag ctg acc aat acc tgc cac gag agc tac      1593
Tyr Met Asp Val Ala Lys Lys Leu Thr Asn Thr Cys His Glu Ser Tyr
                505                 510                 515 gcg cga tcc gag acc aaa ctc ggc cct gaa gca ttc cga ttc tcc aac      1641
Ala Arg Ser Glu Thr Lys Leu Gly Pro Glu Ala Phe Arg Phe Ser Asn
            520                 525                 530 gcg gcc gag gcg cgt gca cag aag agc aat gag aag gtg tac ctc ctg      1689
Ala Ala Glu Ala Arg Ala Gln Lys Ser Asn Glu Lys Val Tyr Leu Leu
        535                 540                 545 cgg ccg gag acg ttc gag agc tac ttc atc atg tgg aga ctc acc aag      1737
Arg Pro Glu Thr Phe Glu Ser Tyr Phe Ile Met Trp Arg Leu Thr Lys
    550                 555                 560 caa cag atg tac cgc gac tgg gcc tgg gag gct gtg cag gct ctg gag      1785
Gln Gln Met Tyr Arg Asp Trp Ala Trp Glu Ala Val Gln Ala Leu Glu
565                 570                 575                 580 aaa cac tgc cgc gtg gag ggc ggc tac acc ggt ctc gtg aac gtc tac      1833
Lys His Cys Arg Val Glu Gly Gly Tyr Thr Gly Leu Val Asn Val Tyr
                585                 590                 595 cac gcc aac cct cag gga gac gac gtg cag cag agc ttc ttc ctc gct      1881
His Ala Asn Pro Gln Gly Asp Asp Val Gln Gln Ser Phe Phe Leu Ala
            600                 605                 610 gag aca ctc aag tac tta tac ctg ata ttc ggt gac gat tcg ttc ctg      1929
Glu Thr Leu Lys Tyr Leu Tyr Leu Ile Phe Gly Asp Asp Ser Phe Leu
        615                 620                 625 ccg ctc gac gag tgg gtg ttc aac acg gaa gcc cat cca ttc ccg atc      1977
Pro Leu Asp Glu Trp Val Phe Asn Thr Glu Ala His Pro Phe Pro Ile
    630                 635                 640 agg ggc aag aac ccg ctg tac cgc gct gtc gac aaaccggtcc tgccagaacc    2030
Arg Gly Lys Asn Pro Leu Tyr Arg Ala Val Asp
645                 650                 655
```

-continued

```
tgcgcatgcg caaacaaca ggatataaga ccgtcactca agtaatttgt ttttaaaaatg    2090 tttcattttg ttagaactga agaagccaga ctgtaccaac agtgtctggt taggtattga    2150
cgagagtaaa tagcaag                                                   2167
```

<210> SEQ ID NO 2
<211> LENGTH: 655
<212> TYPE: PRT
<213> ORGANISM: Artificial Sequence
<220> FEATURE:
<223> OTHER INFORMATION: Description of Artificial Sequence: Synthetic

<400> SEQUENCE: 2

```
Met Thr Gly Ile Leu Pro Thr Tyr Gln Arg Phe Val Asn Gly Val Pro
 1               5                  10                  15

Val Pro Ser Ile Ser Arg Arg Ser Phe Arg Leu Arg Glu Lys Tyr Leu
                20                  25                  30

Ile Val Ser Val Leu Leu Thr Phe Gly Ile Val Trp Leu Gly Ala Leu
            35                  40                  45

Phe Tyr Leu Pro Glu Phe Lys Ser Ser Asn Ser Val Asn Asp Ser Val
     50                  55                  60

Tyr Asn Val Tyr Lys Arg Ile Gln Lys Ala Gly Pro Glu Leu Leu Met
 65                  70                  75                  80

Pro Pro Leu Ala Gln Asn Asp Val Gly Asp Phe Pro Val Ile Gly
                 85                  90                  95

Ile Ala His His Gly Glu Gly Gly Asp Asp Pro His Val Ile Glu Asp
            100                 105                 110

Arg Asn Arg Leu Arg Ala Lys Ile Glu Glu Asp Met Gly Met Lys Val
        115                 120                 125

Leu Glu Arg Pro Gln Phe Asp Val Ala Pro Ser Val Ser Ser Ser Arg
    130                 135                 140

Gly Pro Ser Lys Pro Pro Val Asp Ala Ile Glu Pro Ala Val Gly
145                 150                 155                 160

Asn Asn Ala Ala Asn Lys Asp Val Ser Pro Ser Gly Pro Lys Ala Glu
                165                 170                 175

Ser Ser Asp Lys Phe Val Ala Val Ala Leu Ala Pro Gly Ala Asp Pro
            180                 185                 190

Glu Ile Lys His Lys Leu Glu Thr Val Lys Lys Met Met Leu His Ala
        195                 200                 205

Trp Tyr Asn Tyr Lys Leu Tyr Ala Trp Gly Lys Asn Glu Leu Lys Pro
    210                 215                 220

Met Ser Lys Arg Ala His Leu Ser Ser Val Phe Gly Ala Gly Glu Leu
225                 230                 235                 240

Gly Ala Thr Ile Val Asp Gly Leu Asp Thr Leu Tyr Leu Met Gly Leu
                245                 250                 255

Asn Asp Glu Phe Arg Glu Gly Arg Asp Trp Val Ala Glu His Leu His
            260                 265                 270

Ile Asn Glu Ile Asp Ser Asp Leu Ser Val Phe Glu Thr Thr Ile Arg
        275                 280                 285

Phe Val Gly Gly Leu Leu Ser Cys Tyr Ala Leu Thr Gly Asp Thr Met
    290                 295                 300

Phe Arg Asp Lys Ala Ala Glu Val Gly Asp Ala Leu Leu Pro Ala Phe
305                 310                 315                 320

Asp Thr Pro Thr Gly Leu Pro Tyr Ala Leu Ile Asn Pro Ser Thr Lys
                325                 330                 335
```

-continued

```
Ala Ser Arg Gln Tyr His Trp Ala Gly Pro Asn Ser Ile Leu Ser Glu
            340                 345                 350

Leu Gly Thr Leu His Leu Glu Phe Thr Tyr Leu Ser Asp Val Thr Gly
        355                 360                 365

Arg Asp Ile Tyr Arg Gln Lys Val Ser Arg Ile Arg Glu Val Leu Asp
    370                 375                 380

Gln Ile Asp Lys Pro Gly Asp Leu Tyr Pro Asn Phe Ile Asn Pro Arg
385                 390                 395                 400

Thr Gly Gln Trp Gly Gln Arg His Met Ser Leu Gly Ala Leu Gly Asp
                405                 410                 415

Ser Phe Tyr Glu Tyr Leu Leu Lys Ala Trp Leu Met Ser Gly Gly Ala
            420                 425                 430

Asp Glu Gln Ala Arg Ile Met Phe Asp Thr Ala Met Gln Ala Ala Leu
        435                 440                 445

Asp Lys Met Leu Arg Val Ser Pro Ser Gly Leu Ala Tyr Leu Ala Glu
    450                 455                 460

Leu Lys Tyr Gly Arg Ile Ile Glu Glu Lys Met Asp His Leu Ser Cys
465                 470                 475                 480

Phe Ala Gly Gly Met Phe Ala Leu Ala Ser Thr Thr Leu Asp Asn Ser
                485                 490                 495

Met Ser Glu Arg Tyr Met Asp Val Ala Lys Lys Leu Thr Asn Thr Cys
            500                 505                 510

His Glu Ser Tyr Ala Arg Ser Glu Thr Lys Leu Gly Pro Glu Ala Phe
        515                 520                 525

Arg Phe Ser Asn Ala Ala Glu Ala Arg Ala Gln Lys Ser Asn Glu Lys
    530                 535                 540

Val Tyr Leu Leu Arg Pro Glu Thr Phe Glu Ser Tyr Phe Ile Met Trp
545                 550                 555                 560

Arg Leu Thr Lys Gln Gln Met Tyr Arg Asp Trp Ala Trp Glu Ala Val
                565                 570                 575

Gln Ala Leu Glu Lys His Cys Arg Val Glu Gly Gly Tyr Thr Gly Leu
            580                 585                 590

Val Asn Val Tyr His Ala Asn Pro Gln Gly Asp Val Gln Gln Ser
        595                 600                 605

Phe Phe Leu Ala Glu Thr Leu Lys Tyr Leu Tyr Leu Ile Phe Gly Asp
    610                 615                 620

Asp Ser Phe Leu Pro Leu Asp Glu Trp Val Phe Asn Thr Glu Ala His
625                 630                 635                 640

Pro Phe Pro Ile Arg Gly Lys Asn Pro Leu Tyr Arg Ala Val Asp
                645                 650                 655
```

<210> SEQ ID NO 3
<211> LENGTH: 3748
<212> TYPE: DNA
<213> ORGANISM: Artificial Sequence
<220> FEATURE:
<221> NAME/KEY: CDS
<222> LOCATION: (177)..(3566)
<223> OTHER INFORMATION: Description of Artificial Sequence: Synthetic
      Primer

<400> SEQUENCE: 3

```
ggcttattaa ccctcactaa agggagagtc aggagcacgc tgtggtgttt ggctgtcgca    60
tgcaagtgcg agccgataac ttacactgca gataaataaa taattgactt tatctggagt   120
aaaataaaat gtaaacattg ttttcaaaaa aatcgtgaca taaaaatat tgcaca atg    179
                                                                   Met
```

```
                                                                 1
agg act cgt gtc ctt cgt tgc cgg ccg ttc tcc acc cgg atc ctg ctg      227
Arg Thr Arg Val Leu Arg Cys Arg Pro Phe Ser Thr Arg Ile Leu Leu
            5                  10                  15 ctg ctg cta ttt gtc ctt gcg ttt ggg gtc tac tgc tat ttc tac aat      275
Leu Leu Leu Phe Val Leu Ala Phe Gly Val Tyr Cys Tyr Phe Tyr Asn
        20                  25                  30 gca tct cct cag aac tat aac aaa cca aga atc agt tac cca gcc agt      323
Ala Ser Pro Gln Asn Tyr Asn Lys Pro Arg Ile Ser Tyr Pro Ala Ser
    35                  40                  45 atg gag cac ttc aaa tct tcc ctc act cac acc gtc aag agc cga gac      371
Met Glu His Phe Lys Ser Ser Leu Thr His Thr Val Lys Ser Arg Asp
50                  55                  60                  65 gag cca act ccg gat caa tgc cct gca ttg aag gaa agc gaa gcg gac      419
Glu Pro Thr Pro Asp Gln Cys Pro Ala Leu Lys Glu Ser Glu Ala Asp
                70                  75                  80 atc gac acc gtg gcg ata tac cca act ttt gat ttt cag ccg agc tgg      467
Ile Asp Thr Val Ala Ile Tyr Pro Thr Phe Asp Phe Gln Pro Ser Trp
            85                  90                  95 ttg cgt aca aag gaa ttt tgg gac aag tcc ttc gag gat cgg tat gaa      515
Leu Arg Thr Lys Glu Phe Trp Asp Lys Ser Phe Glu Asp Arg Tyr Glu
        100                 105                 110 aga att cat aac gac act aca cgg cct aga ctg aag gta atc gtg gtt      563
Arg Ile His Asn Asp Thr Thr Arg Pro Arg Leu Lys Val Ile Val Val
    115                 120                 125 cct cac tca cac aac gac ccg gga tgg ctg aag acg ttt gaa cag tac      611
Pro His Ser His Asn Asp Pro Gly Trp Leu Lys Thr Phe Glu Gln Tyr
130                 135                 140                 145 ttc gag tgg aag acc aag aac att atc aac aac ata gtg aac aaa ctg      659
Phe Glu Trp Lys Thr Lys Asn Ile Ile Asn Asn Ile Val Asn Lys Leu
                150                 155                 160 cac cag tac ccc aac atg acc ttc att tgg acc gag ata tcg ttt ctg      707
His Gln Tyr Pro Asn Met Thr Phe Ile Trp Thr Glu Ile Ser Phe Leu
            165                 170                 175 aat gcc tgg tgg gaa agg tcg cac cct gtc aaa caa aag gca ttg aaa      755
Asn Ala Trp Trp Glu Arg Ser His Pro Val Lys Gln Lys Ala Leu Lys
        180                 185                 190 aaa ctt atc aaa gaa ggt cgt ctc gag atc acg acg ggc ggc tgg gtg      803
Lys Leu Ile Lys Glu Gly Arg Leu Glu Ile Thr Thr Gly Gly Trp Val
    195                 200                 205 atg ccg gac gaa gcc tgc acg cat atc tat gcg cta att gac cag ttt      851
Met Pro Asp Glu Ala Cys Thr His Ile Tyr Ala Leu Ile Asp Gln Phe
210                 215                 220                 225 att gaa gga cat cac tgg gtg aaa act aat ctc ggc gtc atc ccg aag      899
Ile Glu Gly His His Trp Val Lys Thr Asn Leu Gly Val Ile Pro Lys
                230                 235                 240 aca gga tgg tct att gac ccc ttc ggc cac ggg gcc act gtg cct tac      947
Thr Gly Trp Ser Ile Asp Pro Phe Gly His Gly Ala Thr Val Pro Tyr
            245                 250                 255 ctg cta gac cag agc ggc ctt gag gga acc att ata cag aga atc cat      995
Leu Leu Asp Gln Ser Gly Leu Glu Gly Thr Ile Ile Gln Arg Ile His
        260                 265                 270 tat gcg tgg aaa cag tgg ctg gcg gag cga cag att gag gag ttt tac      1043
Tyr Ala Trp Lys Gln Trp Leu Ala Glu Arg Gln Ile Glu Glu Phe Tyr
    275                 280                 285 tgg ctg gcg agt tgg gct act acg aag ccg tcc atg ata gtg cac aat      1091
Trp Leu Ala Ser Trp Ala Thr Thr Lys Pro Ser Met Ile Val His Asn
290                 295                 300                 305 cag ccg ttt gat att tat tca ata aaa agc acg tgt ggc ccg cac cct      1139
```

```
                Gln Pro Phe Asp Ile Tyr Ser Ile Lys Ser Thr Cys Gly Pro His Pro
                                310                 315                 320 tca att tgt ctc agt ttc gac ttc agg aag att ccc ggc gaa tat tct        1187
Ser Ile Cys Leu Ser Phe Asp Phe Arg Lys Ile Pro Gly Glu Tyr Ser
        325                 330                 335 gaa tac aca gct aag cac gaa gac atc acg gaa cac aac ttg cac agc        1235
Glu Tyr Thr Ala Lys His Glu Asp Ile Thr Glu His Asn Leu His Ser
            340                 345                 350 aag gca aag act ttg ata gag gag tac gac cgt atc ggg tcc ctg act        1283
Lys Ala Lys Thr Leu Ile Glu Glu Tyr Asp Arg Ile Gly Ser Leu Thr
355                 360                 365 cca cac aac gtg gtg ctg gtg ccg ctc gga gac gac ttc aga tac gag        1331
Pro His Asn Val Val Leu Val Pro Leu Gly Asp Asp Phe Arg Tyr Glu
370                 375                 380                 385 tac agc gtc gag ttt gat gcc caa tac gtc aat tat atg aaa atg ttt        1379
Tyr Ser Val Glu Phe Asp Ala Gln Tyr Val Asn Tyr Met Lys Met Phe
                390                 395                 400 aac tac atc aat gct cac aag gaa atc ttc aac gct gac gta cag ttc        1427
Asn Tyr Ile Asn Ala His Lys Glu Ile Phe Asn Ala Asp Val Gln Phe
            405                 410                 415 gga act cct ctc gat tac ttt aac gcc atg aaa gaa aga cat caa aat        1475
Gly Thr Pro Leu Asp Tyr Phe Asn Ala Met Lys Glu Arg His Gln Asn
            420                 425                 430 ata ccc agc tta aag gga gat ttc ttc gtt tac tcc gat att ttc agc        1523
Ile Pro Ser Leu Lys Gly Asp Phe Phe Val Tyr Ser Asp Ile Phe Ser
435                 440                 445 gaa ggt aaa cca gcg tac tgg tca ggt tac tac act act aga ccc tac        1571
Glu Gly Lys Pro Ala Tyr Trp Ser Gly Tyr Tyr Thr Thr Arg Pro Tyr
450                 455                 460                 465 caa aaa atc ctc gcc cgt cag ttc gaa cac caa ctg cga tcg gca gag        1619
Gln Lys Ile Leu Ala Arg Gln Phe Glu His Gln Leu Arg Ser Ala Glu
                470                 475                 480 att tta ttc acc ctt gta tcg aac tac atc aga cag atg ggt cgc caa        1667
Ile Leu Phe Thr Leu Val Ser Asn Tyr Ile Arg Gln Met Gly Arg Gln
            485                 490                 495 gga gag ttc gga gct tct gag aaa aag tta gaa aaa tct tac gag cag        1715
Gly Glu Phe Gly Ala Ser Glu Lys Lys Leu Glu Lys Ser Tyr Glu Gln
            500                 505                 510 ctt atc tat gct cga cgg aac ttg ggt ctg ttt caa cat cac gat gcg        1763
Leu Ile Tyr Ala Arg Arg Asn Leu Gly Leu Phe Gln His His Asp Ala
515                 520                 525 att act gga aca tca aag tcc agt gtg atg caa gat tac gga acc aaa        1811
Ile Thr Gly Thr Ser Lys Ser Ser Val Met Gln Asp Tyr Gly Thr Lys
530                 535                 540                 545 ctg ttc aca agt ctg tat cac tgc atc cgc ctg cag gag gcc gcg ctc        1859
Leu Phe Thr Ser Leu Tyr His Cys Ile Arg Leu Gln Glu Ala Ala Leu
                550                 555                 560 acc acc atc atg ttg cct gac cag tcg ttg cac tcg cag agc att ata        1907
Thr Thr Ile Met Leu Pro Asp Gln Ser Leu His Ser Gln Ser Ile Ile
            565                 570                 575 caa agc gag gtt gag tgg gaa act tac gga aaa ccg ccc aag aag ctg        1955
Gln Ser Glu Val Glu Trp Glu Thr Tyr Gly Lys Pro Pro Lys Lys Leu
            580                 585                 590 caa gtg tcc ttc att gac aag aag aaa gtt ata ctt ttt aat ccg ttg        2003
Gln Val Ser Phe Ile Asp Lys Lys Lys Val Ile Leu Phe Asn Pro Leu
595                 600                 605 gct gag act cga act gaa gtg gtc acg gtt aga tcc aac acg tcc aac        2051
Ala Glu Thr Arg Thr Glu Val Val Thr Val Arg Ser Asn Thr Ser Asn
610                 615                 620                 625
```

```
atc cgg gtg tac gat aca cac aag agg aag cac gtc ttg tat cag ata    2099
Ile Arg Val Tyr Asp Thr His Lys Arg Lys His Val Leu Tyr Gln Ile
            630                 635                 640 atg ccc agc atc aca atc caa gac aac ggc aag agt atc gta agc gac    2147
Met Pro Ser Ile Thr Ile Gln Asp Asn Gly Lys Ser Ile Val Ser Asp
            645                 650                 655 acc acg ttc gac ata atg ttc gtg gcc acc atc ccg ccc ctc acc tcc    2195
Thr Thr Phe Asp Ile Met Phe Val Ala Thr Ile Pro Pro Leu Thr Ser
            660                 665                 670 atc tcg tac aag ctg cag gag cac acc aac act tcc cac cac tgc gtc    2243
Ile Ser Tyr Lys Leu Gln Glu His Thr Asn Thr Ser His His Cys Val
        675                 680                 685 att ttc tgc aac aac tgc gaa caa tac cag aaa tcc aat gtg ttc caa    2291
Ile Phe Cys Asn Asn Cys Glu Gln Tyr Gln Lys Ser Asn Val Phe Gln
690                 695                 700                 705 att aag aaa atg atg cct ggt gac ata caa tta gaa aat gca gtg cta    2339
Ile Lys Lys Met Met Pro Gly Asp Ile Gln Leu Glu Asn Ala Val Leu
                710                 715                 720 aaa ctt ctc gtt aat agg aac acc ggc ttt ctg aga caa gtc tat aga    2387
Lys Leu Leu Val Asn Arg Asn Thr Gly Phe Leu Arg Gln Val Tyr Arg
            725                 730                 735 aag gac atc cgg aag aga act gtc gtt gac gta caa ttc ggc gca tat    2435
Lys Asp Ile Arg Lys Arg Thr Val Val Asp Val Gln Phe Gly Ala Tyr
            740                 745                 750 caa agt gcc caa aga cat tct ggt gct tac ctc ttc atg cct cat tac    2483
Gln Ser Ala Gln Arg His Ser Gly Ala Tyr Leu Phe Met Pro His Tyr
755                 760                 765 gac tca cct gag aag aat gtt ctg cat ccc tac act aat cag aac aac    2531
Asp Ser Pro Glu Lys Asn Val Leu His Pro Tyr Thr Asn Gln Asn Asn
770                 775                 780                 785 atg caa gat gat aac ata atc ata gtg tcc gga cct att tct acg gaa    2579
Met Gln Asp Asp Asn Ile Ile Ile Val Ser Gly Pro Ile Ser Thr Glu
                790                 795                 800 atc acg acc atg tac ttg ccc ttc ttg gtg cac act att agg ata tac    2627
Ile Thr Thr Met Tyr Leu Pro Phe Leu Val His Thr Ile Arg Ile Tyr
            805                 810                 815 aac gtg ccg gac ccg gta ctg tcg cgt gct att cta tta gag acc gat    2675
Asn Val Pro Asp Pro Val Leu Ser Arg Ala Ile Leu Leu Glu Thr Asp
            820                 825                 830 gta gat ttc gag gcg cca cct aag aac aga gag act gag tta ttt atg    2723
Val Asp Phe Glu Ala Pro Pro Lys Asn Arg Glu Thr Glu Leu Phe Met
835                 840                 845 aga tta cag act gat ata caa aac ggt gac att ccc gaa ttt tac acc    2771
Arg Leu Gln Thr Asp Ile Gln Asn Gly Asp Ile Pro Glu Phe Tyr Thr
850                 855                 860                 865 gat cag aac gga ttc cag tac caa aag agg gtc aaa gtg aat aaa cta    2819
Asp Gln Asn Gly Phe Gln Tyr Gln Lys Arg Val Lys Val Asn Lys Leu
                870                 875                 880 gga ata gaa gct aat tac tac ccg atc act acc atg gcg tgc ctg caa    2867
Gly Ile Glu Ala Asn Tyr Tyr Pro Ile Thr Thr Met Ala Cys Leu Gln
            885                 890                 895 gac gag gag acc cgg ctc act ctg ctg acg aac cac gct caa ggc gct    2915
Asp Glu Glu Thr Arg Leu Thr Leu Leu Thr Asn His Ala Gln Gly Ala
            900                 905                 910 gct gca tac gaa cca gga cgc tta gaa gtc atg ctc gat cgt cga act    2963
Ala Ala Tyr Glu Pro Gly Arg Leu Glu Val Met Leu Asp Arg Arg Thr
        915                 920                 925 ctt tat gat gac ttc aga gga atc ggt gaa gga gta gtc gat aac aaa    3011
Leu Tyr Asp Asp Phe Arg Gly Ile Gly Glu Gly Val Val Asp Asn Lys
930                 935                 940                 945
```

```
ccg acg act ttc cag aac tgg att tta att gaa tcc atg cca ggc gtg      3059
Pro Thr Thr Phe Gln Asn Trp Ile Leu Ile Glu Ser Met Pro Gly Val
                950                 955                 960 acg cga gcc aag aga gac act agt gaa cca ggt ttc aaa ttt gtt aat      3107
Thr Arg Ala Lys Arg Asp Thr Ser Glu Pro Gly Phe Lys Phe Val Asn
            965                 970                 975 gaa cgt cgt ttt ggc ccc ggc cag aag gaa agc cct tac caa gta ccg      3155
Glu Arg Arg Phe Gly Pro Gly Gln Lys Glu Ser Pro Tyr Gln Val Pro
        980                 985                 990 tcg cag act gcg gac tac ctg agc agg atg ttc aat tac ccg gtg aac      3203
Ser Gln Thr Ala Asp Tyr Leu Ser Arg Met Phe Asn Tyr Pro Val Asn
    995                 1000                1005 gtg tac ctg gtg gac act agc gag gtt ggc gag atc gag gtg aag ccg      3251
Val Tyr Leu Val Asp Thr Ser Glu Val Gly Glu Ile Glu Val Lys Pro
1010                1015                1020                1025 tac cag tcg ttc ctg cag agc ttc ccg ccc ggc atc cac ctg gtc acc      3299
Tyr Gln Ser Phe Leu Gln Ser Phe Pro Pro Gly Ile His Leu Val Thr
                1030                1035                1040 ctg cgc acc atc acc gac gac gtg ctc gaa ctc ttc ccc agc aac gaa      3347
Leu Arg Thr Ile Thr Asp Asp Val Leu Glu Leu Phe Pro Ser Asn Glu
            1045                1050                1055 agc tac atg gta ctg cac cga cca gga tac agc tgc gct gtc gga gag      3395
Ser Tyr Met Val Leu His Arg Pro Gly Tyr Ser Cys Ala Val Gly Glu
        1060                1065                1070 aag cca gtc gcc aag tct ccc aag ttt tcg tcc aaa acc agg ttc aat      3443
Lys Pro Val Ala Lys Ser Pro Lys Phe Ser Ser Lys Thr Arg Phe Asn
    1075                1080                1085 ggt ctg aac att cag aac atc act gca gtc agc ctg acc ggc ctg aag      3491
Gly Leu Asn Ile Gln Asn Ile Thr Ala Val Ser Leu Thr Gly Leu Lys
1090                1095                1100                1105 tca ctc cga cct ctc aca ggt ctg agt gac atc cac ctg aac gct atg      3539
Ser Leu Arg Pro Leu Thr Gly Leu Ser Asp Ile His Leu Asn Ala Met
                1110                1115                1120 gag gta aaa act tac aag atc agg ttt taaagactgc tagtagtaat            3586
Glu Val Lys Thr Tyr Lys Ile Arg Phe
                1125                1130 aggtgtaaca catttgtaat tttataatat ttacaaactt tatcgtgaac ttacagcctc    3646
acacctcggc tatgtaagtg gaataagtag gaagatacaa ttttgatggt actttagtag    3706
agcctcgtac taacgggccg cgtaatagta taatggtatt ag                       3748

<210> SEQ ID NO 4
<211> LENGTH: 1130
<212> TYPE: PRT
<213> ORGANISM: Artificial Sequence
<220> FEATURE:
<223> OTHER INFORMATION: Description of Artificial Sequence: Synthetic

<400> SEQUENCE: 4

Met Arg Thr Arg Val Leu Arg Cys Arg Pro Phe Ser Thr Arg Ile Leu
  1               5                  10                  15

Leu Leu Leu Leu Phe Val Leu Ala Phe Gly Val Tyr Cys Tyr Phe Tyr
                 20                  25                  30

Asn Ala Ser Pro Gln Asn Tyr Asn Lys Pro Arg Ile Ser Tyr Pro Ala
             35                  40                  45

Ser Met Glu His Phe Lys Ser Ser Leu Thr His Thr Val Lys Ser Arg
         50                  55                  60

Asp Glu Pro Thr Pro Asp Gln Cys Pro Ala Leu Lys Glu Ser Glu Ala
 65                  70                  75                  80
```

-continued

```
Asp Ile Asp Thr Val Ala Ile Tyr Pro Thr Phe Asp Phe Gln Pro Ser
                 85                  90                  95
Trp Leu Arg Thr Lys Glu Phe Trp Asp Lys Ser Phe Glu Asp Arg Tyr
            100                 105                 110
Glu Arg Ile His Asn Asp Thr Thr Arg Pro Arg Leu Lys Val Ile Val
        115                 120                 125
Val Pro His Ser His Asn Asp Pro Gly Trp Leu Lys Thr Phe Glu Gln
    130                 135                 140
Tyr Phe Glu Trp Lys Thr Lys Asn Ile Ile Asn Asn Ile Val Asn Lys
145                 150                 155                 160
Leu His Gln Tyr Pro Asn Met Thr Phe Ile Trp Thr Glu Ile Ser Phe
                165                 170                 175
Leu Asn Ala Trp Trp Glu Arg Ser His Pro Val Lys Gln Lys Ala Leu
            180                 185                 190
Lys Lys Leu Ile Lys Glu Gly Arg Leu Glu Ile Thr Thr Gly Gly Trp
        195                 200                 205
Val Met Pro Asp Glu Ala Cys Thr His Ile Tyr Ala Leu Ile Asp Gln
    210                 215                 220
Phe Ile Glu Gly His His Trp Val Lys Thr Asn Leu Gly Val Ile Pro
225                 230                 235                 240
Lys Thr Gly Trp Ser Ile Asp Pro Phe Gly His Gly Ala Thr Val Pro
                245                 250                 255
Tyr Leu Leu Asp Gln Ser Gly Leu Glu Gly Thr Ile Ile Gln Arg Ile
            260                 265                 270
His Tyr Ala Trp Lys Gln Trp Leu Ala Glu Arg Gln Ile Glu Glu Phe
        275                 280                 285
Tyr Trp Leu Ala Ser Trp Ala Thr Thr Lys Pro Ser Met Ile Val His
    290                 295                 300
Asn Gln Pro Phe Asp Ile Tyr Ser Ile Lys Ser Thr Cys Gly Pro His
305                 310                 315                 320
Pro Ser Ile Cys Leu Ser Phe Asp Phe Arg Lys Ile Pro Gly Glu Tyr
                325                 330                 335
Ser Glu Tyr Thr Ala Lys His Glu Asp Ile Thr Glu His Asn Leu His
            340                 345                 350
Ser Lys Ala Lys Thr Leu Ile Glu Glu Tyr Asp Arg Ile Gly Ser Leu
        355                 360                 365
Thr Pro His Asn Val Val Leu Val Pro Leu Gly Asp Asp Phe Arg Tyr
    370                 375                 380
Glu Tyr Ser Val Glu Phe Asp Ala Gln Tyr Val Asn Tyr Met Lys Met
385                 390                 395                 400
Phe Asn Tyr Ile Asn Ala His Lys Glu Ile Phe Asn Ala Asp Val Gln
                405                 410                 415
Phe Gly Thr Pro Leu Asp Tyr Phe Asn Ala Met Lys Glu Arg His Gln
            420                 425                 430
Asn Ile Pro Ser Leu Lys Gly Asp Phe Phe Val Tyr Ser Asp Ile Phe
        435                 440                 445
Ser Glu Gly Lys Pro Ala Tyr Trp Ser Gly Tyr Tyr Thr Thr Arg Pro
    450                 455                 460
Tyr Gln Lys Ile Leu Ala Arg Gln Phe Glu His Gln Leu Arg Ser Ala
465                 470                 475                 480
Glu Ile Leu Phe Thr Leu Val Ser Asn Tyr Ile Arg Gln Met Gly Arg
                485                 490                 495
```

```
Gln Gly Glu Phe Gly Ala Ser Glu Lys Lys Leu Glu Lys Ser Tyr Glu
            500                 505                 510

Gln Leu Ile Tyr Ala Arg Arg Asn Leu Gly Leu Phe Gln His His Asp
            515                 520                 525

Ala Ile Thr Gly Thr Ser Lys Ser Ser Val Met Gln Asp Tyr Gly Thr
            530                 535                 540

Lys Leu Phe Thr Ser Leu Tyr His Cys Ile Arg Leu Gln Glu Ala Ala
545                 550                 555                 560

Leu Thr Thr Ile Met Leu Pro Asp Gln Ser Leu His Ser Gln Ser Ile
                565                 570                 575

Ile Gln Ser Glu Val Glu Trp Glu Thr Tyr Gly Lys Pro Lys Lys
            580                 585                 590

Leu Gln Val Ser Phe Ile Asp Lys Lys Val Ile Leu Phe Asn Pro
            595                 600                 605

Leu Ala Glu Thr Arg Thr Glu Val Val Thr Val Arg Ser Asn Thr Ser
            610                 615                 620

Asn Ile Arg Val Tyr Asp Thr His Lys Arg Lys His Val Leu Tyr Gln
625                 630                 635                 640

Ile Met Pro Ser Ile Thr Ile Gln Asp Asn Gly Lys Ser Ile Val Ser
                645                 650                 655

Asp Thr Thr Phe Asp Ile Met Phe Val Ala Thr Ile Pro Pro Leu Thr
                660                 665                 670

Ser Ile Ser Tyr Lys Leu Gln Glu His Thr Asn Thr Ser His His Cys
            675                 680                 685

Val Ile Phe Cys Asn Asn Cys Glu Gln Tyr Gln Lys Ser Asn Val Phe
            690                 695                 700

Gln Ile Lys Lys Met Met Pro Gly Asp Ile Gln Leu Glu Asn Ala Val
705                 710                 715                 720

Leu Lys Leu Leu Val Asn Arg Asn Thr Gly Phe Leu Arg Gln Val Tyr
                725                 730                 735

Arg Lys Asp Ile Arg Lys Arg Thr Val Val Asp Val Gln Phe Gly Ala
            740                 745                 750

Tyr Gln Ser Ala Gln Arg His Ser Gly Ala Tyr Leu Phe Met Pro His
            755                 760                 765

Tyr Asp Ser Pro Glu Lys Asn Val Leu His Pro Tyr Thr Asn Gln Asn
            770                 775                 780

Asn Met Gln Asp Asp Asn Ile Ile Ile Val Ser Gly Pro Ile Ser Thr
785                 790                 795                 800

Glu Ile Thr Thr Met Tyr Leu Pro Phe Leu Val His Thr Ile Arg Ile
                805                 810                 815

Tyr Asn Val Pro Asp Pro Val Leu Ser Arg Ala Ile Leu Leu Glu Thr
            820                 825                 830

Asp Val Asp Phe Glu Ala Pro Lys Asn Arg Glu Thr Glu Leu Phe
            835                 840                 845

Met Arg Leu Gln Thr Asp Ile Gln Asn Gly Asp Ile Pro Glu Phe Tyr
            850                 855                 860

Thr Asp Gln Asn Gly Phe Gln Tyr Gln Lys Arg Val Lys Val Asn Lys
865                 870                 875                 880

Leu Gly Ile Glu Ala Asn Tyr Tyr Pro Ile Thr Thr Met Ala Cys Leu
                885                 890                 895

Gln Asp Glu Glu Thr Arg Leu Thr Leu Leu Thr Asn His Ala Gln Gly
            900                 905                 910

Ala Ala Ala Tyr Glu Pro Gly Arg Leu Glu Val Met Leu Asp Arg Arg
```

-continued

```
                915                 920                 925
Thr Leu Tyr Asp Asp Phe Arg Gly Ile Gly Glu Gly Val Val Asp Asn
            930                 935                 940
Lys Pro Thr Thr Phe Gln Asn Trp Ile Leu Ile Glu Ser Met Pro Gly
945                 950                 955                 960
Val Thr Arg Ala Lys Arg Asp Thr Ser Glu Pro Gly Phe Lys Phe Val
                965                 970                 975
Asn Glu Arg Arg Phe Gly Pro Gly Gln Lys Glu Ser Pro Tyr Gln Val
            980                 985                 990
Pro Ser Gln Thr Ala Asp Tyr Leu Ser Arg Met Phe Asn Tyr Pro Val
                995                1000                1005
Asn Val Tyr Leu Val Asp Thr Ser Glu Val Gly Glu Ile Glu Val Lys
    1010                1015                1020
Pro Tyr Gln Ser Phe Leu Gln Ser Phe Pro Gly Ile His Leu Val
1025                1030                1035                1040
Thr Leu Arg Thr Ile Thr Asp Asp Val Leu Glu Leu Phe Pro Ser Asn
                1045                1050                1055
Glu Ser Tyr Met Val Leu His Arg Pro Gly Tyr Ser Cys Ala Val Gly
                1060                1065                1070
Glu Lys Pro Val Ala Lys Ser Pro Lys Phe Ser Ser Lys Thr Arg Phe
        1075                1080                1085
Asn Gly Leu Asn Ile Gln Asn Ile Thr Ala Val Ser Leu Thr Gly Leu
    1090                1095                1100
Lys Ser Leu Arg Pro Leu Thr Gly Leu Ser Asp Ile His Leu Asn Ala
1105                1110                1115                1120
Met Glu Val Lys Thr Tyr Lys Ile Arg Phe
                1125                1130

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
cagtataaat tgacgttc                                                   18

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
ttttggatcc atagtcactt ggttgtt                                         27

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
gtgactatgg atctagatct gcggccgcag gcctcgcgac tagtttaaac cc             52
```

<210> SEQ ID NO 8
<211> LENGTH: 53
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gtgactatgg atccccgggt ttaaactagt cgcgaggcct gcggccgcag atc          53

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gtgaccgcgg atctagatct gcggccgcag gcctcgcgac tagtttaaac cc           52

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gtgaccgcgg atccccgggt ttaaactagt cgcgaggcct gcggccgcag atc          53

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gtgactatgg atcccgggta ccttctagaa ttccggagcg gccgctgcag atctgatcc    59

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gtgaccgcgg atcccgggta ccttctagaa ttccggagcg gccgctgcag atctgatcc    59

<210> SEQ ID NO 13
<211> LENGTH: 26
<212> TYPE: DNA
<213> ORGANISM: Artificial Sequence
<220> FEATURE:
<221> NAME/KEY: modified_base
<222> LOCATION: (3)..(18)
<223> OTHER INFORMATION: N = Inosine
<221> NAME/KEY: modified_base
<222> LOCATION: (24)
<223> OTHER INFORMATION: N = A, C, G or T/U
<221> NAME/KEY: modified_base

```
<222> LOCATION: (12)
<223> OTHER INFORMATION: H = A, C or T/U
<221> NAME/KEY: modified_base
<222> LOCATION: (15)..(21)
<223> OTHER INFORMATION: Y = C or T/U
<223> OTHER INFORMATION: Description of Artificial Sequence: Synthetic
      Primer

<400> SEQUENCE: 13
ggntggnnna thgayccntt yggnca                                          26

<210> SEQ ID NO 14
<211> LENGTH: 29
<212> TYPE: DNA
<213> ORGANISM: Artificial Sequence
<220> FEATURE:
<221> NAME/KEY: modified_base
<222> LOCATION: (3)
<223> OTHER INFORMATION: N = A, C, G or T/U
<221> NAME/KEY: modified_base
<222> LOCATION: (5)
<223> OTHER INFORMATION: K = G or T/U
<221> NAME/KEY: modified_base
<222> LOCATION: (7)
<223> OTHER INFORMATION: S = G or C
<221> NAME/KEY: modified_base
<222> LOCATION: (8)
<223> OTHER INFORMATION: W = A or T/U
<221> NAME/KEY: modified_base
<222> LOCATION: (12)..(27)
<223> OTHER INFORMATION: R = A or G
<221> NAME/KEY: modified_base
<222> LOCATION: (23)
<223> OTHER INFORMATION: D = G, A or T/U
<221> NAME/KEY: modified_base
<222> LOCATION: (6)..(21)
<223> OTHER INFORMATION: N = Inosine
<223> OTHER INFORMATION: Description of Artificial Sequence: Synthetic
      Primer

<400> SEQUENCE: 14
ggncknswnn nraartancc nsdccarta                                       29

<210> SEQ ID NO 15
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: "5'-phosphorylated, 3'-amino blocked"
<223> OTHER INFORMATION: Description of Artificial Sequence: Synthetic
      Primer

<400> SEQUENCE: 15
tccctttagt gagggttaat tt                                              22

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Asp Pro Ser Arg Phe Ser Gly Ala Lys Glu Ala Lys
  1               5                  10

<210> SEQ ID NO 17
<211> LENGTH: 14
```

```
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 17

Asp Leu Asp Pro Ser Arg Phe Ser Gly Ala Lys Glu Ala Lys
 1               5                  10

<210> SEQ ID NO 18
<211> LENGTH: 26
<212> TYPE: DNA
<213> ORGANISM: Artificial Sequence
<220> FEATURE:
<221> NAME/KEY: modified_base
<222> LOCATION: (3)..(22)
<223> OTHER INFORMATION: Y = C or T/U
<221> NAME/KEY: modified_base
<222> LOCATION: (4)
<223> OTHER INFORMATION: W = A or T/U
<221> NAME/KEY: modified_base
<222> LOCATION: (5)
<223> OTHER INFORMATION: S = G or C
<221> NAME/KEY: modified_base
<222> LOCATION: (6)..(21)
<223> OTHER INFORMATION: N = Inosine
<221> NAME/KEY: modified_base
<222> LOCATION: (24)
<223> OTHER INFORMATION: N = A, C, G or T/U
<221> NAME/KEY: modified_base
<222> LOCATION: (15)
<223> OTHER INFORMATION: R = A or G
<223> OTHER INFORMATION: Description of Artificial Sequence:  Synthetic
      Primer

<400> SEQUENCE: 18
gaywsnttyt aygartayyt nytnaa                                    26

<210> SEQ ID NO 19
<211> LENGTH: 18
<212> TYPE: DNA
<213> ORGANISM: Artificial Sequence
<220> FEATURE:
<221> NAME/KEY: modified_base
<222> LOCATION: (1)..(16)
<223> OTHER INFORMATION: R = A or G
<221> NAME/KEY: modified_base
<222> LOCATION: (4)..(10)
<223> OTHER INFORMATION: N = A, C, R or T/U
<221> NAME/KEY: modified_base
<222> LOCATION: (7)
<223> OTHER INFORMATION: Y = C or T/U
<223> OTHER INFORMATION: Description of Artificial Sequence:  Synthetic
      Primer

<400> SEQUENCE: 19
rtgngcytcn gtrttraa                                             18

<210> SEQ ID NO 20
<211> LENGTH: 26
<212> TYPE: DNA
<213> ORGANISM: Artificial Sequence
<220> FEATURE:
<221> NAME/KEY: modified_base
<222> LOCATION: (1)..(15)
<223> OTHER INFORMATION: R = A or G
<221> NAME/KEY: modified_base
<222> LOCATION: (10)..(19)
<223> OTHER INFORMATION: Y = C or T/U
<221> NAME/KEY: modified_base
<222> LOCATION: (4)..(22)
<223> OTHER INFORMATION: N - Inosine
```

```
<221> NAME/KEY: modified_base
<222> LOCATION: (25)
<223> OTHER INFORMATION: N = A, C, G or T/U
<223> OTHER INFORMATION: Description of Artificial Sequence: Synthetic
      Primer

<400> SEQUENCE: 20
rtanarrtay ttnarngtyt cngcna                                          26

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gcatcatgtt cgacacg                                                    17

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gtggtagacg ttcacgagac                                                 20

<210> SEQ ID NO 23
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ttgcgtctac tgcagtctac gactcactat agggc                                35

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ttgcgtctac tgcagtc                                                    17

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ccttgctatt tactctcgtc                                                 20

<210> SEQ ID NO 26
<211> LENGTH: 19
<212> TYPE: DNA
```

-continued

```
<213> ORGANISM: Artificial Sequence
<220> FEATURE:
<223> OTHER INFORMATION: Description of Artificial Sequence:  Synthetic
      Primer

<400> SEQUENCE: 26
tgtgttcgag acgacgatc                                                   19

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 27
gacatcgagt tgtccagg                                                    18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 28
gtgtaggttc tgtgtttacg                                                  20

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 29
ttcaccatgg tgagcgatc                                                   19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 30
aagtgagctc gcttcgacat                                                  20
```

MODIFYING INSECT CELL GYLCOSYLATION PATHWAYS WITH BACULOVIRUS EXPRESSION VECTORS

This application claims priority to U.S. Provisional Application Ser. No. 60/024,078 filed Aug. 16, 1996.

The government owns rights in the present invention pursuant to grant number GM49734 from the National Institutes of Health.

BACKGROUND OF THE INVENTION

1. Field of the Invention

The present invention relates generally to the field of recombinant DNA vectors, and particularly concerns vectors useful for producing a desired protein of interest in an insect cell that has modifications similar to the same protein produced in mammalian cells. More particularly, it concerns recombinant baculovirus vectors that are used to infect or stably transform insect cells, directing the production of oligosaccharide processing enzymes, other protein modification enzymes and proteins which aid in proper protein folding, thereby obtaining the desired protein. The invention also concerns insect cells with stably integrated protein modification enzymes, and methods utilizing the vectors, viruses and cells disclosed herein.

2. Description of Related Art

One of the major benefits provided by recombinant DNA technology is the ability to express cloned genes in a heterologous host, which facilitates the isolation of large amounts of foreign gene products for further study or direct practical applications. Bacterial systems typically provide high expression levels, but lack eucaryotic protein processing capabilities. Many biomedically important proteins are processed, and the lack of processing can alter their folding, transport, stability and/or function (Welply, 1991). Also, the foreign gene product is often deposited as an insoluble inclusion body. Mammalian systems can provide protein processing, but expression levels are much lower and mammalian cells are much more expensive to cultivate. An ideal system would combine high expression levels, proper protein processing, and still be relatively inexpensive.

Baculoviruses are DNA-containing viruses that infect insects or other invertebrates (Adams and McClintock 1991). Baculovirus vectors usually provide high levels of foreign gene expression, and the insect cell hosts have some eucaryotic protein processing capabilities. Also, while insect cells remain more expensive to cultivate than bacteria, recent developments have significantly reduced the cost of producing foreign gene products in this system. Based on these properties, the baculovirus-insect cell system is a widely used tool for the production of foreign gene products, particularly eucaryotic proteins that must be co- and post-translationally processed (Summers and Smith, 1987; Luckow and Summers, 1988; Miller, 1988; O'Reilly et al., 1992).

However, a major limitation of using the baculovirus-insect cell system for recombinant glycoprotein production is that the N-glycosylation pathway in insect cells differs from the pathway found in higher eukaryotes (Jarvis and Summers, 1992; Kornfeld and Kornfeld, 1985). This is a significant drawback as there is increasing evidence that proper glycosylation imparts important functions to many eukaryotic proteins (Welply, 1991).

Most of the information on the N-glycosylation pathway in insect cells has come from structural studies on foreign glycoproteins expressed in baculovirus-infected cell lines or in larvae (reviewed by Jarvis and Summers, 1992; O'Reilly et al., 1992; Jarvis, 1993a). These studies have demonstrated that insect cells have processing glucosidases and mannosidases which convert high mannose oligosaccharides to trimmed structures with as few as three mannose residues. Several lines of evidence indicate that these cells also have a fucosyltransferase that can add fucose to the core Asn-linked GlcNAc residue (Staudacher et al., 1992).

However, mammalian cells extend such trimmed oligosaccharide structures by adding N-acetylglucosamine, galactose, fucose, and sialic acid residues to produce a complex biantennary structure containing penultimate galactose and terminal sialic acid residues (Kornfeld and Kornfeld, 1985; Paulson and Colley, 1989; Moremen et al., 1994). Insect cells generally do not produce these extended complex structures, indicating that the requisite processing activities are either absent or too low to be generally effective in these cells. This limits the current usefulness of insect cells. Although some recent studies indicate that insect cell lines can produce glycoproteins with certain terminal glycosylation patterns more similar to those found in higher eukaryotes (Kubelka et al., 1994; Ackermann et al., 1995, Ogonah, et al., 1996, Davidson et al., 1990; Davidson and Castellino, 1991a), the vast majority of recombinant proteins produced in insect cells lack these structures.

SUMMARY OF THE INVENTION

The present invention overcomes the drawbacks in the prior art by providing new and improved baculoviral expression vectors, insect cell lines, compositions and various methods of use. The invention first provides a baculovirus expression vector characterized as either: (a) comprising at least a first and a second glycosylation enzyme transcriptional unit, the transcriptional units comprising a first and a second structural gene encoding a first and a second oligosaccharide processing enzyme, each gene operatively positioned under the control of and in frame with a promoter; or (b) comprising at least a first glycosylation enzyme transcriptional unit, the transcriptional unit comprising a structural gene encoding an oligosaccharide processing enzyme, the gene operatively positioned under the control of a baculoviral immediate early, delayed early, early or late promoter.

Recombinant vectors for important aspects of the present invention. The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense or ribozyme constructs. It will naturally be understood that the transcriptional units each comprise the appropriate transcription and translation initiation and termination signals, such as ATG start signals, and are positioned in the proper orientation to allow transcription of the gene.

Where the present invention comprises the vector of part (a) above, it will be understood that the vector may a vantageously further include a third, fourth, fifth, sixth, seventh, eighth and/or a ninth glycosylation enzyme transcriptional unit, the third, fourth, fifth, sixth, seventh, eighth and/or a ninth transcriptional unit comprising a structural gene for a third, fourth, fifth, sixth, seventh, eighth and/or a ninth oligosaccharide processing enzyme, operatively positioned under the control of a promoter.

Equally, where the present invention comprises the vector of part (b) above, the vector may also further include a second, third, fourth, fifth, sixth, seventh, eighth and/or a ninth glycosylation enzyme transcriptional unit, the second, third, fourth, fifth, sixth, seventh, eighth and/or a ninth transcriptional unit comprising a structural gene for a second, third, fourth, fifth, sixth, seventh, eighth and/or a ninth oligosaccharide processing enzyme, operatively positioned under the control of a promoter.

Exemplary oligosaccharide processing enzymes for use in the invention include, but are not limited to α-glucosidases, including α-glucosidase I and α-glucosidase I, α-mannosidases, such as α-mannosidase I and α-mannosidase II, N-acetylglucosaminyltransferases, including, but not limited to N-acetylglucosaminyltransferase and N-acetylglucosaminyltransferase II, fucosyltransferases, galactosyltransferases and sialyltransferases. The oligosaccharide processing enzymes contemplated for use in the present invention include, but are not limited to, the extensive list provided herein below in Table 1.

The oligosaccharide processing enzymes may be used individually, or in any combination. In certain preferred embodiments, the oligosaccharide processing enzyme will be a galactosyltransferase. In other preferred embodiments, a galactosyltransferase will be used in combination with sialyltransferase. In further preferred embodiments, a galactosyltransferase will and a sialyltransferase will be used in conjunction with N-acetylglucosaminyltransferase I and N-acetylglucosaminyltransferase II.

Particularly useful vectors are contemplated to be those vectors in which the coding portion of a DNA segment, whether encoding a full length protein or smaller peptide, is positioned under the transcriptional control of a promoter. A "promoter" refers to a DNA sequence recognized y the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene. Promoters for use in the present invention include insect cell promoters, viral promoters, and preferably baculovirus promoters, such as IE1, IEN (IE2) IE0, 39K, gp64, DA26, ETL, 35K, capsid (p39) p10 and the polyhedrin promoter.

The viral promoters for use in the present invention may be obtained from the viral DNA of *Autographa californica* NPV, *Trichoplusia ni* NPV, *Rachipulsia ou* NPV, *Orgyia pseudosugata* NPV, *Bombyx mori* NPV, *Heliothis zea* NPV, *Spodoptera exigua* NPV or *Galleria mellonella* NPV.

Additionally, the current invention provides for the use of enhancer elements operatively positioned to enhance expression of the transcriptional units. All eukaryotic enhancers are contemplated for use in the present invention, with preferred enhancers being the baculovirus enhancers hr1, hr2, hr3, hr4 and/or hr5, with the viral DNA of *Autographa californica* NPV, *Trichoplusia ni* NPV, *Rachipulsia ou* NPV, *Orgyia pseudosugata* NPV, *Bombyx mori* NPV, *Heliothis zea* NPV, *Spodoptera exigua* NPV or *Galleria mellonella* NPV being the preferred sources for the baculoviral enhancer elements.

Additional proteins that modify or stabilize proteins are contemplated for use in the present invention, either alone, in conjunction with the oligosaccharide processing enzymes. Certain embodiments of the present invention provide a structural gene encoding a modification protein including, but not limited to, a protein kinase, a protein methylase, and proteins involved in acylation, acetylation and/or amidation of proteins, operatively positioned under the control of a promoter. Other embodiments of the present invention provide a structural gene encoding a protein involved in the stabilization or proper folding of proteins, including, but not limited to, protein disulphide isomerase, peptidyl prolyl cis-trans isomerase and/or a chaperone protein, operatively positioned under the control of a promoter referred from this class of proteins is a structural gene for BiP/GRP78, and particularly preferred is BiP/GRP78 from an insect cell.

Further embodiments of the present invention include a structural gene encoding a screenable or selectable marker protein, operatively positioned under the control of a promoter. Exemplary of these screenable marker proteins are β-galactosidase, chloramphenicol acetyltransferase, β-glucuronidase, luciferase and green fluorescent protein. Preferred for use in the present invention are selectable marker proteins, including, but not limited to, antibiotic or toxin resistance genes such as neomycin resistance, hygromycin resistance and dihydrofolate reductase, which confers resistance to methotrexate.

In particular aspects of the present invention, the vectors further comprise a baculovirus structural gene, with gp64, p10 and/or polyhedrin being preferred examples. Further embodiments of the present invention include a cloning restriction site, optionally, and preferably, for insertion of one or more heterologous coding regions or genes that encode one or more proteins or polypeptides to be expressed. In particularly preferred embodiments, the cloning restriction site comprises a DNA insert including a multiple cloning cassette.

Certain embodiments of the present invention include at least one heterologous structural gene encoding a selected protein, the gene operatively positioned under the control of and in frame with, a promoter. Preferred are baculoviral promoters, more preferred are very late baculoviral promoters, and particularly preferred are the polyhedrin and/or p10 promoter. Alternatively the promoter is a promoter naturally associated with the heterologous structural gene.

In additional embodiments of the present invention, the vectors comprise a structural gene encoding an insecticidal protein. Insecticidal proteins preferred for use include, but are not limited to, *Bacillus thuringiensis* crystal toxins, protease inhibitors, lectins, chitinases, proteases, insect-specific neurotoxins and trypsin inhibitors. Particularly preferred are juvenile hormone esterase and the insect-specific toxins *Androctonus australis* toxin (AaIT) and *Leiurus quinquestriatus hebraeus* toxin (LqhIT2).

The present invention additionally provides a 5' end flanking baculovirus viral DNA and a 3' end flanking baculovirus viral DNA, allowing recombination of the transcriptional units into the baculovirus genome, thereby replacing a portion of the baculovirus genome. Preferred portions of the baculovirus genome for replacement are the gp64, p10 and/or polyhedrin loci.

In certain preferred embodiments of the present invention, the first oligosaccharide processing enzyme structural gene encodes a galactosyltransferase and the second oligosaccharide processing enzyme structural gene encodes a sialyltransferase. In preferred embodiments, at least one of the first or second oligosaccharide processing enzyme structural genes is operatively positioned under the control of a baculovirus promoter. Preferred baculovirus promoters are baculovirus immediate early, delayed early and/or early promoters. Further preferred uses of the current invention provide the structural gene encoding N-acetylglucosaminyltransferase I and N-acetylglucosaminyltransferase II, operatively positioned under the control of the above promoters. Particularly preferred embodiments further include a baculoviral enhancer. Preferred embodiments provide these components irrespective of the particular vector construct used. In certain embodiments of the present invention, the vectors are encapsulated within a baculovirus.

Thus in particular aspects the present invention provides a baculovirus expression vector comprising a gene encoding an oligosaccharide processing enzyme, a chaperone protein, a protein stabilization protein and/or another type of protein modification enzyme operatively positioned under the control of a promoter, a baculoviral structural gene, a 5' end flanking baculovirus viral DNA, a 3' end flanking baculovirus viral DNA, and a structural gene encoding a chaperone protein operatively positioned under the control of a promoter.

In further embodiments, the gene encoding the oligosaccharide processing enzyme is operatively positioned under the control of a promoter and a baculoviral enhancer. Additional embodiments include a structural gene encoding a screenable or selectable marker protein operatively positioned under the control of a promoter. In preferred embodiments, the gene encoding the selectable marker protein encodes an antibiotic or toxin resistance gene. Particularly preferred embodiments include a DNA insert including a multiple cloning site. Exemplary embodiments further include a heterologous structural gene inserted into the multiple cloning site.

The present invention also provides a baculovirus particle comprising a baculovirus expression vector characterized as: (a) comprising at least a first and a second glycosylation enzyme transcriptional unit, the transcriptional units comprising a first and a second structural gene encoding a first and a second oligosaccharide processing enzyme, each gene operatively positioned under the control of a promoter; or (b) comprising at least a first glycosylation enzyme transcriptional unit, the transcriptional unit comprising a structural gene encoding an oligosaccharide processing enzyme, the gene operatively positioned under the control of a baculoviral immediate early, delayed early, early or late promoter.

An embodiment of the present invention is an insecticidal composition comprising a population of baculovirus particles, the baculovirus particles comprising a baculovirus expression vector characterized as: (a) comprising at least a first and a second glycosylation enzyme transcriptional unit, the transcriptional units comprising a first and a second structural gene encoding a first and a second oligosaccharide processing enzyme, each gene operatively positioned under the control of a promoter; or (b) comprising at least a first glycosylation enzyme transcriptional unit, the transcriptional unit comprising a structural gene encoding an oligosaccharide processing enzyme, the gene operatively positioned under the control of a baculoviral immediate early, delayed early, early or late promoter.

An additional embodiment of the present invention is an insect cell comprising a baculovirus expression vector characterized as: (a) comprising at least a first and a second glycosylation enzyme transcriptional unit, the transcriptional units comprising a first and a second structural gene encoding a first and a second oligosaccharide processing enzyme, each gene operatively positioned under the control of a promoter; or (b) comprising at least a first glycosylation enzyme transcriptional unit, the transcriptional unit comprising a structural gene encoding an oligosaccharide processing enzyme, the gene operatively positioned under the control of a baculoviral immediate early, delayed early, early or late promoter.

The insect cell may have integrated into its genome one or more functional units from the baculovirus expression vector. Thus, in further embodiments of the current invention, the insect cell is a stably transformed insect cell line or clone that expresses or continually expresses at least a first glycosylation enzyme not normally expressed, or not normally expressed at sufficiently functional levels, in the natural insect cell. Preferred insect cells are Lepidopteran insect cells, and particularly preferred are *Spodoptera frugiperda*, *Bombyx mori*, *Heliothis virescens*, *Heliothis zea*, *Mamestra brassicas*, *Estigmene acrea* or *Trichoplusia ni* insect cells.

In certain aspects, the vectors of the present invention are contemplated for use in the preparation of a recombinant baculovirus. Thus, the present invention provides a baculovirus containing any of the baculovirus expression vectors disclosed herein. The present invention also provides for the use of the vectors of the instant invention in the preparation of a recombinant baculovirus. In further aspects, the invention provides a population of baculovirus particles containing any of the instant baculovirus expression vectors. In other preferred embodiments, a baculovirus containing any of the baculovirus expression vectors disclosed herein are contemplated for use in the preparation of an insecticidal formulation. Thus, the present invention also provides for the use of a baculovirus containing any of the baculovirus expression vectors of the present invention in the preparation of an insecticidal formulation.

Also provided by the present invention is a method for metabolically engineering an insect cell, comprising providing to the cell at least a first baculovirus expression vector characterized as: (a) comprising at least a first and a second glycosylation enzyme transcriptional unit, the transcriptional units comprising a first and a second structural gene encoding a first and a second oligosaccharide processing enzyme, each gene positioned under the control of a promoter operative in the insect cell; or (b) comprising at least a first glycosylation enzyme transcriptional unit, the transcriptional unit comprising a structural gene encoding an oligosaccharide processing enzyme, the gene positioned under the control of a baculoviral immediate early, delayed early, early or late promoter operative in the insect cell.

The invention further provides a method for metabolically engineering an insect cell, comprising providing to an insect any of the baculovirus expression vectors disclosed herein. Also provided are baculovirus expression vectors for use in metabolically engineering an insect cell. Thus, the present invention provides for the use of any of the disclosed baculovirus expression vectors in the metabolic engineering an insect cell.

In further embodiments, the insect cell line is provided with the first baculovirus expression vector by infection. Alternatively, the insect cell line is provided with the first baculovirus expression vector by transfection. In an additional method of practicing the present invention, the first baculovirus expression vector is maintained extrachromosomally in the insect cell to provide an insect cell that transiently expresses the oligosaccharide processing enzyme or enzymes. In an alternate method of the current invention, the first baculovirus expression vector stably integrates into the genome of the insect cell line to provide a stably transformed insect cell that continuously expresses the oligosaccharide processing enzyme or enzymes.

The present invention thus further provides an insect cell containing any of the baculovirus expression vectors disclosed herein. In further aspects, a baculovirus containing any of the disclosed baculovirus expression vectors are provided for use in the preparation of an engineered insect cell. Thus, the present invention provides for the use of a baculovirus containing any of the disclosed baculovirus expression vectors in the preparation of an engineered insect cell. The invention also provides an engineered insect cell that expresses at least a first heterologous oligosaccharide processing enzyme. A further embodiment of the instant invention is an engineered insect cell that expresses at least a first heterologous oligosaccharide processing enzyme and at least a first heterologous gene that encodes a selected protein.

In a preferred method, the first baculovirus expression vector expresses a galactosyltransferase and a sialyltransferase oligosaccharide processing enzyme. Particularly preferred is where the first baculovirus expression vector further expresses N-acetylglucosaminyltransferase II and N-acetylglucosaminyltransferase II. In certain methods of the present invention, the insect cell is a Lepidopteran insect cell. In preferred methods, the insect cell is a cultured insect cell, or in the alternative is housed within a living insect.

In additional methods of the present invention, the insect cell is further provided with a heterologous structural gene that expresses a selected protein in the insect cell. In particular methods, the heterologous structural gene is provided to the insect cell by means of a baculovirus expression vector. In certain methods of the present invention, the heterologous structural gene is comprised within the first baculovirus expression vector. In additional methods, the heterologous structural gene is comprised within a second baculovirus expression vector that is provided to the insect cell.

The present invention provides a method for producing a selected protein in an insect cell, comprising preparing an engineered insect cell that expresses at least a first heterologous oligosaccharide processing enzyme and expressing in the engineered insect cell a heterologous gene that encodes the selected protein. Additional methods comprise collecting the selected protein expressed by the cell.

The present invention also provides a method for producing a selected protein in an insect cell, comprising providing to an insect any of the baculovirus expression vectors of the instant invention and an expressible nucleic acid segment encoding said selected protein. Additionally, baculovirus expression vectors for use in producing an oligosaccharide-containing selected protein in an insect cell are provided. Thus, the present invention provides for the use of any of the disclosed baculovirus expression vectors in the production of an oligosaccharide-containing selected protein in an insect cell. In other embodiments, baculovirus expression vectors are provided for use in preparing a formulation for use in producing an oligosaccharide-containing selected protein in an insect cell. Therefore, the present invention additionally provides for the use of any of the instant baculovirus expression vectors in the preparation of a formulation for use in producing an oligosaccharide-containing selected protein in an insect cell.

The present invention also provides a method for producing a selected protein in an insect cell, comprising providing to the insect cell at least a first baculovirus expression vector that expresses at least a first oligosaccharide processing enzyme in the insect cell, and further providing to the cell a heterologous gene that expresses the selected protein in the insect cell. The method may be characterized as comprising the steps of preparing a first baculovirus expression vector in which an oligosaccharide processing enzyme gene is positioned under the control of a promoter operative in the insect cell, introducing the baculovirus expression vector into an insect cell, and maintaining the insect cell under conditions effective to allow expression of the encoded selected protein. Preferred methods of the present invention include collecting the expressed selected protein and purifying the expressed protein away from total cell components.

In additional methods, the heterologous structural gene is provided to the insect cell by means of a baculovirus expression vector. In alternate methods of the present invention, the heterologous structural gene is comprised within the first baculovirus expression vector, or within a second baculovirus expression vector that is provided to the insect cell.

In a preferred method of the present invention, the first baculovirus expression vector expresses galactosyltransferase and sialyltransferase oligosaccharide processing enzymes. In additional methods, the first baculovirus expression vector further expresses N-acetylglucosaminyltransferase I and N-acetylglucosaminyltransferase II enzymes.

The present invention provides a selected recombinant protein polypeptide prepared by expressing a heterologous gene encoding the protein or polypeptide in a recombinant insect cell, as disclosed herein, and purifying the expressed protein or polypeptide away from total recombinant host cell components.

The present invention further provides a method for producing a selected protein in an insect cell, comprising the steps of creating an engineered insect cell by providing to an insect cell at least a first baculovirus expression vector characterized as comprising at least a first and a second glycosylation enzyme transcriptional unit, the transcriptional units comprising a first and a second structural gene encoding a first and a second oligosaccharide processing enzyme, each gene positioned under the control of a promoter operative in the insect cell, or comprising at least a first glycosylation enzyme transcriptional unit, the transcriptional unit comprising a structural gene encoding an oligosaccharide processing enzyme, the gene positioned under the control of a baculoviral immediate early, delayed early, early or late promoter operative in the insect cell, and expressing in the engineered insect cell a heterologous gene that expresses the selected protein.

The present invention also provides a method for producing a selected protein in an insect cell, comprising preparing a stably transformed insect cell that expresses at least a first oligosaccharide processing enzyme and infecting the stably transformed cell with a baculovirus comprising an expression vector that comprises a heterologous gene that expresses the selected protein in the insect cell.

Additionally, the present invention provides a method for killing an insect cell, comprising contacting the insect cell with at least a first baculovirus expression vector that expresses at least a first oligosaccharide processing enzyme in the insect cell. In a preferred method, the baculovirus expression vector is encapsulated within a baculovirus. Thus in certain embodiments, the invention provides an insect containing one or more of the baculovirus expression vectors disclosed herein.

These methods are generally based upon the classical use of baculovirus alone to kill insects. As the virus life cycle requires the virus to infect an insect cell, to reproduce and ultimately to kill the host insect cell and release new viruses, baculovirus alone is insecticidal. The narrow host cell specificity means that the use of baculovirus in the environment is not generally deleterious to cells, plants and animals other than insect cells.

However, the insect target cells can adapt to be less-sensitive to baculovirus infection. This process is believed to include, at least in part, recognition and activity of glycosylated proteins. Therefore, the new baculovirus expression vectors of the present invention that express at least one oligosaccharide processing enzyme, the enzyme not normally present or significantly present in insect cells, will function to change the glycosylation pattern of the proteins in the cells, which should hamper the ability of the cells to become resistant to baculovirus.

In further methods, the insect cell is housed within a living insect. That is, the methods are applicable to insect cells in culture, and to whole, live insects. In additional methods of the present invention, the baculovirus expression vector is characterized as comprising at least a first and a second glycosylation enzyme transcriptional unit, the transcriptional units comprising a first and a second structural gene encoding a first and a second oligosaccharide processing enzyme, each gene positioned under the control of a promoter operative in the insect cell, or comprising at least a first glycosylation enzyme transcriptional unit, the transcriptional unit comprising a structural gene encoding an oligosaccharide processing enzyme, the gene positioned under the control of a baculoviral immediate early, delayed early, early or late promoter operative in the insect cell.

In preferred methods of the present invention, the baculovirus expression vector further expresses an insecticidal protein in the insect cell. In particularly preferred methods, the insecticidal protein is *Bacillus thuringiensis* crystal toxin, a protease inhibitor, a protease, an insect-specific neurotoxin or other toxins, a lectin, a chitinase, juvenile hormone esterase or a trypsin inhibitor insecticidal protein. In exemplary examples of the present invention, the insecticidal proteins are lectins such as wheat germ agglutinin, rice lectin or stinging nettle lectin, *Bacillus thuringiensis* crystal toxin genes such as CryIA (b) or CryIA(c), or insect-specific toxins such as AaIT or LqhIT2.

In additional methods of the present invention, the vector expresses a glycosylatable insecticidal protein and the oligosaccharide processing enzyme functions to modify the glycosylation pattern of the insecticidal protein, wherein the vector expresses a glycosylatable insecticidal protein that requires a defined glycosylation pattern to achieve significant insecticidal activity and wherein the co-expressed oligosaccharide processing enzyme functions to modify the glycosylation pattern of the insecticidal protein expressed in the insect cell sufficiently to increase its insecticidal activity, i.e., wherein the oligosaccharide processing enzyme modifies the glycosylation pattern of the insecticidal protein by adding one or more terminal glycosyl residues that are not normally added to the protein when the protein alone is expressed in the insect cell.

In preferred methods of the present invention, the vector expresses the insecticidal protein juvenile hormone esterase, AaIT and/or LqhIT2 and the oligosaccharide processing enzyme galactosyltransferase and/or sialyltransferase. In other aspects, the vector expresses a chaperone protein, such as BiP/GRP78, in conjunction with an insecticidal protein, such as the insect-specific toxins AaIT and/or LqhIT2.

The present invention further provides DNA segments that comprise an isolated insect α-mannosidase I and/or α-mannosidase II gene or cDNA, as may be isolated from lepidopteran insect cells, such as Sf9, High Five or Ea cells. The α-mannosidase II or α-mannosidase I genes or cDNAs are DNA segments that comprise gene sequences, or coding regions, that encode α-mannosidase II or α-mannosidase I proteins, polypeptides or peptides.

In certain embodiments, the α-mannosidase II genes and cDNAs will include a contiguous nucleic acid sequence that encodes an α-mannosidase II protein, polypeptide or peptide that comprises a contiguous amino acid sequence from the amino acid sequence of SEQ ID NO:4. In further embodiments, the α-mannosidase II genes and cDNAs will include a contiguous nucleic acid sequence that corresponds to a contiguous nucleic acid sequence from the nucleic acid sequence of SEQ ID NO:3, and preferably, from the open reading frame thereof. Nucleic acid sequences comprising the complement of SEQ ID NO:3 are also provided.

In certain other embodiments, the α-mannosidase I genes and cDNAs will include a contiguous nucleic acid sequence that encodes an α-mannosidase I protein, polypeptide or peptide that comprises a contiguous amino acid sequence from the amino acid sequence of SEQ ID NO:2. In further other embodiments, the α-mannosidase I genes and cDNAs will include a contiguous nucleic acid sequence that corresponds to a contiguous nucleic acid sequence from the nucleic acid sequence of SEQ ID NO:1, and preferably, from the open reading frame thereof. Nucleic acid sequences comprising the complement of SEQ ID NO:1 are also provided.

It will be understood that nucleic acid segments of from 14 to about 10,000 nucleotides in length that hybridize to the nucleic acid segment of SEQ ID NO:3 or SEQ ID NO:1, or the complement thereof, under standard or high stringency hybridization conditions are also included within the present invention. Where the insect α-mannosidase II and I gene constructs encode α-mannosidase II and I polypeptides or peptides, contiguous amino acid sequences of from about 15 to about 50, or from about 15 to about 30 amino acids in length are contemplated. These may be used in, e.g., immunization to generate antibodies to α-mannosidase II and I.

Insect α-mannosidase II and I gene constructs encoding full length proteins will generally be preferred in embodiments concerning the production of active proteins. The insect α-mannosidase II and I genes and cDNAs of the present invention may be positioned under the control of a promoter, preferably a promoter that directs the expression of the α-mannosidase II or I proteins in an insect cell. As such, the present invention also provides recombinant vectors comprising insect α-mannosidase II and I genes and/or cDNAs that express α-mannosidase II and/or I proteins. The present invention also provides recombinant host cells, preferably insect cells, comprising or incorporating DNA segments that comprise isolated α-mannosidase II and/or I genes or cDNAs that encode insect α-mannosidase II and/or I proteins. The genes or cDNAs are preferably introduced by means of a recombinant vector and the cell preferably expresses the vector.

The invention thus further provides methods of using a DNA segment that includes an isolated insect α-mannosidase II and/or I gene or cDNA that encodes an α-mannosidase II and/or I protein, comprising the steps of preparing a recombinant vector in which an insect α-mannosidase II and/or I-encoding DNA segment is positioned under the control of a promoter, introducing the recombinant vector into a recombinant host cell, preferably an insect cell, culturing the recombinant host cell under conditions effective to allow expression of an insect encoded α-mannosidase II and/or I protein or peptide, and collecting the expressed α-mannosidase II and/or I protein or peptide.

Recombinant insect α-mannosidase II and/or I protein, polypeptide or peptide compositions prepared by expressing α-mannosidase II and/or I in a recombinant host cell are also provided, with preferred compositions comprising α-mannosidase II and/or I polypeptide or peptide composition purified, or substantially, purified away from total recombinant host cell components. Antibodies that specifically bind to, i.e., have immunospecificty for insect α-mannosidase II and/or I proteins, polypeptides or peptides are also provided.

Methods for detecting insect α-mannosidase II and/or I sequences in a sample are also provided, which comprise obtaining sample nucleic acids from a sample suspected of containing insect α-mannosidase II and/or I, contacting the sample nucleic acids with a nucleic acid segment that encodes an insect α-mannosidase II and/or I protein or peptide under conditions effective to allow hybridization of substantially complementary nucleic acids, and detecting the hybridized complementary nucleic acids thus formed.

In situ hybridization, Northern and Southern blotting are contemplated. Also, pairs of nucleic acid primers that hybridize to distant sequences from insect α-mannosidase II and/or I nucleic acid sequences may be used, wherein the primers are capable of amplifying an insect α-mannosidase II and/or I nucleic acid segment when used in conjunction with a polymerase chain reaction. In such a polymerase chain reaction, amplification products are created and the amplification products thus formed are then detected. Thus, nucleic acid detection kits are provided which comprise, in suitable container means, one or more isolated insect α-mannosidase II and/or I nucleic acid segments and, optionally, detection reagents.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B and FIG. 1C. Immediate early expression plasmids. FIG. 1A: pIE1HR1–4. FIG. 1B: pAcP(–)IE1TV5 and 6. FIG. 1C: pAcP(+)IE1TV1–4. The key features of the immediate early expression plasmids described herein below are shown in FIG. 1A through FIG. 1C. In each case, the thin lines indicate pUC8 sequences, the open boxes represent the hr5 enhancer, the lightly-shaded boxes represent the ie1 promoter and downstream sequences, and the darkly shaded boxes represent polyhedrin coding and/or flanking sequences. The early transcription unit in each plasmid is indicated by the arrow spanning the ie1 transcriptional initiation (CAGT) and polyadenylation sites. The very late transcription unit in the plasmids shown in FIG. 1C is indicated by the arrow spanning the polyhedrin initiation (ATAAG) and polyadenylation sites. All plasmids within a set (FIG. 1A, FIG. 1B, or FIG. 1C) are identical except for their mcs sequences. Multiple cloning site 1 (mcs1: GTGACTATGGATCTAGATCTGCGGCCG-CAGGCCTCGCGACTAGTTTAAACCC; SEQ ID NO:7) has XbaI, BglII, NotI, StuI, NruI, SpeI and PmeI sites. Multiple cloning site 2 (mcs2: GTGACTATGGATC-CCGGGTTTAAACTAGTCGCGAGGCCT-GCGGCCGCAGATC; SEQ ID NO:8) has PmeI, SpeI, NruI, StuI and NotI sites. Multiple cloning site 3 (mcs3: GTGAC-CGCGGATCTAGATCTGCGGCCGCAGGC-CTCGCGACTAGTTTAAACCC; SEQ ID NO:9) has SacII, XbaI, BglII, NotI, StuI, NruI, SpeI and PmeI sites. Multiple cloning site 4 (mcs4: GTGACCGCGGATCCCCGGGTT-TAAACTAGTCGCGAGGCCTGCGGCCGCAGATC; SEQ ID NO:10) has SacII, PmeI, SpeI, NruI, StuI and NotI sites. Multiple cloning site 5 (mcs5: GTGACTATGGATC-CCGGGTACCTTCTAGAATTCCGGAGCG-GCCGCTGCAGATCTGATCC ; SEQ ID NO:11) has BamHI, SmaI, KpnI, XbaI, NotI, BglII and PstI sites. Multiple cloning site 6 (mcs6: GTGACCGCGGATC-CCGGGTACCTTCTAGAATTCCGGAGCG-GCCGCTGCAGATCT GATCC; SEQ ID NO:12) has SacII, BamHI, SmaI, KpnI, XbaI, NotI, BglII and PstI sites. The number designating each individual plasmid (#1–6) specifies which mcs sequence it contains. pIE1HR–4 (FIG. 1A) are designed for optimal ie1-mediated expression of fused (pIE1HR1 and 2) or nonfused (pIE1HR3 and 4) proteins in uninfected insect cells. Except for StuI and SpeI, all of the restriction sites in the mcs are unique, but the XbaI site in mcs 1 and 3 has an overlapping dam methylation site and can be cut only if the DNA is produced in a dam⁻ strain of E. coli. A foreign gene can be inserted at StuI or SpeI, but the insert must have its own polyadenylation site because there are additional StuI and SpeI sites downstream that result in deletion of a plasmid fragment including the ie1 polyadenylation site. The mcs also includes a SmaI site, but it is only useful for insertions if partial digests are done because there is another SmaI site upstream of the hr5 enhancer element. pAcP(–)IE1TV5 and 6 (FIG. 1B) are designed for the isolation of occlusion-negative recombinant baculoviruses capable of expressing fused (pAcP-IE1TV5) or nonfused (pAcP-IE1TV6) proteins under ie1 control. pAcP(+)IE1TV1–4 (FIG. 1C) are designed for the isolation of occlusion-positive recombinant baculoviruses capable of expressing fused (pAcP+IE1TV1 and 2) or nonfused (pAcP+IE1TV3 and 4) proteins under ie1 control. Each of the restriction sites in the mcs's of the various pAcP-IE1TV and pAcP+IE1TV plasmids are unique and the XbaI site in the AcP-IE1TV plasmids is not blocked by an overlapping dam methylase site. The mcs in pAcP+IE1TV2 and 4 also include BamHI sites, but these are not unique and are not useful for insertions.

FIG. 5A: A diagram of the partial Sf9 α-mannosidase II cDNA clone is shown (top) and a diagram showing the ligation-anchored PCR™ strategy used to isolate the 5' end of the cDNA (bottom). FIG. 5B: Assembly of the full-length Sf9 α-mannosidase II cDNA.

FIG. 7A: α-mannosidase II activity assays were performed on cell extracts with the p-nitrophenyl α-mannosidase substrate (open bars, wild type; cross-hatched bars, recombinant). FIG. 7B: Activity assays also were performed in the presence of various concentrations of swainsonine (dotted lines, wild-type; solid lines; recombinant; open squares, 24 h postinfection; crosses, 36 h postinfection; closed circles, 48 h postinfection).

FIG. 8A is the genetic structure of pAcP(−)IE1GalT. FIG. 8B is the genetic structure of pAcP(+)IE1GalT. The key genetic features of both plasmids are shown in the context of the linear AcMNPV map, in which the polyhedrin open reading frame extends from left to right (Summers and Smith, 1987; O'Reilly et al., 1992). The viral DNA sequences upstream and downstream of the polyhedrin open reading frame are labeled polh-up and polh-dn, respectively. The hr5 enhancer is labeled hr5, the ie1 promoter is labeled IE1, and the polyhedrin promoter is labeled PH. The polyhedrin and β1,4-galactosyltransferase open reading frames are labeled Polh and Gal-T, respectively.

FIG. 10A: Progeny budded virions were partially purified from Sf9 cells infected with wild type AcMNPV and gp64 was extracted and immunoprecipitated as described in Example 3. FIG. 10B: Progeny budded virions were partially purified from Sf9 cells infected with AcP(+)IE1GalT and gp64 was extracted and immunoprecipitated as described in Example 3. The disrupted immunoprecipitates were resolved by SDS-PAGE, transferred to Immobilon, and the blots were cut into strips and probed with various lectins or rabbit anti-gp64 (Ab), as described in Example 3. The lectins were concanavalin A (Con A; binds α-linked mannose or glucose), Aleuria aurantia agglutinin (AAA; binds α-linked fucose), Datura stramonium agglutinin (DSA; binds terminal O-linked N-acetylglucosamine or Gal-β1,4-GalNAc), RCA (binds β-linked Gal), or Sambucus nigra agglutinin (SNA; binds terminal α-2–6-linked sialic acid). Lectins were preincubated in buffer alone (−) or buffer containing excess competing sugar (+) prior to being used to probe the filters as described previously (Jarvis and Finn, 1995). For the DSA lanes marked (+), excess N-acetylglucosamine was used for reaction on the left and excess galactose for the reaction on the right. Lectin or antibody binding was detected with alkaline phosphatase-conjugated secondary antibodies and a standard color reaction, as described in Example 3. The arrows on the right mark the positions of gp64 and the IgG heavy chain, which served as an internal standard for the lectin blots.

FIG. 15A shows the activity levels in cell lysates at various times postinfection. These reaction mixtures included 10 mM $CaCl_2$, and 5 mM $MgCl_2$. FIG. 15B shows assays done under various conditions with cell lysates at 48 hours postinfection. As indicated on the abscissa, the various reaction mixtures included 500 μM dMNJ, 10 mM EDTA, 10 mM $CaCl_2$, and/or 10 mM $MgCl_2$. The arrow (→) indicates cell lysates that were treated with EDTA, then supplemented with $CaCl_2$ and/or $MgCl_2$.

FIG. 20A, FIG. 20B, FIG. 20C and FIG. 20D. Recombinant baculoviruses and transfer plasmids. FIG. 20A. Recombinant baculovirus AcP(+)DIE-GTST. FIG. 20B. Transfer plasmid AcP(−)DIE-GTST. FIG. 20C. Recombinant baculovirus AcSWT-1. FIG. 20D. Recombinant baculovirus AcSWT-2.

FIG. 21A. Expression plasmid pDIE-GTST. FIG. 21B. Expression plasmid pDIE-GlcNAc-TI-II. FIG. 20C. Expression plasmid pIE1GT, used to create stable cell line SfGalT, plus recombinant baculovirus AcP(+)IE1ST, used to infect SfGalT to incorporate ST activity. FIG. 20D. Expression plasmid pIE1GT, used to create stable cell line SfGalT, plus recombinant baculovirus AcP(−)IE1ST, used to infect SfGalT to incorporate ST activity and a desired gene of interest.

DESCRIPTION OF ILLUSTRATIVE EMBODIMENTS

Figure 2:
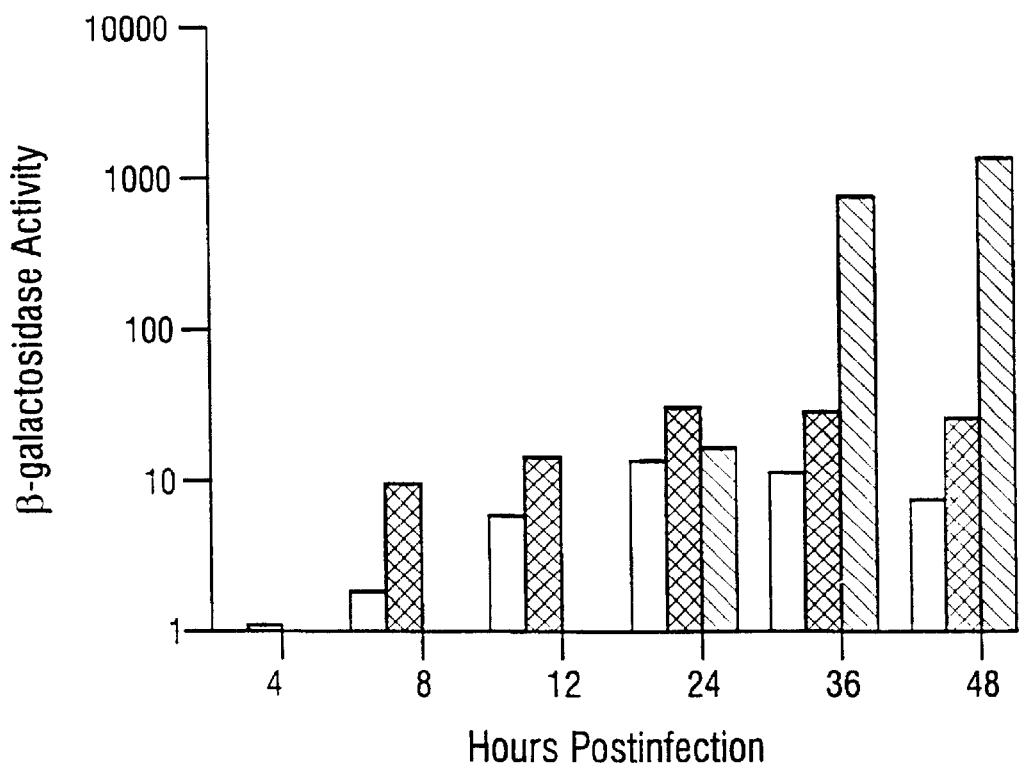
FIG. 2. Production of β-gal activity by immediate early and conventional baculovirus vectors. This log-scale plot shows the relative levels of A-gal activity in cytoplasmic extracts from Sf9 cells infected for various times with AcP(–)IE1βgal (open bars), AcP(+)IE1βgal (stippled bars), 941βgal (cross-hatched bars), or wild-type AcMNPV (closed bars). β-gal activity is expressed as nmol of o-nitrophenol produced per minute per million infected cells.

The baculovirus-insect cell expression system is well-suited for recombinant glycoprotein production because baculovirus vectors can provide high levels of expression and insect cells can modify newly-synthesized proteins in eucaryotic fashion. However, the N-glycosylation pathway in baculovirus-infected insect cells differs from the pathway found in higher eukaryotes, as indicated by the fact that glycoproteins produced in the baculovirus system typically lack complex biantennary N-linked oligosaccharide side chains containing penultimate galactose and terminal sialic acid residues.

Previous work has shown that the N-glycosylation capabilities of other eucaryotic expression systems can be modified by transfecting cells with genes encoding new processing enzymes and isolating stably-transformed clones that express those genes constitutively. For example, clones of stably-transformed CHO or BHK-21 cells have been isolated that express newly-introduced genes encoding $\alpha$-2,6sialyltransferase (Lee et al., 1989; Minch et al., 1995; Grabenhorst et al., 1995) or $\alpha$-1,3-galactosyltransferase (Smith et al., 1990) and produce differentially modified glycoproteins. Similarly, it has been shown that *Aspergillus nidulans* can be transformed to express a heterologous $\beta$-1,2-N-acetylglucosaminyltransferase I gene (Kalsner et al., 1995).

Similar efforts to modify the N-glycosylation pathway in lepidopteran insect cells have been extremely limited. The only published report known to the inventor describes elongation of N-linked oligosaccharides by the addition of an N-acetylglucosamine residue, which was absent on a fowl plague virus glycoprotein expressed in insect cells infected with a conventional baculovirus vector (Wagner et al., 1996b). Addition of the extra monosaccharide was accomplished by coinfecting insect cells with two recombinant baculoviruses, one encoding the fowl plague virus glycoprotein and the other encoding the human processing enzyme, 3-1,2-N-acetylglucosaminyltransferase I. Expression of both foreign genes was controlled by the polyhedrin promoter.

There are at least three limitations associated with the Wagner (1996b) approach. First, it can sometimes be difficult to obtain homogeneous populations of cells coinfected with more than one baculovirus. Second, expression of the processing enzyme will not precede expression of the protein to be processed, so only a subpopulation of the protein of interest will be exposed to the new processing activity. Third, expression of this single enzyme would not be sufficient to convert an expressed heterologous protein to a processed state similar to a mammalian protein. It also should be noted that insect cells contain N-acetylglucosaminyltransferase I activity (Altmann et al., 1993; Velardo et al., 1993), so the study by Wagner et al. (1996b) actually does not describe the introduction of a new processing activity, merely the upregulation of a preexisting processing activity.

The present inventor realized that modification of the insect cell N-linked oligosaccharide processing pathway to the point where these cells will be able to produce glycoproteins with higher eukaryotic-type N-linked side-chains will require the addition of two processing enzymes that are thought to be completely missing in these cells (a galactosyltransferase and a sialyltransferase) and possibly two more that are expressed at very low levels by these cells (N-acetylglucosaminyltransferases I and II). This complexity may explain why there have been so few attempts to modify the insect N-glycosylation pathway given that many genes would need to be introduced into an insect cell, while simultaneously preserving the ability to express a foreign protein of interest. Moreover, the inventor considered the polyhedrin promoter to have limitations in the context of expressing modification enzymes, but promoters capable of providing temporal expression before polyhedrin are not widely used and are relatively unrecognized. Similarly, the use of vectors and methods needed for insect cell transformation, available for more than five years, have generally been limited.

The inventor contemplated that a vector comprising one or more eukaryotic protein processing genes could be used to modify the insect cell N-glycosylation pathway by directing the expression of heterologous processing enzyme(s). The one or more encoded enzyme(s) will then function as part of the insect cell machinery and contribute to the processing of a protein of interest. As shown herein, this approach was demonstrated to have practical utility. The use of a novel baculovirus vector to introduce and express active bovine $\beta$1,4-galactosyltransferase (Harduin-Lepers et al., 1993; Russo et al., 1992) in insect cells is shown herein to modify the N-linked oligosaccharide(s) on gp64, the major baculovirus virion glycoprotein (Examples 11–14).

Furthermore, another novel baculovirus vector was used to create a stably transformed insect cell subclone capable of modifying the N-linked oligosaccharides of the gp64 protein or of human tissue plasminogen activator, when genes encoding these proteins comprised within conventional baculovirus vectors were introduced into the transformed cells by infection (Example 20). Finally, these same cells produced galactosylated and sialylated N-linked oligosaccharides on the gp64 protein when infected with a novel baculovirus vector encoding a sialyltransferase and the gp64 protein (Example 21).

The current invention takes advantage of the present discovery of altered protein processing in insect cells through the introduction of heterologous processing enzymes, thus providing various novel improvements to the baculovirus expression system.

I. Baculovirus Expression Vehicles

A baculovirus expression vehicle (BEV) is a recombinant baculovirus with a double-stranded circular DNA genome that has been genetically modified to include a foreign gene of interest. BEVs are viable and can infect susceptible hosts, usually cultured lepidopteran insect cells or larvae, in a helper-independent fashion. Therefore, BEVs can efficiently transfer foreign genes into these eukaryotic host cells. The foreign gene is usually a chimeric construct with the sequence encoding a protein of interest placed under the transcriptional control of a viral promoter. This arrangement enables viral functions to transcribe the gene during infection. The resulting mRNA is translated and the newly-synthesized protein modified by host-encoded biosynthetic machinery. In essence, then, BEVs and their insect cell hosts are two separate components of a binary eukaryotic expression system, which will be referred to as "the BEV system" herein below.

The BEV system is among the best tools currently available for the expression of recombinant genes in a eukaryotic host. The BEV system has contributed immensely to basic research, as it has been used to produce hundreds of different recombinant proteins for further studies. This system also holds great promise for the industrial production of proteins with direct applications as vaccines, therapeutic agents, and/or diagnostic reagents. Finally, BEVs are being developed as improved biological pest control agents.

The most significant advantage of the BEV system over other expression systems is that it can be used to produce exceptionally large amounts of functional foreign proteins. The production levels provided by the BEV system are often comparable to those provided by prokaryotic systems and, at late times after infection, the recombinant protein usually constitutes a significant proportion of the total protein in the host cell. Unlike prokaryotic expression systems, however, the BEV system has eukaryotic protein processing capabilities, which enables it to produce more authentic foreign proteins. Thus, it is the potential of this system to provide prokaryotic levels of foreign gene expression in a eukaryotic background that makes it so powerful and attractive. Finally, the actual process of isolating BEVs has become increasingly fast, simple, and efficient as more sophisticated molecular tools have been developed. Additional background information on baculoviruses and the BEV system are available (Montreuil et al., 1995; Richardson, 1995; King and Possee, 1992; O'Reilly et al., 1992; Adams and McClintock, 1991; Blissard and Rohrmann, 1990; Luckow and Summers, 1988; Miller, 1988; Summers and Smith, 1987).

A. Baculoviruses

The family Baculoviridae consists of a large group of double-stranded DNA-containing viruses that infect arthropods (Volkman et al., 1995). The majority of these viruses infect insects and the type species is *Autographa californica* nuclear polyhedrosis virus (AcMNPV). There are two phenotypically distinct forms of AcMNPV, occluded virus (OV) and budded virus (BV). OV consists of rod-shaped nucleocapsids enclosed by an envelope and embedded within a polyhedral-shaped crystalline matrix, or polyhedron. The "M" in AcMNPV indicates that one enveloped OV particle can contain multiple nucleocapsids. BV also consists of rod-shaped nucleocapsids enclosed by an envelope, but BV particles contain only one nucleocapsid and are released as free, nonoccluded virions by budding from the surface of the infected cell. OV and BV have different relative infectivities for insect larvae or cultured insect cells, which reflects their distinct roles in baculovirus infections, as discussed further below.

AcMNPV was originally isolated (Vail et al., 1971) as a mixture of genotypic variants with different restriction patterns (Lee and Miller, 1978) and different variants were used by investigators who went on to study this baculovirus and develop the first BEVs. Other nucleopolyhedroviruses also have been used to develop BEVs. Among these, BEVs derived from *Bombyx mori* nuclear polyhedrosis virus (BmNPV) are notable for their frequent use for foreign gene expression in insect larvae (Maeda, 1989). The discussion in this section will focus on generic "baculoviruses" and "BEVs" except where it is important to be more specific.

Natural baculovirus infections begin when a susceptible insect ingests OV in the form of polyhedra-contaminated food. The crystalline polyhedral matrix dissociates in the insect midgut and the liberated virus particles infect columnar epithelial and regenerative cells (Keddie et al., 1989). The infected midgut cells produce BV progeny that invade the insect circulatory and respiratory systems (Engelhard et al., 1994; Keddie, et al., 1989), where they initiate secondary infections and produce both BV and OV. BV progeny are produced when newly-assembled viral nucleocapsids migrate from the nucleus and bud from the infected cell surface. These virions acquire a lipid envelope and plasma membrane-bound glycoproteins during the process of budding. OV progeny are produced when nucleocapsids are enveloped within the nucleus (Stoltz et al., 1973) and the resulting virions are surrounded by the polyhedral matrix. Polyhedra remain in the nuclei of infected cells until being released when the cell dies. Baculovirus-infected insect larvae are ultimately liquefied by virus-encoded digestive enzymes (Hawtin et al., 1995; Ohkawa et al., 1994) and when the cuticle ruptures, BV and polyhedra are released into the environment. Occluded virions are protected by the crystalline polyhedral matrix and, as a result, are relatively resistant to inactivation by adverse environmental conditions. Moreover, this form of the virus is significantly more infectious than BV for orally-inoculated insect larvae (Volkman and Summers, 1977). Accordingly, OV is responsible for horizontal transmission of baculovirus infection in nature and is used to experimentally infect larvae via the oral route. Conversely, BV is significantly more infectious than OV for cultured insect cells (Volkman and Summers, 1977; Volkman et al., 1976) and is used to experimentally infect these cells in the laboratory.

The complete nucleotide sequences of AcMNPV (C6 isolate; Ayres et al., 1994; GenBank Accession No. L22858) and BmNPV (GenBank Accession No. L33180) have been determined. The AcMNPV genome is a double-stranded circular DNA molecule consisting of 133,894 nucleotides that probably encode about 150 proteins. Viral genes are distributed evenly throughout the genome on both strands of the DNA and are expressed in a temporally regulated fashion after infection. The immediate early genes, such as ie1 (Guarino and Summers, 1987), are expressed immediately after infection in the absence of other viral functions. At least some of the immediate early genes encode transcription factors that function to stimulate the expression of other early genes like 39K (Guarino and Smith, 1990). The early phase of baculovirus infection is followed by viral DNA replication and the onset of late viral gene expression. Many baculovirus late genes encode proteins needed for the assembly of progeny virions. For example, vp39 is a late gene which encodes the major nucleocapsid structural protein (Thiem and Miller, 1989) and p6.9 is a late gene which encodes a basic, protamine-like protein found in association with viral DNA (Wilson et al., 1987). Late gene expression is followed by expression of the very late genes, including polh (Hooft van Iddekinge et al., 1983) and p10 (Kuzio et al., 1984), which are needed for the assembly and envelopment of polyhedra, respectively.

There have been significant advances in the understanding of baculovirus gene expression during the past decade. The immediate early genes are transcribed by host cell factors and transcription of later classes of viral genes is increasingly influenced by virus-encoded factors. In particular, studies have identified nearly twenty virus-encoded proteins that are required for late and very late gene expression (Lu and Miller, 1995; Todd et al., 1995; McLachlin and Miller, 1994) and at least some of these must assemble into a virus-modified or -encoded transcriptional complex (Beniya et al., 1996; Passarelli el al., 1994; Fuchs et al., 1983). This is an important concept because it is the nature of the transcriptional complex that is assembled during the very late phase of baculovirus infection, together with the structure of the promoters in baculovirus very late genes (Qin et al., 1989; Weyer and Possee, 1989; Rankin et al., 1988; Possee and Howard, 1987), that determines one of the most attractive properties of BEVs-their ability to express foreign genes at extremely high levels.

By the end of the baculovirus replication cycle, the nucleus occupies most of the volume of the infected host cell and it is literally stuffed with polyhedra. The major component of polyhedra is a protein called polyhedrin (Rohrmann, 1986), which forms the crystalline matrix. Thus, baculoviruses must be able to produce copious amounts of polyhedrin protein. In fact, polyhedrin comprises at least 25% of the total protein in baculovirus-infected insect cells during the very late phase of infection (Smith et al., 1983c). The ability to produce such large amounts of polyhedrin reflects the availability of a huge pool of polyhedrin mRNA, which represents about 25% of the total polyadenylated RNA in the cell during the very late phase of infection (Adang and Miller, 1982).

The polh promoter contains a critical core sequence, TAAG, which also serves as the transcriptional initiation site and is conserved in baculovirus very late and late promoters (Rohrmann, 1986). However, very late promoters are transcribed later in infection and produce more mRNA than late promoters (Thiem and Miller, 1990). Therefore, the very late promoters and/or the very late transcriptional complex must have additional features, in addition to the TAAG sequence, which account for these differences. Indeed, studies have identified a region in the polh promoter (Ooi et al., 1989) and a virus-encoded factor (McLachlin and Miller, 1994) that specifically enhance very late transcription and transcriptional complexes have been isolated that exhibit preferential activity towards late or very late promoters in vitro (Xu et al., 1995). Furthermore, various differences in the behavior of the polh and p10 promoters have been reported (Tomita et al., 1995; McLachlin and Miller, 1994; Roelvink et al., 1992; Min and Bishop, 1991) indicating that even individual very late promoters are not functionally homologous.

The ability to produce large amounts of polyhedrin during infection was the fundamental property of baculoviruses that led to their development as expression vehicles. The AcMNPV polh gene was mapped, cloned, and sequenced (Hooft van Iddekinge, et al., 1983; Adang and Miller, 1982; Vlak et al., 1981) and, together with the establishment of marker rescue in the baculovirus system (Miller, 1981), these studies provided some of the molecular tools that were needed to develop BEVs. In addition, the polh gene was shown to be nonessential for virus replication in cultured insect cells (Smith et al., 1983a). This indicated that one could create a BEV simply by replacing the polh open reading frame in the wild-type viral genome with a nucleotide sequence encoding a foreign protein of interest. The resulting BEV could be phenotypically distinguished from wild-type by its inability to produce polyhedra. Moreover, the BEV would be viable and could be used to infect cultured insect cells, in which the foreign coding sequences would be expressed under the transcriptional control of the polh promoter and large quantities of the foreign protein would be produced. The feasibility of this concept was demonstrated when it was shown that BEVs could be isolated and used to express human β-interferon (Smith et al., 1983b) or E. coli β-galactosidase (Pennock et al., 1984) in cultured insect cells.

B. Producing BEVs

The first step in the original procedure used to produce a BEV is to clone the sequences encoding a protein of interest into a suitable "transfer plasmid". A classic transfer plasmid contains the polh promoter and long upstream and downstream flanking sequences, but lacks some or all of the polh open reading frame, which is usually replaced by a convenient cloning site. Once the DNA sequence encoding a protein of interest has been inserted into this site, the recombinant transfer plasmid is purified, mixed with genomic DNA from wild-type baculovirus, and the mixture is cotransfected into cultured insect cells. Upon entering the cell, the viral DNA will be replicated and wild-type progeny will be produced.

In addition, homologous recombination can occur between the polh flanking sequences in the transfer plasmid and the same sequences in the viral DNA. This process, called "allelic replacement", produces recombinant viral DNAs in which the polh open reading frame in the parental virus has been replaced by sequences from the recombinant transfer plasmid encoding the protein of interest. These viral DNAs are replicated and packaged to produce recombinant viral progeny. Allelic replacement of polh occurs at a maximum frequency of only about 1% (Smith, et al., 1983a), but this is no problem because it is relatively easy to distinguish wild-type and recombinant progeny by their plaque phenotypes. The mixture of viruses is simply harvested from the cotransfected cells and resolved in a plaque assay. The wild-type progeny, which retain the polyhedrin gene, produce polyhedron-positive plaques, whereas the recombinant progeny, which lack the polyhedrin gene, produce polyhedron-negative plaques. Once identified, recombinant viral clones can be further plaque-purified, amplified, and characterized, then large BV stocks can be produced and used to infect cultured insect cells for foreign gene expression and foreign protein production.

1. Transfer Plasmids

There are many different transfer plasmids that can be used to construct a chimeric gene and insert it into the baculovirus genome by allelic replacement. This section describes the general features of some of these plasmids. Maps and more detailed descriptions are available in several other places, including the primary literature (cited below), technical manuals (Richardson, 1995; King and Possee, 1992; O'Reilly, et al., 1992; Summers and Smith, 1987), and commercial literature and catalogs from various scientific supply houses, including Clontech (Palo Alto), InVitroGen (San Diego), Novagen (Madison), Pharmingen (San Diego), and Stratagene (La Jolla). Many different transfer plasmids can be purchased from these companies.

The first transfer plasmids were designed to produce BEVs in which the polh gene had been replaced by a new, chimeric gene consisting of the very late polh promoter and the sequence encoding the protein of interest positioned downstream, as described above (Pennock, et al., 1984; Smith, et al., 1983b). These transfer plasmids were constructed before it was clearly determined precisely which sequences from the 5' untranslated region (UTR) of the polh gene were needed for optimal levels of polh promoter-mediated transcription (Rankin, et al., 1988; Matsuura et al., 1987; Possee and Howard, 1987). Once this information became available, it was easier to ensure that the transfer plasmid included all of the critical promoter sequences and to decide exactly where to place multiple cloning sites to facilitate subcloning of the foreign coding sequence. The polh promoter and multiple cloning site in the transfer plasmid must be flanked by sequences which normally flank the polh gene in the viral genome, as these sequences are needed for homologous recombination between the transfer plasmid and the viral DNA. This process mediates allelic replacement of the polh gene, as described above. Transfer plasmids containing the polh promoter are still the most widely used tools for the production of BEVs. However, the increased popularity of the BEV system has led to the design and construction of many variations on this basic theme.

For example, there are transfer plasmids that can be used to produce BEVs which will express a foreign gene under the control of the very late p10 promoter. Some of these transfer plasmids contain both the p10 promoter and p10 flanking sequences and, after the sequence encoding the protein of interest has been inserted, the resulting plasmid is used to replace the nonessential baculovirus p10 gene (Vlak et al., 1990). This approach requires special screening procedures to identify recombinant viruses, as loss of the viral p10 gene is not accompanied by an easily distinguishable change in plaque phenotype. Usually, this type of transfer plasmid includes a marker gene, such as *E. coli* lacZ, which is incorporated together with the chimeric gene of interest into the recombinant virus genome during allelic replacement.

Another approach is to use a hybrid transfer plasmid, in which the p10 promoter is embedded within polh flanking sequences, to construct the chimeric gene and insert it into the polh region of the baculovirus genome (Weyer el al., 1990). This latter approach takes advantage of the simple visual screen that can be used to distinguish between parental (occlusion-positive plaques) and recombinant (occlusion-negative plaques) viruses whenever polh is used as the target for allelic replacement. The p10 promoter has been used to produce BEVs for foreign protein production (Bozon et al., 1995; Tomita, et al., 1995; van Lier et al., 1994; Roelvink, et al., 1992; Vlak, et al., 1990), but it provides lower levels of foreign gene expression and is used much less frequently than the polh promoter for this purpose. The p10 promoter is more commonly used to construct BEVs for biopesticide applications because allelic replacement of p10 is one way to produce recombinants that can express a foreign gene without deleting the polh gene (McCutchen et al., 1991; Stewart et al., 1991; Merryweather et al., 1990). This is important because BEVs intended for use as pesticides must be able to produce polyhedra to infect insect larvae naturally in the field.

Other transfer plasmids can be used to construct BEVs that will express foreign genes under the transcriptional control of alternative promoters, including both viral and cellular promoters. These plasmids typically contain the promoter of choice embedded within polh flanking sequences and are used for allelic replacement of the polh gene as described above. Baculoviral promoters that have been used most commonly for this purpose include the late p6.9 (Hill-Perkins and Possee, 1990) and vp39 (Thiem and Miller, 1990) promoters and the early etl (Morris and Miller, 1992) and ie1 (Examples 1–5 below) promoters. Cellular promoters include Drosophila hsp70 (Vlak, et al., 1990) and *B. mori* actin (Johnson et al., 1992). Transfer plasmids with a hybrid vp39-polh promoter (Thiem and Miller, 1990) or tandem polh-etl promoters (Xia et al., 1993) also have been described. Except for the last two, none of these promoters are as strong as the polh promoter (Examples 1–5 below; Morris and Miller, 1992; Thiem and Miller, 1990).

Considering that high-level expression is one of the most attractive features of the BEV system, it might seem foolish to use any promoter besides polh for baculovirus-mediated foreign gene expression. But, there are some good reasons to do this. BEVs cannot produce all classes of foreign proteins in equal abundance or quality under polh control. Generally, secretory pathway proteins are produced at much lower levels than other types of proteins and some are biologically inactive and/or insoluble when expressed under polh control (Pajot-Augy et al., 1995; Rankl et al., 1994; Arp et al., 1993; Xie et al., 1992; Tsao et al., 1990). This might reflect the adverse effects of baculovirus infection on host cell secretory pathway functions, which have already begun to decay by the start of the very late phase of infection (Murphy et al., 1990; Jarvis and Summers, 1989). Alternatively, it might reflect saturation of the protein folding and secretory capacity of the host cell due to high-level foreign gene expression, as has been documented in a yeast system (Parekh et al., 1995).

Either way, it has been shown that the p6.9 (Chazenbalk and Rapoport, 1995; Lawrie et al., 1995; Bonning et al., 1994; Rankl, et al., 1994; Sridhar et al., 1993) and ie1 (Examples 1–5 below; Jarvis et al., 1990) promoters, which are expressed earlier and produce less mRNA, and even the p10 promoter (Bozon, et al., 1995), which is expressed only slightly earlier and produces only slightly less mRNA, can sometimes be used to produce larger amounts of biologically active and/or soluble foreign protein than the polh promoter. The use of these alternative promoters to produce BEVs that can express foreign genes earlier in infection also represents a good approach for biopesticide applications, as the main idea is to produce a virus with a new gene that will help it to kill insects or stop their feeding more quickly (Jarvis, et al., 1996; Examples 1–5 below).

Sometimes, it is important to be able to express more than one foreign protein simultaneously to study protein-protein interactions, assemble functional protein complexes, or reconstruct biochemical pathways. The BEV system is especially useful for this purpose. One approach is to use a mixture of two or more BEVs, each containing one foreign gene of interest, to coinfect host cells (St. Angelo et al., 1987). Theoretically, this approach can be used to vary the ratios of the different proteins being produced. However, a problem with this approach is that it is difficult to obtain a reasonably uniform population of cells coinfected with each virus. Another approach is to use transfer plasmids containing multiple promoters to produce a single BEV that can express multiple foreign genes. The first transfer plasmids of this type contained two copies of the polh promoter and were used to produce "dual" BEVs that could express two different foreign genes in a single cell (Emery and Bishop, 1987). Later, transfer plasmids were constructed that contained various combinations of different viral promoters, including the polh, p10, and vp39 promoters, and these could be used to produce BEVs capable of expressing up to five different foreign proteins in the same infected cell (Belyaev et al., 1995; Wang et al., 1991; Weyer and Possee, 1991).

One of the first specialized functions to be built into transfer plasmids was a marker gene that could be used to identify BEVs. The marker was designed to be incorporated along with the gene of interest during allelic replacement. The resulting BEV would express this marker and produce a protein that could be detected with a chromogenic substrate and identify recombinant viral plaques. This was mandatory for the identification of BEVs with allelic replacements in p10 (Vlak, et al., 1990), but it also facilitated the identification of BEVs with allelic replacements in polh (Vialard et al., 1990), because many investigators had trouble seeing the occlusion-negative plaques produced by those recombinants. The first marker used for this purpose was *E. coli* lacZ and its expression was controlled variously by baculovirus p10, ie11, etl, or Drosophila hsp70 promoters. Other markers that have been used for this purpose include luciferase (Oker-Blom et al., 1993) and β-glucuronidase (Bishop et al., 1995).

The sheer diversity of transfer plasmids that have become available, with their diverse array of multiple cloning sites, has greatly simplified the process of subcloning a foreign coding sequence for insertion into the baculovirus genome. Some transfer plasmids include translational initiation signals and can be used to construct chimeric genes encoding fusion proteins. Others lack these signals and are used to construct genes encoding nonfused proteins. Still others can be used either way, depending on where the foreign coding sequence is inserted. Some transfer plasmids also have been streamlined by shortening the flanking sequences to the minimum lengths needed for efficient homologous recombination. This approach has been used to reduce the size of a transfer plasmid by nearly half, which facilitates the subcloning process by leaving more room for the insertion of larger foreign protein coding sequences (Pharmingen and In Vitrogen catalogs).

Some of the newest transfer plasmids are designed for ligation-independent cloning of a foreign protein coding sequence to be incorporated into a BEV (Bishop, et al., 1995, Pharmingen catalog). This approach circumvents the need to subclone the sequence of interest into the transfer plasmid and amplify it in E. coli prior to cotransfection with viral DNA. Transfer plasmids designed for ligation-independent cloning have long single-stranded overhangs that can anneal to complementary single-stranded overhangs on a PCR™ amplification product encoding the foreign protein of interest. The annealed products are mixed with viral DNA and the mixture is used to cotransfect insect cells for production of BEVs by allelic replacement. This ligation-independent cloning approach is also called "direct" cloning. However, a transfer plasmid serves as an intermediate, which differentiates this approach from truly direct cloning by ligation of a DNA fragment encoding a protein of interest with restriction-digested viral DNA (Lu and Miller, 1996; Ernst et al., 1994; and below).

One of the biggest challenges faced in using any expression system is purification of the overexpressed heterologous protein. This has led to the development of various generic protein purification methods (Ford et al., 1991). The usual approach is to design the expression vector to include a short nucleotide sequence which encodes a short amino acid sequence that can be used as an affinity "tag" to purify any protein. The sequence encoding the protein of interest is inserted into the vector in such a way that it will be expressed as a fusion protein with the affinity tag on its N- or C-terminus. Then, the fusion protein can be solubilized and affinity-purified with a reagent that specifically recognizes and binds to the tag. A problem with this approach is that the affinity tag sometimes interferes with the biological activities of the protein of interest. Hence, some vectors also include sequences which encode a short amino acid sequence between the affinity tag and the protein of interest that can be specifically cleaved by treating the purified fusion protein with a protease.

A variety of different transfer plasmids have been constructed and used to isolate BEVs that produce affinity-tagged proteins. Many different affinity tags have been used in the BEV system. Various affinity tags can be used effectively in this system to purify recombinant proteins to varying degrees, ranging from about 80% to homogeneity. Also, antibodies against some affinity tags can be used to monitor the expression and localization of foreign proteins in BEV-infected insect cells by immunocytochemical techniques. This idea has been taken one step further with the development of transfer plasmids that can be used to produce BEVs which encode fusion proteins containing a naturally fluorescent protein, such as green fluorescent protein (Pharmingen catalog). Fluorescent protein tags permit direct visualization of the fusion protein in unfixed BEV-infected cells with a fluorescence microscope.

Some transfer plasmids include sequences that encode signal peptides which can mediate secretion of a foreign protein from BEV-infected insect cells. The coding sequence of interest is inserted downstream and in-frame and the resulting construct encodes the protein of interest with a cleavable N-terminal signal peptide. The signal peptides used to direct secretion are sometimes derived from insect glycoproteins, including honeybee prepromellitin (Tessier et al., 1991) and baculovirus gp64 and egt (Murphy et al., 1993) and it has been found that insect-derived signal peptides can increase the efficiency of secretion of some recombinant proteins from BEV-infected insect cells. However, mammalian signal peptides also can be used, sometimes with better success, to direct secretion of recombinant proteins in this system (Mroczkowski et al., 1994; Jarvis et al., 1993; Andersons et al., 1991). Some transfer plasmids provide both an N-terminal signal peptide and a C-terminal affinity tag to facilitate purification of recombinant proteins from the growth medium (Kuhn and Zipfel, 1995).

Additionally, some transfer plasmids can be used to produce BEVs that will express a foreign protein which can be incorporated into the envelope of recombinant BV particles (Boublik et al., 1995). These BEVs are eukaryotic versions of bacteriophage "display" vectors, which have been used to select rare recombinants from mixed virus populations by using ligands that bind to the protein of interest (Winter et al., 1994). The transfer vectors contain the sequence encoding gp64, the major BV envelope glycoprotein embedded within polh flanking sequences. The sequence encoding the protein of interest is inserted between the sequences encoding the signal peptide and mature portions of gp64. The resulting plasmid is used for allelic replacement of polh to produce a BEV that will express the protein of interest as a fusion protein which can be incorporated into the BV envelope and "displayed" for interactions with specific ligands or antibodies.

2. Sequences Encoding Foreign Proteins

The promoter in the transfer plasmid is only one component of the chimeric gene that must be assembled and inserted into the baculovirus genome in order to produce a BEV by allelic replacement. Another requirement is the sequence encoding the protein of interest, which could be either a cDNA or genomic DNA sequence. The vast majority of BEVs contain cDNA inserts, but there are a few reports of BEVs that contain and can express foreign DNA sequences containing introns (Davrinche et al., 1993; Iatrou et al., 1989; Jeang et al., 1987) and at least one baculovirus gene has introns that are removed by splicing in infected insect cells (Kovacs et al., 1991; Chisholm and Henner, 1988). However, there is evidence that RNA splicing is very inefficient at late times of baculovirus infection (Kovacs, et al., 1991) and it has been reported that a human papillomavirus gene failed to be spliced when expressed in the BEV system (Park et al., 1993). Thus, it is probably prudent to use cDNAs to construct BEVs.

Publication of the entire AcMNPV nucleotide sequence was accompanied by the identification of 337 open reading frames of at least 150 bp in length (Ayres, et al., 1994). Among these, 154 were included in a selected set deemed most likely to be expressed during baculovirus infection. Analysis of the predicted translational initiation sites in this selected set of open reading frames revealed that 41% did not conform to Kozak's rules (1986). This might indicate that biosynthesis of some viral proteins is down-regulated by the absence of an optimal translational initiation site. Or, it might indicate that Kozak's rules do not accurately define the signals required for optimal translational initiation in baculovirus-infected insect cells. The latter interpretation is supported by experimental evidence which showed that Kozak's rules could be broken with no reduction in the levels of foreign protein produced by a BEV (Hills and Crane-Robinson, 1995).

Furthermore, three different proteins were expressed at higher levels by BEVs when fused to a bacterial leader sequence that had a pyrimidine instead of a purine at position-3 relative to the initiation codon (Peakman et al., 1992a). A putative baculovirus translational initiation consensus sequence has been elucidated by computer analysis of 23 viral genes and this sequence includes a purine at position-3 (Ranjan and Hasnain, 1995). However, considering the experimental observations cited above, it is difficult to know how accurately this consensus sequence defines a translational initiation site in the BEV system. Overall, it seems that the rules governing translational initiation in this system remain unclear. Similarly, analysis of codon usage in the selected set of AcMNPV open reading frames revealed some bias, but it is not clear whether this influences the levels of foreign protein production in the BEV system (Ayres, et al., 1994).

One clear finding is that AUU can sometimes serve as an inefficient translational initiation codon in baculovirus-infected insect cells (Beames et al., 1991). This was discovered when a BEV was used to express hepatitis B virus core protein and about one-fifth of the end-product had a polh amino acid sequence fused to its N-terminus. The BEV had been produced with a transfer plasmid in which the polyhedrin ATG was changed to ATT and the sequence encoding the core protein, which had its own ATG, was inserted downstream and in-frame. It was discovered that the fusion protein was produced as a result of translational initiation at the upstream ATT (AUU in the transcript). This problem might be related to the fact that the AUU was located in precisely the same position formerly occupied by the polh AUG and, in any case, it can be avoided simply by cloning coding sequences out-of-frame with respect to this upstream ATT or by using a transfer plasmid that does not have the ATT in this position.

The chimeric gene in a BEV also must have appropriate signals for transcriptional termination and RNA processing. These signals might be included in the 3' untranslated region of the foreign sequence inserted into the transfer plasmid. Or, they can be provided by the transfer plasmid itself, which includes the 3' untranslated region of the polh gene. mRNA processing signals have not been extensively analyzed in the baculovirus system, but several baculovirus genes, including polh, contain the 3' motif (AAUAAA) that serves as a polyadenylation signal in higher eukaryotes (Westwood et al., 1993). As in higher eukaryotes, this motif alone is insufficient for mRNA processing in baculovirus-infected insect cells. Also, heterologous mRNA processing signals from the SV40 early region or a rabbit β-globin gene have been included in some transfer plasmids and are functional in the BEV system (Westwood, et al., 1993). These findings suggest that baculovirus-infected insect cells and higher eukaryotes have the same or similar mechanisms for transcriptional termination and mRNA processing.

3. Viral DNAs for Allelic Replacement

Besides the transfer plasmid, the other critical component in an allelic replacement reaction is baculoviral DNA. Baculoviral DNA is usually isolated from BV particles partially purified from the extracellular medium of wild-type baculovirus-infected insect cells, as described elsewhere (Richardson, 1995; O'Reilly, et al., 1992; Summers and Smith, 1987). Historically, a major problem with using wild-type viral DNA to isolate BEVs was that the frequency of allelic replacement is low and many investigators had trouble finding recombinant virus plaques among the high background of parental virus plaques. This problem was addressed by incorporating marker genes into transfer plasmids, as described above. However, this approach did not reduce parental virus background.

This problem was solved by the development of linearizable viral DNAs that could be used as the targets for allelic replacement. The first linearizable viral DNA was created by constructing an occlusion-negative recombinant virus with a unique Bsu36I site in the polh region (Kitts el al., 1990). The circular genomic DNA from this recombinant could be linearized by digestion with Bsu36I, which significantly reduced its infectivity. Thus, when linearized viral DNA is mixed with a transfer plasmid and used to cotransfect insect cells, the recircularized recombinant viral DNAs produced by allelic replacement have a strong replicative advantage over the linear parental DNA molecules. The net result is an increase in the maximum efficiency of BEV production from about 1% to about 30%. An occlusion-positive linearizable viral DNA has been described that provides the same high efficiency of BEV production while preserving the ability to identify recombinants by using the classic visual screen (Hartig et al., 1992). There also is a viral DNA that can be linearized at a unique Bsu36I site in the p10 region and used for high efficiency production of BEVs with allelic replacements in that region (Martens et al., 1995).

The development of linearizable viral DNAs was followed by the development of a viral DNA that can provide even higher efficiencies of BEV production (Kitts and Possee, 1993). This viral DNA has an *E. coli* lacZ insert in the polh region and Bsu36I sites in the two flanking genes on each side. Therefore, Bsu36I digestion actually deletes a fragment of the viral DNA, including part of the ORF 1629 gene located downstream of polh, which encodes an essential nucleocapsid-associated phosphoprotein (Vialard and Richardson, 1993). This effectively inactivates the viral DNA, but it can be rescued by homologous recombination with the transfer plasmid, which simultaneously introduces the coding sequence of interest, restores ORF 1629, and recircularizes the viral genome. The efficiency of BEV production with these Bsu36I-gapped viral DNAs is routinely over 90%.

Another type of baculovirus DNA that is currently being developed as a target for allelic replacement is one in which various "auxiliary" genes have been deleted (Bishop, et al., 1995). These genes encode proteins that are needed for baculoviruses to infect insect larvae, but are nonessential for the replication of these viruses in cultured insect cells. The idea behind the development of these viral DNAs is that expression of the auxiliary genes might interfere with the production of a protein of interest by a BEV. For example, it would be a good idea to delete the baculoviral cathepsin-like protease gene, as this protease could degrade some BEV-expressed recombinant proteins. Similarly, deletion of the viral protein phosphatase gene (Kim and Weaver, 1993) might improve the quality of phosphoproteins produced in the BEV system.

4. Producing BEVs by Allelic Replacement

After being subcloned into an appropriate transfer plasmid or annealed to a ligation-independent transfer plasmid, a sequence encoding a protein of interest is incorporated into the baculovirus genome by mixing it with viral DNA and transferring the mixture into cultured insect cells, where allelic replacement can occur by homologous recombination, as discussed above. The production of BEVs by the allelic replacement method relies upon the homology between sequences flanking the polh (or p10) genes in the viral DNA and the same sequences flanking the gene of interest in the transfer plasmid. The frequency with which BEVs are produced by this method is determined by the choice of target viral DNA, as described above, and selectable markers are not usually used. However, some selectable markers have been used to increase the frequency of BEV production, including negative selection of parental viruses containing the herpes simplex virus thymidine kinase gene (Godeau et al., 1992) and positive selection of recombinant viruses containing neomycin resistance or p35 genes (Lerch and Friesen, 1993).

5. Isolating, Identifying, and Characterizing BEVs

The most common way to resolve the mixture of parental and recombinant baculovirus progeny obtained from cotransfected cells is by using a conventional viral plaque assay (Summers and Smith, 1987). However, limiting dilution (Reed and Muench, 1938) and fluorescence-activated cell sorting (Peng et al., 1993) also have been used for this purpose. The classic approach used to identify BEVs in viral plaque assays is direct visualization of occlusion-negative plaques, as described above. This screen can be used only if the parental virus had an intact polh gene and the transfer plasmid was designed to replace that gene. Other ways to identify BEVs in plaque assays are to do plaque-lifts with nucleic acid or antibody probes (Capone, 1989; Summers and Smith, 1987) or to rely on visualization of marker gene that was introduced during allelic replacement, as described above.

Conversely, BEVs produced using Bsu36I-gapped viral DNA can be tentatively identified by the loss of the lacZ marker in the parental viral DNA (Kitts and Possee, 1993). When limiting dilution is used as the isolation method, BEVs are usually identified by using nucleic acid or antibody probes in dot-blot formats (Manns and Grosse, 1991; Pen et al., 1989; Summers and Smith, 1987). Finally, BEVs can be identified by direct sequencing (Slightom and Sieu, 1992; Wang and Fraser, 1991) or PCR™ analysis (Sisk et al., 1992; Malitschek and Schartl, 1991; Webb et al., 1991) of viral DNAs.

After a BEV has been isolated and identified by one of the above methods, it can be amplified in insect cells, titered, and used to produce the foreign protein of interest by infecting a fresh cell culture. However, it is important to carefully characterize BEVs before proceeding with foreign gene expression, as there are some traps in the isolation and screening process. The most serious trap is that recombinants are produced far more frequently by single crossovers than by allelic replacement, which requires a double crossover between the viral DNA and transfer vector (O'Reilly, et al., 1992). Single-crossover recombinants contain the entire transfer plasmid at a random site in the viral genome and are genetically unstable. Depending on which screening method was used, single crossover recombinants can be mistakenly identified as BEVs in which the target gene in the parental viral DNA has been properly replaced by the gene of interest. True allelic replacement must be confirmed by verifying the location of the inserted gene in the BEV genome and/or the absence of the gene it was intended to replace. This can be done by using any of several different methods to analyze the viral DNA, including restriction mapping, Southern blotting, or PCR™. Using linearized or gapped viral DNAs for BEV production minimizes the problem of single crossover recombination because double crossover recombination at the appropriate site is necessary to regenerate a circular viral DNA molecule that can efficiently replicate. However, single crossover recombinants can be obtained if digestion of the viral DNA is incomplete.

Standard methods of protein analysis can be used to assess foreign protein production by BEV-infected insect cells. If expression levels are high, as expected, foreign proteins can be identified in electrophoretic profiles of total lysates prepared at late times after infection. In the best cases, this can be done simply by staining protein gels with Coomassie Brilliant Blue. More sensitive methods can be used to detect proteins produced at lower levels, including electrophoretic analysis of total protein lysates from radiolabeled cells, western blotting, radiolabeling and immunoprecipitation, or specific activity assays.

6. Alternative Ways to Produce BEVs

The development of new transfer plasmids and linearizable and gappable viral DNAs for the production of BEVs by allelic replacement significantly increased the rate and efficiency and simplified the process of BEV production. Alternatives to the allelic replacement approach also have been developed to facilitate BEV production.

The first alternative method described for producing BEVs involved homologous recombination and selection of recombinant viral DNAs in yeast (Patel et al., 1992). A recombinant baculovirus was constructed with a yeast autonomous replication sequence, centromere, and selectable marker in the polh region. This viral DNA was introduced into yeast, where it replicates as a stable, low copy number episome. A second marker, SUP4-o, which can be selected either for or against, was then added to produce the viral DNA molecule that serves as the target for homologous recombination. Recombination occurs when yeast cells containing this viral DNA are transfected with a transfer plasmid designed to replace the SUP4-o marker with a sequence encoding the foreign protein of interest. Yeast transformants are counterselected for the absence of SUP4-o and used as a source of the recombinant viral DNA, which can be isolated and transfected onto insect cells to produce BEVs.

Another alternative method that can be used to produce BEVs is enzymatic recombination with the Cre-lox system (Peakman et al., 1992b). These investigators constructed a recombinant baculovirus and transfer plasmid with LoxP sites that can mediate site-specific in vitro recombination by purified Cre recombinase. This method produces recombinant viral DNAs at a frequency of up to 50% and BEVs can be isolated by cotransfecting insect cells and resolving the recombinant and parental progeny by plaque assay. BEVs can be identified by the presence of a lacZ marker donated by the transfer plasmid. This approach provided a way to produce BEVs with high frequency before gapped viral DNAs became available. It also circumvents the single crossover problem associated with conventional allelic replacements in vivo.

Site-specific transposition of a foreign coding sequence into the baculovirus genome is another method that can be used for highly efficient and rapid production of BEVs (Luckow et al., 1993). This approach requires the use of a "bacmid", which is a recombinant baculoviral DNA containing a mini-F replicon, selectable marker, and Tn7 transposition site. Thus, a bacmid can replicate autonomously in *E. coli* and strains harboring the bacmid and a helper plasmid that encodes the Tn7 transposase functions can be used to produce BEVs. This is done by introducing a donor plasmid containing the desired cDNA sequence and a second selectable marker positioned between the left and right arms of Tn7. The transposition functions provided by the helper plasmid will move the cDNA and selectable marker from the donor plasmid to the bacmid. This produces a recombinant bacmid that can be selected, isolated, and transfected onto cultured insect cells to produce BEVs. The bacmid system is available commercially from Life Technologies (Gaithersburg, Md.). In addition, a modified bacmid system that uses an *E. coli* host strain with an occupied Tn7 attachment site and a temperature-sensitive selection step has been described (Leusch et al., 1995).

Finally, baculovirus DNAs designed for the direct insertion of a foreign gene into unique cloning sites have been described (Lu and Miller, 1996; Ernst, et al., 1994). Due to their large size (130 Kb), it is difficult to construct viral DNAs with unique restriction sites and to efficiently ligate linearized viral DNA with a foreign DNA fragment in vitro. However, due to the replicative advantage enjoyed by the recircularized viral DNA, direct cloning can be used successfully for highly efficient production of BEVs. Direct cloning of cDNAs into baculovirus vectors containing an appropriate promoter upstream of the insertion site has been proposed as a way to produce baculovirus-based cDNA expression libraries (Lu and Miller, 1996).

C. Using BEVs

1. Expression Levels

The ability to produce foreign proteins at exceptionally high levels is one of the hallmark features of the BEV system. These high production levels mainly reflect the ability of the transcriptional complex and polh promoter to produce large pools of mRNA during the very late phase of infection. Thus, BEVs that express a foreign coding sequence under the control of a different promoter will usually provide lower production levels. The production levels provided by polh-based BEVs are usually measured in the hundreds of mgs of recombinant protein per liter of infected cells (about $1 \times 10^9$ cells). However, this crude generalization must be immediately qualified with a reminder that production levels vary widely from protein to protein. Secretory pathway proteins are produced at lower levels, often only 1 to 5 mg/liter of infected cells. The block to high-level production of secretory pathway proteins is probably post-transcriptional, as BEVs encoding these proteins can produce large amounts of the foreign mRNA (Jarvis, et al., 1993). However, the nature of this block is unknown. Possibilities include saturation of secretory pathway functions, malfolding of newly-synthesized proteins, and adverse effects of baculovirus infection (Jarvis, et al., 1993; Jarvis and Summers, 1989). It is unlikely that high-level production of all secretory pathway proteins is blocked at one key step, however, because this system can produce some secretory pathway proteins at high levels. Finally, even though they produce less mRNA than the polh promoter, alternative promoters can sometimes produce larger amounts of biologically active secretory pathway proteins, as discussed above.

2. Hosts

Besides the protein to protein variation, production levels in the BEV system depend on the host being used (Hink el al., 1991). Historically, the most widely used hosts were the established insect cell lines IPLB-Sf21-AE ("Sf21"), originally derived from *Spodoptera frugiperda* ovaries (Vaughn et al., 1977), and its clonal derivative, Sf9 (Summers and Smith, 1987). However, in 1992 it was reported that BTI-TN-5B1-4, an insect cell line derived from *Trichoplusia ni* eggs, provided higher levels of foreign protein production (Wickham et al., 1992). Subsequent studies on a larger sample of recombinant proteins generally supported this claim. As a result, BTI-TN-5B1-4 cells, more commonly known as "High Five®" cells (a tradename of InVitroGen), have become another widely-used host for BEVs. Recent data suggest that subclones of yet another established insect cell line, BTI-EaA, derived from *Estigmene acrea* (Granados and Naughton, 1975), can provide more extensive N-glycosylation of foreign glycoproteins expressed by BEVs (Ogonah et al., 1996). Thus, in addition to providing different levels of foreign protein production, different cell lines also can provide different levels of processing in the BEV system.

Insect cells must be perfectly healthy to provide optimal levels of BEV-mediated foreign protein production. This requires high quality growth media, routine subculturing, and careful monitoring of cell doubling times and viability's. Insect cell growth media are available from several different companies and serum-free media have been developed (Maiorella et al., 1988). Insect cell lines may be grown as monolayer cultures in T-flasks, as suspension cultures in shake flasks or spinner flasks, or as large-scale cultures in stirred tank or airlift bioreactors (Shuler et al., 1995; Weiss et al., 1995a; Weiss et al., 1995b). The development of scaleup methods was challenging because insect cells have an unusually high oxygen demand and large cultures must be aerated, but aeration can damage the cells because they are extremely sensitive to shear stress. This problem was solved when it was found that a nonionic surfactant, Pluronic® F68, could protect insect cells from shear stress (Maiorella, et al., 1988; Murhammer and Goochee, 1988). The physical and nutritive conditions needed for optimal foreign protein production by large-scale insect cell cultures have been studied extensively (Shuler et al., 1995; Taticek et al., 1994; Tramper et al., 1993). Among many other interesting results, it has been found that perfusion techniques can be used to obtain extremely high-density cultures ($>5 \times 10^7$ cells/ml) that can produce larger amounts of recombinant protein (Deutschmann and Jager, 1994) and that oxygen demand rises even higher after baculovirus infection (Wong et al., 1994).

Two disadvantages associated with the use of established insect cell lines as hosts for foreign protein production by BEVs are that animal cell culture media are expensive and individual insect cell lines might not have all the protein processing capabilities found in higher eukaryotes (see below). Sometimes, these problems can be circumvented by using insect larvae as an alternative host. BmNPV has been extensively developed for this purpose and is commonly used as a BEV to express foreign proteins in silkworm larvae (Maeda, 1989; Maeda et al., 1985). Methods for rearing and infecting larvae have been described (Choudary et al., 1995; O'Reilly, et al., 1992). However, most investigators use established cell lines this method is more familiar and it is easier to purify recombinant proteins from cultured cells than from insect larvae. Moreover, although larvae are usually cheaper to cultivate than established insect cell lines, their use does not always solve protein processing problems (Pajot-Augy, et al., 1995).

3. Protein Processing

The other hallmark feature of the BEV system is its ability to process proteins. Biosynthesis of many eukaryotic proteins includes co- and/or post-translational processing, which can be critical for protein solubility and function, and insect cells have most of the protein processing pathways associated with higher eukaryotes. In fact, development of the BEV system has contributed immensely to the knowledge of protein processing in insect cells. Most reports of foreign protein production in the BEV system include structural analyses of the end-product and its covalent chemical modifications. These are often simple qualitative analyses designed to determine if a specific modification took place and whether there are gross differences in the structures of the recombinant and native proteins (e.g. differences in electrophoretic mobility). However, some studies include more detailed structural analyses, which have provided extremely valuable information on protein processing pathways in insect cells.

This information comes with a caveat, though, which is that it must be applied specifically to the protein processing pathway of a specific baculovirus-infected host. This is important because baculovirus infection probably alters cellular protein processing pathways in various ways (Velardo et al., 1993; Davidson et al., 1991; Murphy, et al., 1990; Jarvis and Summers, 1989) and the specific protein processing capabilities of different hosts, including different insect cell lines, can be quite different (Ogonah, et al., 1996; Kuroda et al., 1989). The chemical modifications found on many different recombinant proteins have been catalogued elsewhere (Luckow, 1991; Luckow and Summers, 1988). A few selected results that have provided the most definitive information are summarized below.

a. Proteolytic Cleavages

Many secretory pathway proteins have short, N-terminal signal peptides that are proteolytically cleaved during biosynthesis. Signal peptide cleavage has been carefully evaluated by directly sequencing the N-termini of many different foreign proteins produced in the BEV system. The results indicate that insect cells can accurately remove native signal peptides of plant or animal secretory pathway proteins. Insect cells also can accurately cleave heterologous signal peptides that are encoded by some transfer plasmids and used to direct secretion, as discussed above. Thus, insect cells clearly have secretory signal peptide recognition and cleavage machinery. However, the relationship between this machinery and that of other eukaryotes remains unclear because some foreign signal peptides are nonfunctional in insect cells (Pajot-Augy, et al., 1995) and insect cell-derived signal peptides sometimes, but not always provide better secretion, as discussed above.

Many eukaryotic proteins also have prosequences, which are usually short amino acids sequences that need to be removed to convert a protein to its biologically active form. Prosequences may or may not be accurately and efficiently cleaved from foreign proteins produced in the BEV system. For example, the N-terminal prosequence of human tissue plasminogen activator was efficiently cleaved (Furlong et al., 1988), but the N-terminal prosequences of other proteins, including a frog alpha-amidating enzyme (Suzuki et al., 1990), were not. The C-terminal prosequence of the gastrin-releasing peptide precursor was cleaved at the proper site, but also at several other sites (Lebacq-Verheyden et al., 1988). These problems probably reflect limiting levels of the appropriate proteases in baculovirus-infected insect cells, as well as differences in their substrate specificities.

Proteolytic cleavages at internal dibasic amino acid sites occur inefficiently in cultured insect cells. For example, influenza virus hemagglutinin (Kuroda et al., 1986) and HIV gp160 (Hu et al., 1987) were cleaved slowly and/or inefficiently in the BEV system. This suggests that insect cell lines have limiting amounts of the kex-2 family of processing proteases needed for these internal cleavages. This conclusion is supported by the findings that hemagglutinin was cleaved more efficiently in insect larvae (Kuroda, et al., 1989) and gp160 was cleaved more efficiently when furin is coexpressed in this system (Yamshchikov et al., 1995).

b. Glycosylation

Many eukaryotic proteins are modified by the covalent addition of carbohydrate side-chains. There are three well-defined protein glycosylation pathways in eukaryotic cells: N-glycosylation, O-glycosylation, and addition of O-linked N-acetylglucosamine (O-GlcNAc; Montreuil, et al., 1995; Hart, 1992). Insect cells have all of these pathways, but they are not necessarily the same as those found in higher eukaryotes (Marz et al., 1995).

N-glycosylation begins with cotranslational addition of a preassembled oligosaccharide precursor, $Glc_3Man_9GlcNAc_2$, to a nascent polypeptide chain (Kornfeld and Kornfeld, 1985). The glucose residues are removed by glucosidases I and II to produce a "high mannose" side chain, which can be the finished end-product. In mammalian cells, however, high mannose side chains can be converted to "complex" structures. This requires class I α-mannosidases, which remove the α-1,2-linked mannose residues to produce $Man_5GlcNAc_2$, GlcNAc transferase I, which adds a GlcNAc residue to produce $GlcNAcMan_5GlcNAc_2$, and α-mannosidase II, which removes two mannose residues to produce $GlcNAcMan_3GlcNAc_2$. This key intermediate is then elongated by glycosyltransferases that add GlcNAc, galactose, fucose, and sialic acid residues to complete the complex side chain.

The overall conclusion from most structural data on N-linked oligosaccharides from glycoproteins produced in insect cells, together with biochemical data on the processing activities of these cells, is that the insect cell N-glycosylation pathway is a truncated version of the mammalian pathway (Jarvis and Finn, 1995; Marz, et al., 1995; and references therein). Insect cells clearly can add N-linked precursors to newly-synthesized proteins and convert them to trimmed and fucosylated structures. But, these cells usually do not elongate the side-chains further to produce complex structures. Interestingly, insect cells have GlcNAc transferase I and II activities (Altmann et al., 1993; Velardo, et al., 1993), indicating that they should be able to add GlcNAc residues to the trimmed structures. This idea is supported by the finding that some glycoproteins produced in insect cells have N-linked side chains consisting of $GlcNAcMan_3GlcNAc_2$.

It has been proposed that $GlcNAcMan_3GlcNAc_2$ is a transient intermediate needed for fucosylation and that the terminal GlcNAc is subsequently removed to produce the fucosylated $Man_3GlcNAc2$ structure seen on many insect cell-derived glycoproteins. This possibility is supported by the discovery that some insect cells contain a membrane-bound N-acetylglucosaminidase activity (Altmann et al., 1995). Alternatively, if they have the requisite glycosyltransferases, insect cells could convert $GlcNAcMan_3GlcNAc_2$ to complex structures with penultimate galactose and terminal sialic acids, like those produced by mammalian cells. This possibility is supported by structural data on two foreign glycoproteins produced in BEV-infected insect cells which showed that they had N-linked side-chains with terminal galactose (Ogonah, et al., 1996) or sialic acid (Davidson et al., 1990).

It has been proposed that the synthesis of complex N-linked oligosaccharide side chains by insect cells requires induction of cellular processing enzymes resulting from baculovirus infection (Velardo, et al., 1993; Davidson, et al., 1991). However, the total glycopeptide profiles of uninfected and infected Sf9 cells are similar (Kretzschmar et al., 1994) and it is generally thought that baculoviruses turn cellular gene expression off (Ooi and Miller, 1988). Another proposal is that only a select few recombinant glycoproteins can acquire complex N-linked side-chains due to special structural properties which make them excellent substrates for extremely low levels of glycosyltransferase activities or poor substrates for the processing N-acetylglucosaminidase in baculovirus-infected insect cells (Jarvis and Finn, 1995).

Although they might have different N-linked oligosaccharide side-chains, most foreign glycoproteins produced in the BEV system are biologically active and antigenically authentic (Luckow and Summers, 1988). However, it has been shown that a recombinant human glycoprotein with insect cell-derived N-linked glycans is cleared more rapidly from the mammalian circulatory system (Sareneva et al., 1993). Another problem with N-glycosylation in the BEV system is that it can be inefficient, particularly at later times of infection, and the nonprocessed subpopulation of the protein of interest is often insoluble and/or inactive (Jarvis, et al., 1996; Murphy, et al., 1990).

O-glycosylation occurs in the Golgi apparatus and results in the post-translational addition of relatively small glycans O-linked through N-acetylgalactosamine (GalNAc) to serine or threonine (Montreuil, et al., 1995). Structural analyses of recombinant O-glycosylated proteins produced in the BEV system reveal that the major O-linked side-chain consists of just the monosaccharide, GalNAc (Marz, et al., 1995). A subpopulation of these proteins have O-linked Gal-GalNAc, but the sialylated Gal-GalNAc trisaccharides produced by mammalian cells have not been detected. Further analysis showed that various insect cell lines have comparable levels of UDP-GalNAc:polypeptide GalNAc transferase activity, but different levels of UDP-Gal:GalNAc β-1,3 galactosyl-transferase activity (Thompsen et al., 1990). Sf9 cells have the lowest levels of the latter activity, which probably explains why GalI is the major O-linked side-chain produced by these cells. Overall, the O-glycosylation pathway in baculovirus-infected insect cells appears to be incomplete, due to the absence of sialyltransferases, and inefficient, due to limiting levels of transferase activities.

Many proteins are post-translationally glycosylated by a cytoplasmic enzyme which adds a single GlcNAc via O-linkage to serine or threonine residues (Hart, 1992). This process is reversible and probably regulates the functions of many nuclear and cytosolic proteins. The BEV system clearly can add O-GlcNAc to foreign proteins, as demonstrated for mammalian keratins (Ku and Omary, 1994), nucleoporins (Bailer et al., 1995), and c-myc (Chou et al., 1995), among others. However, the addition of O-GlcNAc to one keratin was less efficient in this system than in mammalian cells.

c. Phosphorylation

Phosphorylation is another reversible covalent chemical modification that can regulate protein function. Phosphorylation of many different foreign proteins has been documented in the BEV system. The more detailed studies have led to the general conclusion that foreign phosphoproteins can be accurately phosphorylated in this system, but phosphorylation of specific sites is sometimes inefficient. For example, the same sites were phosphorylated on SV40 large T-antigen produced in SV40-infected monkey or BEV-infected insect cells, but certain serine residues recognized by nuclear kinases were relatively underphosphorylated in insect cells (Hoss et al., 1990). Considering that T-antigen is localized in the nucleus of BEV-infected insect cells, it appeared that the levels of these kinases might be too low to process all of the T-antigen being produced by these cells. However, another factor to consider is that baculoviruses encode a protein phosphatase and kinase (Ayres, et al., 1994), which could alter the structures of recombinant phosphoproteins in unexpected ways. In fact, one recent study concluded that underphosphorylation of recombinant proteins in the BEV system may result from unusually high phosphatase activities rather than saturation of kinases with recombinant substrate (Fuchs et al., 1995). Another study showed that recombinant kinases involved in cellular signaling were activated by site-specific phosphorylation in the absence of kinases which lie upstream in the signaling pathway, probably by baculovirus-encoded or -induced kinase activity (Kozma et al., 1993). Finally, it is worth mentioning that various growth factor receptors expressed in the BEV system are accurately tyrosine phosphorylated, as this has led people to use this system to express multiple proteins that functionally reconstitute cellular signaling pathways (Agarwal et al., 1995).

d. Other Covalent Chemical Modifications

Acylation. Many eukaryotic proteins are modified by the addition of lipid side-chains, including myristate, palmitate, isoprenoids, and glycosylphosphatidylinositols (GPIs). Studies of various foreign proteins have shown that each of these lipid modifications can occur in BEV-infected insect cells. Myristylation is dependent on protein synthesis, occurs at the expected sites, and can produce side-chains with the expected structures, as shown by site-directed mutagenesis, hydroxylamine resistance, and direct structural analyses (Risinger et al., 1992; Delchambre et al., 1989). Palmitylation is independent of protein synthesis and can produce structurally authentic, hydroxylamine-sensitive side-chains, but it can be quite inefficient in BEV-infected insect cells (Veit et al., 1994; Page et al., 1989). One study showed that palmitylation is sensitive to pharmacological regulation, suggesting that the insect and mammalian cell pathways are similar (Mouillac et al., 1992). This conclusion is supported by the finding that palmitylation of some recombinant proteins produced in the BEV system is dependent upon prior isoprenylation, as in higher eukaryotes (Lowe et al., 1992). Isoprenylation is inefficient in BEV-infected insect cells, but occurs at the same recognition sites and produces the same side-chains, suggesting that prenyl-transferase functions are conserved in insect cells and higher eukaryotes (Kalman et al., 1995; Buss el al., 1991). Finally, studies on several recombinant proteins, including human CD59 antigen (Davies and Morgan, 1993), have shown that BEV-infected insect cells can produce GPI anchors. Like many other types of protein processing provided by this system, GPI addition was inefficient, and large subpopulations of these products were unanchored and secreted into the extracellular growth medium.

N-terminal acetylation. N-terminal protein modifications are often a nuisance in protein sequencing projects, but N-acetylation is sometimes required for protein function. The BEV system can produce N-acetylated proteins and this system was used to show that N-acetylation is required for the function of alpha tropomyosin (Urbancikova and Hitchcock-DeGregori, 1994). Another N-terminal modification that can occur in the BEV system is removal of an N-terminal methionine, followed by acetylation of the formerly penultimate alanine (Han et al., 1995) or serine (Becker et al., 1994).

C-terminal methylation. About half of the Kirsten-ras p21 protein produced in the BEV system was modified by C-terminal methylation, as well as isoprenylation (Lowe et al., 1991).

Alpha-amidation. Alpha-amidation is one of the few covalent chemical modifications that does not occur in BEV-infected Sf9 (Lebacq-Verheyden, et al., 1988) or other insect cell lines, including High Five (Vakharia et al., 1995). This covalent chemical modification results from a complex, multistep pathway which begins with proteolytic cleavage of a C-terminal prosequence, followed by the removal of additional amino acids to produce a C-terminal glycine. The glycine residue is then hydroxylated and amidated by two distinct activities. The C-terminal prosequence can be removed in BEV-infected insect cells, but alpha-amidation does not occur, suggesting that these cells lack a subsequent step(s) in this processing pathway. By contrast, alpha-amidation can occur in BEV-infected insect larvae (Hellers et al., 1991).

e. Supramolecular Assembly

Supramolecular protein assembly is one of the best-documented capabilities of the BEV system. Individual proteins can assemble into higher order structures via disulfide bond formation, which is virtually complete in some cases (Giese et al., 1989), but not in others (Domingo and Trowbridge, 1988). This indicates that BEV-infected insect cells have protein disulfide isomerase activity, but perhaps too little to completely process highly-expressed foreign proteins. Proteins also can assemble by noncovalent interactions in BEV-infected insect cells at rates similar to (Lanford, 1988) or lower than (Kuroda et al., 1991) native rates.

Hetero-oligomeric protein complexes can be assembled by infecting insect cells with multiple BEVs (St. Angelo, et al., 1987) or with a single BEV encoding multiple foreign genes (Emery and Bishop, 1987). Both of these approaches have been used to produce functional IgG heterodimers with normal heavy and light chain composition in the BEV system (Hasemann and Capra, 1990). The ability of this system to produce larger, even more complex oligomeric assemblies, including virus-like particles, is well-documented. Subviral particles consisting of hepatitis B virus, bluetongue virus, or rotavirus proteins were among the first to be described (Urakawa and Roy, 1988; Estes et al., 1987; Kang el al., 1987). This was followed by an example of protein processing in which a BEV was used to express the poliovirus genome in insect cells and the resulting polyprotein was properly cleaved and assembled into stable, noninfectious poliovirus-like particles (Urakawa et al., 1989).

These early studies led to widespread use of the BEV system to express multiple viral proteins and produce many different types of virus-like particles that hold great promise as noninfectious vaccines and diagnostic reagents (Pearson and Roy, 1993). Most recently, potential multivalent vaccines have been produced by incorporating heterologous epitopes into the virus-like particles or other supramolecular protein complexes that can be assembled in this system (Garnier et al., 1995b; Belyaev and Roy, 1992). Virus-like particles containing exogenous DNA also have been produced and used to efficiently transfer DNA into eukaryotic cells, indicating that these particles could be good tools for gene therapy (Forstova et al., 1995).

f. Protein Targeting

Protein targeting signals had not been widely investigated in insect systems when the BEV system was first developed, so it was not known whether insect cells would be able to recognize protein targeting signals in foreign proteins. Today, it is known that insect cells can recognize heterologous targeting signals, which suggests that these cells have similar protein trafficking machinery. Foreign proteins destined for secretion or the cell surface can enter the insect cell secretory pathway and native or heterologous signal peptides can be cleaved accurately, as discussed above. Polarized cell-surface expression of foreign proteins can occur in midgut epithelial cells of insect larvae (Kuroda, et al., 1989). Mitochondrial proteins localize to the mitochondria (Takagi et al., 1992) and nuclear proteins localize to the nuclei of BEV-infected insect cells and two baculovirus-encoded nuclear proteins contain nuclear targeting signals similar to those found in higher eukaryotes (Broussard et al., 1996; Jarvis et al., 1991). However, lysosomal enzymes produced in the BEV system lack the lysosomal targeting signal, mannose-6-phosphate, and are secreted by default (Boose et al., 1990; Martin et al., 1988). Biochemical assays indicate that Sf9 cells lack the phosphotransferase activity responsible for this modification (Aeed and Elhammer, 1994). A curious feature of protein trafficking in insect cells is that they secrete the intracellular domain of rabbit prolactin receptor, which lacks a typical signal peptide (Garnier et al., 1995a). Furthermore, this domain can mediate secretion and ubiquitination of heterologous proteins, which suggests that lepidopteran insect cells have an unusual secretory pathway, that can respond to this novel targeting signal.

g. Variation and the Art of Molecular Genetics

Structural analyses of recombinant proteins and biochemical analyses of cellular protein processing activities have produced a wealth of information on protein processing pathways in the BEV system. However, it is important to recognize the limitations of these biochemical approaches. They are indirect and provide only a retrospective view of protein processing pathways, which must be inferred from the structures of the end-products or the presence or absence of processing activities. These conclusions can be confused by degradative pathways, which might alter the product of the biosynthetic pathway and lead to misinterpretations. Also, the inability to detect a processing activity clearly does not prove the absence of that activity. Conclusions drawn from structural data on any one recombinant protein need to be applied only to that protein and not to the pathway in general. These conclusions also should be applied only to the specific host that was used to produce the recombinant protein under analysis. Finally, the possible effects of baculovirus infection on the host need to be considered.

An alternative approach which circumvents many of these problems is to use molecular genetics to isolate genes encoding insect cell processing enzymes. This makes it possible to study these genes, their expression, the conditions that influence their expression, and, ultimately, the properties of the enzymes they encode. Examples herein below detail the isolation and characterization of class I and II α-mannosidase cDNAs from Sf9 cells.

Overall, the biochemical evidence suggests that foreign proteins can be appropriately processed in the BEV system. However, it is important to recognize that there are some exceptions and caveats to this generalization. BEV-infected cell lines clearly lack certain protein processing capabilities, like alpha-amidation and lysosomal targeting. There also are clear differences in the structures of the N-linked glycans found on most recombinant glycoproteins produced in this system. Inefficient processing of recombinant proteins is a common problem in the BEV system. Nonetheless, this problem does not preclude the use of this expression system because, if adequate yields of a perfectly processed recombinant protein can be obtained, a high background of unprocessed material can be irrelevant. The "inefficiency" of protein processing in this system might reflect adverse effects of baculovirus infection or the inability of the cellular processing machinery to cope with the high levels of foreign gene transcription provided by BEVs. There also might be subtle differences in the protein processing machinery of insect cells and higher eukaryotes, which reduce the functional efficiency of foreign protein processing in this expression system. Theoretically, any of these protein processing problems can be addressed by metabolic engineering, which could be used to improve the BEV system, as discussed further below.

4. Selected Applications of BEV-Expressed Proteins a. Vaccines

One of the best-recognized applications of the BEV system is vaccine production. There are far too many examples of this application to discuss here and a comprehensive list with references is available (Luckow, 1991).

However, it is appropriate to summarize some general conclusions and new discoveries that have arisen from immunological studies on recombinant proteins produced in this system. Recombinant proteins from BEV-infected insect cells are invariably recognized by antibodies produced against the corresponding native proteins, indicating that they are antigenically authentic. Moreover, recombinant proteins from the BEV system usually induce protective immunity in laboratory animals. HIV gp160 produced in this system has been used extensively for human clinical trials and the results indicate that this product is safe and immunogenic. Unfortunately, although gp160 can induce both humoral and cell-mediated immune responses, these are usually weak, transient, and non-neutralizing. On the positive side, clinical trials on BEV-expressed recombinant gp 160 showed that it has a therapeutic effect in previously infected individuals and the new concept of "vaccine therapy" emerged from these results (Redfield et al., 1991). It also was found that stronger humoral and cell-mediated immune responses could be obtained by using a combined vaccine regimen involving priming with a live recombinant vaccinia virus encoding gp160 and boosting with BEV-expressed recombinant gp160 (Cooney et al., 1993; Graham et al., 1993).

b. Diagnostic Tests

Another exciting application of recombinant proteins produced in the BEV system is diagnostic testing. Recombinant proteins produced in the BEV system have been used to develop diagnostic tests for many different infectious agents, including viruses, protozoa, rickettsia, and bacteria, as well as tests for human autoantibodies and cancer markers. Diagnostic testing with recombinant proteins from the BEV system has progressed beyond the developmental state, as these proteins have been used for several large epidemiological studies (Numata et al., 1994).

c. Three Dimensional Structural Analyses

The BEV system is being used with increasing frequency to produce recombinant proteins for three dimensional structural analyses. Rat acid phosphatase was one of the first recombinant proteins to be crystallized (Vihko et al., 1993) and, subsequently, many recombinant proteins have been crystallized and analyzed by x-ray diffraction. In addition, the three-dimensional structures of many of the virus-like particles produced in this system have been examined by x-ray crystallography (Roy, 1996; Agbandje et al., 1991) and electron cryomicroscopy (Prasad el al., 1994).

D. Preventing Adverse Effects of Baculovirus Infection

BEVs ultimately kill the host that is producing the foreign protein of interest. Thus, recombinant protein production with the BEV system is a "batch" process and fresh cells and virus must be used to produce each batch of recombinant protein. BEVs also have adverse effects on host protein processing pathways long before they kill the cells and encode at least one protease and phosphatase that might degrade or dephosphorylate the foreign protein being produced.

One way to address these problems is to use viral promoters to develop insect cell expression systems that avoid using a BEV altogether. This can be done by producing stably-transformed insect cells that express a foreign gene constitutively under the control of baculovirus early promoters (Jarvis, et al., 1990). The production levels obtained with transformed insect cells are usually lower than those obtained by infecting insect cells with polh-based BEVs. However, where polh-based BEVs fail to produce high levels of a foreign protein, as in the case of many secretory pathway proteins, transformed insect cells can provide similar levels of recombinant product. Furthermore, stably-transformed cells can produce these proteins continuously over a long time period and process them faster and more efficiently than infected cells. Thus, stably-transformed insect cells hold promise for foreign protein production, but this approach would be significantly more attractive if it could provide higher production levels. This may be accomplished by developing gene amplification methods or using stronger promoters.

Another way to circumvent the adverse effects of baculovirus infection is to develop BEVs that can provide high-level foreign gene expression without the cytopathic effects. One example is a "miniviral replicon": a baculovirus-based DNA molecule encoding only the cis- and trans-acting functions needed for autonomous replication and transcription of strong viral promoters in insect cells. This replicon lacks all other viral functions. It replicates as an episome and produce a foreign protein(s) of interest at high levels, but has no adverse side-effects on the host cell and produce no progeny virus. Efforts to identify the functions required for baculovirus DNA replication and late/very late transcription are proceeding at a rapid pace. Thus, these efforts may lead to the development of a miniviral replicon expression vector.

E. Metabolic Engineering

Another reason for the relatively lower levels of secretory pathway protein production in baculovirus-infected insect cells is that host protein processing activities might be saturated. If specific cellular processing activities are limiting, it should be possible to improve the system by "metabolic engineering" to increase available levels of these activities. One approach would be to use insect cells that have been stably-transformed to overexpress processing activities as modified hosts for conventional BEVs, as proposed previously (Jarvis, et al., 1990). However, this approach is complicated by the unexpected finding that baculovirus infection shuts down expression of integrated genes, even when their expression is controlled by a viral promoter that is normally active throughout infection (Jarvis, 1993). An alternative approach is to use modified BEVs that include and can overexpress genes encoding cellular protein processing enzymes.

This latter approach was used to try to improve the assembly of steroid receptors (Alnemri and Litwack, 1993) and immunoglobulins (Hsu et al., 1994), both of which were inefficiently processed and formed insoluble protein aggregates when overexpressed in BEV-infected insect cells. Coexpression of the steroid receptors and hsp90 or hsp70 failed to enhance assembly and prevent aggregation. Coexpression of immunoglobulins with immunoglobulin binding protein produced higher levels of soluble intracellular immunoglobulin, but failed to increase secretion.

As provided herein by the present invention, metabolic engineering of protein glycosylation pathways is another way to improve the BEV system. Insect cell glycosylation pathways are modified by increasing the levels of existing processing activities or by adding new processing activities thought to be missing in these cells. Modified host cells or modified viruses can be used for either purpose, as described herein.

II. Baculovirus Expression

A. Vectors

Baculovirus expression vectors are useful tools for the production of proteins for a variety of applications (Summers and Smith, 1987; O'Reilly et al, 1992; also U.S. Pat. Nos. 5,077,214 (Guarino and Jarvis) and U.S. Pat. No. 5,162,222, (Guarino and Jarvis), each incorporated herein by reference). Baculovirus expression vectors are recombinant insect vectors in which the coding region of a particular gene of interest is placed behind a promoter in place of a nonessential baculoviral gene. The classic approach used to isolate a recombinant baculovirus expression vector is to construct a plasmid in which the foreign gene of interest is positioned downstream of the polyhedrin promoter. Then, via homologous recombination, that plasmid can be used to transfer the new gene into the viral genome in place of the wild-type polyhedrin gene (Summers and Smith, 1987; O'Reilly et al., 1992).

The resulting recombinant virus can infect cultured lepidopteran insect cells or larvae and express the foreign gene under the control of the polyhedrin promoter, which is strong and provides very high levels of transcription during the very late phase of infection. The strength of the polyhedrin promoter is an advantage of the use of recombinant baculoviruses as expression vectors because it usually leads to the synthesis of large amounts of the foreign gene product during infection.

Ironically, while it is an advantage of conventional baculovirus expression vectors, the present inventor reasoned that the use of the polyhedrin promoter also presents some clear limitations. These limitations stem from the fact that this promoter requires virus-encoded factors for its transcriptional activity that only become available during the very late phase of infection (Huh and Weaver, 1990; Passarelli and Miller, 1993; McLachlin and Miller, 1994; Lu and Miller, 1995; Todd et al., 1995; Xu et al., 1995). Thus, while the polyhedrin promoter ultimately can provide high expression levels, it cannot provide any expression until the viral replication cycle is nearly complete. This is undesirable for foreign glycoprotein production as evidence suggests that cellular glycoprotein processing pathways are compromised at late times of infection (Jarvis and Summers, 1989; Jarvis et al., 1990; Murphy et al., 1990).

B. Methods

The present invention contemplates the use of a vector comprising one or more eukaryotic oligosaccharide processing genes to modify the insect cell N-glycosylation pathway by directing the expression of heterologous processing enzyme(s). The one or more encoded enzyme(s) then function as part of the insect cell oligosaccharide processing machinery. This contributes to the production of a protein of interest that has a complex biantennary oligosaccharide structure containing penultimate galactose and terminal sialic acid residues, similar to that obtained from mammalian cell culture techniques.

The baculovirus expression vectors of the present invention also contemplate the use of additional promoter and enhancer elements, heterologous genes encoding proteins which aid in protein folding and/or other post translational modifications, and additional features which expand the breadth and utility of the current baculovirus expression vectors. Each of these features of the present invention will be discussed in greater detail below.

The present invention contemplates at least four different modes of using the novel baculovirus expression vectors. While each of the vectors will have common features, each of these modes of use requires different features to be incorporated into the vector of choice for the desired application. 1. Vectors for Use in Coinfection Method The first method of use contemplated for the present invention would take advantage of the heterologous coding sequence of interest already being cloned into a current baculovirus expression vector, behind a promoter. The present invention provides a second baculovirus expression vector, which in a preferred embodiment supplies all of the oligosaccharide processing enzyme coding regions required to produce a protein of interest with the desired oligosaccharide structure. These two vectors are used independently to make recombinant baculoviruses, which are then used to coinfect an insect cell host.

This class of vector is the least complex, comprising only the common elements of all five classes. This class of vector comprises one or more oligosaccharide processing enzyme transcription unit(s), further comprising appropriate promoter and enhancer elements to achieve optimal temporal expression (discussed in greater detail below). These vectors further comprise expression unit(s) encoding protein(s) which aid in the protein of interest folding or being otherwise modified properly in the cellular host. Additional embodiments of these vectors comprise 5' and 3' flanking DNA segments, for directing the replacement of the recombinant baculovirus expression vector into the baculovirus host. These vectors further comprise baculovirus structural genes and promoters, providing a method to identify recombinant baculoviruses, or providing essential gene function to the recombinant baculoviruses. Additional embodiments comprise selectable markers which can also be used to identify recombinant baculoviruses. These vectors are discussed in detail in Example 22 below.

2. Vectors for Infection Method

The second method of use contemplated for the present invention comprises all of the features of the first vectors, and would further comprise a cloning site, preferably a multiple cloning site, for the insertion of the heterologous gene or cDNA encoding the protein of interest. A preferred embodiment of the second vectors would include a promoter element functionally positioned upstream of the multiple cloning site, and would further comprise an enhancer element to increase transcription of the heterologous coding region. This vector is used alone to produce recombinant baculoviruses, which are used to infect an insect cell host. These vectors are discussed in detail in Example 22 below.

3. Additional Vectors for Infection Method

The third method of use contemplated for the present invention represents an improvement over the first vectors. In addition to comprising one or more oligosaccharide processing enzyme transcription unit(s) as described for the first vectors, these vectors further comprise features that allow for the more efficient insertion of one or more genes encoding any protein of interest, under the control of a promoter. The insertion is carried out using conventional baculovirus transfer plasmids and a conventional method involving linearization of the viral DNA by digestion with Bsu36I. The resulting recombinants, which are produced at a much higher efficiency than previous methods, are used to express the protein of interest during infection of conventional insect cell lines. These vectors are discussed in detail in Example 22 below.

4. Vectors that Create a Stably Transformed Insect Cell Line

The fourth method of use contemplated for the present invention produces a stable insect cell line, which incorporates all of the desired features of the first vectors. These vectors comprise all of the features of the first vectors, wherein the selectable marker provides the insect cell host resistance to a cellular toxin. The selectable marker which provides the insect cell host resistance to a cellular toxin can be either on the same vector as the rest of the elements, in which case the single vector would be transfected into the host cell, or on a separate vector from the rest of the elements, in which case co-transfection of the two vectors would be used. A further embodiment of the present invention comprises using multiple baculovirus expression vectors with different toxin resistance markers and different regions of their genomes replaced to stepwise or in combination stably incorporate all of the desired features described above into an insect cell line. The stably transformed insect cell line is then infected with baculoviruses produced from a standard baculovirus expression vector, wherein the heterologous coding sequence of interest is cloned behind a promoter. Further, these stable cell lines can also be used for infection with one or more of the novel recombinant baculoviruses described herein.

The particular features of the four classes of baculovirus expression vectors will now be discussed in greater detail.

III. Oligosaccharide Processing

A. Oligosaccharide Processing Pathway

Insect cells and higher eukaryotes begin oligosaccharide processing along a similar pathway. Both add $Glc_3$-$Man_9$-$GlcNAc_2$ precursors to appropriate recognition sites in nascent polypeptides followed by the trimming of glucose residues to produce $Man_9$-$GlcNAc_2$. The four α-1,2-linked mannose residues are removed by "class I" α-mannosidases, producing a $Man_5GlcNAc_2$ structure (Moremen et al., 1994). Following the addition of a single GlcNAc residue by N-acetylglucosaminyltransferase I, two more mannose residues are removed by α-mannosidase II, a "class II" mannosidase to produce $GlcNAc$-$Man_3$-$GlcNAc_2$ (Moremen et al., 1994).

At this point in the pathway, insect cells and higher eukaryotes diverge. In higher eukaryotes, $GlcNAc$-$Man_3$-$GlcNAc_2$ can be extended by N-acetylglucosaminyltransferase II, galactosyltransferase, and sialyltransferase to produce a complex biantennary structure containing penultimate galactose and terminal sialic acid residues (Kornfeld and Kornfeld, 1985). However, in insect cells $GlcNAc$-$Man_3$-$GlcNAc_2$ appears to be converted to $Man_3$-$GlcNAc_2$ by a novel insect cell β-N-acetylglucosaminidase (Licari et al., 1993; Altmann et al., 1995; Wagner et al., 1996a). This final structure is found either with or without fucose linked to the chitobiose core (Butters and Hughes, 1981; Hsieh and Robbins, 1984; Ryan et al., 1985; Nagao et al., 1987; Kuroda et al., 1990; Chen et al., 1991; Wathen et al., 1991; Williams et al., 1991; Knepper et al., 1992; Grabenhorst et al., 1993; Yeh et al., 1993; Kubelka et al., 1994; Manneberg et al., 1994).

The widely-used host cell lines for baculovirus vectors are Sf21 (Vaughn et al., 1977), Sf9 (Summers and Smith, 1987), and High Five (Wickham et al., 1992) and these are reported to have low levels of the glucosaminyltransferases I and II (Altmann et al., 1993; Velardo et al., 1993), but no galactosyl- or sialyltransferase activities. There are two reports of lectin blotting analyses which claim to demonstrate sialic acid on insect cell-expressed glycoproteins (Davis and Wood, 1995; Sridhar et al., 1993), but these are completely invalid as controls were not included to show that the lectins were binding to sugars. There is one report of β1,4-galactosyltransferase activity in insect cells (Ogonah et al., 1996) and one group which has found penultimate galactose and terminal sialic acid on one human glycoprotein (Davidson et al., 1990; Davidson and Castellino, 1991a). However, it is clear that this observation is peculiar to the glycoprotein used in that study as it has not been convincingly demonstrated by any other researchers for any other glycoprotein in the intervening five years even though this is a highly desirable result. Thus, although insect cells are theoretically capable of producing oligosaccharide structures similar to those produced in higher eukaryotes, this has yet to yield practical benefits. The unpredictability of the glycosylation pattern for any given protein and the differences in the glycosylation pattern from protein to protein are clear limitations of the current system.

B. Oligosaccharide Processing Genes

Figure 13:
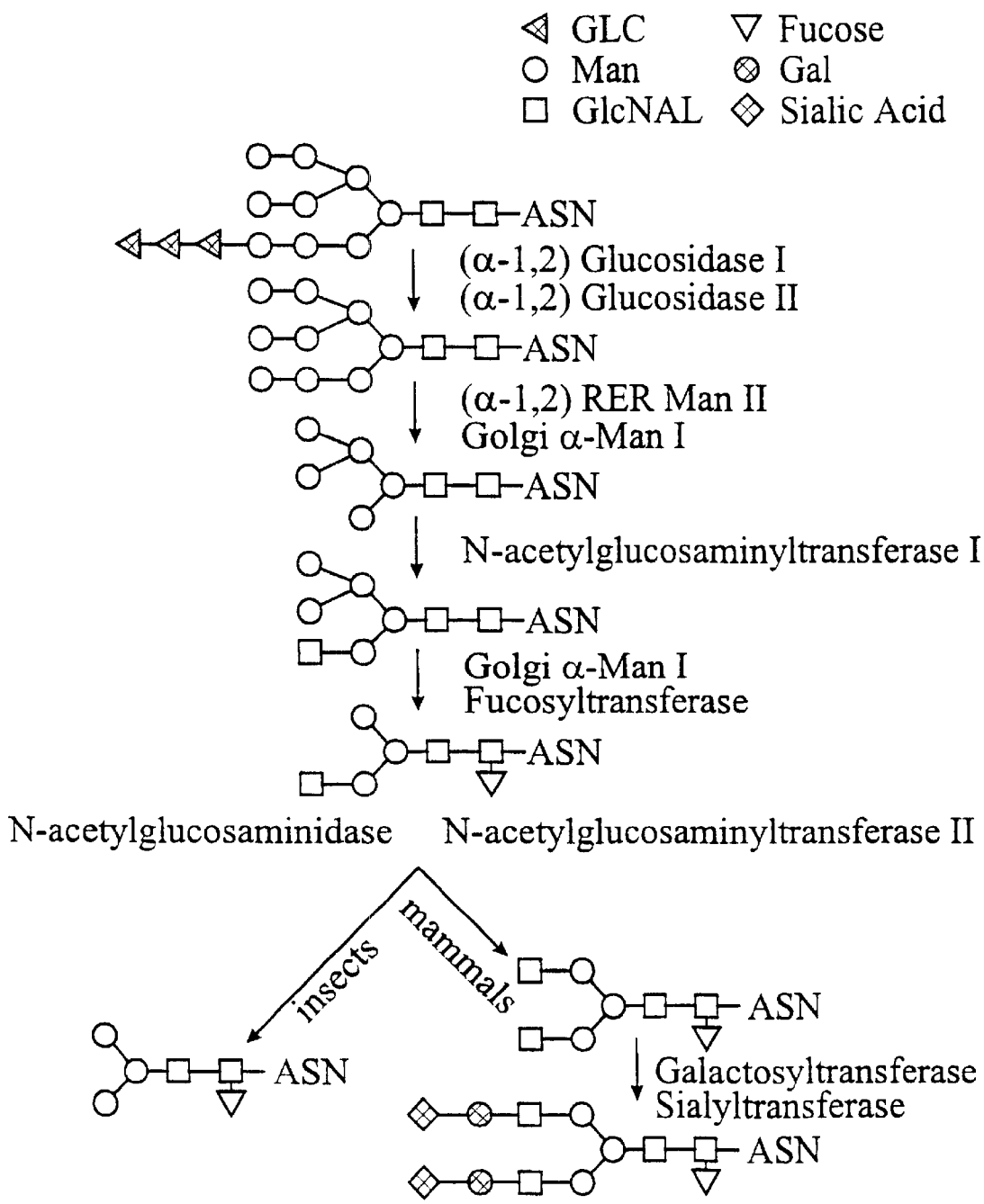
FIG. 13. N-linked oligosaccharide processing. The oligosaccharide processing steps in insect cells (left branch) or higher eukaryotes (right branch) is shown. N-acetylglucosamine residues are depicted as open squares, mannose residues are depicted as open circles, glucose residues are depicted as stippled triangles, fucose residues are depicted as open triangles, galactose residues are depicted as stippled circles and sialic acid residues are depicted as stippled diamonds. The enzymes catalyzing each step are listed.

There are at least seven different enzymes responsible for the complete processing of N-linked oligosaccharides to form a complex biantennary structure containing penultimate galactose and terminal sialic acid residues (FIG. 13). A table containing cloned glycosyltransferases, along with the source of the clone and the GenBank accession number is shown below (Field and Wainwright, 1995).

TABLE 1

| Enzyme | EC designation | GenBank accession |
|---|---|---|
| Sialyltransferases | | |
| α2,3-sialyltransferase | H. sapiens: cDNA | X74570 |
| α2,3-sialyltransferase | H. sapiens: cDNA | L23768 |
| α2,3-sialyltransferase | H. sapiens: cDNA | L23767 |
| α2,3-sialyltransferase | S. scrofa: cDNA | M97753, M98463 |
| α2,3-sialyltransferase | R. rattus | M97754 |
| α2,3-sialyltransferase | M. musculus: cDNA | X73523 |
| α2,3-sialyltransferase | M. musculus: cDNA | X76988, X76988 |
| α2,3-sialyltransferase | M. musculus: cDNA | D28941 |
| α2,3-sialyltransferase | G. gallus: cDNA | X77775 |
| α2,3-sialyltransferase | G. gallus: cDNA | X74946 |
| α2,6-sialyltransferase | H. sapiens | A17362 |
| α2,6-sialyltransferase | H. sapiens: cDNA | X17247 |
| α2,6-sialyltransferase | H. sapiens: cDNA | X62822 |
| α2,6-sialyltransferase | H. sapiens: cDNA | S55693, S55689 |
| α2,6-sialyltransferase | H. sapiens: cDNA | X54363 |
| α2,6-sialyltransferase | H. sapiens: cDNA | L11720 |
| α2,6-sialyltransferase | H. sapiens: cDNA | M38193 |
| α2,6-sialyltransferase | R. rattus: cDNA | M83142, M83143, M83141 |
| α2,6-sialyltransferase | R. rattus: cDNA | M73985, M73986, M73987 |
| α2,6-sialyltransferase | R. rattus: genomic | M54999 |
| α2,6-sialyltransferase | R. rattus: cDNA | M18769 |
| α2,6-sialyltransferase | M. musculus: cDNA | D16106 |
| α2,6-sialyltransferase | G. gallus: cDNA | X75558 |
| α2,8-sialyltransferase | H. sapiens | X77922 |
| α2,8-sialyltransferase | H. sapiens | D26360 |
| Sialyltransferase | H. sapiens: cDNA | U14550 |
| Sialyltransferase | H. sapiens: cDNA | D13972 |
| Fucosyltransferases | | |
| α1,2fucosyltransferase | H. sapiens: cDNA | M35531 |
| α1,2fucosyltransferase | R. norwegicus: cDNA | L26009, L26010 |
| α1,3fucosyltransferase III | H. sapiens: cDNA | X53578 |
| α1,3fucosyltransferase IV | H. sapiens: genomic | S52967, S52968 |
| α1,3fucosyltransferase IV | H. sapiens | L01698 |
| α1,3fucosyltransferase VI | H. sapiens: cDNA | M98825 |
| α1,3fucosyltransferase VII | H. sapiens: cDNA | X78031 |
| α1,3fucosyltransferase VII | H. sapiens: cDNA | U08112, U11282 |
| α1,3fucosyltransferase | H. sapiens | M65030 |
| α1,3fucosyltransferase | H. sapiens: genomic | S65161 |
| α1,3fucosyltransferase | H. sapiens | M81485 |
| α1,3fucosyltransferase | H. sapiens: cDNA | M58596, M58597 |
| Galactosyltransferases | | |
| α1,3galactosyltransferase | H. sapiens: genomic | J05421 |
| α1,3galactosyltransferase | H. sapiens | M65082 |
| α1,3galactosyltransferase | H. sapiens | M60263 |
| α1,3galactosyltransferase | H. sapiens | J05421 |
| α1,3galactosyltransferase | B. taurus: cDNA | J04989 |

TABLE 1-continued

| Enzyme | EC designation | GenBank accession |
|---|---|---|
| α1,3galactosyltransferase | M. musculus | M26925 |
| α1,3galactosyltransferase | M. musculus: cDNA | M85153 |
| α1,3galactosyltransferase | C. aethiops | M73307 |
| α1,3galactosyltransferase | P. paniscus | M72526 |
| α1,3galactosyltransferase | E. patos | M73308 |
| α1,3galactosyltransferase | G. gorilla | M73304 |
| α1,3galactosyltransferase | M. mulatta | M73306 |
| α1,3galactosyltransferase | A. geoffrovi | M73309 |
| α1,3galactosyltransferase | P. pygmucus | M73305 |
| α1,3galactosyltransferase | S. scieureus | M73310 |
| α1,3galactosyltransferase | A. curaya | M73311 |
| β1,4galactosyltransferase | H. sapiens: cDNA | M22921, X14085 |
| β1,4galactosyltransferase | H. sapiens: cDNA | X51589 |
| β1,4galactosyltransferase | H. sapiens: cDNA | X55415 |
| β1,4galactosyltransferase | H. sapiens: cDNA | X13223 |
| β1,4galactosyltransferase | H. sapiens: cDNA | U10472, U10473, U10474 |
| β1,4galactosyltransferase | H. sapiens | M14624 |
| β1,4galactosyltransferase | H. sapiens: genomic | M70427, M70428, M70429, M70430, M70432, M70433 |
| β1,4galactosyltransferase | B. taurus | J05217 |
| β1,4galactosyltransferase | B. taurus: cDNA | M25398 |
| β1,4galactosyltransferase | B. taurus: cDNA | M13569 |
| β1,4galactosyltransferase | B. taurus: cDNA | X14558 |
| β1,4galactosyltransferase | M. musculus | L16840 |
| β1,4galactosyltransferase | M. musculus: cDNA | D00314, D00315 |
| β1,4galactosyltransferase | M. musculus: cDNA | D37790, D37791 |
| β1,4galactosyltransferase | M. musculus: genomic | M27917 through M27923 |
| β1,4galactosyltransferase | M. musculus | M36289 |
| β1,4galactosyltransferase | M. musculus | J03880 |
| β1,4galactosyltransferase | G. gallus: cDNA | L12565 |
| β1,4galactosyltransferase | G. gallus: cDNA | X16336 |
| Galactosyltransferase | H. sapiens: cDNA | M13701 |
| Galactosyltransferase | B. taurus: cDNA | M13214 |
| Galactosyltransferase | R. norwegicus: cDNA | L21698, S66862 |
| Galactosyltransferase | R. norwegicus: cDNA | U07683 |
| Galactosyltransferase | C. elegans: genomic | Z29095 |
| Galactosyltransferase | L. donovani: genomic | L11348 |
| N-Acetylglucosaminyltransferases | | |
| GlcNActransferaseNAG1PTase | M. musculus: genomic | U03603 |
| GlcNActransferaseNAG1PTase | M. musculus: cDNA | X65603, S41875 |
| GlcNActransferaseNAG1PTase | C. longicaudarus: cDNA | J05590, M22755 |
| GlcNActransferaseNAG1PTase | L. mexicana | M96635 |
| GlcNActransferaseNAG1PTase | S. cerevisiae | Y00126 |
| GlcNActransferaseNAG1PTase | S. pombe | U09454 |
| β1,2GlcNActransferase | C. elegans: genomic | Z46381 |
| β1,4GlcNActransferase | L. stagnalis: cDNA | X80228 |
| β1,6GlcNActransferase | H. sapiens: cDNA | M97347 |
| β1,6GlcNActransferase | H. sapiens: cDNA | Z19550, L19656 |
| β1,6GlcNActransferase | M. musculus: cDNA | U19295 |
| β1,6GlcNActransferase | C. elegans: genomic | Z36752 |
| β1,6GlcNActransferase | C. elegans: genomic | Z37092 |
| GlcNActransferaseI | H. sapiens: cDNA | M55621 |
| GlcNActransferaseI | H. sapiens: cDNA | T08544 |
| GlcNActransferaseI | H. sapiens | M61829 |
| GlcNActransferaseI | R. rattus: cDNA | D16302 |
| GlcNActransferaseI | M. musculus: genomic | M73491 |
| GlcNActransferaseI | M. musculus: genomic | L07037 |
| GlcNActransferaseI | O. cuniculus: cDNA | M57301 |
| GlcNActransferaseI | C. elegans | Z46381 |
| GlcNActransferaseII | R. rattus: cDNA | U21662 |
| GlcNActransferaseII | H. sapiens: genomic | U15128, L36537 |
| GlcNActransferaseIII | H. sapiens | D13789 |
| GlcNActransferaseIII | R. rattus: cDNA | D10852 |
| GlcNActransferaseV | H. sapiens: cDNA | D17716 |
| GlcNActransferaseV | R. rattus: cDNA | L14284 |
| N-Acetylgalactosaminyltransferases | | |
| α1,3GalNActransferase | H. sapiens: cDNA | J05173 |
| α1,3GalNActransferase | H. sapiens: cDNA | S44054 |
| β1,4GalNActransferase | H. sapiens: cDNA | M83651 |
| Protein: GalNActransferase | B. taurus: cDNA | L07780 |
| Protein: GalNActransferase | B. taurus: cDNA | L17437, L16925 |
| Mannosyltransferases | | |
| Mannosyltransferase | C. elegans: cDNA | M75918 |
| Mannosyltransferase | S. cerevisiae: genomic | L19169, L19700 |
| Mannosyltransferase | S. cerevisiae: genomic | L05146 |
| Mannosyltransferase | S. cerevisiae | J04184 |
| α1,2mannosyltransferase | S. cerevisiae: cDNA | M81110 |
| α1,6mannosyltransferase | S. cerevisiae: genomic | D11095 |
| β1,4mannosyltransferase | S. cerevisiae | J05416, Z35979 |
| Mannosyltransferase | S. cerevisiae: genomic | L17083 |
| Mannosyltransferase | S. cerevisiae | X62941 |
| Mannosyltransferase | S. cerevisiae | X62647 |
| Mannosyltransferase | S. cerevisiae | |
| Mannosyltransferase | S. cerevisiae | L23753 |
| Mannosyltransferase | S. cerevisiae | L23752 |
| Mannosyltransferase | S. cerevisiae | Z38059 |
| Mannosyltransferase | S. cerevisiae | Z46728 |

The combination of α-glucosidase I and α-glucosidase II cleave the three glucose residues from the $Glc_3$-$Man_9$-$GlcNAc_2$ precursors. α-glucosidase I and α-glucosidase II from eukaryotic sources are preferred for use in the present invention. The enzyme from *Aspergillus oryzae* (Minetoki et al., 1995) is an example.

The next step in the pathway is catalyzed by "class I" α-mannosidases, producing a $Man_5GlcNAc_2$ structure. Eukaryotic α-mannosidase genes or cDNAs are generally preferred for use in the present invention. Those from yeast (Camirand et al., 1991), Aspergillus (Inoue et al., 1995), Penicillium (Yoshida and Ichishima, 1995), Drosophila (Kerscher et al., 1995), rabbit (Lal et al., 1994), mouse (Herscovics et al., 1994; Lal et al., 1994) and human (Bause et al., 1993) are examples. Particularly preferred is the α-mannosidase cDNA from Spodoptera (Example 6; SEQ ID NO:1).

Next, N-acetylglucosaminyltransferase I catalyzes the addition of a single GlcNAc residue to $Man_5$-$GlcNAc_2$. Genes or cDNAs encoding N-acetylglucosaminyltransferase I from eukaryotic sources are preferred for use in the present invention. Those from rabbit (Sarkar et al., 1991), mouse (Pownall et al., 1992; Kumar et al., 1992), rat (Fukada et al., 1994) and human (Kumar et al., 1990) are examples.

The next step in the pathway is the removal of two more mannose residues by α-mannosidase II, a "class II" mannosidase to produce $GlcNAc$-$Man_3$-$GlcNAc_2$. Preferred for use in the present invention is α-mannosidase II from eukaryotic sources. Examples are the yeast vacuolar mannosidase (Yoshihisa and Anraku, 1989; Accession no. M29146), rat ER α-mannosidase (Bischoff et al., 1990; Accession no. M57547), mouse α-mannosidase II (Moremen and Robbins, 1991; Accession no. X61172), human α-mannosidase II (Misago et al., 1995; Accession no.

U31520), human α-mannosidase II$^x$ (Misago et al., 1996; Accession no. D55649) and Drosophila α-mannosidase II (Foster et al., 1995; Accession no. X77652). Particularly preferred is the α-mannosidase II cDNA from lepidopteran insect (Sf9) cells (Example 6; SEQ ID NO:3).

Concomitant with the removal of the two mannose residues is the addition of a fucose residue, catalyzed by fucosyltransferase. Eukaryotic genes or cDNAs which encode fucosyltransferase are preferred for use in the present invention. The human cDNA (Larsen et al., 1990) is an example.

At this point, in insect cells, N-acetylglucosaminidase converts one of the intermediates in the oligosaccharide processing pathway to a structure which not a substrate for the enzymes which add the penultimate galactose and terminal sialic acid residues. *Estigmene acrea* lacks this enzyme (Wagner, 1996a), which should lead to the accumulation of the intermediate which is a substrate for N-acetylglucosaminyltransferase II, the committed step in the production of complex oligosaccharide side chains containing penultimate galactose and terminal sialic acid residues. The inventor contemplates deleting the N-acetylglucosaminidase gene from a Spodoptera cell line using standard gene knockout techniques, or using antisense technology to reduce the levels of protein production in the insect cell.

The conversion of GlcNAc-Man$_3$-GlcNAc$_2$ to GlcNAc$_2$-Man$_3$-GlcNAc$_2$ is catalyzed by N-acetylglucosaminyltransferase II. Eukaryotic genes or cDNAs encoding N-acetylglucosaminyltransferase II are generally preferred for use in the current invention. Those from rat (D'Agostaro et al., 1995) and human (Tan et al., 1995) are examples.

The next step in the pathway is the addition of a galactose residue to each branch of the oligosaccharide structure. This reaction is catalyzed by the enzyme β1,4-galactosyltransferase. β1,4-galactosyltransferase genes or cDNAs from eukaryotic sources are preferred for use in the present invention. Those from mouse (Nakazawa et al., 1988), human (Masri et al., 1988; Chatterjee et al., 1995), rat (Bendiak et al., 1993) and Lymnaea stagnalis (Bakker et al., 1994) are examples. More preferred is the full-length cDNA encoding the short protein isoform of bovine β1,4-galactosyltransferase (Harduin-Lepers et al., 1993; Russo et al., 1992.

The final processing step in the formation of complex biantennary oligosaccharide structures is the addition of sialic acid residues to each galactose residue at the end of the oligosaccharide branches. This reaction is catalyzed by various sialyltransferases. Eukaryotic cDNAs or genes encoding α2,6-sialyltransferase are preferred for use in the present invention. The human gene (Wang et al., 1993) is an example.

C. Oligosaccharide Gene Combinations

The present invention provides to insect cells high levels of one or more of the enzymes needed to produce the complex oligosaccharide found in higher eukaryotes. A preferred method is by providing eukaryotic cDNAs or genes encoding α-glucosidase I, α-glucosidase II, α-mannosidase I, N-acetylglucosaminyltransferase I, α-mannosidase II, fucosyltransferase, N-acetylglucosaminyltransferase II, a galactosyltransferase and a sialyltransferase. A further embodiment is to provide various combinations of the coding sequences for these enzymes, to specifically design the oligosaccharide pattern of choice. A particularly preferred embodiment is to provide eukaryotic cDNAs or genes encoding the enzymes which are barely detectable or absent in insect cells, N-acetylglucosaminyltransferase I, N-acetylglucosaminyltransferase II, β1,4-galactosyltransferase and sialyltransferase.

It will be understood that where the use of two or more oligosaccharide processing genes is contemplated, the genes may be combined in the vector in any desired combination. There is no requirement for any particular gene to be inserted before or after any other particular gene, when considering the DNA sequence in the 5' to 3' direction. One may therefore insert two or more genes into the vectors of the present invention in any order that is convenient, as may be determined by different cloning strategies or restriction enzyme sites.

In embodiments of the invention where different promoters are used to express two or more oligosaccharide processing genes, it may be preferred in certain embodiments to use a baculovirus early promoter to express genes that encode protein products that act at earlier steps in the glycosylation pathways. This may be useful in ensuring that the required partially processed recombinant polypeptide is available to act as a substrate for the processing enzymes that catalyze subsequent steps in the overall pathway. However, it will be understood that this is by no means a limitation of the present invention and is simply provided as one embodiment thereof.

D. Assays for the Effects of Glycosylation on Protein Substrates

While it is known that glycosylation of a protein in general can alter the functional aspects of the protein (Welply, 1991), delineation of the precise effects of individual glycosylation steps requires the use of enzyme inhibitors (Elbein, 1991), for example tunicamycin, castanospermine (which inhibits glucosidase I), deoxymannojirimycin (which inhibits α-mannosidase I) or swainsonine (which inhibits α-mannosidase II; Moremen et al., 1994). However, some of the enzymes in the oligosaccharide processing pathway have no known inhibitors. The present invention provides a method for using conventional and modified baculovirus expression systems to study the influence of N-linked oligosaccharide processing on glycoprotein function. Example 14 shows that there was no significant difference in the in vitro growth properties of wild type AcMNPV and an immediate early recombinant expressing β1,4-galactosyltransferase, which contained nongalactosylated and galactosylated gp64, respectively. This approach can be used to produce nongalactosylated and galactosylated versions of any recombinant glycoprotein for interesting functional comparisons. This is an important application because there are no specific β1,4-galactosyltransferase inhibitors that can be used to study the function of this late step in N-linked oligosaccharide processing.

The present invention provides for sequential addition of oligosaccharide residues to a protein of interest by adding additional processing enzyme coding units into the baculovirus expression vector. A preferred embodiment of the present invention is to use vectors that contain step-wise additions of N-acetylglucosaminyltransferase I, N-acetylglucosaminyltransferase II, β1,4-galactosyltransferase and sialyltransferase expression units, to study the effect of adding N-acetylglucosamine, galactose and sialic acid on protein function.

It will be therefore understood that it is not a requirement of this invention to produce one or more recombinant proteins that are modified exactly in the manner that the counterpart mammalian or human protein appears in its natural environment. Even where a functional protein with complete or moderate biological activity is desired, it may still be the case that the glycosylation pattern does not have to directly correspond to that of the natural protein. Proteins that are modified to any degree further than those previously expressed in insect cells will naturally represent an advance in this technology. Proteins that more closely resemble the naturally occurring mammalian or human proteins will, of course, be preferred in many embodiments.

However, as outlined above, it is not always required or even desired to produce a protein with complete or even substantial biological activity. In fact, in terms of identifying inhibitors of particular glycosylation enzymes, all that is required is to produce a protein which may be analyzed to determine which sugar groups it contains. This provides a ready means for conducting screening assays to identify various inhibitors.

To conduct such a screening assay, one would generally provide to an insect cell a particular glycosylation enzyme and test the effect of the enzyme on a protein from the cell that lends itself to ready analysis. The glycosylation enzyme for use in such embodiments will be chosen so that it catalyzes a glycosylation step that is not readily conducted in the natural insect cell. Expression of the enzyme will thus result in a protein with a different glycosylation pattern. Once this has been confirmed, the recombinant insect cell can then be exposed to a "candidate substance". A candidate substance that reduces the level of the newly modified protein, and results in the production of larger amounts of proteins that correspond to those produced in natural insect cells, will then be identified as having the ability to inhibit the expressed glycosylation enzyme and is therefore categorized as a "inhibitory substance".

IV. Genes Which Encode Accessory Proteins That Aid in Protein Folding

The proper folding of a protein into its correct three-dimensional structure is important for the proper function of the protein. For large, glycosylated proteins, folding in vivo is a complex process that requires other proteins. Many of these proteins belong to families which are evolutionarily conserved. These protein families fall into two major classes (Gething and Sambrook, 1992, incorporated herein by reference, including the incorporation of each of the references cited therein). The first class includes enzymes which catalyze isomerization reactions which are rate limiting in the folding process of some proteins. The second class includes chaperone proteins which associate with other proteins during the folding process to prevent the formation of incorrect intermediate structures.

There are two rate determining steps in the in vitro folding of proteins, thiol/disulphide interchange reactions and proline cis-trans isomerization. These reactions are catalyzed by protein disulphide isomerase and peptidyl prolyl cis-trans isomerase, respectively. Protein disulphide isomerase has been described from a number of sources, including *E. coli*, plants, yeast, Drosophila and higher eukaryotes. Likewise, peptidyl prolyl cis-trans isomerase has been detected in both prokaryotes and eukaryotes.

Protein chaperones generally fall into three major classes, which are all highly conserved between plants, prokaryotes and eukaryotes. These classes are referred to as chaperonin-60, stress-70 and stress-90 (Gething and Sambrook, 1992). Examples of proteins which belong to the chaperonin-60 class are *E. coli* GroEL and the yeast and mammalian Hsp60. Representatives of the stress-70 class are *E. coli* DnaK and the BiP/GRP78 homologs from plants, yeast (Normington et al., 1989), Drosophila (Rubin et al., 1993), and higher eukaryotes such as rat (Munro and Pelham, 1986) and hamster (Ting et al., 1987). The stress-90 class is represented by Hsp83 from Drosophila, yeast and mammals, and the Grp94 protein from mammals.

A potential method of improving protein processing in insect cells is by providing increased levels of proteins which assist in protein folding in the cell. For example, it has been demonstrated that coexpression of BiP (GRP78) resulted in an increase in the intracellular levels of functional immunoglobulin IgG (Hsu, 1994). However the promoter used in the previous example was the very late polyhedrin promoter.

The present invention contemplates the administration of proteins such as protein disulphide isomerase, peptidyl prolyl cis-trans isomerase and chaperone proteins, either alone or in conjunction with the oligosaccharide processing enzymes. A preferred method is by providing eukaryotic cDNAs or genes encoding eukaryotic protein disulphide isomerase, peptidyl prolyl cis-trans isomerase and chaperone proteins. Another preferred embodiment is a eukaryotic BiP/GRP78 gene. A particularly preferred embodiment is a eukaryotic BiP/GRP78 gene functionally positioned downstream from a baculovirus immediate-early promoter. The present invention further contemplates the cloning of the insect homolog of BiP/GRP78 (see section XI below). After identifying an appropriate DNA molecule, it may be inserted into any one of the many vectors in the present invention.

The present invention additionally contemplates the administration of additional protein modification enzymes, such as those involved in phosphorylation, acylation, acetylation, methylation and amidation, as described in Section I above.

V. Promoters and Enhancers

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

There are two basic procedures for expressing cloned genes from promoters, which are both useful in insect cell systems. In transient systems, the gene of interest is introduced into the insect cell by infection with a recombinant baculovirus. In the most widely used systems, the gene of interest is under the control of the polyhedrin promoter. The polyhedrin promoter is a very late promoter, which means that the expression of the gene of interest does not start until the late phase of the baculovirus infection. The expression levels are high, but transient as the baculovirus infection eventually leads to cell death.

The second method for expressing cloned genes from control regions is stable transfection. Stable transfection may allow for moderate expression levels from a transfected gene to be obtained in a long term continuous culture. In this method the recombinant DNA molecule and promoter/enhancer combination is introduced via transfection, with a gene encoding a selectable marker protein either on the same vector (transfection), or on a separate vector (co-transfection; Jarvis et al., 1990). After selection for clones which express the marker protein, the cells are assayed for the presence of the gene of interest (for example by Southern analysis of the genomic DNA, northern analysis of the RNA or western analysis of the protein product). Cells which have the gene of interest incorporated into the genomic DNA of the host cell will stably express the gene.

In any event, it will be understood that promoters are DNA elements which when positioned functionally upstream of a gene leads to the expression of that gene. Each heterologous gene in the vector of the present invention is functionally positioned downstream of a promoter element. Promoters which are active in insect cells to drive transcription are intended for use in the present invention. Preferred are viral promoters, more preferred are baculoviral promoters, and a particularly preferred embodiment uses immediate-early promoters.

A. Eukaryotic and Viral Promoters and Enhancers

Below are a list of viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

TABLE 2

| ENHANCER | REFERENCES |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ a and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, #99O |
| a-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |

TABLE 2-continued

| ENHANCER | REFERENCES |
|---|---|
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immuno-deficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 3

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | E1a | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| a-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1a, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

B. Cellular Promoters and Enhancers

Vector constructs incorporating insect cellular promoters have been used successfully, including Drosophila HSP70 (Vlak et al., 1990; Zuidema et al., 1990) and *Bombyx mori* actin (Johnson et al., 1992). Multiple genes have also been successfully coexpressed in insect cells coinfected with more than one recombinant baculovirus (O'Reilly and Miller, 1988; St Angelo et al., 1987). Cellular promoter and enhancer elements which are active in insect cells are preferred for use in the present invention.

C. Baculoviral Promoters and Enhancers

There are four distinct phases of a baculovirus infection, termed immediate-early, delayed-early, late and very late. Therefore, different baculovirus genes may be classified according to the phase of the viral infection during which they are expressed. Also there are a class of genes which have been defined as early genes, which have not been subcatagorized as either immediate-early or delayed-early. Different classes of promoters control each class of gene.

1. Immediate-Early Promoters

This class of promoters are distinguished by needing only host cell factors to drive expression. Examples are the ie 1 (Guarino and Summers, 1987), ieN (ie2; Carson et al., 1991) and ie0 promoters, with the ie 1 promoter being particularly preferred for use in the present invention.

2. Delayed-Early Promoters

This class of promoters are distinguished by needing only products of the immediate-early genes, in addition to host cell factors to drive expression. Examples are the 39K (Guarino and Smith, 1990) and gp64 (Blissard and Rohrmann, 1989; Whitford et al., 1989) promoters, with the 39K promoter particularly preferred for use in the present invention.

3. Early Promoters

This class of promoters have not been placed into the specific immediate-early of delayed-early class. Examples include the DA26, ETL and 35K promoters.

4. Late Promoters

This class of promoters requires products of the delayed-early and immediate-early genes, as well as other host cell factors, to drive expression. Examples are the gp64 (Blissard and Rohrmann, 1989; Whitford et al., 1989), p6.9 (Wilson et al., 1987) and capsid (p39; Thiem and Miller, 1989) promoters.

5. Very Late Promoters

This class of promoters requires a number of baculovirus gene products, in addition to other host cell factors, to drive expression. Examples of promoters from this class are the polyhedrin (Hooft van Iddekinge et al., 1983) and the p10 (Kuzio et al., 1984) promoters. The best characterized and most often used baculoviral promoter is the polyhedrin promoter. The use of the polyhedrin promoter is a preferred embodiment of the present invention.

As mentioned, enhancers are DNA elements which can be positionally located to enhance transcription from a given promoter. Enhancers which are active in insect cells to drive transcription are preferred in the present invention. Preferred are viral enhancers, and most preferred are baculoviral enhancers.

Examples of baculoviral enhancers include hr1, hr2, hr3, hr4 and hr5 (Guarino et al., 1986), with the use of the hr5 enhancer being a particularly preferred embodiment.

VI. Selectable Marker Genes

The present invention also provides recombinant candidate screening methods which are based upon whole cell assays and which, preferably, employ a reporter gene that confers on its recombinant hosts a readily detectable phenotype that emerges only under conditions where a general DNA promoters positioned upstream of the reporter gene is functional.

Generally, reporter genes encode a polypeptide not otherwise produced by the host cell which is detectable by analysis of the cell culture, e.g., by fluorometric, radioisotopic or spectrophotometric analysis of the cell culture. Exemplary enzymes include esterases, phosphatases, proteases (tissue plasminogen activator or urokinase) and other enzymes capable of being detected by their activity, as will be known to those skilled in the art. Preferred examples are the enzyme chloramphenicol acetyltransferase (CAT) which may be employed with a radiolabelled substrate, firefly and bacterial luciferase, and even green fluorescent protein (GFP) as a marker for gene expression (Chalfie et al., 1994). The use of GFP does not need exogenously added substrates, only irradiation by near UV or blue light, and thus has significant potential for use in monitoring gene expression in living cells.

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978) along with many others well known in the art (Kaufman, 1990).

It is the genes or cDNAs encoding drug resistance proteins, which allow for the selection of recombinant clones in the preparation of stable cell lines, that are particularly preferred in the present invention.

VII. Baculovirus Structural Genes and Flanking Baculovirus DNA

There are three main locations in the baculovirus genome into which recombinant expression cassettes can be transplaced. These are the gp64, the p10 and the polyhedrin loci. The baculovirus gp64 gene plays a central role in baculovirus infection, apparently mediating penetration of the virus into host cells during adsorptive endocytosis (Volkman and Goldsmith, 1985; Volkman et al., 1984; Volkman, 1986; Blissard and Wenz, 1992; Charlton and Volkmnan, 1993). The present invention contemplates incorporating a functional copy of the baculovirus gp64 structural gene and promoter, as well as 5' and 3' flanking gp64 DNA segments, for constructs which use the gp64 locus of the baculovirus host for replacement of the recombinant baculovirus expression vector.

The polyhedrin gene can be used as a method for screening recombinant baculovirus constructs (Summers and Smith, 1987; Webb and Summers, 1990; Miller 1988). Further embodiments of the present invention comprise the 5' and 3' flanking polyhedrin DNA segments, for constructs which use the polyhedrin locus of the baculovirus host for replacement of the recombinant baculovirus expression vector. These recombinant vectors can be identified in plaque assays by their occlusion-negative phenotypes. A further embodiment would comprise the polyhedrin structural gene and promoter, enabling the recombinant viruses to be identified in plaque assays by their occlusion-positive phenotypes.

The present invention contemplates incorporating 5' and 3' flanking p10 DNA segments, either with or without a functional copy of the baculovirus p1 0 structural gene, for constructs which use the p10 locus of the baculovirus host for replacement of the recombinant baculovirus expression vector. Further embodiments of the present invention incorporate the necessary flanking DNA segments and structural genes and promoters into separate baculovirus expression vectors so that any combination of the three loci described above can be used for replacement of multiple recombinant baculovirus expression vectors.

The present invention also contemplates the use of immediate early and conventional baculovirus vectors as biocontrol agents, based on the idea that expression of appropriate foreign genes earlier in infection should allow immediate early recombinants to kill insect larvae faster or stop their feeding earlier than conventional polyhedrin- or p10-based recombinants. An immediate early vector designed to express an insect-specific toxin under iel control failed to kill insect larvae faster than a conventional vector designed to express the same toxin under p10 control, but the vector actually reduced feeding activity more effectively than the conventional vector. Infection of live insects or larvae require the products of the p10 and polyhedrin loci. This embodiment of the present invention contemplates incorporating a functional copy of the baculovirus p10 or polyhedrin structural gene and promoter when these loci are used for replacement of the recombinant vectors.

VIII. Heterologous Structural Genes

A vast number of heterologous cDNAs have been expressed using the baculovirus expression system. Particularly preferred for use in the present invention is any heterologous coding region encoding for a protein in which oligosaccharide processing is desired. Below is a list of selected cloned structural genes that could be used in the present invention. The list is not in any way meant to be interpreted as limiting, only as exemplary of the types of structural genes contemplated for use in the present invention.

TABLE 4

| | Selected Cloned Structural Genes | |
|---|---|---|
| Gene | Clone Type* | Reference |
| activin | porcine-cDNA | Mason AJ, Nat, 318:659, 1985 |
| adenosine deaminase | h-cDNA | Wiginton DA, PNAS, 80:7481, 1983 |
| angiotensinogen I | r-cDNA | Ohkubo H, PNAS, 80:2196, 1983 |
| | r-gDNA | Tanaka T, JBC, 259:8063, 1984 |
| antithrombin III | h-cDNA | Bock SC, NAR 10:8113, 1982 |
| | h-cDNA and gDNA | Prochownik EV, JBC, 258:8389, 1983 |
| antitrypsin, alpha I | h-cDNA | Kurachi K, PNAS, 78:6826, 1981 |
| | h-gDNA | Leicht M, Nat, 297:655, 1982 |
| | RFLP | Cox DW, AJHG, 36:134S, 1984 |
| apolipoprotein A-I | h-cDNA, h-gDNA | Shoulders CC, NAR, 10:4873, 1982 |
| | RFLP | Karathanasis SK, Nat, 301:718, 1983 |
| | h-gDNA | Kranthanasis SK, PNAS, 80:6147, 1983 |
| apolipoprotein A-II | h-cDNA | Sharpe CR, NAR, 12:3917, 1984 |
| | Chr | Sakaguchi AY, AJHG, 36:207S, 1984 |
| | h-cDNA | Knott TJ, BBRC, 120:734, 1984 |

TABLE 4-continued

Selected Cloned Structural Genes

| Gene | Clone Type* | Reference |
| --- | --- | --- |
| apolipoprotein C-I | h-cDNA | Knott TJ, NAR, 12:3909, 1984 |
| apolipoprotein C-II | h-cDNA | Jackson CL, PNAS, 81:2945, 1984 |
| | h-cDNA | Mykelbost O, JBC, 259:4401, 1984 |
| | h-cDNA | Fojo SS, PNAS, 81:6354, 1984 |
| | RFLP | Humphries SE, C Gen, 26:389, 1984 |
| apolipoprotein C-III | h-cDNA and gDNA | Karanthanasis SK, Nat, 304:371, 1983 |
| | h-cDNA | Sharpe CR, NAR, 12:3917, 1984 |
| apolipoprotein E | h-cDNA | Breslow JL, JBC, 257:14639, 1982 |
| atrial natriuretic | h-cDNA | Oikawa S, Nat, 309:724, 1984 |
| factor | h-cDNA | Nakayama K, Nat, 310:699, 1984 |
| | h-cDNA | Zivin RA, PNAS, 81:6325, 1984 |
| | h-gDNA | Seidman CE, Sci, 226:1206, 1984 |
| | h-gDNA | Nemer M, Nat, 312:654, 1984 |
| | h-gDNA | Greenberg BI, Nat, 312:665, 1984 |
| chorionic | h-cDNA | Fiddes JC, Nat, 281:351, 1981 |
| gonadotropin, alpha chain | RFLP | Boethby M, JBC, 256:5121, 1981 |
| chorionic | h-cDNA | Fiddes JC, Nat, 286:684, 1980 |
| gonadotropin, | h-gDNA | Boorstein WR, Nat, 300:419, 1982 |
| beta chain | h-gDNA | Talmadge K, Nat, 307:37, 1984 |
| chymosin, pro (rennin) | bovine-cDNA | Harris TJR, NAR, 10:2177, 1982 |
| compiement, factor B | h-cDNA | Woods DE, PNAS, 79:5661, 1982 |
| | h-cDNA and gDNA | Duncan R, PNAS, 80:4464, 1983 |
| complement C2 | h-cDNA | Bentley DR, PNAS, 81:1212, 1984 |
| | h-gDNA (C2, C4, and B) | Carroll MC, Nat, 307:237, 1984 |
| complement C3 | m-cDNA | Domdey H, PNAS, 79:7619, 1983 |
| | h-gDNA | Whitehead AS, PNAS, 79:5021, 1982 |
| complement C4 | h-cDNA and gDNA | Carroll MC, PNAS, 80:264, 1983 |
| | h-cDNA | Whitehead AS, PNAS, 80:5387, 1983 |
| complement C9 | h-cDNA | DiScipio RC, PNAS, 81:7298, 1984 |
| corticotropin | sheep - cDNA | Furutani Y, Nat, 301:537, 1983 |
| releasing factor | h-gDNA | Shibahara S, EMBO J, 2:775, 1983 |
| epidermal growth factor | m-cDNA | Gray A, Nat, 303:722, 1983 |
| | m-cDNA | Scott J, Sci, 221:236, 1983 |
| | h-gDNA | Brissenden JE, Nat, 310:781, 1984 |
| epidermal growth factor receptor, oncogene c-erb B | h-cDNA and Chr | Lan CR, Sci, 224:843, 1984 |
| epoxide dehydratase | r-cDNA | Gonzalez FJ, JBC, 256:4697, 1981 |
| erythropoietin | h-cDNA | Lee-Huang S, PNAS, 81:2708, 1984 |
| esterase inhibitor, | h-cDNA, | Stanley KK, EMBO J, 3:1429, 1984 |
| C1 factor VIII | h-cDNA and gDNA | Gitschier J, Nat, 312:326, 1984 |
| | h-cDNA | Toole JJ, Nat, 312:342, 1984 |
| factor IX, Christmas factor | h-cDNA | Kutachi K, PNAS, 79:6461, 1982 |
| | h-cDNA | Choo KH, Nat, 299:178, 1982 |
| | RFLP | Camerino G, PNAS, 81:498, 1984 |
| | h-gDNA | Anson DS, EMBO J, 3:1053, 1984 |
| factor X | h-cDNA | Leytus SP, PNAS, 81:3699, 1984 |
| fibrinogen A alpha, | h-cDNA | Kant JA, PNAS, 80:3953, 1983 |
| B beta, gamma | h-gDNA (gamma) | Fornace AJ, Sci, 224:161, 1984 |
| | h-cDNA (alpha gamma) | Imam AMA, NAR, 11:7427, 1983 |
| | h-gDNA (gamma) | Fornace AJ, JBC, 259:12826, 1984 |
| gatrin releasing peptide | h-cDNA | Spindel ER, FNAS, 81:5699, 1984 |
| glucagon, prepro | hamster-cDNA | Bell GI, Nat, 302:716, 1983 |
| | h-gDNA | Bell GI, Nat, 304:368, 1983 |
| growth hormone | h-cDNA | Martial JA, Sci, 205:602, 1979 |
| | h-gDNA | DeNoto FM, NAR, 9:3719, 1981 |
| | GH-like gene | Owerbach D, Sci, 209:289, 1980 |
| growth hormone RF, | h-cDNA | Gubler V, PNAS, 80:4311, 1983 |
| somatocrinin | h-cDNA | Mayo KE, Nat, 306:86:1983 |
| hemopexin | h-cDNA | Stanley KK, EMBO J, 3:1429, 1984 |
| inhibin | porcine-cDNA | Mason AJ, Nat, 318:659, 1985 |
| insulin, prepro | h-cDNA | Ullrich a, Sci, 209:612, 1980 |
| insulin-like growth factor I | h-cDNA | Jansen M, Nat, 306:609, 1983 |
| | h-cDNA | Bell GI, Nat, 310:775, 1984 |
| | Chr | Brissenden JE, Nat, 310:781, 1984 |
| insulin-like growth factor II | h-cDNA | Bell GI, Nat, 310:775, 1984 |
| | h-gDNA | Dull TJ, Nat, 310:777, 1984 |
| | Chr | Brissenden JE, Nat, 310:781, 1984 |
| interferon, alpha | h-cDNA | Maeda S, PNAS, 77:7010, 1980 |
| (leukocyte), multiple | h-cDNA (8 distinct) | Goeddel DV, Nat, 290:20, 1981 |
| | h-gDNA | Lawn RM, PNAS, 78:5435, 1981 |
| | h-gDNA | Todokoro K, EMBO J, 3:1809, 1984 |
| | h-gDNA | Torczynski RM, PNAS, 81:6451, 1984 |

TABLE 4-continued

Selected Cloned Structural Genes

| Gene | Clone Type* | Reference |
| --- | --- | --- |
| interferon, beta | h-cDNA | Taniguchi T, Gene, 10:11, 1980 |
| (fibroblast) | h-gDNA | Lawn RM, NAR, 9:1045, 1981 |
| | h-gDNA (related) | Sehgal PB, PNAS, 80:3632, 1983 |
| | h-gDNA (related) | Sagar AD, Sci, 223:1312, 1984 |
| interferon, gamma | h-cDNA | Gray PW, Nat, 295:503, 1982 |
| (immune) | h-gDNA | Gray PW, Nat, 298:859, 1982 |
| interleukin-1 | m-cDNA | Lomedico PT, Nat, 312:458, 1984 |
| interleukin-2, T-cell | h-cDNA | Devos R, NAR, 11:4307, 1983 |
| growth factor | h-cDNA | Taniguchi T, Nat, 302:305, 1983 |
| | h-gDNA | Hollbrook NJ, PNAS, 81:1634, 1984 |
| | Chr | Siegel LF, Sci, 223:175, 1984 |
| interluekin-3 | m-cDNA | Fung MC, Nat, 307:233, 1984 |
| kininogen, two forms | bovine-cDNA | Nawa H, PNAS, 80:90, 1983 |
| | bovine-cDNA and gDNA | Kitamura N, Nat, 305:545, 1983 |
| luteinizing hormone, beta subunit | h-gDNA and Chr | Talmadge K, Nat, 207:37, 1984 |
| luteinizing hormone releasing hormone | h-cDNA and gDNA | Seeburg PH, Nat, 311:666, 1984 |
| lymphotoxin | h-cDNA and gDNA | Gray PW, Nat, 312:721, 1984 |
| mast cell growth factor | m-cDNA | Yokoya T, PNAS, 81:1070, 1984 |
| nerve growth factor, | m-cDNA | Scott J, Nat, 302:538, 1983 |
| beta subunit | h-gDNA | Ullrich A, Nat, 303:821, 1983 |
| | Chr | Franke C, Sci, 222:1248, 1983 |
| oncogene, c-sis, | h-gDNA | Dalla-Favera R, Nat, 295:31, 1981 |
| PGDF chain A | h-cDNA | Clarke MF, Nat, 208:464, 1984 |
| pancreatic polypeptide and icosapeptide | h-cDNA | Boel B, EMBO J, 3:909, 1984 |
| parathyroid | h-cDNA | Hendy GN, PNAS, 78:7365, 1981 |
| hormone, prepro | h-gDNA | Vasicek TJ, PNAS, 80:2127, 1983 |
| plasminogen | h-cDNA and gDNA | Malinowski DP, Fed P, 42:1761, 1983 |
| plasminogen | h-cDNA | Edlund T, PNAS, 80:349, 1983 |
| activator | h-cDNA | Pennica D, Nat, 301:214, 1983 |
| | h-gDNA | Ny T, PNAS, 81:5355, 1984 |
| prolactin | h-cDNA | Cook NE, JBC, 256:4007, 1981 |
| | r-gDNA | Cooke NE, Nat, 297:603, 1982 |
| proopiomelanocortin | h-cDNA | DeBold CR, Sci, 220:721, 1983 |
| | h-gDNA | Cochet M, Nat, 297:335, 1982 |
| protein C | h-cDNA | Foster D, PNAS, 81:4766, 1984 |
| prothrombin | bovine-cDNA | MacGillivray RTA, PNAS, 77:5153, 1980 |
| relaxin | h-gDNA | Hudson P, Nat, 301:628, 1983 |
| | h-cDNA (2 genes) | Hudson P, EMBO J, 3:2333, 1984 |
| | Chr | Crawford RJ, EMBO J, 3:2341, 1984 |
| renin, prepro | h-cDNA | Imai T, PNAS, 80:7405, 1983 |
| | h-gDNA | Hobart PM, PNAS 81:5026, 1984 |
| | h-gDNA | Miyazaki H, PNAS, 81:5999, 1984 |
| | Chr | Chirgwin JM, SCMG, 10:415, 1984 |
| somatostatin | h-cDNA | Shen IP, PNAS, 79:4575, 1982 |
| | h-gDNA and Ri-IP | Naylot SI, PNAS, 80:2686, 1983 |
| tachykinin, prepro, | bovine-cDNA | Nawa H, Nat, 306:32, 1983 |
| substances P & K | bovine-gDNA | Nawa H, Nat, 312:729, 1984 |
| urokinase | h-cDNA | Verde P, PNAS, 81:4727, 1984 |
| vasoactive intestinal peptide, prepro | h-cDNA | Itoh N, Nat, 304:547, 1983 |
| vasopressin | r-cDNA | Schmale H, EMBO J, 2:763, 1983 |

Key to Table 4: *cDNA - complementary DNA; Chr - chromosome; gDNA - genomic DNA; RFLP - restriction fragment polymorphism; h - human; m - mouse; r - rat

IX. Cloning Site

Cloning sites allow for the insertion and proper orientation of a heterologous gene of interest. Cloning sites are DNA regions comprising a recognition site for a DNA restriction endonuclease. Multiple cloning sites are DNA regions comprising two or more recognition sites for DNA restriction endonucleases, improving the utility of vectors which contain them. DNA fragments containing multiple cloning sites are commercially available or easily synthesized, and well known to practicioners in the art. A multiple cloning site comprising the recognition sites for five, six, seven, eight, nine, ten or more DNA restriction endonucleases is preferred for use in the present invention. A multiple cloning site positioned downstream from a promoter element is a particularly preferred embodiment of the present invention.

X. Insect Cell Lines

Insect cell lines which contain appropriate transcriptional factors to drive expression of the structural genes provided in the baculovirus expression vectors of the present invention are preferred for use. Examples include *Spodoptera frugiperda, Bombyx mori, Heliothis virescens, Heliothis zea, Mamestra brassicas, Estigmene acrea* and *Trichoplusia ni.*

XI. Methods for Transfection, Infection, Cell Culture, and Protein Production and Purification General methods involved in the use of the present invention, including methods for cell growth and maintenance, production of recombinant baculoviruses, infection of insect cells, and analysis of expressed proteins in insect cells are provided in detail in the Examples below. Also, good general references on the various techniques needed to practice the current invention are available (O'Reilly et al., 1992).

XII. α-Mannosidase I and α-Mannosidase II DNA Segments

Further aspects of the present invention concern isolated DNA segments and recombinant vectors encoding α-mannosidase I and α-mannosidase II, and the creation and use of recombinant host cells through the application of DNA technology, that express α-mannosidase I and α-mannosidase II.

The present invention concerns DNA segments, isolatable from uninfected *Spodoptera frugiperda* Sf-9 cells, that are free from total genomic DNA and are capable of conferring α-mannosidase I and α-mannosidase II activity to a recombinant host cell when incorporated into the recombinant host cell. As used herein, the term α-mannosidase I and α-mannosidase II activity indicates the ability to cleave mannose residues from $Man_9$-$GlcNAc_2$ to produce $Man_5$-$GlcNAc_2$ (α-mannosidase I) and the ability to cleave two mannose residues from $Man_5$-$GlcNAc_2$ to produce $Man_3$-$GlcNAc_2$ (α-mannosidase II).

As used herein, the term "DNA segment" refers to a DNA molecule that has been isolated free of total genomic DNA of a particular species. Therefore, a DNA segment encoding α-mannosidase I and α-mannosidase II refers to a DNA segment that contains α-mannosidase I and α-mannosidase II coding sequences yet is isolated away from, or purified free from, total genomic DNA of *Spodoptera frugiperda*. Included within the term "DNA segment", are DNA segments and smaller fragments of such segments, and also recombinant vectors, including, for example, plasmids, cosmids, phage, viruses, and the like.

Similarly, a DNA segment comprising an isolated or purified α-mannosidase I or α-mannosidase II gene refers to a DNA segment including α-mannosidase I or α-mannosidase II gene coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case α-mannosidase I or α-mannosidase II gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an α-mannosidase I or α-mannosidase II gene that includes within its amino acid sequence a contiguous amino acid sequence from SEQ ID NO:2 (α-mannosidase I) and SEQ ID NO:4 (α-mannosidase II), corresponding to *Spodoptera frugiperda*.

Naturally, where the DNA segment or vector encodes a full length α-mannosidase I or α-mannosidase II protein, or is intended for use in expressing the α-mannosidase I or α-mannosidase II protein, the most preferred sequences are those that are essentially as set forth in the full length contiguous sequence of SEQ ID NO:2 (α-mannosidase I) and SEQ ID NO:4 (α-mannosidase II), and that encode a protein that retains α-mannosidase I or α-mannosidase II activity, e.g., as may be determined by the α-mannosidase assay, as disclosed herein (Example 10).

Sequence of the present invention will substantially correspond to a contiguous portion of SEQ ID NO:2 (α-mannosidase I) and SEQ ID NO:4 (α-mannosidase 11), and have relatively few amino acids that are not identical to, or a biologically functional equivalent of, the amino acids of SEQ ID NO:2 (α-mannosidase I) and SEQ ID NO:4 (α-mannosidase II). The term "biologically functional equivalent" is well understood in the art and is further defined in detail herein (Section XVI).

Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 (α-mannosidase I) and SEQ ID NO:4 (α-mannosidase II) will be sequences that are "essentially as set forth in SEQ ID NO:2 (α-mannosidase I) and SEQ ID NO:4 (α-mannosidase II).

In certain other embodiments, the invention concerns isolated DNA segments and recombinant vectors that include within their sequence a contiguous nucleic acid sequence from SEQ ID NO:1 (α-mannosidase I) and SEQ ID NO:3 (α-mannosidase II). This definition is used in the same sense as described above and means that the nucleic acid sequence substantially corresponds to a contiguous portion of SEQ ID NO:1 (α-mannosidase I) and SEQ ID NO:3 (α-mannosidase II) and has relatively few codons that are not identical, or functionally equivalent, to the codons of SEQ ID NO:1 (α-mannosidase I) and SEQ ID NO:3 (α-mannosidase II). Again, DNA segments that encode proteins exhibiting α-mannosidase I or α-mannosidase II activity will be most preferred. The term "functionally equivalent codon" is used herein to refer to codons that encode the same amino acid, such as the six codons for arginine or serine, and also refers to codons that encode biologically equivalent amino acids. See Table 5 below.

TABLE 5

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 79%; or more preferably, between about 80% and about 89%; or even more preferably, between about 90% and about 99% of nucleotides that are identical to the nucleotides of SEQ ID NO:1 (α-mannosidase I) and SEQ ID NO:3 (α-mannosidase II) will be sequences that are "essentially as set forth in SEQ ID NO:1 (α-mannosidase I) and SEQ ID NO:3 (α-mannosidase II). Sequences that are essentially the same as those set forth in SEQ ID NO:1 (α-mannosidase I) and SEQ ID NO:3 (α-mannosidase II) may also be functionally defined as sequences that are capable of hybridizing to a nucleic acid segment containing the complement of SEQ ID NO:1 (α-mannosidase I) and SEQ ID NO:3 (α-mannosidase II) under relatively stringent conditions. Suitable relatively stringent hybridization conditions will be well known to those of skill in the art and are clearly set forth herein (Example 7).

Naturally, the present invention also encompasses DNA segments that are complementary, or essentially complementary, to the sequence set forth in SEQ ID NO:1 (α-mannosidase I) and SEQ ID NO:3 (α-mannosidase II). Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:I (α-mannosidase I) and SEQ ID NO:3 (α-mannosidase II) under relatively stringent conditions such as those described herein in Example 7.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1 (α-mannosidase I) and SEQ ID NO:3 (α-mannosidase II), such as about 14 nucleotides, and that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid and amino acid sequences of SEQ ID NO:1 and SEQ ID NO:2 (α-mannosidase I) and SEQ ID NO:3 and SEQ ID NO:4 (α-mannosidase II), respectively. Recombinant vectors and isolated DNA segments may therefore variously include the α-mannosidase I and α-mannosidase II coding regions themselves, coding regions bearing selected alterations or modifications in the basic coding region, or they may encode larger polypeptides that nevertheless include α-mannosidase I and α-mannosidase II-coding regions or may encode biologically functional equivalent proteins or peptides that have variant amino acids sequences.

The DNA segments of the present invention encompass biologically functional equivalent α-mannosidase I and α-mannosidase II proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test α-mannosidase I and α-mannosidase II mutants in order to examine α-mannosidase I and α-mannosidase II activity at the molecular level.

If desired, one may also prepare fusion proteins and peptides, e.g., where the α-mannosidase I and α-mannosidase II coding regions are aligned within the same expression unit with other proteins or peptides having desired functions, such as for purification or immunodetection purposes (e.g., proteins that may be purified by affinity chromatography and enzyme label coding regions, respectively).

XIII. Cloning Insect Oligosaccharide Processing and Protein Folding Accessory Genes The present inventor contemplates cloning oligosaccharide processing and protein folding accessory genes or cDNAs from insect cells, and particularly, α-glucosidase I and α-glucosidase II, N-acetylglucosaminyltransferase I, N-acetylglucosaminyltransferase II, protein disulphide isomerase, peptidyl prolyl cis-trans isomerase and BiP/GRP78. The insect cells contemplated for use include Sf-9, High Five and Ea cells.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as, in the present case, a lambda ZAP II™ cDNA library from uninfected Sf-9 cells. The screening procedure may be an expression screening protocol employing antibodies directed against the protein, or activity assays. For example, antibody screening is very routinely employed. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, for example, in Sambrook et al. (1989), incorporated herein by reference. Moreover, as the present invention encompasses the cloning of genomic segments as well as cDNA molecules, it is contemplated that suitable genomic cloning methods, as known to those in the art, may also be used.

XIV. Use in Insect Control

Baculoviruses have been used throughout this century for insect pest control. The present invention contemplates two novel uses of baculoviruses in this manner. The gp64 protein is involved in the infectivity and virulence of baculovirus, mainly through the oligosaccharide side chains. The current invention provides for a method of alteration of the oligosaccharides on gp64 (Example 13 and 14). An embodiment of the current invention is to use the vectors described herein to alter the glycoprotein structure, thereby altering the infectivity and virulence of the recombinant baculoviruses. A further embodiment includes delivering known insect toxins, such as *Bacillus thuringiensis* crystal toxin, protease inhibitor II, rice lectin, AaIT, LqhIT2 or juvenile hormone esterase, with juvenile hormone esterase particularly preferred.

XV. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman el al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes an oligosaccharide processing enzyme. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coil* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected oligosaccharide processing gene using site-directed mutagenesis is provided as a means of producing potentially useful oligosaccharide processing enzyme species and is not meant to be limiting as there are other ways in which sequence variants of the oligosaccharide processing enzyme may be obtained. For example, recombinant vectors encoding the desired oligosaccharide processing enzyme gene may be treated with mutagenic agents to obtain sequence variants (see, e.g., a method described by Eichenlaub, 1979) for the mutagenesis of plasmid DNA using hydroxylamine.

XVI. Protein Purification

Further aspects of the present invention concern the purification, and in particular embodiments, the substantial purification, of a recombinant heterologous protein. The term "purified recombinant heterologous protein" as used herein, is intended to refer to a recombinant heterologous protein composition, isolatable from recombinant host insect cells, wherein the recombinant heterologous protein is purified to any degree relative to its naturally-obtainable state, i.e., in this case, relative to its purity within a natural extract. A purified recombinant heterologous protein therefore also refers to a recombinant heterologous protein free from the environment in which it may naturally occur.

Generally, "purified" will refer to a recombinant heterologous protein composition which has been subjected to fractionation to remove various non-insect cell components such as other cell components. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Methods exhibiting a lower degree of relative purification may have advantages in total recovery of protein product, or in maintaining the activity of an expressed protein. Inactive products also have utility in certain embodiments, such as, e.g., in antibody generation.

Partially purified recombinant heterologous protein fractions for use in such embodiments may be obtained by subjecting a insect cell extract to one or a combination of the steps described above. Substituting certain steps with improved equivalents is also contemplated to be useful. For example, it is appreciated that a cation-exchange column chromatography performed utilizing an HPLC apparatus will generally result in a greater-fold purification than the same technique utilizing a low pressure chromatography system.

XVII. Biological Functional Equivalents

As mentioned above, modification and changes may be made in the structure of oligosaccharide processing enzymes and still obtain a molecule having like or otherwise desirable characteristics. For example, certain amino acids may be substituted for other amino acids in a protein structure without appreciable loss of oligosaccharide processing capabilities. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of oligosaccharide processing proteins or peptides (or underlying DNA) without appreciable loss of their biological utility or activity.

In terms of functional equivalents, It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged.

Conservative substitutions well known in the art include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within +1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. use this shorter portion for non- immunological stuff It is understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on fuctionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Construction of pIE1HR1, 2, 3, and 4

These four plasmids are designed to facilitate the expression of foreign gene products under ie1 control in stably-transformed or transiently transfected lepidopteran insect cells. The ie1 5' untranslated region and most of the open reading frame were deleted from the *Autographa californica* multicapsid nuclear polyhedrosis virus (AcMNPV) ie1 gene by digesting pAcIE1 (Guarino and Summers, 1986) with SmaI and HincII. The deleted fragment was replaced with a blunt-ended PCR™ amplimer containing the 5' end of the ie1 gene from −84 to +3. The primers used to produce this amplimer (IE1–84+: 5'-CAGTATAAATTGACGTTC-3' (SEQ ID NO:5); and IE1+3−: 5'-TTTTGGATCCATAGTCACTTGGTTGTT-3' (SEQ ID NO:6)) were designed to add a BamHI site just downstream of the initiation codon in the ie1 gene (the first base of this ATG is defined as position +1).

The sequence of the cloned PCR™ amplimer was checked by direct sequencing of double-stranded templates using a commercial sequencing kit (Sequenase™ 2.0; United States Biochemical Corp., Cleveland, Ohio). The resulting plasmid, pIE184Bam, was used to isolate a DNA fragment containing the 5' end of the ie1 gene from −38 to +2 followed immediately by a BamHI site (GGATCC), a short cap sequence (AAAA) from the downstream PCR™ primer (IE1+3−; SEQ ID NO:6), a sequence from the 3' end of the ie1 gene (from position +1255 to +2491), and a short sequence from the pUC8 vector (from HindIII in the multiple cloning site to NarI in the lacZ gene). This 1431 bp fragment was used to replace the corresponding fragment in pAcIE1, which resulted in regeneration of the ie1 untranslated region from position −600 to −1, followed by the ATG, an overlapping BamHI site, the short cap sequence, the 3' end of the ie1 gene from position +1255 to +2491, which includes a polyadenylation site, and the pUC8 vector.

This new plasmid, pIE1600PreBam, was linearized with BamHI, the overhangs were removed with mung bean nuclease, and a blunt-ended MluI fragment from pHR5, which contains the AcMNPV hr5 enhancer element (Guarino et al., 1986), was inserted. This produced pIE1600BamHR, in which the enhancer element is oriented in the same direction as the ie1 promoter at the upstream BamHI site (position −600). A synthetic oligonucleotide encoding a multiple cloning site (mcs) was inserted into the single remaining BamHI site of pIE1600BamHR to produce pIE1HR1 and pIE1HR2 (FIG. 1A), which have the insert in opposite orientations with respect to the ie1 promoter (mcs1 (SEQ ID NO:7) and mcs2 (SEQ ID NO:8)). This same linker also was inserted into the unique BamHI site of pIE1600BamHRDATG, in which the ie1 translational initiation site (ACTATG) of pIE1600BamHR had been changed to ACCGCG by site-directed mutagenesis (Kunkel, 1985). This produced pIE1HR3 and pIE1HR4 (FIG. 1A), which lack the ie1 initiation codon and contain the mcs in opposite orientations with respect to the ie1 promoter (mcs3 (SEQ ID NO:9) and mcs4 (SEQ ID NO:10)).

The pIE1HR plasmids (FIG. 1A) are designed to facilitate transient expression of a foreign gene in uninfected insect cells (Guarino and Summers, 1986) or isolation of transformed insect cell clones that can express a foreign gene constitutively, in the absence of baculovirus infection (Jarvis et al., 1990; Jarvis, 1993; Jarvis and Guarino, 1995; Kleymann et al., 1993; Joyce et al., 1993; Vulsteke et al., 1993; Cartier et al., 1994. Each of these plasmids has the AcMNPV hr5 enhancer element (483 bp; Guarino et al., 1986) positioned upstream and in the same orientation as the ie1 promoter. In pIE1HR1 and 2, the ie1 promoter sequence extends from position −600 to +3, with +1 defined as the first nucleotide of the ie1 ATG (Guarino and Summers, 1987). In pIE1HR3 and 4, the promoter sequence extends from position −600 to −2. Thus, pIE1HR1 and 2 include the ie1 translational initiation site and can be used to produce fusion proteins, while pIE1HR3 and 4 lack this site and can be used to produce native proteins. The ie1 promoter in these four plasmids is followed by a mcs with several unique restriction sites. The mcs found in each plasmid is designated by a number (mcs1, mcs2, mcs3, or mcs4) that matches the number of the plasmid (pIE1HR1, pIE1HR2, pIE1HR3, or pIE1HR4) and the sequence of each mcs region, beginning at position −6 of the ie1 promoter, is shown in the brief description of FIG. 1 herein above. Each mcs is followed by the 3' end of the ie1 gene (positions +1255 to +2491), which includes a polyadenylation site. These plasmids are all derivatives of pUC8 (Vieira and Messing, 1982), which carries an ampicillin resistance marker and has the pMB1 replicon.

The immediate early expression plasmids shown in FIG. 1A facilitate transient expression assays in insect cells or the production of stably-transformed insect cells by providing flexibility in cloning foreign genes under ie1 control. These plasmids include all the promoter sequences that have been shown to be important for ie1-mediated gene expression in uninfected insect cells (Pullen and Friesen, 1995). They also include the hr5 enhancer element, which has been shown to stimulate ie1-mediated foreign gene expression (Pullen and Friesen, 1995; Rodems and Friesen, 1993; Guarino and Dong, 1994). Therefore, these plasmids provide optimal levels of foreign gene transcription in transiently-transfected or stably-transformed insect cells (Cartier et al., 1994; Pullen and Friesen, 1995; Rodems and Friesen, 1993). In addition to their potential utility as a tool for foreign glycoprotein production, stably-transformed insect cells produced using these plasmids can be used as helper cells to facilitate studies on essential baculovirus, or as modified hosts to study insect cell biology and the baculovirus-host cell interaction (Cartier et al., 1994; Jarvis, 1993).

Construction of pAcP(−)IE1TV5 and 6 and pAcP (+)IE1TV1, 2, 3, and 4

The pAcP(−)IE1TV5 and 6 plasmids are designed to facilitate the isolation of occlusion-negative recombinant baculoviruses in which a foreign gene of interest can be expressed under the control of the ie1 promoter during the immediate early phase of infection. pAcP(−)IE1TV5 was constructed by replacing the EcoRV-BamHI fragment of pVL1393 (O'Reilly et al., 1992) with the SmaI-BamHI fragment of pIE1600BamHR. This effectively replaced the polyhedrin sequence from −92 to +177 with the ie1 sequence from −600 to +3, regenerated an overlapping unique BamHI site, and maintained some additional unique cloning sites immediately downstream (FIG. 1B). This same strategy was used to construct pAcP(−)IE1TV6, except the EcoRV-BamHI fragment from pVL1393 was replaced with the SmaI-BamHI fragment of pIE1600BamHRDATG, in which the ie1 ATG had been eliminated by site-directed mutagenesis.

The pAcP(+)IE1TV1, 2, 3, and 4 plasmids are designed for the isolation of occlusion-positive recombinants that can express a foreign gene under ie1 control during the immediate early phase of infection. First pAcPo1h was constructed, which contained the full-length AcMNPV polyhedrin gene with about 2 Kb and 1.5 Kb of 5' and 3' flanking sequences, respectively, and ultimately served as the target for inserting a DNA fragment encoding the hr5 enhancer, ie1 promoter, and mcs. A precursor, pAcPolh-5', was constructed by inserting the XhoI-BamHI fragment of pAcPstI-D into the SalI-BamHI sites of pUC18 (Yanisch-Perron et al., 1985), then the 1.94 Kb BamHI fragment of pAcPstI-D was inserted into the unique BamHI site of pAc-Polh-5' to produce pAcPolh. pAcP(+)IE1TV1, 2, 3, or 4 (FIG. 1C) were constructed by inserting the hr5-ie1-mcs fragments from pIE1HR1, 2, 3, or 4, respectively, into the unique EcoRV site of pAcPo1h. pAcP(+)IE1TV1 and 2 contain the hr5 enhancer element, the ie1 promoter from −600 to −1, and the ie1 ATG, followed by mcs1 or mcs2. pAcP(+)IE1TV3 and 4 have the enhancer and the ie1 promoter from −600 to −2, followed by mcs3 or mcs4, but lack the ie1 ATG.

The pAcP(−)IE1TV (FIG. 1B) and pAcP(+)IE1TV (FIG. 1C) transfer plasmids are designed for the production of occlusion-negative or -positive recombinant baculovirus vectors, respectively, that can express a foreign gene beginning immediately after infection. Each of these plasmids has the hr5 enhancer and ie1 promoter from positions −600 to +3 or −600 to −2, as described above. Thus, some include the ie1 translational start site and can be used to express fusion proteins, whereas others lack it and can be used to express native proteins. The ie1 promoter in each plasmid is followed by a mcs with several unique restriction sites; as above, the number following the name of the plasmid indicates which mcs it contains and the various mcs sequences are shown in the brief description of FIG. 1 herein above.

In the pAcP(−)IE1TV plasmids, the mcs is followed by sequences which begin in the middle of the polyhedrin open reading frame (at position +177 with respect to the polyhedrin ATG) and extend about 2.8 Kb downstream through the polyhedrin polyadenylation site. The sequence on the other side of the hr5-ie1-mcs complex in the pAcP(−)IE1TV plasmids begins at the EcoRV site in the polyhedrin promoter region (position −92 with respect to the polyhedrin ATG) and extends about 4.0 kb in the 5' direction with respect to the polyhedrin ATG. Thus, as in conventional polyhedrin-based baculovirus transfer plasmids, these long flanking sequences will target the foreign gene to the polyhedrin locus where it can be inserted by homologous recombination. This produces polyhedrin-negative recombinants, which can be identified in plaque assays by their occlusion-negative phenotypes.

By contrast, the mcs in the pAcP(+)IE1TV plasmids is followed by sequences that begin at the EcoRV site in the promoter region of the polyhedrin gene (position −92) and extend about 2.1 kb in the 5' direction with respect to the polyhedrin ATG (FIG. 1C). The sequences preceding the hr5-ie1-mcs complex in the pAcP(+)IE1TV plasmids begin at the EcoRV site and extend about 2.2 Kb in the 3' direction with respect to the polyhedrin ATG. Thus, these plasmids have an intact polyhedrin promoter, open reading frame, and 3' flanking sequence positioned upstream and in opposite orientation to the hr5-ie1-mcs and a long flanking sequence from the 5' side of the polyhedrin gene positioned downstream and in opposite orientation to the hr5-ie1-mcs. As with the pAcP(−)IE1TV plasmids, the pAcP(+)IE1TV plasmids can be used to insert the foreign gene into the polyhedrin locus by homologous recombination. However, these latter transfer plasmids will produce occlusion-positive recombinants that can be distinguished by their plaque phenotypes only if genomic DNA from an occlusion-negative virus is used as the target for homologous recombination.

The immediate early baculovirus transfer plasmids shown in FIG. 1B and FIG. 1C are designed to facilitate the isolation of either occlusion-negative or -positive recombinant baculoviruses that can be used to express foreign genes during the early phase of infection. The availability of multiple plasmids designed to produce recombinants with either plaque phenotype provides flexibility in the choice of screening techniques and allows one to produce either environmentally labile (occlusion-negative) or stable (occlusion-positive) recombinants for use as biopesticides (Section XIII). It should be noted that the pAcP(−)IE1TV and pAcP(+)IE1TV transfer plasmids will target the ie1-driven foreign gene for insertion into the viral genome in opposite orientations and the sequences, including potential polyadenylation sites, downstream of the inserts will be completely different. These differences might influence the levels of expression that can be obtained with immediate early baculovirus vectors produced with these different types of transfer plasmids.

EXAMPLE 2

Isolation and Analysis of Immediate Early Baculovirus Vectors that Express E. coli β-gal The E. coli lacZ gene was inserted into pAcP(−)IE1TV1 or pAcP(+)IE1TV1 and the resulting plasmids were used to isolate immediate early baculovirus vectors. The BamHI fragment of pVL1393-βgal was inserted into the unique BamHI site of pAcP(−)IE1TV5 or BglII site of pAcP(+)IE1TV1 to produce pAcP(−)IE1βgal or pAcP(+)IE1βgal, respectively. pAcP(−)IE1βgal is designed to express a fusion protein under the influence of the hr5 enhancer and ie1 promoter which initiates at the ie1 ATG and has two linker amino acids (D-P) fused to amino acids 10–1024 of β-gal. pAcP(+)IE1βgal is identical, except it encodes a fusion protein with four linker amino acids (D-L-D-P) fused to β-gal and also has an intact polyhedrin gene oriented in the opposite direction.

Working stocks of these viruses were prepared, titered, and used as follows. Occlusion-negative or -positive recombinant viruses were isolated after calcium phosphate-mediated cotransfection of Sf9 cells with a mixture of the appropriate transfer plasmid and viral DNA, as described previously (Summers and Smith, 1987). The transfer plasmids used to isolate occlusion-negative recombinants expressing β-gal, CAT (Example 3), or t-PA (Example 4) were pAcP(−)IE1βgal, pAcP(−)IE1CAT, and pAcP(−)IE1tPA, respectively. The viral DNA was from wild-type AcMNPV and recombinants were identified by their occlusion-negative blue (β-gal) or white (CAT and t-PA; Examples 3 and 4) phenotypes in plaque assays containing X-gal (Research Organics Inc., Cleveland, Ohio). The transfer plasmids used to isolate occlusion-positive recombinants were pAcP(+)IE1βgal, pAcP(+)IE1CAT, pAcP(+)IE1tPA, or pAcP(+)IE1SfManII, respectively. The viral DNA was Bsu36I-linearized BAKPAK6 (32), and recombinants were identified by their occlusion-positive blue (β-gal) or white (CAT, t-PA, and SfManII; Examples 3, 4 and 5) phenotypes in plaque assays containing X-gal. Once the desired recombinants were identified, well-isolated plaques were picked, taken through one additional round of plaque purification, and working virus stocks were prepared and titered in Sf9 cells, as described below.

Sf9 cells were routinely maintained as a spinner culture in TNM-FH medium supplemented with fetal bovine serum, antibiotics, and pluronic F68, as previously described (Summers and Smith, 1987). The E2 strain of wild-type AcMNPV and the recombinant baculoviruses used were routinely propagated and titrated by plaque assay in Sf9 cells and working virus stocks were stored frozen in the dark at −85° C. (Summers and Smith, 1987, Jarvis and Garcia, 1994). The recombinant viruses used as controls for this study, which express β-gal (VL941-βgal), CAT (Ac360CAT; Example 3), t-PA (PreProTPA; Example 4), or the Sf9 a-mannosidase II protein (AcSfManII; Example 5) under the influence of the polyhedrin promoter, have been described previously (Jarvis et al., 1993; Luckow and Summers, 1988, 1989; Example 6–10).

Working stocks of these viruses were used to compare the kinetics and levels of β-gal expression obtained in infected Sf9 cells to those obtained with a conventional polyhedrin-based baculovirus vector. Sf9 cells were grown in suspension to a density of $1 \times 10^6$ cells per ml and infected with the appropriate virus at a multiplicity of infection of 5 plaque-forming units per cell. The virus was allowed to adsorb for one hr at 28° C., then the inoculum was removed and the cells were washed twice with TN-MFH medium supplemented with 10% serum, antibiotics, and pluronic F68 and twice with Grace's medium (Summers and Smith, 1987) supplemented with 0.5% serum, antibiotics, and pluronic F68. The infected cells were resuspended in the latter medium at a density of $1\times10^6$ per ml, returned to the spinner, and samples containing $5\times10^7$ or $5\times10^6$ cells were removed at various times after infection for extraction of total RNA or protein, respectively.

Total RNA was prepared (Chirgwin et al., 1979) and 20 μg, 10 μg and 5 μg aliquots were analyzed by dot blot assays on nitrocellulose filters (Schleicher and Schuell, Inc.; Keene, NH; Luckow and Summers, 1988), as described previously. The probe was a 625 bp internal HincII fragment of the *E. coli* lacZ gene that was twice gel-purified and radiolabeled by the random primer method (Feinberg and Vogelstein, 1983).

For analysis of β-gal, CAT (Example 3), and SfManII (Example 5) expression, total protein was extracted from infected cell pellets by trituration in protein disruption buffer (50 mM Tris-HCl, pH 6.8; 4% sodium dodecyl sulfate; 4% β-mercaptoethanol) through a syringe equipped with a 22 ga needle followed by boiling for 3 min. For t-PA (Example 4), extracellular medium was harvested, clarified, freeze-dried, and redissolved by boiling in protein disruption buffer. Proteins were subsequently resolved by sodium dodecyl sulfate polyacrylamide gel electrophoresis using the discontinuous buffer system (Laemmli 1970), and either stained with Coomassie Brilliant Blue or transferred to Immobilon™ PVDF filters (Millipore Corporation, Bedford, Mass.) using a standard wet electrophoretic transfer method (Towbin et al., 1979). The filters were incubated overnight at 4° C. with blocking buffer (50 mM Tris-HCl, pH 7.5; 150 mM NaCl; 1% NP40; 5% nonfat dry milk), then probed in the same buffer containing appropriately diluted rabbit anti-β-gal, rabbit anti-CAT (Example 3), or goat anti-t-PA (Example 4). After washing away the unbound primary antibodies, the filters were incubated with appropriately diluted goat or rabbit secondary antibody conjugated to alkaline phosphatase. The unbound secondary antibody was washed away, then the immunoblots were rinsed and developed using a standard color reaction (Blake et al., 1984).

β-gal, CAT (Guarino and Summers, 1986; Example 3), and Sf9 α-mannosidase II (Example 5) activities were measured by biochemical assays done on cytosolic extracts of infected cells prepared by freeze-thaw or detergent lysis at various times after infection, as described previously. Human t-PA activity (Example 4) was measured by a fibrin agar plate lysis assay done on clarified extracellular medium from infected cells isolated at various times after infection, as described previously (Jarvis et al., 1993).

Immunoblotting analysis showed that β-gal could be detected in cells infected with either immediate early vector (AcP(+)IE1βgal or AcP(−)IE1βgal) as early as 4 hr postinfection. In both cases, the β-gal protein accumulated with increasing time of infection and reached peak steady-state levels at 24 hr postinfection. The occlusion-positive immediate early vector produced larger amounts of β-gal than the occlusion-negative vector, particularly at earlier times after infection. β-gal was not detected in cells infected with a conventional baculovirus vector (941βgal; polyhedrin promoter) until 24 hr postinfection and, at that time point, the amount of accumulated β-gal produced by that vector was lower than the amount produced by the immediate early vectors. However, at later times after infection, the conventional baculovirus vector provided higher levels of accumulated β-gal protein. It was previously demonstrated that immunoblotting provided reasonably quantitative estimates of the relative levels of total β-gal protein in insect cell lysates (Jarvis et al., 1990), but it is possible that the difference in the amounts observed at 48 hr postinfection is underrepresented by this analysis.

The amounts of β-gal enzyme activity produced by the immediate early or conventional baculovirus vectors were also compared and the results, which were consistent with the immunoblotting results, are shown on a log scale plot in FIG. 2. The immediate early vectors produced β-gal activity earlier, with a peak at 24 hr postinfection, and the occlusion-positive vector produced more activity than the occlusion-negative vector. The occlusion-positive immediate early vector produced about twice as much β-gal activity as the conventional vector by 24 hr postinfection, but about 25-fold and 50-fold lower activity by 36 and 48 hr postinfection, respectively. The reason for the difference in RNA levels was unclear, but a major difference between the two types of immediate early vector was the orientation of the ie1-controlled foreign gene with respect to the rest of the viral genome. Whereas the foreign genes in the occlusion-positive vectors are oriented from right to left on the AcMNPV map (Summers and Smith, 1987; O'Reilly et al., 1992), the same genes are oriented from left to right in the occlusion-negative vectors. This was not a specifically designed difference between the two different types of immediate early vectors; rather, it was a by-product of the desire to position the ie1 and polyhedrin promoters in the occlusion-positive vectors in back-to-back orientation.

Transcriptional analysis of lacZ expression by dot blot assays showed that lacZ-specific RNA was detectable as early as 4 hr postinfection in cells infected with either immediate early baculovirus vector. Cells infected with the occlusion-positive vector contained more lacZ RNA than cells infected with the occlusion-negative vector. In both cases, lacZ RNA levels reached plateaus at 24 hr postinfection and, at this time point, cells infected with the immediate early vectors contained more lacZ RNA than cells infected with a conventional vector. LacZ RNA was first detected in cells infected with a conventional vector at 24 hr postinfection and the levels continued to rise to 48 hr postinfection. These results were consistent with the results observed for expression of β-gal protein and enzymatic activity.

EXAMPLE 3

Isolation and Analysis of Immediate Early Baculovirus Vectors that Express *E. coli* CAT Occlusion-negative and -positive immediate early baculovirus vectors containing the *E. coli* CAT gene were produced. The BamHI fragment of pCAT#3 was inserted into the unique BamHI site of pAcP(−)IE1TV5 or the BglII site of pAcP(+)IE1TV1 to produce pAcP(−)IE1CAT or pAcP(+)IE1CAT, respectively. pAcP(−)IE1CAT is designed to express CAT as a fusion protein which initiates at the ie1 ATG and has twelve linker amino acids (D-P-S-R-F-S-G-A-K-E-A-K; SEQ ID NO:16) fused to amino acids 1–219 of the CAT protein. pAcP(+)IE1CAT encodes a fusion protein which initiates at the ie1 ATG and has fourteen linker amino acids (D-L-D-P-S-R-F-S-G-A-K-E-A-K; SEQ ID NO:17) joined to the CAT sequence and also includes the intact polyhedrin gene oriented in the opposite direction.

Figure 3:
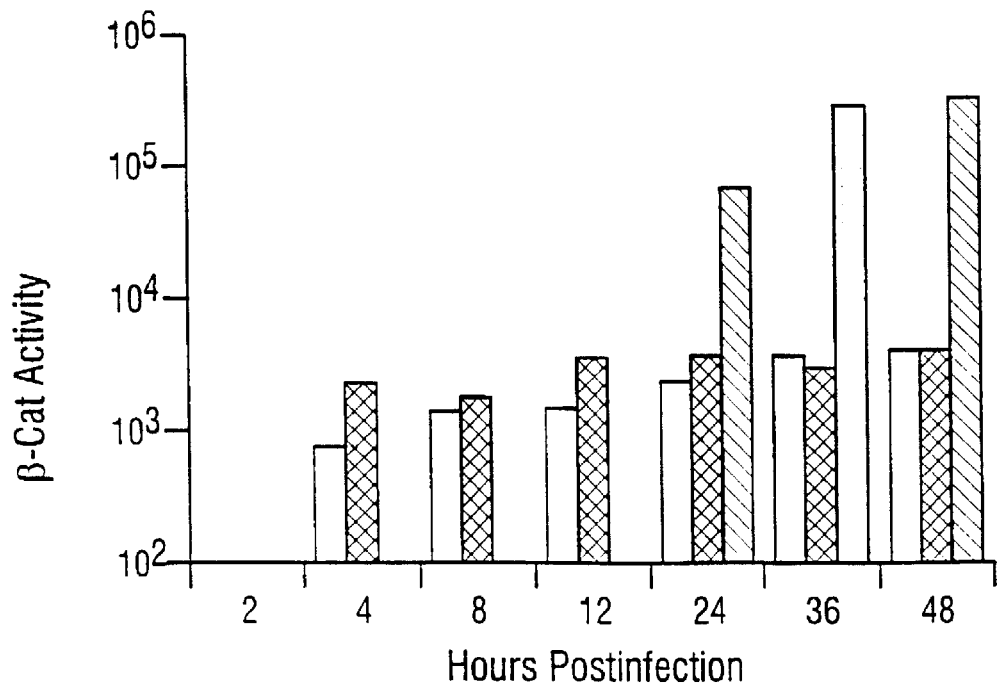
FIG. 3. Production of E. coli CAT activity by immediate early and conventional baculovirus vectors. This log scale plot shows the relative levels of CAT activity in cytoplasmic extracts from Sf9 cells infected for various times with AcP(–)IE1CAT (open bars), AcP(+)IE1CAT (light stippled bars), or Ac360CAT (dark stippled bars). CAT activity is expressed as pmol of acetylated chloramphenicol produced per 30 min per million infected cells.

The kinetics and levels of CAT protein expression provided by these vectors was compared to those provided by a conventional baculovirus vector (Ac360CAT; polyhedrin promoter). The immediate early vectors produced the foreign protein at earlier times after infection, with a plateau at 24 hr postinfection, and the occlusion-positive recombinant produced larger amounts than the occlusion-negative recombinant. CAT protein was first detected in cells infected with a conventional baculovirus vector at 24 hr postinfection and, even at that time point, the conventional vector produced more CAT than either of the immediate early vectors. These results were consistent with the results of CAT activity assays, which showed that the immediate early vectors produced about 10-fold less activity at 24 hr postinfection and about 80-fold less activity by 36 hr postinfection (FIG. 3). These results also were consistent with previous results (Morris and Miller, 1992), which indicated that CAT activity was expressed at very low levels under ie1 control.

EXAMPLE 4

Isolation and Analysis of Immediate Early Baculovirus Vectors that Express Human t-PA The results in Examples 2 and 3 showed that immediate early baculovirus vectors could produce two different prokaryotic enzymes earlier in infection, but that conventional baculovirus vectors containing the polyhedrin promoter could ultimately provide higher levels of both protein and enzymatic activity. Previous findings had indicated that earlier expression would probably be advantageous for foreign glycoprotein expression (Jarvis and Summers, 1989; Jarvis et al., 1990; Murphy et al., 1990; Sridhar et al., 1993), but this idea had never been tested by using the ie1 promoter to express a foreign glycoprotein gene in baculovirus-infected insect cells. Therefore, immediate early recombinants capable of expressing human t-PA, a foreign secreted glycoprotein, under ie1 control were produced. This also provided a test of immediate early baculovirus vectors designed to express unfused, native proteins.

The native t-PA gene was inserted into pAcP(−)IE1TV6 and pAcP(+)IE1TV3 and the resulting plasmids were used to isolate immediate early baculovirus vectors. The BamHI-KpnI fragment of pPrePro-t-PA (Jarvis et al., 1993) was inserted into the BamHI-KpnI sites of pAcP(−)IE1TV6 to produce pAcP(−)IE1tPA, which is designed to express the native t-PA protein under the influence of the hr5 enhancer and ie1 promoter. A similar strategy was used to produce pAcP(+)IE1tPA, except the KpnI site was blunt-ended with T4 DNA polymerase and the BamHI-KpnI (blunt) fragment was inserted into the BglII-StuI sites of pAcP(+)IE1TV3.

These vectors were used to infect Sf9 cells and the amounts of t-PA protein in the extracellular fraction of these cells were monitored by immunoblotting. As had been observed with β-gal and CAT, the immediate early vectors produced extracellular t-PA starting at 4 hr postinfection, with a peak at 24 hr postinfection, and the occlusion-positive vector produced larger amounts than the occlusion-negative vector. The conventional baculovirus vector (PreProTPA; polyhedrin promoter) first produced extracellular t-PA at 24 hr postinfection and, at that time point, the amount was similar to the amount produced by the occlusion-negative immediate early vector and lower than that produced by the occlusion-positive immediate early vector. At 36 hr postinfection, the medium from cells infected with the occlusion-positive immediate early vector still contained more t-PA than medium from cells infected with the conventional vector. By 48 hr postinfection, there was a clear reduction in the amount of extracellular t-PA in the medium of cells infected by either immediate early vector, which probably reflected turnover of the extracellular t-PA product, and, at that time, the medium from cells infected with the conventional baculovirus vector contained more immunoreactive t-PA protein.

The results of t-PA activity assays showed that the immediate early vectors produced t-PA activity earlier than the conventional vectors and that the levels of activity produced by the former were about equal to those produced by the latter, even at 48 hr postinfection. Thus, unlike β-gal and CAT, a conventional baculovirus vector was unable to produce significantly more extracellular human t-PA protein or activity than the immediate early vectors described herein.

EXAMPLE 5

Isolation and Analysis of Immediate early Baculovirus Vectors that Express Sf9 α-mannosidase II An occlusion-positive immediate early baculovirus vector capable of expressing a membrane-bound secretory pathway glycoprotein, α-mannosidase II, was isolated. The BglII-NotI fragment of pSfManII (Example 6) was inserted into the BglII-NotI sites of pAcP(+)IE1TV3 to produce pAcP(+)IE1SfManII, which is designed to express the native Sf9 cell α-mannosidase II protein under the influence of the hr5 enhancer and ie1 promoter. Since no antibody is available, a comparison of the amounts of total Sf9 α-mannosidase II protein expressed by immediate early or conventional baculovirus vectors (AcSfManII; polyhedrin promoter) was limited to SDS-PAGE and Coomassie Brilliant Blue staining of infected cell lysates.

Figure 4:
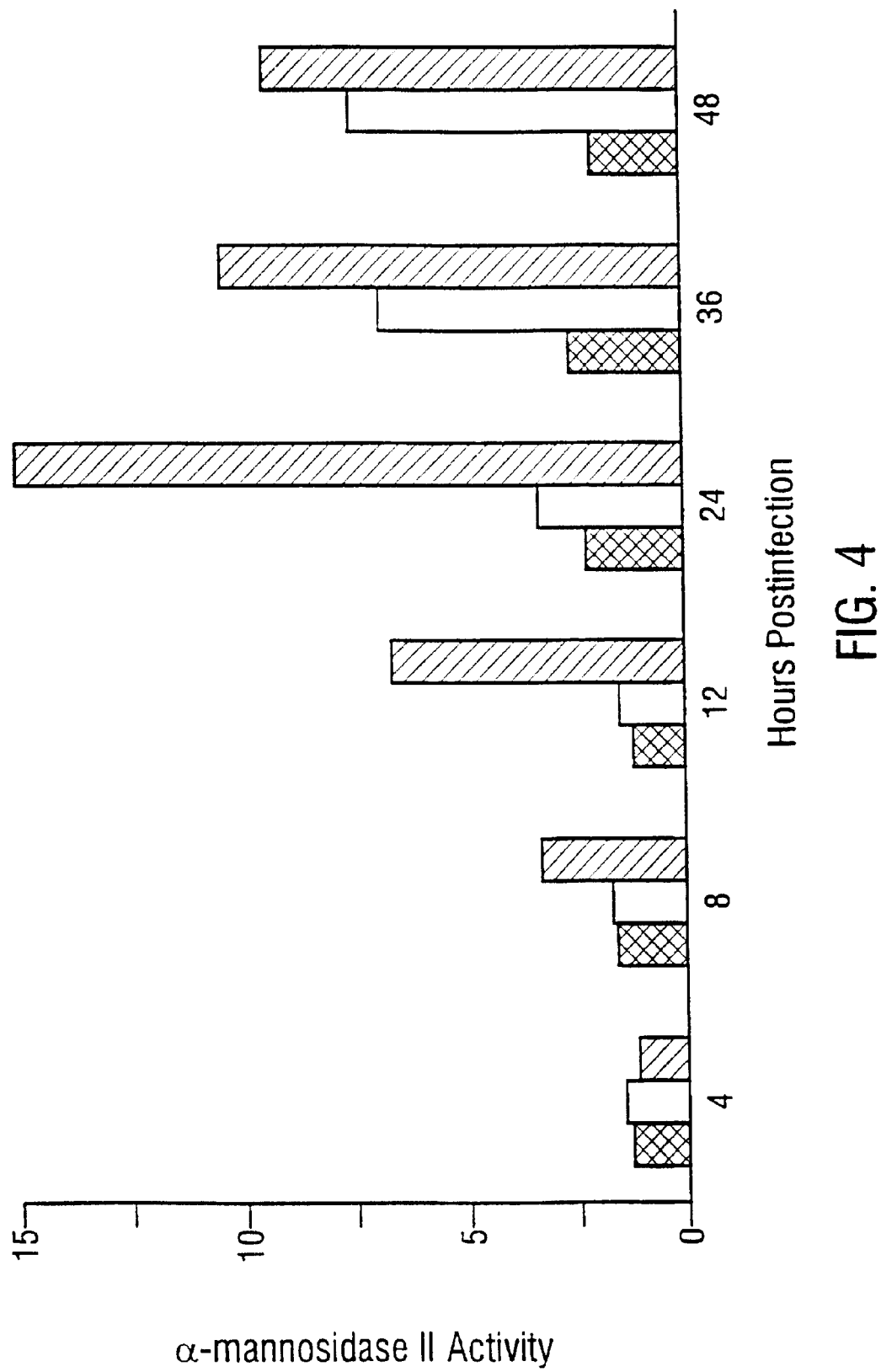
FIG. 4. Production of α-mannosidase II activity by immediate early and conventional baculovirus vectors. This plot shows the relative levels of α-mannosidase II activity in total extracts of Sf9 cells infected for various times with wild-type AcMNPV (closed bars), AcSfManII (open bars), or AcP(+)SfManII (cross-hatched bars). Activity is expressed as nmol of p-nitrophenol produced per min per ml of cell extract.

The results showed that the Sf9 α-mannosidase II protein, which has an $M_r$ of approximately 131,000, could only be seen against the background of other infected cell proteins in lysates from cells infected for 48 hr with the conventional vector. However, when α-mannosidase II activity in these same lysates was measured, the immediate early baculovirus vector produced activity earlier, with a peak at 24 hr postinfection, and at higher levels than the conventional vector at all time points examined (FIG. 4). Thus, the immediate early baculovirus vector produced less total Sf9 α-mannosidase II protein, but more enzymatically active protein than the conventional vector, even as late as 48 hr postinfection. This might be related to adverse effects of baculovirus infection on the host cell secretory pathway at late times of infection (Jarvis and Summers, 1989; Jarvis et al., 1990; Murphy et al., 1990). Alternatively, it might indicate that the levels of newly synthesized protein expressed under polyhedrin control at late times of infection exceed the capabilities of the host protein processing machinery and only a relatively small proportion can be processed to an enzymatically active form.

EXAMPLE 6

Isolation and Characterization of α-mannosidase II and α-mannosidase I cDNAs from Sf9 Cells An α-mannosidase II cDNA from lepidopteran insect (Sf9) cells was isolated using a degenerate oligonucleotide PCR™ approach (Moremen, 1989). Genomic DNA was isolated from Sf9 cells by a standard method (Sambrook et al., 1989) and used for PCR™ (Saiki et al., 1985) with degenerate oligonucleotide primers (GGITGGIIIATHGAYCCITTYGGNCA; SEQ ID NO:13, and GGNCKISWIIIRAA RTAICCISDCCARTA; SEQ ID NO:14) designed against conserved amino acid sequences in two class II α-mannosidases (Moremen et al., 1994), namely, murine Golgi α-mannosidase II (Moremen and Robbins, 1991) and the lysosomal α-mannosidase from *Dictyostelium discoideum* (Schatzle et al., 1992). PCRs™ were done in a total volume of 25 ml containing 10 mM Tris-HCl (pH 8.3), 50 mM KCl, 2.5 mM $MgCl_2$, 0.01% (w/v) gelatin, 0.2 mM dNTP's, 1 mM primers, 1 mg of genomic DNA, and 2.5 U of Taq polymerase (Perkin-Elmer Corp., Norwalk, Conn.). After 40 cycles of denaturation (45 sec at 92° C.), annealing (45 sec at 45° C.), and extension (3 min at 72° C.) in a Perkin-Elmer thermal cycler, a final extension was done for 5 min at 72° C. and the amplification products were analyzed on 1% agarose gels.

The resulting 669 bp amplification product was identical in size to a positive control RT-PCR™ product derived from murine liver mRNA. Similar RT-PCR™ products were obtained using mRNA isolated from either uninfected or baculovirus-infected Sf9 cells. The PCR™ product from Sf9 genomic DNA was cloned a plasmid vector designed to facilitate direct cloning of PCR™ products (PCRII™; Invitrogen, San Diego, Calif.), and its sequence was determined by the chain termination method (Sanger et al., 1977). The translation of the amplimer sequence was compared to a translation of the GenBank sequence database.

The cDNA sequence was assembled using the sequence assembly package of Staden (1987). The sequence of the amplimer translation was compared to the six frame translation of the GenBank non-redundant DNA sequence database (version 91) using the TFASTA subroutine of the University of Wisconsin Genetics Computer Group (GCG) software package (Program Manual for the Wisconsin Package, Version 8.1, Genetics Computer Group, Madison, Wis.). The pairwise sequence comparisons were performed using the Bestfit subroutine and multiple sequence alignments and dendrograms were prepared using the Pileup and Boxshade subroutines of the GCG software package. Only class II mannosidases, including murine and human α-mannosidase II (42.3% and 43.3% identity, respectively) and D. discoideum and human lysosomal α-mannosidase (29.4% and 26.1% identity, respectively), were identified by this analysis. This suggested that the Sf9 amplimer was derived from a gene that is related to the class II mannosidases and is more similar to the Golgi processing than the lysosomal mannosidases.

The Sf9 amplimer DNA sequence was used to design exact-match primers against the putative Sf9 α-mannosidase II coding region and these primers were used for PCRs™ with total λ DNA from an unfractionated Sf9 cDNA library. Electrophoretic analysis of the reaction products revealed one major DNA fragment of about the same size as the RT-PCR™ product. The same result was obtained with total λ DNA from an unfractionated Sf9 genomic DNA library or with the pCRII clone containing the Sf9 amplimer, but not in negative controls which lacked template DNA or contained one specific and one nonspecific primer. These results indicated that the uninfected Sf9 cell cDNA library included a clone containing the putative Sf9 α-mannosidase II coding region. This cDNA was isolated by using a sibling selection and PCR™ screening approach (Moremen, 1989).

Briefly, an Sf9 cDNA library in λZAPII™ (Short et al., 1988; Stratagene, La Jolla, Calif.) was split into 43 pools of 50,000 clones, each pool was amplified in E. coli, and total λ DNA was prepared from 2×10⁶ progeny using a commercial anti-lambdaphage immunosorbent (Lambdasorb), according to the manufacturer's instructions (Promega Corp., Madison, Wis.). These DNAs were used as templates for PCRs™ with the exact-match primers to determine which pools included an Sf9 α-mannosidase II clone. One positive pool was split into eight subpools of 10,000 clones, each subpool was reamplified in E. coli, total λ DNA was isolated, and the PCR™ screening process was repeated. Finally, one positive subpool, which theoretically included an Sf9 α-mannosidase II clone at a frequency of at least 1 in 10,000, was screened by plaque hybridization (Benton and Davis, 1977; Sam brook, 1989). The hybridization probe, which was the original Sf9 α-mannosidase II PCR™ amplimer that had been cloned into pCRII™, was excised with EcoRI, gel-purified twice, and uniformly labeled by the random primer method (Feinberg and Vogelstein, 1983).

Positive plaques from high-density plates were taken through two additional rounds of low density plaque hybridization for further purification and screening. The cDNA inserts in two λZAPII™ clones that remained positive through all three rounds of screening were excised as Bluescript™-based plasmid subclones by coinfection with M13R408 helper phage, as described previously (Short et al., 1988). The resulting plasmids were isolated by standard alkaline lysis extraction and CsCl-EtBr gradient centrifugation procedures (Sambrook et al., 1989) and used as templates to sequence the cDNA inserts with universal and gene-specific primers (Sanger et al., 1977). The largest cDNA (about 6.5 Kb) was sequenced with universal and gene-specific primers and compared to mammalian α-mannosidase II DNA sequences. This analysis revealed extensive similarities, but indicated that the cDNA clone lacked the 5' end of the α-mannosidase II coding region.

Figure 5A:
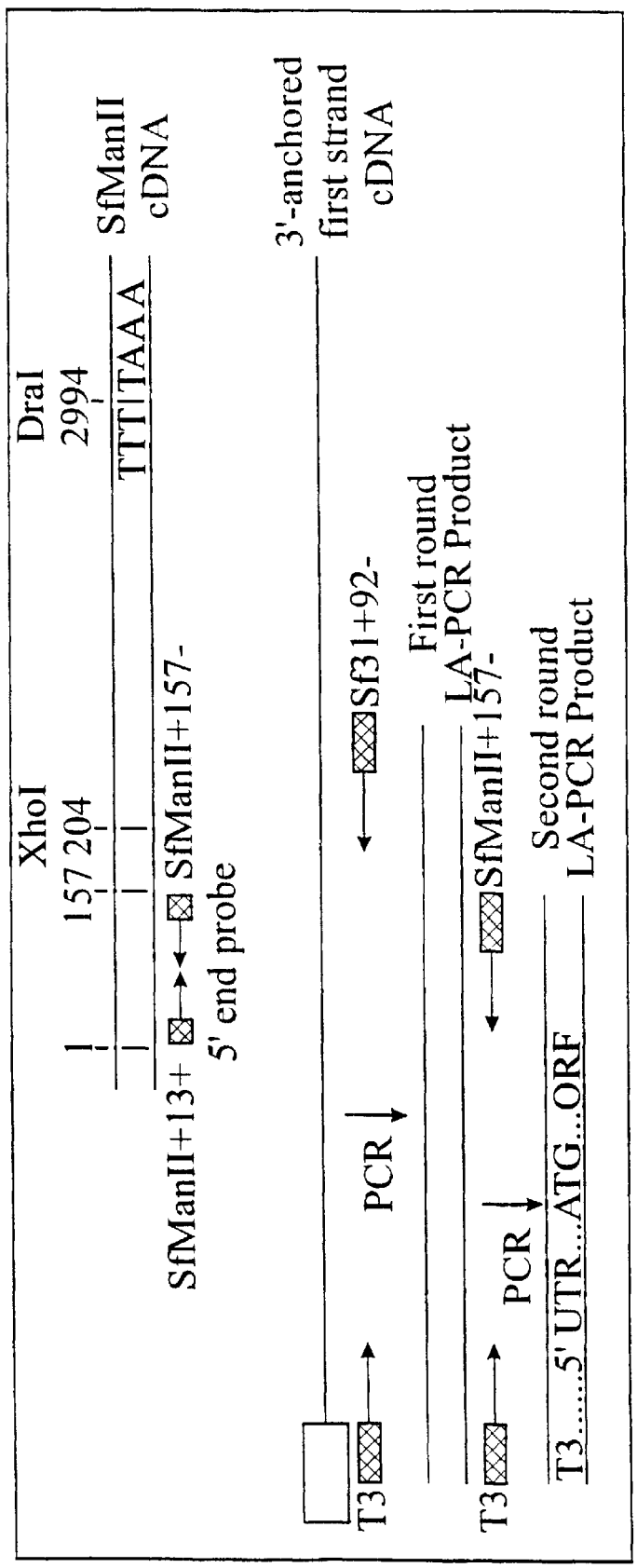
FIG. 5A and FIG. 5B. Isolation of the Sf9 α-mannosidase II cDNA.

The 5' end of the Sf9 α-mannosidase II cDNA was isolated by using ligation-anchored PCR™ (Troutt et al., 1992) as outlined in FIG. 5A. Total RNA was prepared from a log phase culture of uninfected Sf9 cells by the method of Chirgwin and coworkers (1979) and used to prepare poly A+ RNA by oligo-dT cellulose column chromatography (Aviv and Leder, 1972). One microgram of the poly A+ RNA was used for first-strand cDNA synthesis with random hexamer primers and an RNase H-minus form of MoMuLV reverse transcriptase (Superscript™ II; Life Technologies, Gaithersburg, Md.). After reverse transcription, the RNA was digested with RNAse H and the reaction mixture was diluted and desalted by ultrafiltration in a Microcon™ 100 filter (Amicon, Inc., Beverly, Mass.). The single-stranded cDNA was recovered and a 5'-phosphorylated, 3'-blocked primer complementary to the T3 primer (5'-TCCCTTTAGTGAGGGTTAATTT-NH2-3' SEQ ID NO:15) was ligated to its 3' end with T4 RNA ligase (New England Biolabs, Beverly, Mass.).

The resulting anchored first-strand cDNA product was used as the template for a PCR™ with T3 as the upstream primer and an Sf9 α-mannosidase II-specific oligonucleotide (Sf31+92- in FIG. 5A) as the downstream primer, under the conditions described by Apte and Siebert (1993). The amplification product was extracted with phenol-chloroform and a fraction was used as the template for a secondary PCR™ under the same conditions as the primary PCR™ with T3 as the upstream primer and a different Sf9 α-mannosidase II-specific oligonucleotide (SfManII+157- in FIG. 5A) as the downstream primer. The secondary products were extracted with phenol-chloroform, gel-purified on a 1% agarose gel, and a band of interest identified by Southern blotting with the gene-specific 5' end probe shown in FIG. 5A. After the second round of PCR™ amplification, several products were observed by ethidium bromide staining, but only two (175 and 750 bp) hybridized with the 5' end probe. The 750 bp product was cloned into PCRII™, sequenced, and the results showed that it overlapped and extended the 5' end of the Sf9 α-mannosidase cDNA clone by an additional 681 bp.

Figure 5B:
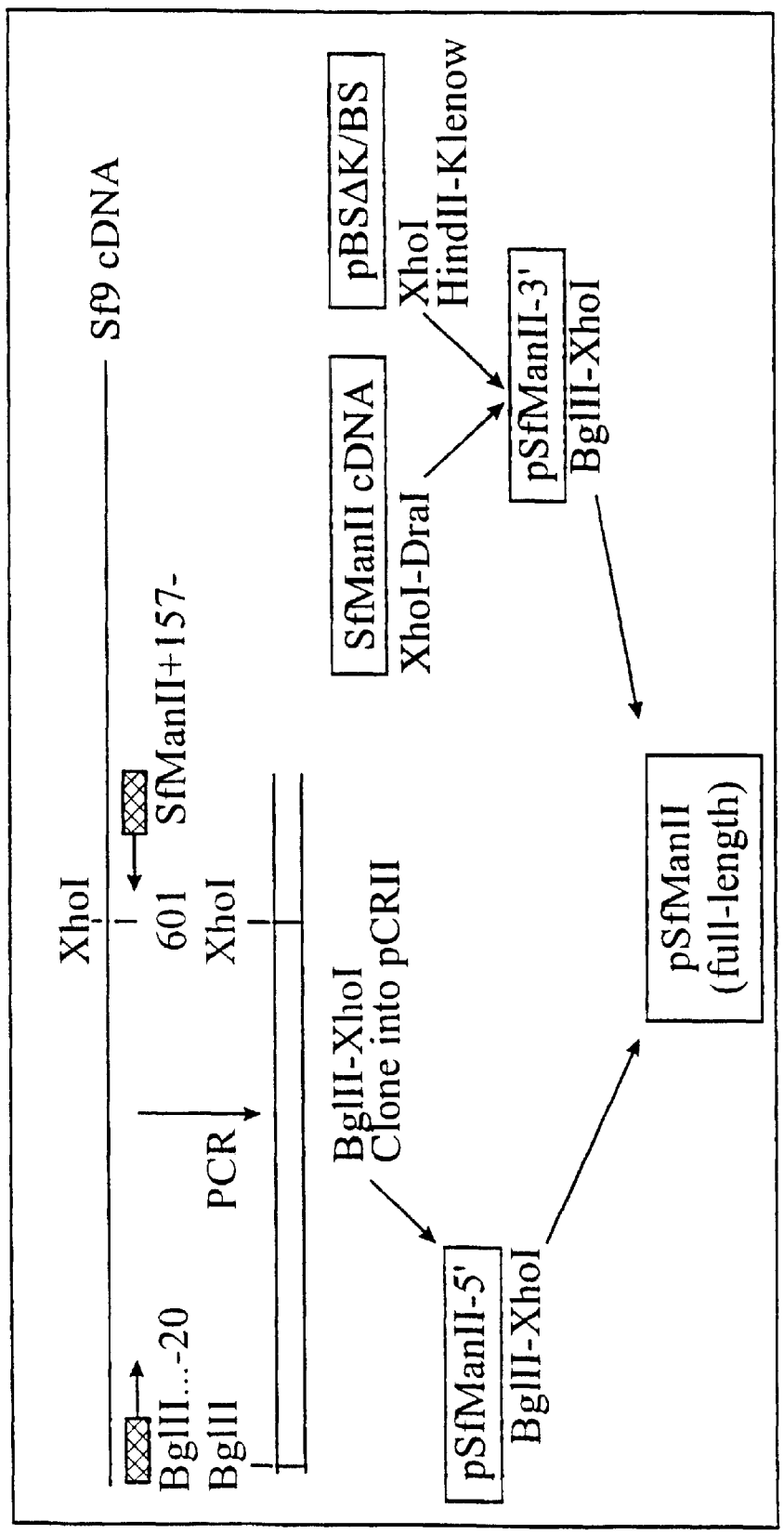

The resulting sequence information was used to design exact-match primers for amplification of the 5' end of the putative x-mannosidase II cDNA from the original Sf9 cell cDNA preparation, as diagrammed in FIG. 5B. The 5' primer (BglII . . . −20 in FIG. 5B) was designed to incorporate a unique BglII site at position −20, with respect to the putative translational initiation site, and the 3' primer (SfManII-A1 in FIG. 5B) was located downstream of a unique XhoI site. This amplification product was cloned into PCRII™ to produce pSfManII-5', several independent transformants were sequenced, and the BglII-XhoI fragment from a representative clone was excised and gel-purified. In parallel, the XhoI-DraI fragment of the partial α-mannosidase II cDNA clone from the Sf9 library was subcloned into a modified form of pBSKS™+ (pBSDK/BS in FIG. 5B) to produce pSfManII-3'. Finally, the full-length Sf9 α-mannosidase II cDNA was assembled by inserting the BglII-XhoI fragment of pSfManII-5' into BglII-XhoI-digested pSfManII-3' to produce pSfManII, as shown in FIG. 5B. The complete sequence of the Sf9 α-mannosidase II cDNA was assembled and analyzed using version 8.1 of the University of Wisconsin Genetics Computer Group software package (Program Manual for the Wisconsin Package, Version 8.1, Genetics Computer Group, Madison, Wis.).

The assembled full-length open reading frame of the Sf9 α-mannosidase II cDNA, together with 176 bp of 5' and 179 bp of 3' sequence, is shown in SEQ ID NO:3. The 3393 bp open reading frame encodes a polypeptide of 1130 amino acids (SEQ ID NO:4) with a 37% identity to murine Golgi α-mannosidase II (Moremen and Robbins, 1991). The first in-frame ATG in the long open reading frame is preceded by a purine at the critical −3 position, suggesting that it serves as the translation initiation site (Kozak, 1983, 1986a). Hydropathy analysis (Kyte and Doolittle, 1982) revealed a potential transmembrane domain between amino acids 14 and 34 and predicted a type II transmembrane topology similar to all other cloned Golgi processing hydrolases and glycosyltransferases (Paulson and Colley, 1989, Lowe, 1991; Moremen et al., 1994). In addition, the putative Sf9 α-mannosidase protein would have seven potential N-glycosylation sites.

The protein encoded by the Sf9 α-mannosidase cDNA was compared to the protein sequences of other class II α-mannosidases. An optimized multiple sequence alignment was generated using the Pileup and Boxshade subroutines, as described above. Protein sequences included in the alignment were the yeast vacuolar mannosidase (Yoshihisa and Anraku, 1989; Accession no. M29146), rat ER α-mannosidase (Bischoff et al., 1990; Accession no. M57547), *Dictyostelium discoideum* lysosomal α-mannosidase (Schatzle et al., 1992; Accession no. M82822), human lysosomal (α-mannosidase (Nebes and Schmidt, 1994, Accession no. U05572), mouse α-mannosidase II (Moremen and Robbins, 1991; Accession no. X61172), human α-mannosidase II (Misago et al., 1995; Accession no. U31520), human α-mannosidase II$^x$ (Misago et al., 1996; Accession no. D55649), Drosophila α-mannosidase II (Foster et al., 1995; Accession no. X77652), and Sf9 α-mannosidase II (SEQ ID NO:4).

Figure 6:
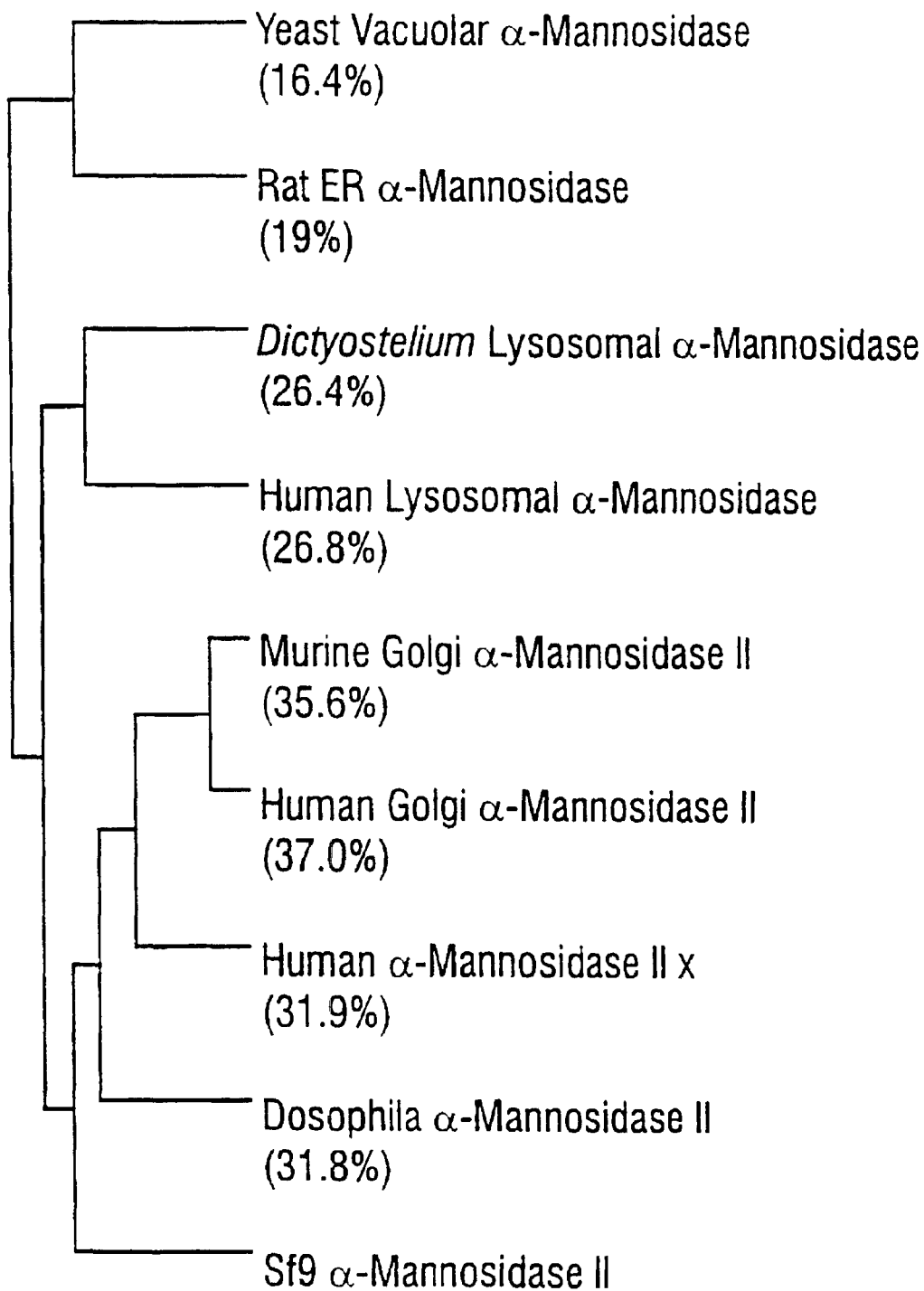
FIG. 6. A dendogram of the α-mannosidase polypeptide sequences generated with the Pileup subroutine as described in Example 6. The numbers in parentheses represent the percent identity of the indicated sequence to the Sf9 α-mannosidase II polypeptide.

The protein encoded by the Sf9 α-mannosidase cDNA has extensive amino acid sequence similarity to a subclass of the class II mannosidases (Moremen et al., 1994). This subclass is typified by the mammalian Golgi glycoprotein processing enzyme, α-mannosidase II, and a recently cloned homolog, α-mannosidase II$^x$ (Misago et al., 1995; FIG. 6). The regions of lowest sequence similarity are localized to the NH$_2$ terminal 124 amino acids of the Sf9 α-mannosidase polypeptide, which encode the putative cytoplasmic tail, transmembrane domain, and "stem region". These regions were previously shown to be unessential for the catalytic activity of mammalian α-mannosidase II (Moremen et al., 1991), indicating that there would be little selective pressure to maintain their primary sequences during evolution. Surprisingly, the predicted Sf9 α-mannosidase protein is more similar to the mammalian x-mannosidase II proteins than to the putative α-mannosidase II protein encoded by a cDNA recently isolated from Drosophila (Foster et al., 1995).

Using the same general methodology described above, an α-mannosidase I cDNA was isolated from Sf9 cells (Examples 15 through 19 below). The nucleic acid sequence is shown in SEQ ID NO:1, and the amino acid sequence is shown in SEQ ID NO:2.

EXAMPLE 7

Southern Blotting Analysis of the Sf9 α-mannosidase II Gene

Southern blotting analyses were done to examine the structure of the Sf9 α-mannosidase II gene and its relationship to α-mannosidase II genes from other insects and higher eukaryotes. Genomic DNA from the lepidopteran insect cell lines Sf9, Sf21, High Five, Ea, Bm, and Md and from a mammalian cell line COS was isolated by a standard method (Sambrook et al., 1989). Twenty micrograms of the genomic DNA samples were digested with HindIII, which does not cut the Sf9 α-mannosidase II cDNA, or with PstI, which cuts this cDNA five times, and the digests were resolved on a 1% agarose gel.

The DNA was transferred to a positively charged nylon filter (Zetaprobe™; Bio-Rad Laboratories, Hercules, Calif.) under alkaline conditions (Southern, 1975; Reed and Mann, 1985) and the filter was prehybridized for at least one hour at 68° C. in a buffer containing 1.5×SSPE (15 mM NaPO$_4$, pH 7.0; 270 mM NaCl, and 15 mM EDTA), 1% (w/v) sodium dodecyl sulfate (SDS), 0.5% (w/v) nonfat dry milk, and 150 μg/ml of sheared salmon sperm DNA (Sigma). High stringency hybridizations were done overnight at 68° C. in the same buffer with a twice gel-purified, random primer-labeled (Feinberg and Vogelstein, 1983), XhoI-DraI fragment of the Sf9 α-mannosidase II cDNA clone (FIG. 5A). After hybridization, the filters were washed for 15 min at room temperature with 2×SSC plus 0.1% SDS, then with 0.5×SSC plus 0.1% SDS, then with 0.1×SSC plus 0.1% SDS, and finally, for 30 min with 0.1×SSC plus 1% SDS that had been prewarmed to 50° C. For low stringency hybridizations, the hybridization temperature was reduced to 55° C. and the last wash was done at room temperature. After washing, the filters were sealed in plastic bags and exposed to Kodak (Rochester, N.Y.) X-OMAT AR™ film with Fisher (Pittsburgh, Pa.) intensifying screens for various times at −85° C.

The HindIII digests of DNA from Sf9, Sf21, Bm, and Md cells produced single bands with similar hybridization intensities, suggesting that these cells have single copy, closely related α-mannosidase II genes. PstI digests of DNA from these four cell lines produced identical multiple banding patterns (there were only four bands because two of the six expected PstI fragments were too small to be retained by the gel) with similar hybridization intensities, supporting the idea that they all have closely related α-mannosidase II genes. By contrast, HindIII and PstI digests of genomic DNA from High 5 and Ea cells produced different banding patterns and weaker hybridization signals, suggesting that the α-mannosidase II genes in these cell lines differ from the α-mannosidase II genes in the former cell lines. This conclusion was supported by the Southern blotting results obtained after digesting genomic DNA from Sf9, High 5, and Ea cells with six different enzymes (EcoRI, HindIII, PstI, SspI, StyI and XbaI), which revealed significant differences in the restriction maps of the α-mannosidase II genes in these cell lines. The Sf9 probe failed to hybridize with DNA from COS cells, indicating that the Sf9 α-mannosidase II gene is less closely related to the α-mannosidase II genes in these mammalian cells than it is to the α-mannosidase II genes in the various lepidopteran insect cell lines. When the blots were stripped and rehybridized under lower stringency, the hybridization signals obtained with DNA from the various lepidopteran insect cells were approximately equal, but no hybridization was detected with COS cell DNA.

The nearly full-length Sf9 α-mannosidase II probe also was used for low stringency hybridizations on Southern blots of HindIII and PstI digests of genomic DNA from insects belonging to the Orders Lepidoptera (*H. virescens* and *H. zea*), Coleoptera (*T. molitor*), Orthoptera (*S. gregaria*), Blattaria (*B. discoidalis*), and Diptera (*D. melanogaster*), and from *Xenopus laevis*. The results showed that the probe hybridized with DNA from two different lepidopteran insects, *Heliothis virescens* (tobacco budworm) and *Helicoverpa zea* (corn earworm), but the hybridization signal was weaker and the digestion patterns were different, when compared to the Sf9 cell controls. The Sf9 α-mannosidase II probe failed to detectably hybridize to any non-lepidopteran insect DNA, including beetle (Coleoptera), locust (Orthoptera), cockroach (Blattaria), and fruitfly (Diptera), or to frog (Xenopus) DNA. These results supported the idea that the Sf9 α-mannosidase II gene is more closely related to the α-mannosidase II genes of other lepidopteran insects than to these same genes in animals outside of the Order Lepidoptera.

EXAMPLE 8

Transcription of the Sf9 α-mannosidase II Gene

Initially, Northern blotting was used to try to examine transcription of the Sf9 α-mannosidase II gene in uninfected and baculovirus-infected Sf9 cells, but this approach failed even using 20 mg of poly A+RNA, despite being able to obtain specific RT-PCR™ products from these RNAs. Therefore, the inventors turned to the use of a more sensitive technique, ribonuclease protection (Lee and Costlow, 1987), with a 431 bp antisense riboprobe consisting of 19 bp of vector sequence followed by 412 bp of sequence from the middle of the Sf9 α-mannosidase II cDNA (positions 966–1384 in SEQ ID NO: 3).

Sf9 cells were grown in 500 ml spinner flasks (Bellco Glass Co., N.J.) to a density of 1×10⁶ cells per ml and either mock-infected or infected with wild-type baculovirus (*Autographa californica* multicapsid nuclear polyhedrosis virus) at a multiplicity of five plaque-forming units per cell. After adsorption for one hour at 28° C., the cells were separated from the inoculum by low speed centrifugation, gently resuspended in 500 ml of TN-MFH medium supplemented with 10% serum, antibiotics, and pluronic F68, and returned to the spinner flask. Total RNA either was extracted immediately from the mock-infected cells or was extracted 12, 24, or 48 h later from the infected cells and used to isolate poly A+RNA, as described in Example 6.

Twenty microgram samples of each mRNA preparation were analyzed by RNase protection assays using a commercial kit according to the manufacturer's instructions (Ambion, Inc., Austin Tex.). The riboprobe for these assays was synthesized in vitro with T7 RNA polymerase (Melton et al., 1984) and [α-$^{32}$P]-GTP (800 Ci/mmol; DuPont NEN, Boston, Mass.) using a commercial kit (Ambion) according to the manufacturer's instructions. The DNA template for the transcription reactions was pSfManIIDBst, a derivative of pSfManII (FIG. 5B), linearized at the PmlI site. Transcription of this template produced a 431 bp antisense RNA consisting of 19 bp from the vector followed by 412 bp beginning at the BstXI site and ending at the PmlI site of the Sf9 α-mannosidase II cDNA (positions 1384 and 966, respectively, in SEQ ID NO: 3). Protected fragments were analyzed on 5% acrylamide-7M urea gels, as described previously (Jarvis, 1993b), and the gels were dried and exposed to Kodak X-OMAT AR™ film with intensifying screens for various times at −85° C.

The results showed that RNA from mock-infected Sf9 cells protected a 412 bp fragment of the probe, indicating that the α-mannosidase II gene is expressed in these cells. The steady state levels of β-mannosidase II-specific RNA must be very low, since no protection was detected in assays with 20 μg of total RNA and large amounts (10 μg) of poly A+RNA produced only a relatively weak signal. The signals observed with poly A+RNA from infected cells were even weaker than the signal obtained from uninfected cells and little, if any, protection was observed with RNA from cells infected for 48 hours. Ethidium bromide staining of the poly A+RNA samples used for this study indicated that equal amounts had been loaded, suggesting that steady state levels of Sf9 α-mannosidase II RNA are reduced by baculovirus infection.

EXAMPLE 9

In vitro Translation and Processing of the Sf9 α-mannosidase II Protein

To obtain further evidence that the Sf9 α-mannosidase II open reading frame encodes a protein, a plasmid construct containing the Sf9 α-mannosidase II cDNA was linearized, transcribed in vitro, and the resulting RNA was used for in vitro translation studies. For these studies, the full-length Sf9 α-mannosidase II open reading frame was subcloned downstream of an SP6 promoter in the plasmid pGem7Zf+™ (Promega) to produce pGemSfManII. RNA was synthesized in vitro from XbaI-linearized pGemSfManII as described above, except SP6 RNA polymerase was used instead of T7 RNA polymerase and the [α-$^{32}$P]-GTP was replaced by nonradioactive rGTP.

A portion of the in vitro transcribed RNA was used for in vitro translation reactions in a rabbit reticulocyte lysate (Promega) in the presence or absence of canine pancreatic microsomal membranes (Blobel and Dobberstein, 1975; Promega), as described previously (Moremen and Robbins, 1991). Subsequently, translation reactions were treated with water, 100 mg/ml trypsin, or trypsin plus 0.1% (v/v) Nonidet-P40 (Zilberstein et al., 1980), as described previously (Moremen and Robbins, 1991). The reaction products were acetone-precipitated and the precipitates were dried, redissolved in protein disruption buffer [50 mM Tris-HCl, pH 6.8; 4% (w/v) SDS; 4% (v/v) β-mercaptoethanol], and heated at 65° C. for 10 min. Total solubilized proteins were analyzed by SDS-PAGE using the discontinuous buffer system (Laemmli 1970) and the gels were fluorographed with Autofluor (National Diagnostics, Atlanta, Ga.), dried, and exposed to Kodak X-OMAT AR™ film at −85° C.

The results showed that a protein of about the expected size was produced when a rabbit reticulocyte lysate was primed with Sf9 α-mannosidase II RNA. Several additional lower molecular weight proteins were also observed, which had been seen previously in translations of murine cc-mannosidase II cDNA (Moremen and Robbins, 1991), and might be explained by premature translational termination or degradation of the full-length product. When translations were done in the presence of canine pancreatic microsomal membranes, a new product was observed that was larger than the largest product translated in the absence of microsomes. Unlike the smaller products, this one was not degraded by subsequent trypsin treatment, but was converted to a slightly smaller form.

This result indicated that the majority of the protein was oriented towards the lumen of the microsomes, where it was protected from trypsin as a result of co-translational translocation during synthesis. In support of this conclusion, this product was completely degraded when trypsin treatments were performed in the presence of a nonionic detergent to solubilize the membranes. The larger size of the translation product prior to proteolysis also suggested that one or more of the potential N-glycosylation sites are utilized during synthesis. Together, these results indicate that the Sf9 α-mannosidase II cDNA encodes a protein with the characteristics of a type II membrane glycoprotein.

EXAMPLE 10

Expression of the Sf9 α-mannosidase II Protein in the Baculovirus System

In vivo evidence that the Sf9 α-mannosidase II cDNA encodes a protein was obtained by using a recombinant baculovirus to express the cDNA under the control of the strong polyhedrin promoter in infected Sf9 cells. A standard method was used to isolate a recombinant baculovirus containing the Sf9 α-mannosidase II cDNA (Summers and Smith, 1987; O'Reilly et al., 1992). The intact Sf9 c-mannosidase II open reading frame was excised from pSfManII and subcloned into the baculovirus transfer vector, pVL1392 (Webb and Summers, 1990). The resulting plasmid, in which the Sf9 α-mannosidase II cDNA was positioned downstream of the strong polyhedrin promoter, was mixed with wild type viral DNA and the mixture was used to cotransfect Sf9 cells by a modified calcium phosphate precipitation method (Summers and Smith, 1987). Viral progeny were harvested five days after transfection and resolved by plaque assay in Sf9 cells, as described previously (Summers and Smith, 1987). Recombinants were identified by their occlusion-negative plaque phenotypes and taken through two additional rounds of plaque-purification. Virus stocks were prepared and titered by plaque assay in Sf9 cells and stored frozen in the dark at −85° C. (Jarvis and Garcia, 1994).

The procedures used for baculovirus infections and analysis of recombinant protein biosynthesis have been described previously (Jarvis and Summers, 1989; Jarvis et al., 1991). Briefly, Sf9 cells were seeded into 6-well plates (Corning Glass Works, Corning, N.Y.) at a density of $1 \times 10^6$ cells per well, mock-infected or infected at a multiplicity of about 5 plaque-forming units per cell, and incubated at 28° C. until 24, 36, 48, or 72 h postinfection. At these time points, the cells were gently squirted off the plastic into the medium, pelleted, 0.5 ml of protein disruption buffer was added, and the cell pellets were triturated through a 1 ml syringe equipped with a 22 ga needle. The sheared lysates were boiled for 3 min, total solubilized proteins were resolved by SDS-PAGE, and the gels were stained with Coomassie Brilliant Blue, destained, and photographed.

Figure 7A:
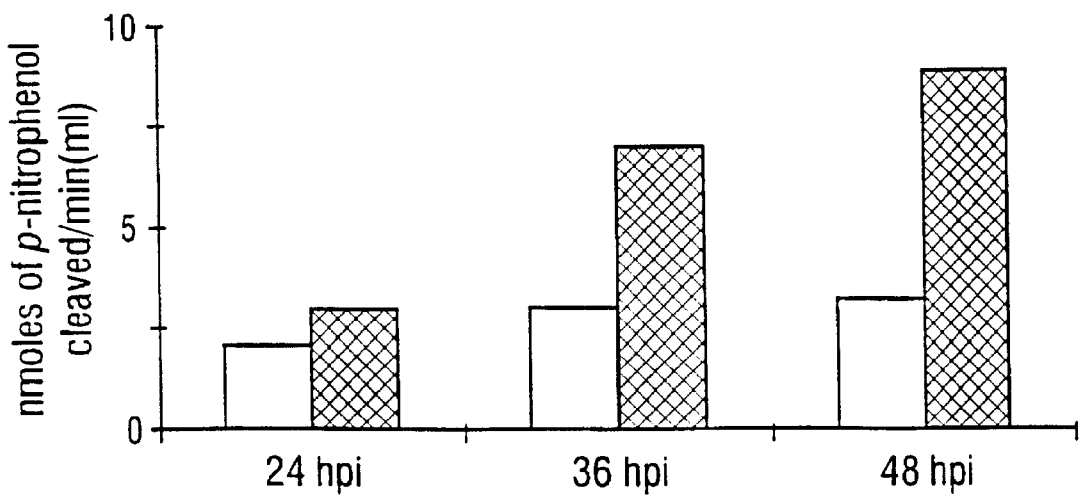
FIG. 7A and FIG. 7B. Enzymatic activity of the Sf9 α-mannosidase II protein in baculovirus-infected Sf9 cells.
Figure 7B:
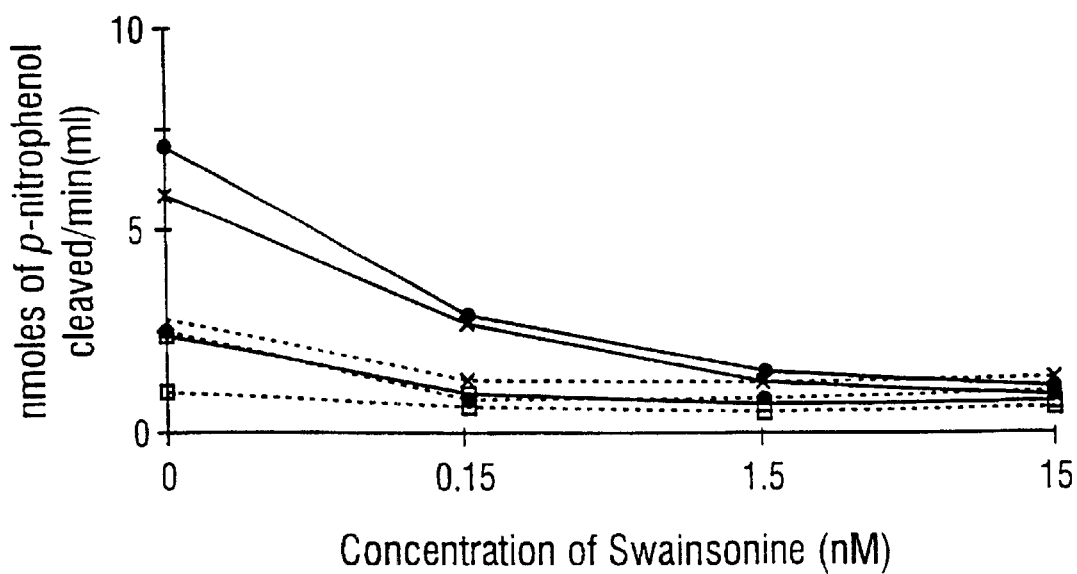

SDS-PAGE analysis of total protein lysates of Sf9 cells infected for 48 or 72 h with this recombinant virus revealed large amounts of a new protein of about the expected size, which was not detected in mock or wild-type virus-infected lysates at any time after infection. This result, together with the kinetics of appearance and accumulation of this protein during recombinant baculovirus infection, suggested that this protein is the product of the Sf9 α-mannosidase II cDNA. Evidence that the protein encoded by the Sf9 α-mannosidase II cDNA is actually an ac-mannosidase II was obtained by biochemical activity assays with p-nitrophenyl-α-D-mannopyranoside as the substrate (FIG. 7A and FIG. 7B).

Sf9 cells were infected with wild-type or recombinant baculoviruses were harvested by centrifugation at various times after infection, and pellets containing $1 \times 10^6$ cells were resuspended in 100 µl of assay buffer (0.1 M MES, pH 6.3; 0.5% Triton-X-100). The cell suspensions were assayed for o-mannosidase activity by mixing 25 µl of the cell extracts with 25 µl of 10 mM p-nitrophenyl α-D-mannopyranoside in the presence or absence of various concentrations of swainsonine. The reaction mixtures were incubated in a microtiter plate for 1 hr at 37° C. with gentle agitation, then quenched by the addition of 200 µl of stop solution (133 mM glycine, 67 mM NaCl, 83 mM $Na_2CO_3$). Absorbance was measured at 410 nm on a plate reader (Dynatech Model MR 5000), corrected for light scattering at 570 nm, and the corrected absorbance values were converted to nmol p-nitrophenol using a standard curve produced on the same plate reader.

Extracts from Sf9 cells infected with the recombinant baculovirus clearly contained higher levels of pNP-α-mannosidase activity than extracts from wild-type virus-infected controls. The levels of α-mannosidase activity increased with increasing time of infection with the recombinant, but not the wild type virus. The putative SfManII protein accumulated in the recombinant virus-infected cells to levels that could be detected by SDS-PAGE and Coomassie blue staining of total cell lysates prepared at 48 hr postinfection. At this very late time after infection, the overexpressed protein had low specific activity. However, this was not unexpected, as previous studies have shown that production of enzymatically active secretory pathway proteins in the baculovirus system is inefficient due to adverse effects of virus infection on host cell secretory pathway function (Jarvis and Summers, 1989; Example 5). Finally, the α-mannosidase activity detected in the recombinant baculovirus-infected cell extracts was sensitive to swainsonine, a known inhibitor of class II α-mannosidases (Moremen et al., 1994).

EXAMPLE 11

Construction of Immediate Early Baculovirus Vectors Containing a β1,4-galactosyltransferase cDNA A bovine β1,4-galactosyltransferase cDNA was subcloned into two different immediate early baculovirus transfer vectors. A full-length cDNA encoding the short protein isoform of bovine β1,4-galactosyltransferase (Harduin-Lepers et al., 1993; Russo et al., 1992) was excised from pSP65 (Promega Corp., Madison, Wis.) and the resulting 1.5 Kb BamHI fragment was gel-purified, recovered, and inserted into the unique BamHI or BglII sites of the immediate early transfer vectors pAcP(−)IE1TV2 and pAcP(+) IE1TV3, respectively (Example 1).

The resulting plasmids (FIG. 8A and FIG. 8B) contained the β1,4-galactosyltransferase cDNA under the control of the viral ie1 promoter, which is active immediately after the virus enters the cell. These plasmids also included the Autographa californica nuclear polyhedrosis virus (AcMNPV) hr5 enhancer to maximize iel-mediated transcription (Guarino et al., 1986; Rodems and Friesen, 1993) and upstream and downstream flanking sequences from the AcMNPV polyhedrin gene to target the new DNA sequences to this nonessential region of the viral genome (Smith et al., 1983a). The major differences between these two plasmids were the presence or absence of the polyhedrin open reading frame, which determines whether recombinant viruses will be occlusion positive or negative, and the orientation of the iel-β1,4-galactosyltransferase sequence with respect to other viral DNA sequences.

EXAMPLE 12

Expression of β1,4-galactosyltransferase Activity

Figure 8A:
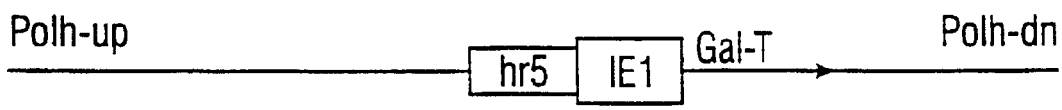
FIG. 8A and FIG. 8B. Genetic structures of the plasmids used to produce immediate early recombinant baculoviruses.
Figure 8B:
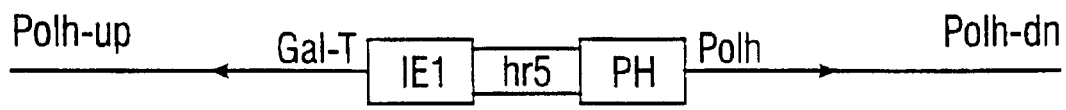

The two plasmids shown in FIG. 8A and FIG. 8B were used to produce recombinant baculoviruses and the ability of these viruses to produce β1,4-galactosyltransferase activity during infection of Sf9 cells was examined as described below. The resulting plasmids, pAcP(−)IE1GalT and pAcP(+)IE1GalT (FIG. 8A and FIG. 8B), were mixed with AcMNPV viral DNA or Bsu36I-digested BakPak6 viral DNA (Kitts and Possee, 1993), respectively, and the mixtures were cotransfected onto Sf9 cells using a modified calcium phosphate precipitation method (Summers and Smith, 1987; O'Reilly et al., 1992). Several days later, the growth media were recovered from the cotransfected cells, progeny viruses were resolved by plaque assay on Sf9 cells, and recombinant viruses were visually identified by their distinctive plaque phenotypes. This was straightforward because the occlusion negative recombinant, AcP(−) IE1GalT, was derived from an occlusion-positive parent (AcMNPV) and the occlusion positive recombinant, AcP(+) IE1GalT, was derived from an occlusion-negative parent (BakPak6). Putative recombinants were plaque-purified twice more, passaged once, and screened for the production of β1,4-galactosyltransferase activity.

Cell extracts were assayed for β1,4-galactosyltransferase activity by adapting previously described methods (Berger et al., 1986; Whiteheart et al., 1989). Briefly, Sf9 cells were grown to a density of about $2.5 \times 10^6$ in 25 cm$^2$ flasks (Corning Glass Works, Corning, N.Y.) and mock-infected or infected at a multiplicity of about 5 plaque-forming units per cell. After a 1 hr adsorption period at 28° C., the inocula were removed and the cells were rinsed and fed with fresh medium. The flasks were incubated for various times at 28° C., then the cells were dislodged and pelleted in a clinical centrifuge (IEC Model HN-SII; Needham Heights, Mass.). The cells were washed with cold Tris-buffered saline (25 mM Tris-HCl, pH 7.4; 140 mM NaCl), resuspended in cold assay buffer (10 mM HEPES, pH 7.4; 140 mM NaCl; 5 mM MnCl$_2$, and 0.5% NP40), and frozen at −85° C. The frozen extracts were slow-thawed, clarified for 10 min in a microcentrifuge (Fisher Model 235C; Fisher Scientific Co., Pittsburgh, Pa.), and total protein concentrations in the supernatants were measured using the bicinchoninic acid method (Smith et al., 1985; Pierce Chemical Company; Rockford, Ill.) with BSA as the standard.

Triplicate samples of the clarified extracts, each containing 100 μg of protein, were assayed for β1,4-galactosyltransferase activity in a total volume of 0.11 ml of fresh assay buffer containing 0.3 μCi of uridine diphosphate [6-$^3$H] Gal (15 Ci/mmol; American Radiolabeled Chemicals, Inc.; St. Louis, Mo.) and 450 μg/ml of ovalbumin (Grade V, Sigma). After 1 hr at 37° C., the reaction mixtures were quenched with 0.4 ml of cold assay buffer and spotted onto glass fiber filters (Whatman GF/D; Hillsboro, Oreg.). The filters were dried and washed once with cold 10% (w/v) trichloroacetic acid, twice with cold 5% (w/v) trichloroacetic acid, and once with cold 95% (v/v) ethanol, then the filters were redried, placed in vials containing liquid scintillation cocktail (Packard UltimaGold; Meriden, Conn.), and radioactivity was measured in a liquid scintillation counter (Beckman Model LS6000-IC; Fullerton, Calif.).

Figure 9:
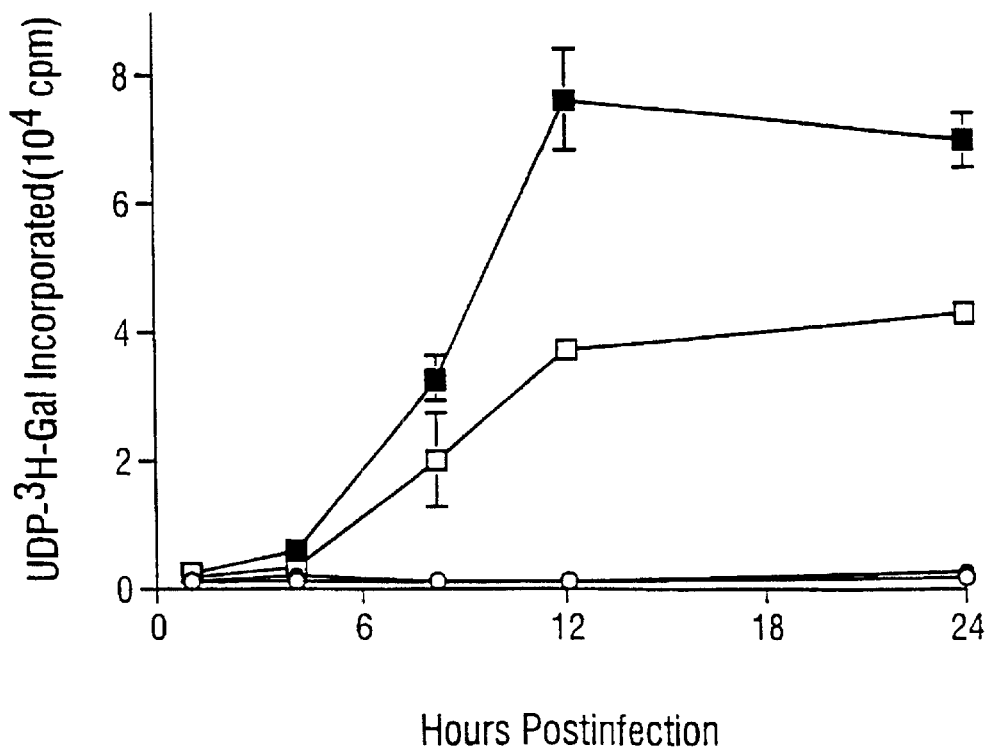
FIG. 9. Expression of β1,4-galactosyltransferase activity by immediate early recombinant baculoviruses. Sf9 cells were mock-infected (open circles) or infected with wild type AcMNPV (closed circles), AcP(−)IE1GalT (open squares), or AcP(+)IE1GalT (closed squares), and cell extracts were prepared at various times after infection. Triplicate samples of each extract were assayed for β1,4-galactosyltransferase activity as described in Example 2. The results were plotted as average $^3$H-galactose counts per minute (cpm) incorporated versus time of infection with standard errors indicated by the bars. The absence of error bars for some time points indicates that the margin of error is too small to be indicated on the present scale.

No activity was detected in extracts from mock- or wild type AcMNPV-infected cells, but activity was detected in extracts from recombinant virus-infected cells beginning at 4 hr postinfection and rising to a plateau at 12 hr postinfection (FIG. 9). These results were similar to those observed with analogous recombinants expressing E. coli β-galactosidase, chloramphenicol acetyltransferase, human tissue plasminogen activator, or Sf9 α-mannosidase II under iel control (Examples 2–5).

EXAMPLE 13

Modification of the Insect Cell N-glycosylation Pathway

The inventor contemplated that the novel immediate early recombinant baculoviruses could be used to modify the N-linked oligosaccharide processing capabilities of lepidopteran insect cells. The strategy was to use the viral iel promoter (Jarvis et al., 1996) to express a bovine β1,4-galactosyltransferase cDNA (Harduin-Lepers et al., 1993; Russo et al., 1992) early in infection and determine if this enzyme could contribute to the insect cell N-glycosylation pathway and modify a foreign glycoprotein synthesized later in infection.

The gp64 protein is the major structural glycoprotein in progeny virions that bud from the surface of AcMNPV-infected cells (Volkman, 1986). Biosynthesis of AcMNPV gp64 peaks at 24 hr postinfection and at least one of its N-linked oligosaccharide side chains is processed to an endo-β-D-N-acetylglucosaminidase H-resistant form (Jarvis and Garcia, 1994), but it contains no galactose (Jarvis and Finn, 1995). Thus, if gp64 from recombinant virions contained galactose, this would indicate that the β1,4-galactosyltransferase encoded by the recombinant virus had contributed to the host cell processing pathway and extended one or more of the N-linked oligosaccharide side chains on gp64.

Sf9 cells were grown to a density of about $1 \times 10^6$ cells per ml in 100 ml spinner flasks (BelIco Glass Inc., Vineland, N.J.) and infected with wild-type or recombinant baculovirus at a multiplicity of about 4 plaque-forming units per cell. At 48 hr postinfection, the infected cells were harvested, pelleted, and progeny budded virus particles were partially purified from the cell-free supernatant as described previously (Jarvis and Garcia, 1994). The budded virus preparations were treated for 10 min on ice with cold extraction buffer [50 mM Tris, pH 8.0; 100 mM NaCl, 1% (v/v) NP40, 0.2 mM leupeptin], the extracts were clarified in a microcentrifuge (Fisher Model 235C).

The gp64 protein was immunoprecipitated from the supernatants with a monoclonal antibody (AcV1; 54) as described previously (Jarvis and Summers, 1989). The immunoprecipitates were washed, disrupted, resolved by discontinuous SDS-PAGE (Laemmli, 1970), and proteins were transferred to Immobilon™ membranes (Millipore Corp.; Bedford, Mass.). The membranes were cut into strips corresponding to individual lanes and the strips were probed with either digoxigenylated lectins (Boehringer Mannheim Biochemicals; Indianapolis, Ind.) or rabbit anti-gp64, as described previously (Jarvis and Finn, 1995). Bound lectins or antibodies were detected by secondary reactions with alkaline phosphatase-conjugated anti-digoxigenin (Boehringer) or alkaline phosphatase-conjugated goat anti-rabbit IgG (Sigma), respectively, followed by an alkaline phosphatase color reaction (Blake et al., 1984). For some lectin blotting studies, gp64 was pretreated with peptide:N-glycosidase F (New England Biolabs, Beverly, Mass.) as described previously (Jarvis and Finn, 1995).

Figure 10A:
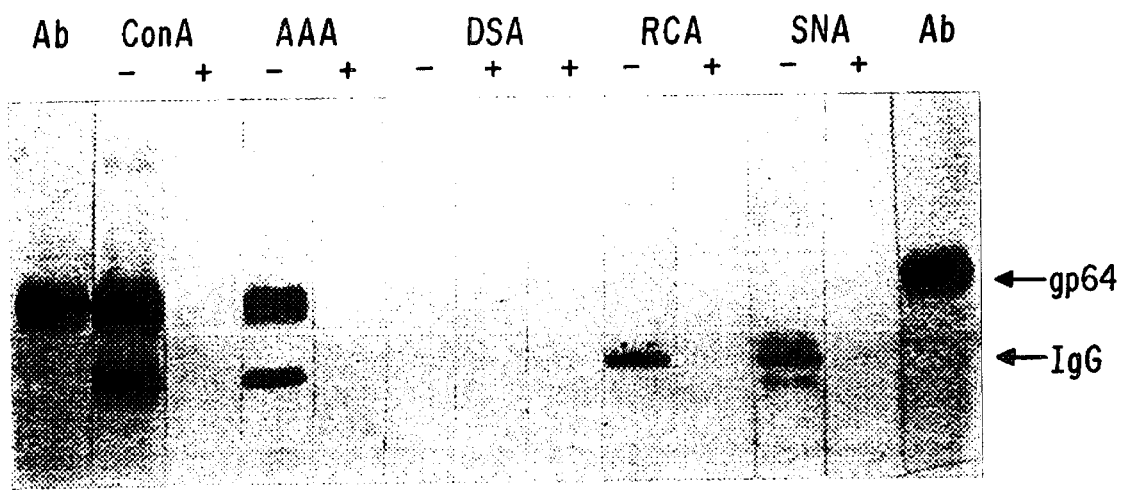
FIG. 10A and FIG. 10B. Modification of the insect cell N-glycosylation pathway by an immediate early recombinant baculovirus.
Figure 10B:
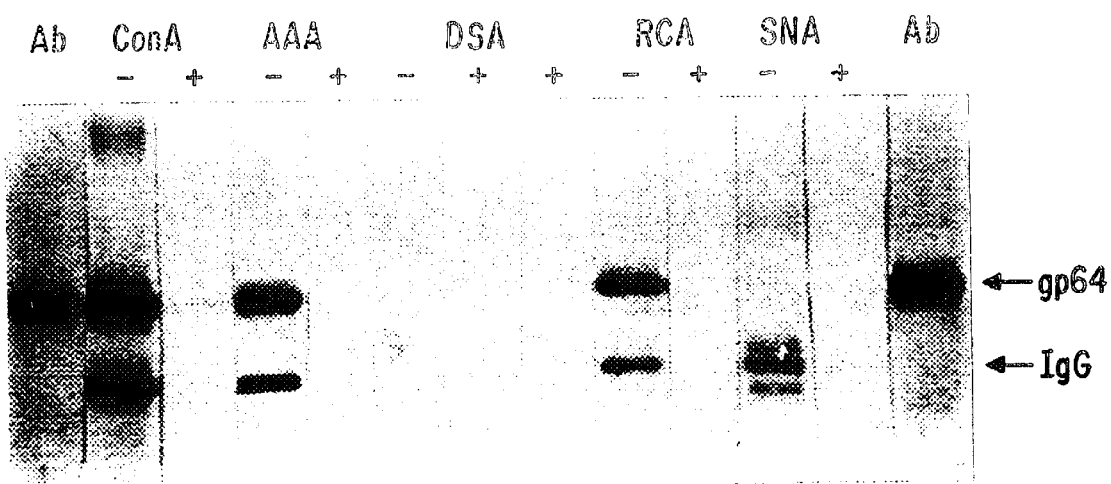
Figure 11:
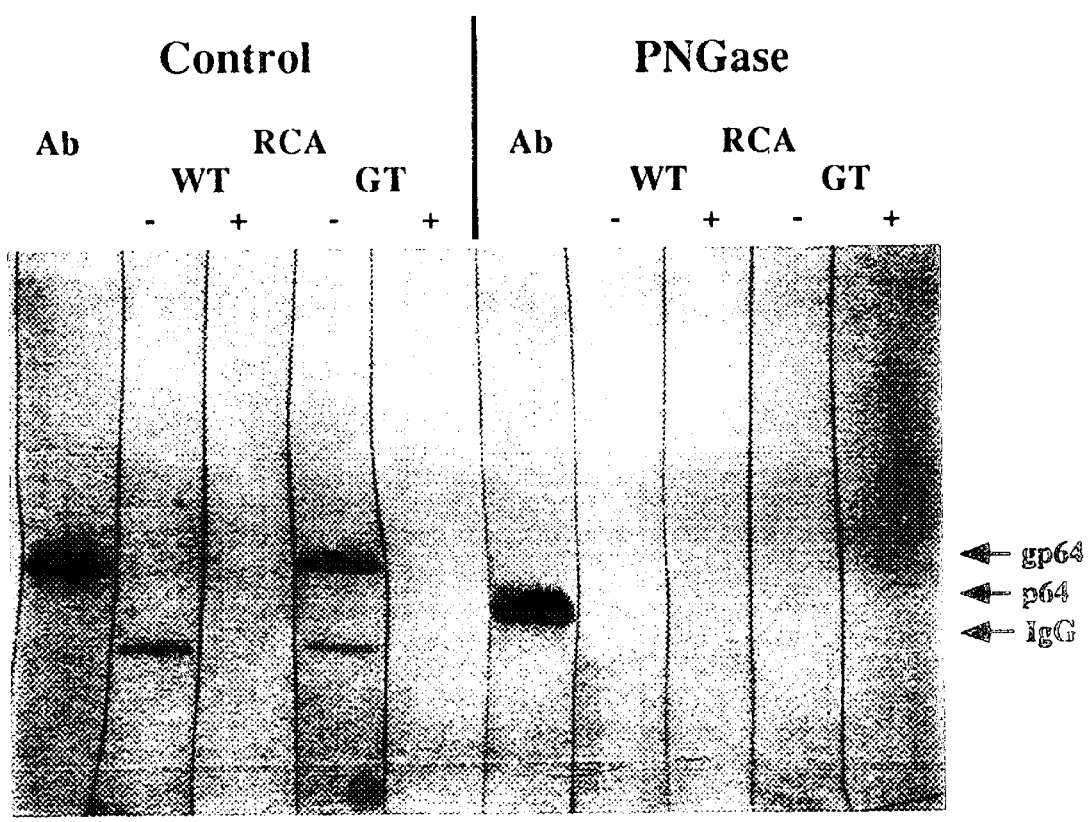
FIG. 11. Linkage of galactose-containing oligosaccharides on gp64 from recombinant virions. gp64 was isolated from either wild type AcMNPV (WT) or AcP(+)IE1GalT (GT) virions and treated with buffer (Control) or peptide:N-glycosidase F (PNGase) as described in Example 3. The reaction products were resolved by SDS-PAGE and analyzed by either immunoblotting with rabbit anti-gp64 (Ab) or RCA lectin blotting (RCA) in the absence (−) or presence (+) of competing galactose as described in the description of FIG. 10A and FIG. 10B. The arrows on the right indicate the positions of glycosylated gp64 (gp64), deglycosylated gp64 (p64), and IgG heavy chain (IgG).

Lectin blotting analyses showed that Ricinus communis agglutinin (RCA), which binds to β-linked galactose, bound strongly to gp64 from recombinant virions (FIG. 10B). Binding was carbohydrate-specific, as indicated by the inability of RCA to bind to gp64 from wild type virions (FIG. 10A) or to gp64 from recombinant virions when the reaction was done in the presence of competing galactose (FIG. 10B). RCA binding was not observed after pretreatment of gp64 from recombinant virions with peptide:N-glycosidase F, which showed that the galactose on gp64 was part of an N-linked oligosaccharide side chain (FIG. 11).

EXAMPLE 14

Influence of Galactose Addition on Glycoprotein Function

The AcMNPV gp64 protein plays a key role in baculovirus infection, serving as a fusogen which apparently mediates penetration of budded virus particles into the host cell during adsorptive endocytosis (Volkman, 1986; Blissard and Wenz, 1992; Volkman and Goldsmith, 1985; Volkman et al., 1986). This led to the question of whether galactosylation of gp64 and/or other virion glycoproteins influenced the growth of the immediate early recombinant virus.

Figure 12:
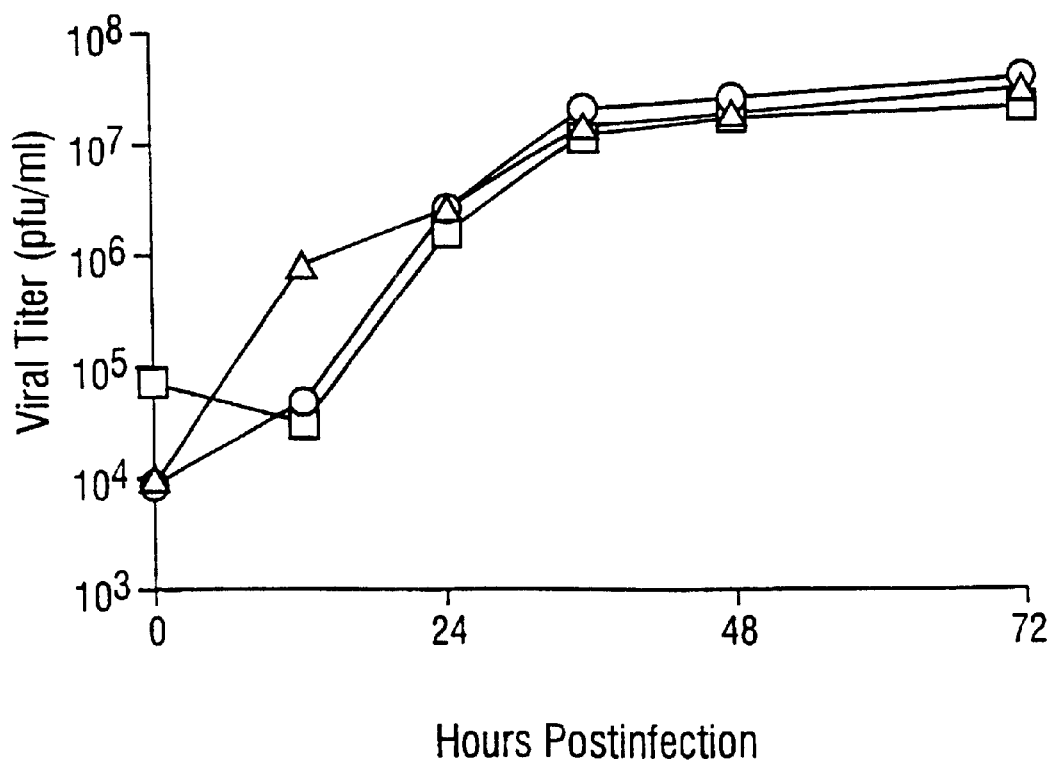
FIG. 12. Influence of galactosylation on glycoprotein function. One-step growth curves were done by infecting triplicate Sf9 cell cultures with wild-type AcMNPV (circles), AcP(+)IE1GalT (squares), or AcP(+)IE1βgal (triangles) at a multiplicity of infection of 5 plaque-forming units per cell. After a 1 hr adsorption period, the inocula were removed and the cells were washed and fed with fresh growth medium. At various times postinfection, the media from triplicate cultures were harvested, pooled, and clarified by low speed centrifugation. The supernatants were titered by TCID$_{50}$ assays on Sf9 cells and the data were converted to average plaque forming units (pfu) per ml and plotted against time of infection, as described in Example 4.

To address this question, the one-step growth curves of wild type AcMNPV and immediate early recombinants expressing β1,4-galactosyltransferase or β-galactosidase under ie1 control were compared. For the one-step growth studies, viral titers were determined by $TCID_{50}$ assays and the results were converted to plaque-forming units per ml using a Microsoft® Excel spreadsheet (Summers and Smith, 1987; O'Reilly et al., 1992). The results showed that there was no significant difference in the growth rates or numbers of infectious progeny produced by any of these viruses during in vitro infection of cultured Sf9 cells (FIG. 12).

EXAMPLE 15

Isolation and Characterization of an α1,2-Mannosidase cDNA from Sf9 Cells

The presence of different types of oligosaccharide side-chains is one source of functional and structural diversity in glycoproteins. During the past ten years, a large number of genes encoding the enzymes that modify N-linked glycans have been cloned and characterized (Moremen et al., 1994; Field and Wainwright, 1995). Glycoproteins acquire their N-linked oligosaccharide side-chains in the lumen of the endoplasmic reticulum (ER) by the transfer of a preassembled $Glc_3Man_9GlcNAc_2$ precursor from dolichol pyrophosphate to specific asparagine residues in the nascent polypeptide. These side-chains are then remodeled by the action of processing enzymes. In mammals, this involves trimming of the glucose residues and up to six of the nine mannose residues followed by the addition of fucose, N-acetylglucosamine, galactose, and sialic acid residues (reviewed by Kornfeld and Kornfeld, 1985). One part of this pathway that is being intensively investigated is trimming of the α1,2-linked mannose residues. Studies have shown that this is accomplished by a family of α1,2-mannosidases that act on glycoproteins in both the ER and Golgi apparatus (Moremen et al., 1994).

It is generally accepted that insect cells, like mammalian cells, can trim N-linked glycans and extend them by adding fucose and N-acetylglucosamine. However, data suggest that insect cells differ from higher eukaryotes by their inability to add antennary galactose or sialic acid to these side-chains (Marz et al., 1995). Insect cells clearly have α1,2-mannosidase activity involved in the trimming of N-linked glycans. This was demonstrated by the ability of 1-deoxymannojirimycin (dMNJ), a specific inhibitor of class I α-mannosidases, to block the processing of N-linked glycans on gp64, the major virion glycoprotein produced in baculovirus-infected lepidopteran cells (Jarvis and Garcia, 1994). More direct evidence was provided by Ren and coworkers (1995), who purified an enzymatically active α1,2-mannosidase from a membrane fraction of baculovirus-infected lepidopteran insect cells (Ren et al., 1995). Finally, a putative α1,2-mannosidase gene was recently cloned from Drosophila (Kerscher et al., 1995), although it was not proven that this gene actually encodes an active enzyme. Cloning and characterization of the genes encoding these enzymes from various organisms will help to elucidate the structural and functional relationships among these enzymes. The present Example details the cloning of an α1,2-mannosidase cDNA homolog from a lepidopteran insect cell-line Sf9 cDNA library.

This cDNA contains an open reading frame which encodes a 670 amino acid protein with a calculated molecular weight of 75,225 Da and, like other α1,2-mannosidases, is predicted to be a type II integral membrane protein with a short N-terminal cytoplasmic domain and a large C-terminal catalytic domain. This protein has two potential N-glycosylation sites, two consensus calcium binding sequences, and is predicted to be a type II integral membrane protein with a 22 amino acid transmembrane domain (residues 31 to 52). The amino acid sequence of this protein is 35–57% identical to Drosophila, human, murine and yeast α1,2-mannosidases. A transcript of approximately six kilobases was detected by Northern blot analysis of Sf9 mRNA. Genomic Southern blots probed with an intron-free fragment of the β1,2-mannosidase gene indicated that there are at least two copies or cross-hybridizing variants of this gene in the Sf9 genome. In vivo expression of the cDNA using a recombinant baculovirus produced a protein which released [$^3$H]mannose from [$^3$H]Man9GlcNAc. This activity required calcium, but not magnesium, and was inhibited by 1-deoxymannojirimycin. These results indicate that Sf9 cells encode and express an α1,2-mannosidase with properties similar to those of other eukaryotic processing α1,2-mannosidases.

A 675 bp fragment of an α1,2-mannosidase homolog was amplified by polymerase chain reaction (PCR™) from an Sf9 cDNA library in λ ZapII. Degenerate oligonucleotide 1 (GAYWSITTYTAYGARTAYYTIYTNAA; SEQ ID NO: 18) and degenerate oligonucleotide 2 (RTGNGCYTCNGTRTTRAA; SEQ ID NO: 19), corresponding to conserved amino acid sequences in yeast (Camirand et al., 1991) and rabbit (Lal et al., 1994) α1,2-mannosidases (Herscovics et al., 1994) were used to amplify a putative β1,2-mannosidase fragment from an Sf9 cDNA library in 1-ZAPII (Short et al., 1988; Stratagene, La Jolla, Calif.). The template for the polymerase chain reactions (PCRs™; Saiki el al., 1985) was 2.5 ml of a clarified λ-ZAPII plate lysate (5×10⁷ pfu/ml) prepared in SM buffer (50 mM Tris-HCl pH 7.5, 100 mM NaCl, 8 mM MgSO₄) and the reactions were done in a total volume of 50 ml containing final concentrations of 10 mM Tris-HCl (pH 8.3), 50 mM KCl, 1.5 mM MgCl₂, 0.2 mM dNTP's, 1.25 units of Taq polymerase, and 1 mM of each primer. PCRs™ were performed in a Perkin-Elmer thermal cycler (Perkin-Elmer Corp., Norwalk, Conn.) programmed for 5 min at 94° C. followed by 40 cycles of 1 min at 94° C., 1 min at 45° C., 3 min at 72° C., and a final extension of 7 min at 72° C.

The identity of the PCR™ amplimer as a putative α1,2-mannosidase fragment was confirmed by Southern blotting (Southern, 1975; Sambrook et al., 1989), with an end-labeled degenerate oligonucleotide (RTAIARRTAYTTIARIGTYTCIGCNA; SEQ ID NO: 20) designed against a third conserved amino acid sequence located between the two conserved regions used to design the PCR™ primers. The PCR™ amplimer was gel-purified, cloned into pBSKS+ (Stratagene), and sequenced using the chain termination method (Sanger et al., 1977).

The sequencing results were used to design exact-match oligonucleotide primers (SfManI+1310+ (GCATCATGTTCGACACG; SEQ ID NO: 21) and Sf ManI+1791-(GTGGTAGACGTTCACGAGAC; SEQ ID NO: 22); the numbers identify the position of the 5' end of the oligo with respect to the start of the Sf9 α1,2-mannosidase ORF, and the signs following these numbers indicate sense (+) or anti-sense (−)) to isolate an α1,2-mannosidase clone from the Sf9 cDNA library by sibling selection and PCR™, as described previously (Moremen, 1989; Example 6 above). The PCR™ reaction conditions were as described above except the annealing step was done at 54° C. instead of 45° C. The library was initially split into 22 subpools of 50,000 clones. A positive subpool of 50,000 was further split into 15 "daughter" subpools of 5,000 clones, and a positive subpool of 5,000 was finally split into 12 daughter subpools of 2,000 clones. A positive subpool of 2,000 was then screened by plaque hybridization (Benton and Davis, 1977) with the cloned PCR™ amplimer, which had been excised from the vector, gel-purified twice, and uniformly labeled with [α-³²P]dATP (Feinberg and Vogelstein, 1983).

A positive clone was identified and plaque purified once more. The cDNA was excised in vivo as a pBluescript-based subclone by coinfecting E. coli XLI-Blue (Stratagene) with this λ-ZAPII isolate plus M13-R408 helper phage. Double-stranded plasmid DNA was prepared and sequenced using the ABI PRISM™ Dye Terminator cycle sequencing method with AmpliTaq® DNA polymerase (Perkin-Elmer Corp.).

Figure 14:
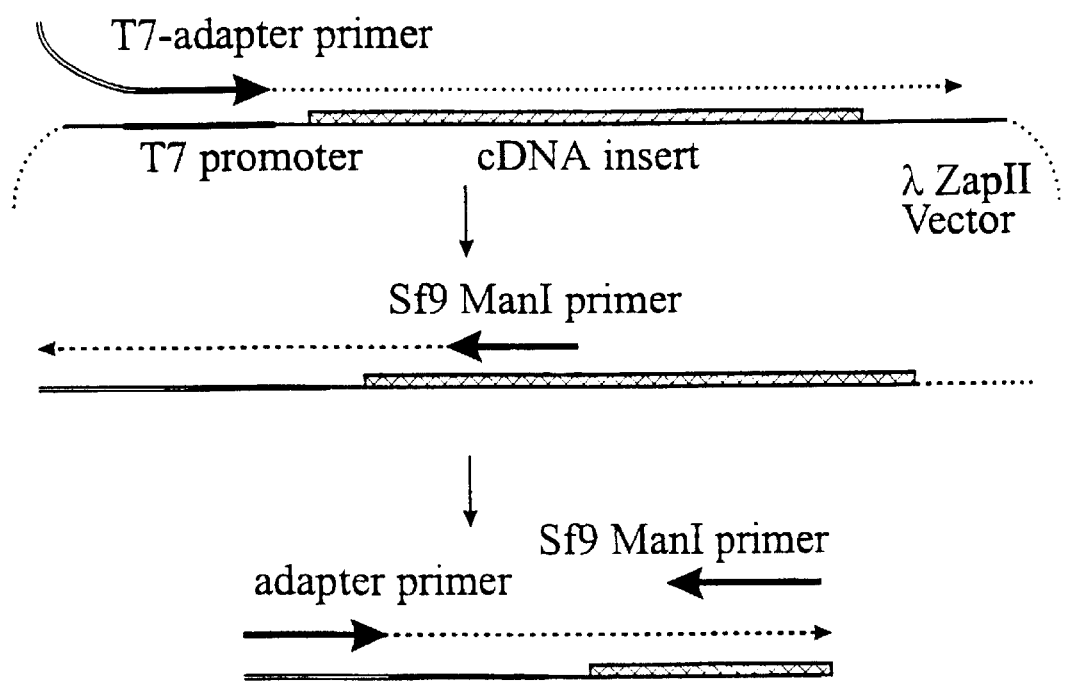
FIG. 14. Modified 5'-RACE procedure used to screen the Sf9 cDNA library for a full-length α1,2-mannosidase clone. T7-adapter primer (SEQ ID NO:23) is complementary to the T7 promoter sequence in the λ-ZAP II vector and also includes a 17-base adapter sequence at its 5' end. Sf9 ManI primer (SEQ ID NO:30) is complementary to an internal sequence near the 5' end of the partial Sf9 α1,2-mannosidase cDNA clone. Adapter primer (SEQ ID NO:24) consists of just the adapter sequence at the 5' end of the T7-adapter primer. In the first step, the T7-adapter primer anneals to the T7 promoter in the λ-ZAP II vector portion of every cDNA clone and is extended by Taq DNA polymerase. Next, the Sf9 ManI primer anneals only to those single-stranded DNAs derived from cDNA clones containing Sf9 α1,2-mannosidase sequences and is extended in the antisense direction. This generates a product that can be amplified with the adapter primer and Sf9 ManI primer, as shown in the last step. The size of the amplification product is determined by how far the cDNA sequence extends upstream of the position of the Sf9 ManI primer in the clone being amplified.

This initial cDNA clone lacked about 600 bp from the 5' end of the putative α1,2-mannosidase ORF. Hence, the 22 subpools (50,000 clones each) of the cDNA library were re-screened for a full-length clone using a modified 5' rapid amplification of cDNA ends (5'-RACE) procedure (Frohman et al., 1988), as outlined in FIG. 14. Briefly, a T7-adapter primer (TTGCGTCTACTGCAGTCTACGACTCACTATAGGGC; SEQ ID NO: 23) was designed to be complementary to the T7 promoter sequence in the λ-ZAP II vector and to include a 17-base adapter sequence at its 5' end. This primer could anneal to the T7 promoter sequence of every cDNA clone in the library. The other primers in the reaction were an Sf9 α1,2-mannosidase-specific primer (AAGTGAGCTCGCTTCGACAT; SEQ ID NO: 30) complementary to an internal sequence near the 5' end of the partial cDNA clone and a primer corresponding to the adapter sequence at the 5' end of the T7-adapter-primer. These two primers could anneal only to clones containing the Sf9 α1,2-mannosidase cDNA. The size of the amplimer produced by this procedure reveals the length of the cDNA sequence located upstream of the Sf9 α1,2-mannosidase-specific primer in the clone being amplified.

PCRs™ were done as described above with 54° C. for annealing and the following primer concentrations: 70 nM of the T7-adapter-primer (SEQ ID NO: 23), 1 mM of the 17-base adapter primer (TTGCGTCTACTGCAGTC; SEQ ID NO: 24), and 1 mM of the sequence-specific primer. A subpool that included a putative full-length α1,2-mannosidase clone was identified and the clone was isolated by sibling selection and plaque hybridization as described above except the modified RACE procedure was used to screen the various subpools. Finally, the cDNA was excised and sequenced as described above and was found to contain a complete ORF encoding a putative α1,2-mannosidase. Computer analyses of the cDNA sequence were carried out using the Fragment Assembly System, Peptide structure, and GAP subroutines of the University of Wisconsin Genetics Computer Group software package (Program Manual for the Wisconsin Package, Version 8, September 1994, Genetics Computer Group, 575 Science Drive, Madison, Wis., USA 5371 1).

This screening procedure identified a full-length α1,2-mannosidase cDNA clone which contains an ORF that begins with an ATG in a favorable sequence for translational initiation (SEQ ID NO: 1; Kozak, 1984, 1986; Cavener and Ray, 1991). This ORF encodes a 670 amino acid protein (SEQ ID NO: 2) with a calculated molecular weight of 75,225 Da. The amino acid sequence of this putative Sf9 β1,2-mannosidase is 57%, 47%, 46%, 46%, and 35% identical to Drosophila (Kerscher et al., 1995; GenBank Accession # X82640), mouse IA (Lal et al., 1994; GenBank Accession # U04299), mouse IB (Herscovics et al., 1994; GenBank Accession # U03458), human (Bause et al., 1993; GenBank Accession # X74837), and yeast (Camirand et al., 1991; GenBank Accession # M63598) processing α1,2-mannosidases, respectively. The putative Sf9 α1,2-mannosidase is predicted to be a type II integral membrane protein with a 22 amino acid transmembrane domain (residues 31 to 52). It contains two potential N-glycosylation sites (residues 61 and 332) and two putative calcium binding sequences (residues 258 to 269 and 273 to 284) as defined by Marsden and coworkers (1990). In addition, there are several other potential calcium binding sequences, but these have less than three acidic residues available for binding calcium and are therefore less likely to be significant (Marsden et al., 1990).

The N-glycosylation pathway in insects is thought to be a truncated version of the mammalian pathway, lacking the ability to add antennary galactose or sialic acid to oligosaccharide side-chains (reviewed in Marz et al., 1995). On the other hand, there have been a few reports which indicate that baculovirus-infected lepidopteran insect cells can produce N-linked glycans containing penultimate galactose and terminal sialic acid (Davidson et al., 1990) and that this process might be facilitated by baculovirus induction of an α1,2-mannosidase with preferential activity toward Man₆GlcNAc₂ (Davidson et al., 1991). An enzyme with this activity was recently purified from a membrane fraction of baculovirus-infected lepidopteran insect cells by Ren and coworkers (1995). However, since the gene encoding this enzyme has not been isolated, the relationship, if any, between this enzyme and the instant α1,2-mannosidase is unclear.

EXAMPLE 16

PCR™ Screening of Introns within the Sf9 α1,2-mannosidase Gene and Genomic Southern Blotting Preliminary PCR™ studies using primers corresponding to selected regions in the Sf9 α1,2-mannosidase sequence were done to identify an intron-free region in the Sf9 α1,2-mannosidase gene that could be used as an unambiguous probe for genomic Southern blots. Several pairs of exact-match primers corresponding to various regions in the Sf9 α1,2-mannosidase cDNA were used for PCR's™ on Sf9 genomic DNA to determine if it contained any introns. The primer pairs were: pair 1, Sf MI+1310+(SEQ ID NO:m 21) and Sf MI+2123-(CCTTGCTATTTACTCTCGTC; SEQ ID NO: 25); pair 2, Sf MI+843+ (TGTGTTCGAGACGACGATC; SEQ ID NO: 26) and Sf MI+1492-(GACATCGAGTTGTCCAGG; SEQ ID NO: 27); and finally pair 3, Sf MI–25+ (GTGTAGGTTCTGTGTTTACG; SEQ ID NO: 28) and Sf MI+306-(TTCACCATGGTGAGCGATC; SEQ ID NO: 29). PCR's™ were done as described above, except the template was 100 ng of Sf9 genomic DNA isolated as described previously (Sambrook, 1989). The presence of introns was indicated by an increase in the size of the product amplified from the genomic DNA template relative to the size of the product amplified from the cDNA clone. The identity of the PCR™ products as fragments of the α1,2-mannosidase gene was confirmed by Southern blotting (Southern, 1975) with the full-length Sf9 α1,2-mannosidase cDNA, which had been excised from the vector, gel purified twice, and uniformly labeled with [α-$^{32}$P]dATP (Feinberg and Vogelstein, 1983).

These studies identified two regions containing introns, as indicated by an increase in the size of the product amplified from Sf9 genomic DNA relative to the size of the product amplified from the cDNA. It is important to note that there could be other intron-containing regions within the gene, since the PCR™ screening was not comprehensive. However, one region of this gene, corresponding to positions –25 to +306 contained no detectable introns. Therefore, the inventors used a 302 bp SnaBI (position –6)-NcoI (position +296) fragment from this region as a probe for genomic Southern blotting analyses.

Genomic DNA from Sf9, Bm, High Five, Ea, or COS cells was digested with either NcoI alone, or with both SnaBI and NcoI, and analyzed by Southern blotting under high stringency conditions. Sf9 cells are derived from the IPLB-Sf21-AE cell line, which was originally isolated from *Spodoptera frugiperda* (fall armyworm) ovaries (Vaughn et al., 1977). Sf9 cells were maintained as a suspension culture at densities between 0.3 and 3.0×10⁶ cells per ml in TNM-FH medium (Summers and Smith, 1987) supplemented with 10% (v/v) heat-inactivated fetal bovine serum (Sigma Chemical Co., St. Louis, Mo.), 1.25 mg/ml amphotericin B (Sigma), 25 mg/ml gentamicin (Sigma), and 0.1% (w/v) pluronic F68 (BASF Wynandotte Corp., Parsippany, N.J.; Murhammer and Goochee, 1988). The other lepidopteran insect cell lines used in this study were BTI-Tn-5B1-4 (High Five; Wickham et al., 1992), derived from *Trichoplusia ni* (cabbage looper) eggs; Bm 5 (Bm; Grace, 1967), derived from *Bombyx mori* (silkmoth) ovaries; and BTI-EaA (Ea; Granados and Naughton, 1975), derived from *Estigmene acrea* (saltmarsh caterpillar). COS-1 (Gluzman, 1981) is an SV40-transformed monkey kidney cell line.

Approximately seven mg of genomic DNA from Sf9, Bm, High Five, Ea, and COS cells were digested with either NcoI only or with both SnaBI and NcoI. The DNA's were resolved on 1% agarose gels, depurinated by soaking in 0.25 M HCl for 10 min, and transferred to positively charged nylon membranes (Zeta-Probe®; Bio-Rad Laboratories, Hercules, Calif.) in 0.4 M NaOH (Southern, 1975; Reed and Mann, 1985).

The membranes were prehybridized for one hour in a solution of 7%(w/v) SDS, 0.12 M Na$_2$HPO$_4$ (pH 7.2), 0.25 M NaCl, 1 mM EDTA, and a formamide concentration of 50%, 42%, or 35% for decreasing levels of stringency. Hybridization was carried out overnight at 43° C. in the same solution using a fragment of the Sf9 α1,2-mannosidase cDNA prepared as described above. For these analyses, however, the probe was an internal 302 bp, SnaBI-NcoI fragment corresponding to positions –6 (SnaBI) to +296 (NcoI) of the cDNA with respect to the start of the ORF. PCR™ analysis of Sf9 genomic DNA had shown that there were no introns within this region of the genomic copy of the α1,2-mannosidase gene. After hybridization, the membranes were rinsed in 2×SSC then washed successively with vigorous agitation for 15 min in each of the following solutions: 2×SSC/0.1% SDS at room temperature; 0.5×SSC/0.1% SDS at room temperature; 0.1×SSC/0.1% SDS at either 65° C. for high stringency (50% formamide) or room temperature for low stringency (42% or 35% formamide). The membranes were then blotted dry and exposed to Kodak (Rochester, N.Y.) BioMax MS film for 24 hours with an intensifying screen.

The probe hybridized with two fragments from the NcoI-digested Sf9 DNA, suggesting that there are two copies or two cross-hybridizing variants of the α1,2-mannosidase gene in the Sf9 genome. The same probe hybridized with a single 302 bp fragment of the SnaBI and NcoI doubly-digested Sf9 DNA, indicating that the two α-mannosidase genes differ with respect to the positions of their upstream NcoI sites, and that the positions of the SnaBI and downstream NcoI sites are conserved. Similar results were obtained with genomic DNA from Bm cells, except the upper fragment detected in the NcoI digest was lighter. Very light hybridization was detected with DNA from High Five cells, and no hybridization was detected with DNA from Ea or COS cells. These results indicated that the α1,2-mannosidase genes present in High Five, Ea, and COS cells are significantly different from those present in Sf9 and Bm cells. This might help to explain why these cell lines have differing N-glycan processing capabilities (Davis et al., 1993; Ogonah et al., 1996).

To further investigate these differences, the Southern blotting analyses of Sf9, High Five, and Ea genomic DNA were repeated under less stringent conditions (42% formamide and 35% formamide). Under these conditions, the probe hybridized with three major fragments of NcoI-digested Sf9 DNA, one major fragment of NcoI-digested High Five cell DNA, and several fragments of NcoI-digested DNA from Ea cells. The probe hybridized with multiple fragments of various sizes with SnaBI and NcoI double-digests of the DNA from these three insect cell lines.

EXAMPLE 17

Expression of the α1,2-mannosidase Gene

To study the expression of the α1,2-mannosidase gene, Northern blotting analysis of Sf9 mRNA was conducted with the full-length Sf9 α1,2-mannosidase ORF as a probe. Total RNA from approximately 2×10⁸ Sf9 cells was prepared by the method of Chirgwin and coworkers (1979) and messenger RNA was isolated on an oligo-dT cellulose column (Aviv and Leder, 1972). Ten mg of the Sf9 mRNA were resolved on a 1.2% agarose/0.66 M formaldehyde gel and transferred to a positively charged nylon membrane (Zeta-Probe®; Bio-Rad) in 50 mM NaOH. Prehybridization, hybridization, washing, and autoradiography were done as described in Example 16, except 10% (w/v) PEG-8000 (Sigma) was used in the hybridization solution and the probe contained the complete ORF of the Sf9 α1,2-mannosidase gene.

Northern blotting analysis of Sf9 mRNA with the full-length Sf9 α1,2-mannosidase ORF as a probe revealed a single transcript of about 6 kb. Since the α1,2-mannosidase ORF is only about 2 kb in length, most of the remaining 4 kb is probably 3' untranslated region in the mRNA transcript. This speculation is supported by the fact that the initial (partial) Sf9 α1,2-mannosidase cDNA clone contained about 3 kb of 3' untranslated sequence.

EXAMPLE 18

Baculovirus-mediated Overexpression of the Sf9 α1,2-mannosidase

A recombinant baculovirus was produced that encoded the Sf9 α1,2-mannosidase cDNA under the control of the strong polyhedrin promoter and used to express the Sf9 α1,2-mannosidase protein. The Sf9 α1,2-mannosidase ORF was subcloned into a baculovirus transfer plasmid (pVL1393; Webb and Summers, 1990) downstream of the polyhedrin promoter. The resulting plasmid was used to produce a baculovirus expression vector encoding the Sf9 α1,2-mannosidase gene under polyhedrin control by using standard methods (Summers and Smith, 1987; O'Reilly et al., 1992). The viral DNA used as the target for homologous recombination was BacPAK6 (Kitts and Possee, 1993) that had been digested with Bsu36I (New England Biolabs, Beverly, Mass.). Recombinant viruses were plaque purified twice, titered by plaque assay, and used to infect Sf9 cells. Expression of the α1,2-mannosidase protein was assessed by discontinuous SDS-polyacrylamide gel electrophoresis (PAGE) and Coomassie-blue staining of total protein lysates, as described previously (Laemmli, 1970; Jarvis et al., 1996).

A protein with an apparent molecular weight of about 68 kDa was observed in total lysates from cells infected with the recombinant baculovirus, but not in lysates from mock-infected or wild-type baculovirus-infected cells at 48 and 72 hours postinfection. The 29 kDa polyhedrin protein was detected only in lysates from wild-type baculovirus-infected cell lysates at 48 and 72 hours postinfection. These results are consistent with those expected of a recombinant baculovirus encoding a foreign protein under the control of the polyhedrin promoter.

EXAMPLE 19

α-mannosidase Activity Assays

Sf9 cell lysates were used for α1,2-mannosidase activity assays with [3H]Man$_9$GlcNAc as described previously (Herscovics and Jelinek-Kelly, 1987) with some modifications. The cells were seeded into 25 cm tissue culture flasks (Corning Glass Works, Corning, N.Y.) at a density of 3 million cells per flask and infected at a multiplicity of infection of 10 plaque forming units per cell with either a recombinant baculovirus encoding the Sf9 α1,2-mannosidase cDNA under the control of the polyhedrin promoter, or wild type baculovirus as a control. The cells were harvested by centrifugation at selected times after infection, washed with 100 mM Na$^+$MES (pH 6.0), and lysed using 1 ml per 30,000 cells of the same buffer containing 0.5% Triton X-100 with or without 80 mM EDTA.

Five ml of the lysates were used in each reaction of the α1,2-mannosidase activity assays. Cell lysates for negative control reactions were boiled for 3 min prior to being added to the reactions. All reactions were carried out in a total volume of 40 ml containing 75 mM Na$^+$MES (pH 6.0), 0.0625% Triton X-100, and 6000 cpm of [$^3$H]Man$_9$GlcNAc. In addition, some reactions contained CaCl$_2$, MgCl$_2$, EDTA, or dMNJ. The reactions were incubated at 37° C. for 2.5 hours, boiled for 2 min, and 250 ml of a 5 mM solution of CaCl$_2$, MgCl$_2$, and MnCl$_2$, and 175 ml of a 2.25 mg/ml solution of concanavalin A (Boehringer-Mannheim, Indianapolis, Ind.) in 3.8 M NaCl were added to each reaction. The solutions were vortexed gently and incubated at room temperature for two minutes, then 1 ml of 25% PEG-8000 was added and the solutions were vortexed and incubated for another 5 min at room temperature. The solutions were then centrifuged for 2 min at 10,000×g, 1 ml of the supernatant was added to 4 ml of a scintillation cocktail (Ultima Gold™; Packard Instrument Company, Meriden, Conn.), and radioactivity was measured using a Beckman liquid scintillation counter (Model LS 60001C; Beckman Instruments, Inc., Fullerton, Calif.).

Figure 15A:
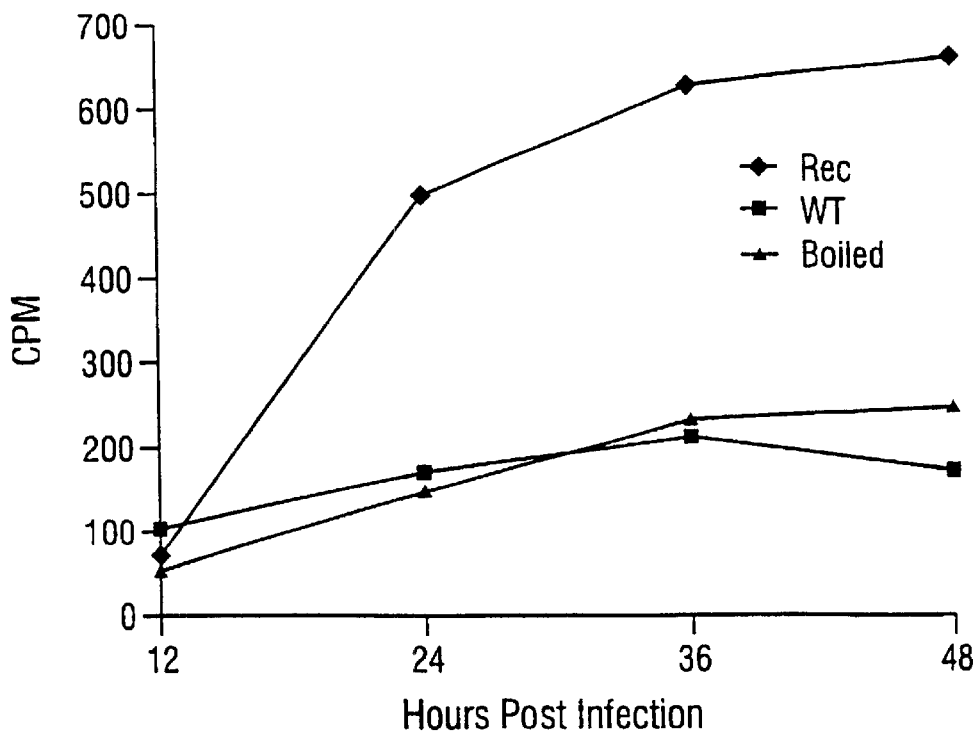
FIG. 15A and FIG. 15B. Enzymatic activity of the protein encoded by the Sf9 α1,2-mannosidase cDNA. Sf9 cells were infected with wild-type baculovirus (WT) or a recombinant (Rec) encoding the Sf9 α1,2-mannosidase cDNA under the control of the polyhedrin promoter. Lysates were prepared at the indicated times postinfection and used for α-mannosidase activity assays, as described in Example 19. A portion of the lysates from cells infected with the recombinant virus was boiled and used as a negative control. α-mannosidase activity was measured in counts per minute (cpm) of [$^3$H]mannose released from [$^3$H]Man$_9$GlcNAc, as described in Example 19.
Figure 15B:
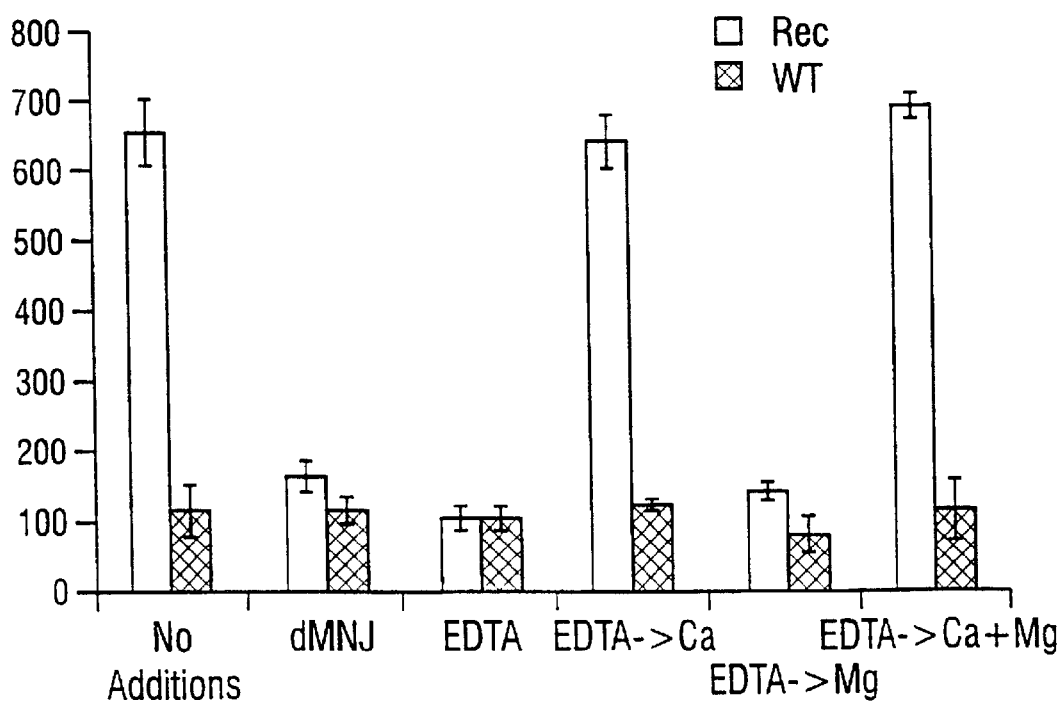

Using this assay, there was no difference in the levels of α-mannosidase activity detected in lysates from wild-type virus-infected cells or in boiled lysates (FIG. 15A). This result indicated that the endogenous activity in wild type virus-infected cells was too low to be detected by this assay. By contrast, recombinant virus-infected cells contained significantly higher levels of activity than boiled lysates. Activity was detected at 24, 36, and 48, but not at 12 hours postinfection, and more activity was detected at 36 and 48 than at 24 hours postinfection (FIG. 15A). Like the protein profiles, these results were consistent with those expected of a recombinant baculovirus encoding a foreign enzyme under the control of the polyhedrin promoter. The α-mannosidase activity observed in recombinant baculovirus-infected cells was strongly inhibited by dMNJ, an inhibitor of class I α-mannosidases, and by EDTA (FIG. 15B). The inhibition by EDTA could be reversed by the addition of calcium, but not magnesium. These properties are identical to those of α1,2-mannosidases from other eukaryotes (Moremen et al., 1994).

EXAMPLE 20

Isolation and Characterization of Stably-transformed Sf9 Cells that Express Mammalian β1, 4-galactosyltransferase Expression plasmids and methods have been described that can be used to produce stably-transformed insect cell subclones that express foreign genes constitutively (Jarvis et al., 1990; Jarvis and Guarino, 1995; Examples 1–5 above). Briefly, various expression plasmids were constructed containing a baculovirus IE1 promoter and hr5 enhancer that can be used to express any gene of interest or selectable marker in uninfected insect cells. Sf9 cells were cotransfected with derivatives of these constructs containing various genes of interest, selected for neomycin resistance, and subclones were produced by limiting dilution. After amplification, the subclones were screened for their ability to express the gene of interest.

This general procedure was used to successfully produce a variety of stably-transformed Sf9 subclones that express different gene products, including E. coli β-galactosidase, human tissue plasminogen activator, and the baculovirus IE2, pp31, and gp64 proteins (Jarvis et al., 1990, Examples 1–5 above). Other labs also have used this approach to produce stably-transformed insect cells that express various foreign gene products (Cartier et al., 1994; Henderson et al., 1995; Joyce et al., 1993). As described above, it has been demonstrated that IE1β-based recombinant baculovirus vectors could be used to express a bovine β1,4-galactosyltransferase (β4-GT) cDNA and modify the Sf9 cell N-glycosylation pathway, as detailed above (Examples 11–14 above). The present Example describes the isolation of a stably-transformed Sf9 cell subclone that constitutively expresses β4-GT.

Sf9 cells were cotransfected with immediate-early expression plasmids containing the β4-GT or neo genes positioned under IE1 control. The cotransfected cells were selected in neo, as described above, and extracts from ten independent subclones were screened for β4-GT activity, as previously described (Examples 11–14 above). The results showed that all ten of these subclones produced β4-GT activity, though expression levels were quite variable. Subclone 9, which expressed the highest levels of activity was designated SfGalT and further characterized by genomic Southern blotting. The results showed that these cells have multiple tandem duplications of the expression plasmid integrated at one site and a single copy inserted at one additional site.

Figure 16A:
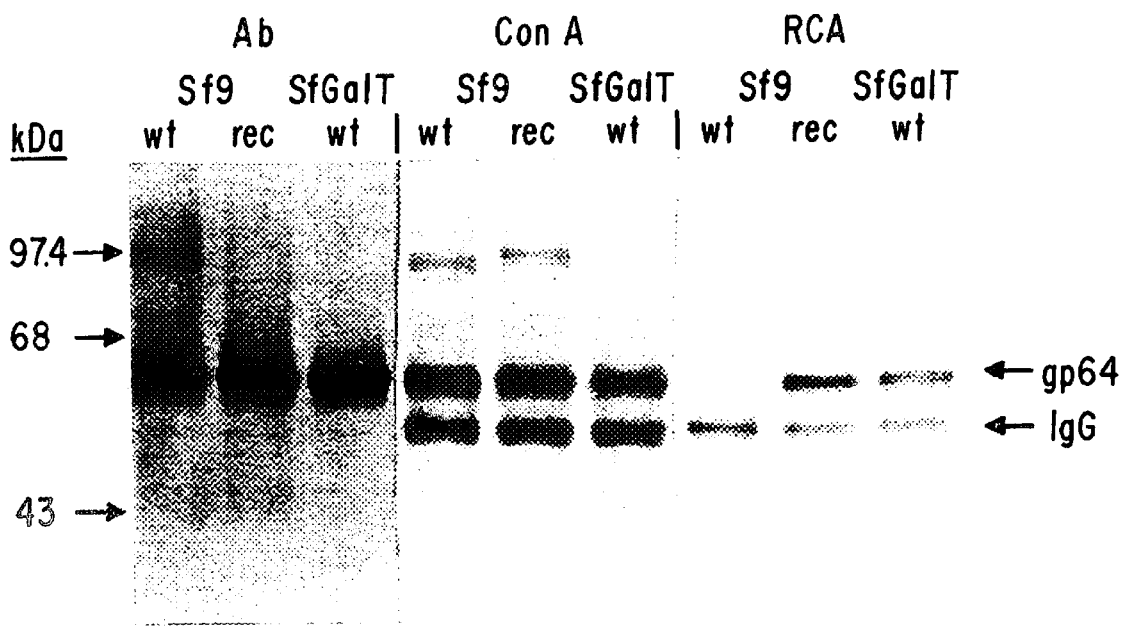
FIG. 16A and FIG. 16B. Extended N-glycosylation pathway of SfGalT cells. Progeny budded virions were partially purified from Sf9 or SfGalT cells infected with wild type baculovirus (wt) or AcP(+)IE1GalT (rec) and gp64 was extracted and immunoprecipitated. The disrupted immunoprecipitates were resolved by SDS-PAGE, transferred to immobilon, and the blots were cut into strips and probed with rabbit anti-gp64 (Ab) or the lectins Con A (binds α-linked mannose or glucose) or RCA (binds β-linked Gal). Each lectin was preincubated in buffer alone (FIG. 16A) or buffer containing excess competing sugar (FIG. 16B) prior to being used to probe the filters. Lectin or antibody binding was detected with alkaline phosphatase-conjugated secondary antibodies and a standard color reaction. The arrows on the right mark the positions of gp64 and the IgG heavy chain, which served as an internal standard for the lectin blots. The results show clearly that only the gp64 produced in SfGalT cells bound to RCA, indicating that only these cells were able to produce a galactosylated end-product.
Figure 16B:
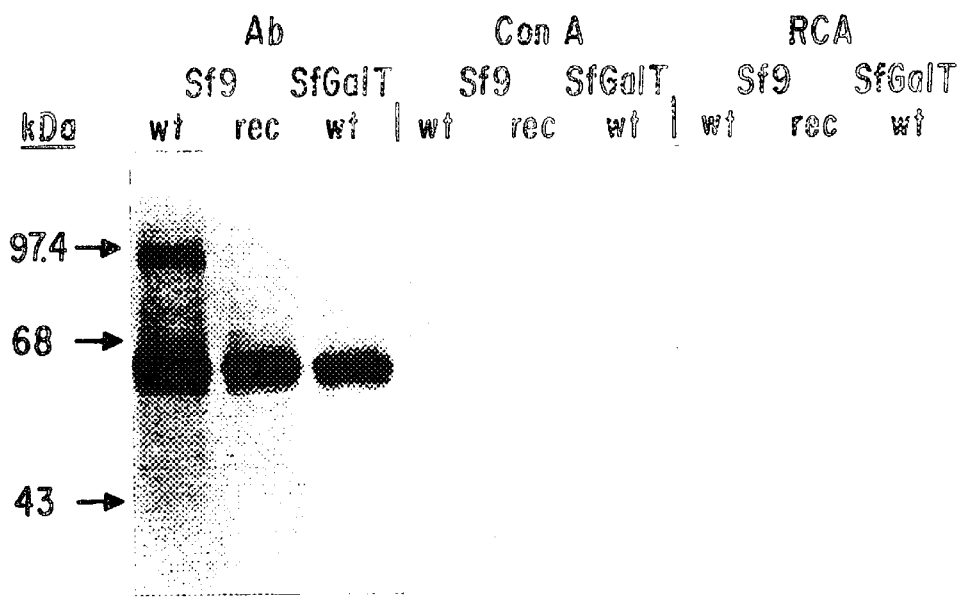

The ability of these cells to modify a foreign glycoprotein was demonstrated by comparing the lectin blotting profiles of gp64 isolated from progeny virions from either Sf9 or SfGalT cells infected with wild-type baculovirus. The results of the lectin blots showed that RCA failed to bind specifically to gp64 from the progeny from Sf9 cells, whereas it clearly bound to gp64 from the progeny from SfGalT cells (FIG. 16A and FIG. 16B). These results indicated that gp64 produced by Sf9 cells lacks β-linked galactose, while gp64 produced by SfGalT cells contains β-linked galactose. Thus, a stably-transformed insect cell subclone has been successfully produced which has an N-glycosylation pathway that has been genetically and biochemically engineered to include mammalian β4-GT activity.

Figure 17A:
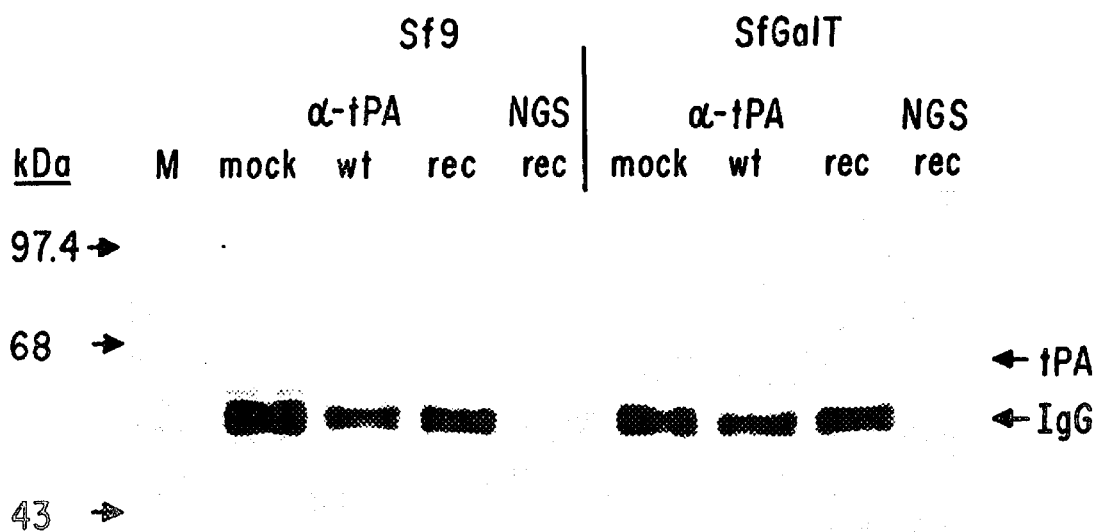
FIG. 17A, FIG. 17B, FIG. 17C and FIG. 17D. Galactosylation of a human glycoprotein expressed by a recombinant baculovirus in SfGalT cells. Sf9 or SfGalT cells were mock-infected (mock), infected with wild type baculovirus (wt), or infected with Ac941t-PA (rec), which is a conventional recombinant baculovirus that encodes human tissue plasminogen activator under the transcriptional control of the polyhedrin promoter. The cells were radiolabeled from 24–48 hr postinfection and the extracellular fraction was collected and immunoprecipitated with a goat antibody against t-PA (α-tPA) or normal goat serum (NGS). The disrupted immunoprecipitates were resolved by SDS-PAGE, transferred to immobilon, and the blots were probed with the lectin RCA, which is specific for β-linked galactose. The lectin was preincubated in buffer alone (FIG. 17A) or buffer containing excess competing galactose (FIG. 17B) prior to being used to probe the filters. Lectin binding was detected with alkaline phosphatase-conjugated secondary antibodies and a standard color reaction. Autoradiographs of the lectin blot of FIG. 17A is shown in FIG. 17C, and of the lectin blot of FIG. 17B is shown in FIG. 17D. The arrows on the right mark the positions of t-PA and the IgG heavy chain, which served as an internal standard for the lectin blots. The results clearly show that t-PA was produced, secreted, and specifically immunoprecipitated from either Sf9 or SfGalT cells infected with the recombinant virus. However, only the t-PA from the recombinant virus-infected SfGalT cells bound to RCA, indicating that only these cells produced a galactosylated end-product.
Figure 17B:
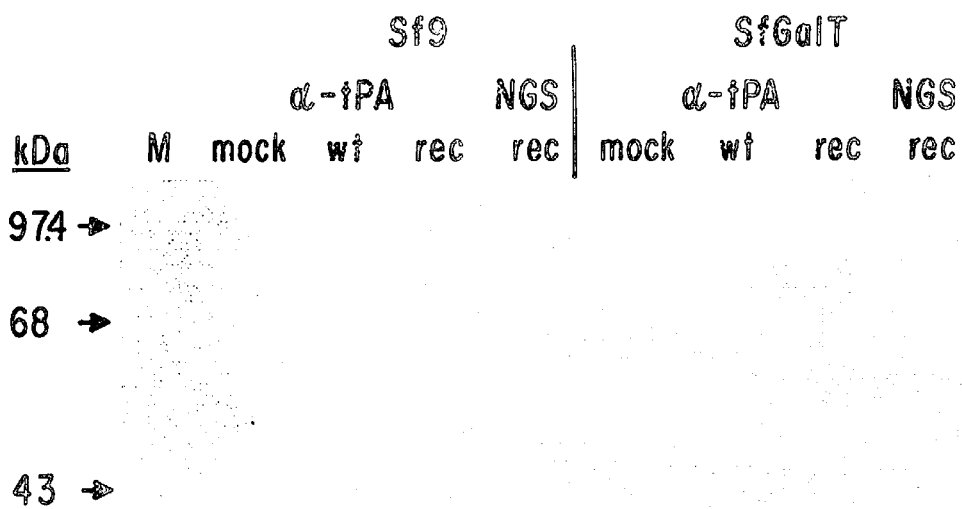
Figure 17C:
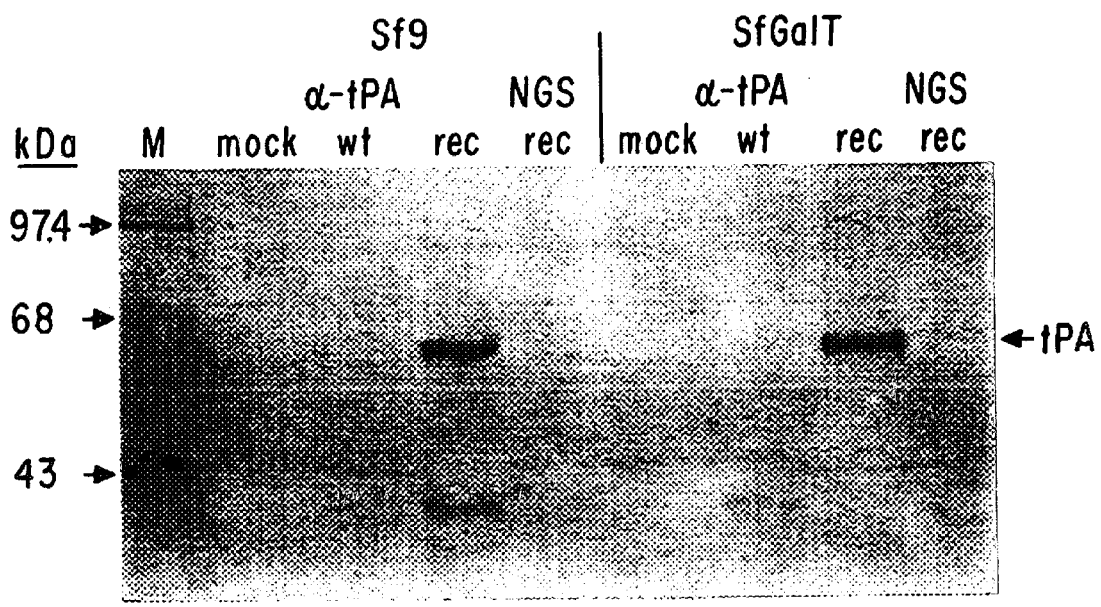
Figure 17D:
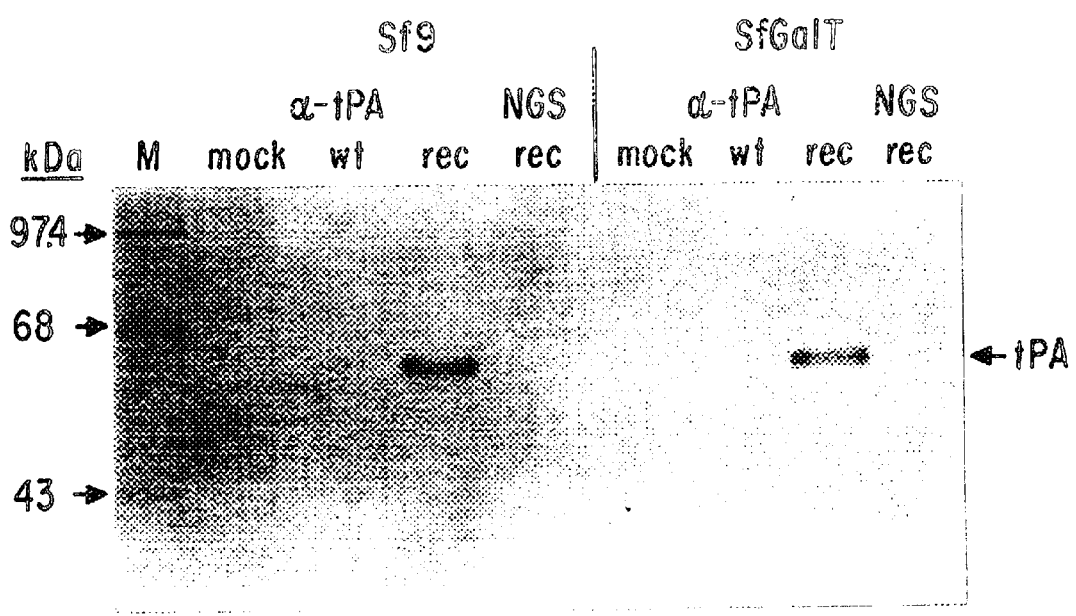

Lectin blotting results also showed that the SfGalT cells differentially modified human tissue plasminogen activator, which was expressed when these cells were infected with a conventional recombinant baculovirus expression vector. Tissue plasminogen activator produced under the control of the polyhedrin promoter in Sf9 cells failed to bind to RCA, whereas the same protein produced by the same virus in SfGalT cells bound to RCA (FIG. 17A and FIG. 17B). These results indicate that SfGalT cells can be used to produce more extensively N-glycosylated foreign glycoproteins when used in conjunction with conventional baculovirus expression vectors.

EXAMPLE 21

Isolation and Characterization of Stably-transformed Sf9 Cells that Express Mammalian β1, 4-glactosyltransferase and α2,6-sialyltransferase This example describes the production of a new Sf9 cell subclone that has both mammalian β4-GT and α2,6-sialyltransferase (α2,6-ST) activity. A new immediate early expression plasmid was constructed that contains two copies of the IE1 promoter. The starting materials were pIE1HR4 and pAcP(−)IE1TV6 (Examples 1–5 above), which were recombined to produce an expression plasmid with two back-to-back IE1 promoters separated by the hr5 enhancer element. Each promoter is followed by at least one unique restriction site, which was used for the subsequent insertion of bovine β4-GT (Shaper et al., 1988) and rat α2,6-ST (Weinstein et al., 1987) cDNAs.

The ability of the resulting plasmid to express β4-GT and rat α2,6-ST is tested by transient transfection assays. Briefly, Sf9 cells are transfected with 10 μg of plasmid DNA, detergent extracts are prepared at 24 hr after transfection, and β4-GT and rat β2,6-ST activities are measured. Cell extraction and radioassay methods for both enzyme activities have been described (Examples 11–14 above; Paulson et al., 1977). Control transfections are done using the dual expression plasmid with no inserts, or IE1 expression plasmids containing the individual β4-GT and rat α2,6-ST cDNAs.

Next, the plasmid was used for coselection of an Sf9 cell subclone, as described in Example 19 above. Sf9 cells were cotransfected with the dual IE1 expression plasmid plus IE1Neo, and transformants were isolated by selection in neomycin followed by limiting dilution. Subclones are amplified and screened for both activities. Subclones that have both activities are characterized by genomic Southern blotting to evaluate the nature of the genetic modification. The ability of these cells to differentially glycosylate gp64 is assessed first by lectin-blotting assays designed to specifically detect β-linked galactose or α2,6-linked sialic acid. The same proteins expressed in untransformed Sf9 cells with the same recombinant viruses and lectins preincubated in the presence of competing sugars are used as controls.

EXAMPLE 22

Recombinant Baculoviruses and Transfer Plasmids
1. AcP(+)DIE-GTST

Figure 20C:
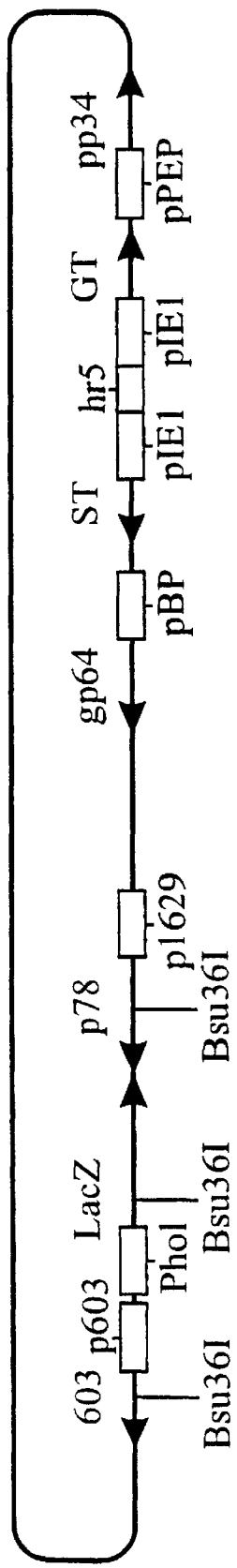

AcP(+)DIE-GTST (FIG. 20A) is a recombinant baculovirus that contains early-promoted and hr-enhanced galactosyltransferase (GT) and sialyltransferase (ST) genes in the polyhedrin region. This virus is used together with a conventional recombinant baculovirus to coinfect conventional host cell lines. AcP(+)DIE-GTST expresses GT and ST early in infection and extends the insect cell N-glycosylation pathway. This occurs before the protein of interest is expressed, preferably under the control of a late or very late baculovirus promoter by the conventional recombinant baculovirus. The protein of interest is more extensively processed by the modified N-glycosylation pathway, resulting in the production of a more authentic recombinant protein.

The inventor contemplates a number of variations for use with this novel recombinant baculovirus. First, any early viral or constitutive cellular promoter may be used to express GT and ST. Second, any enhancer may be used to increase expression of GT and ST. Third, the relative positions of the GT, ST, and polh genes are unimportant. Fourth, similar embodiments provide other types of protein processing (e.g., folding, phosphorylation, acylation, acetylation, methylation or amidation).

2. pAcP(−)DIE-GTST pAcP(−)DIE-GTST (FIG. 20B) is a recombinant transfer plasmid that contains early-promoted and hr-enhanced GT and ST genes and a late-promoted gene encoding any protein of interest, all embedded within polyhedrin flanking sequences. This plasmid is used to produce recombinant baculoviruses that are used, in turn, to infect conventional host cell lines. These recombinant viruses express GT and ST earlier in infection, extending the insect N-glycosylation pathway. These same recombinants also express the protein of interest, preferably later in infection. This design provides more extensive processing of the protein of interest and produces a more authentic recombinant protein without having to resort to coinfection.

The inventor additionally contemplates a number of variations for use with this novel recombinant transfer plasmid. First, any early viral or constitutive cellular promoter may be used to express GT and ST. Second, any enhancer may be used to increase expression of GT and ST. Third, any promoter, preferably a late or very late viral promoter, may be used to express protein of interest. Fourth, the relative positions of the GT, ST, and polh genes are unimportant. Fifth, the precise nature of the multiple cloning site is unimportant. And sixth, similar embodiments provide other types of protein processing, as detailed above.

3. AcSWT-1

AcSWT-1 (FIG. 20C) is a recombinant baculovirus that contains early-promoted and hr-enhanced GT and ST genes inserted into the gp64 region of the baculoviral genome together with multiple Bsu36I sites in ORF-603, polh-LacZ, and ORF-1629. The genes are inserted into the gp64 locus using the transfer plasmid (pAc64DIE-GTST). This recombinant viral DNA is used as a target for the insertion of one or more genes encoding any protein of interest, under the control of a promoter, preferably a late or very late promoter. The insertion is carried out using conventional baculovirus transfer plasmids and a conventional method involving linearization of the viral DNA by digestion with Bsu36I. The resulting recombinants are used to express the protein of interest during infection of conventional insect cell lines. Unlike existing baculoviral vectors, however, recombinant baculoviruses produced with AcSWT-1 viral DNA express GT and ST early in infection, which extends the insect cell N-glycosylation pathway. Thus, the protein of interest that is expressed, preferably later in infection, is more authentic due to virus-mediated modification of the host protein processing machinery.

The inventor also contemplates a number of variations for use with this novel recombinant baculovirus. First, any early viral or constitutive cellular promoter may be used to express GT and ST. Second, any enhancer may be used to increase expression of GT and ST. Third, the GT and ST genes may be inserted into other nonessential locations in viral genome (e.g., p10, see below). Fourth, any promoter, preferably a late or very late viral promoter, may be used to express the protein of interest. Fifth, the relative positions of the GT and ST genes are unimportant. And sixth, as above, similar embodiments provide other types of protein processing.

4. AcSWT-2

Figure 20D:
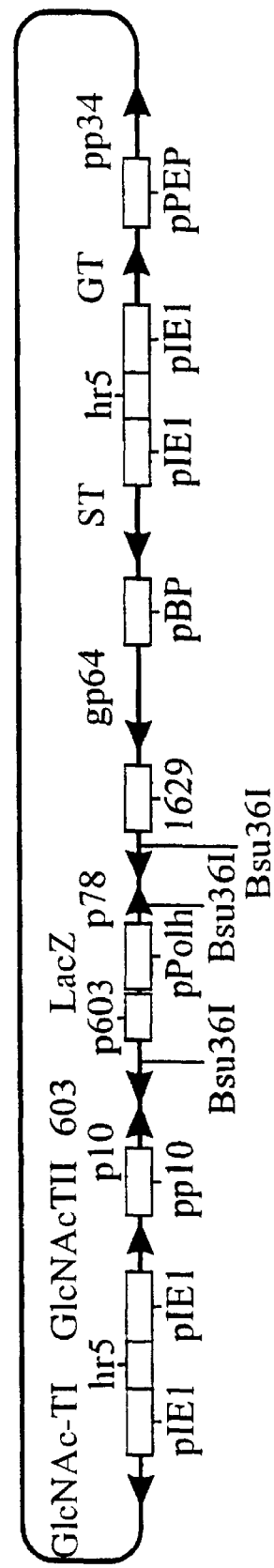

AcSWT-2 (FIG. 20D) is a recombinant baculovirus that contains early-promoted and hr-enhanced GT and ST genes inserted into the gp64 region of the baculovirus genome, early-promoted and enhanced N-acetylglucosaminyltransferase (GlcNAc-T) I and II genes inserted into the p10 region of the baculovirus genome, and multiple Bsu36I sites in ORF-603, polh-LacZ, and ORF-1629. This recombinant viral DNA is used exactly as described above for AcSWT-1. However, in addition to providing GT and ST, which are believed to be absent in insect cells, AcSWT-2 also provides GlcNAc-TI and GlcNAc-TII, which are present only at very low levels in insect cells. Thus, recombinant baculoviruses produced with AcSWT-2 viral DNA express GlcNAc-TI, GlcNAc-TII, GT, and ST early in infection, which increase the levels of existing activities and add new activities to the insect cell N-glycosylation pathway. The protein of interest that is expressed, preferably later in infection, is more authentic due to virus-mediated enhancement and extension of host protein processing machinery.

As with the embodiments above, any early viral or constitutive cellular promoter may be used to express processing enzymes, and any enhancer may be used to increase expression of processing enzymes. The GT and ST genes may be inserted into other nonessential locations in viral genome, and the relative positions of the GT, ST, GlcNAc-TI and GlcNAc-TII genes are unimportant. Any promoter, preferably a late or very late viral promoter, may be used to express the protein of interest, and similar embodiments provide other types of protein processing.

EXAMPLE 23

Production and Use of Insect Cells With Stably Integrated Glycosylation Genes

1. SfGalT plus AcP(+)IE1ST

Figure 18A:
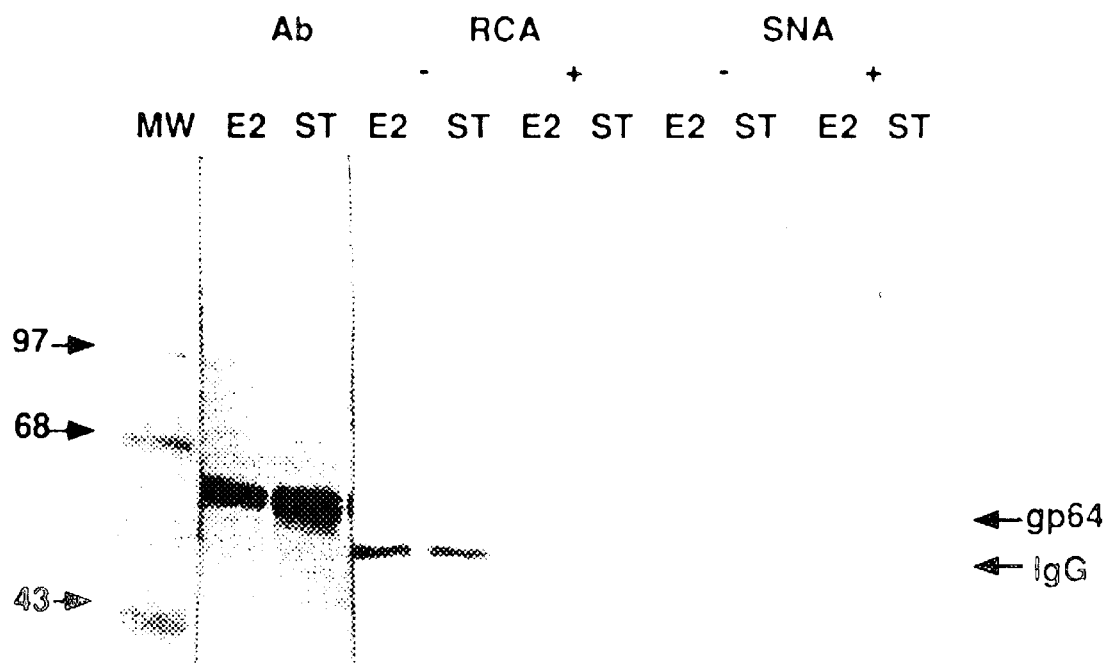
FIG. 18A and FIG. 18B. Further extension of the N-glycosylation pathway in SfGalT cells. Progeny budded virions were partially purified from Sf9 (FIG. 18A) or SfGalT (FIG. 18B) cells infected with wild type baculovirus (E2) or AcP(+)IE1ST, which is an immediate early recombinant baculovirus that encodes rat α2,6-sialyltransferase cDNA under the transcriptional control of the IE1 promoter (ST). gp64 was extracted and immunoprecipitated and the disrupted immunoprecipitates were resolved by SDS-PAGE and transferred to immobilon. The blots were cut into strips and probed with rabbit anti-gp64 (Ab) or the lectins RCA (binds β-linked Gal) or SNA (binds to α2,6-linked sialic acid). Each lectin was preincubated in buffer alone (−) or buffer containing excess competing sugars (+) prior to being used to probe the filters. Lectin or antibody binding was detected with alkaline phosphatase-conjugated secondary antibodies and a standard color reaction. The arrows on the right mark the positions of gp64 and the IgG heavy chain, which served as an internal standard for the lectin blots. The results show clearly that only the gp64 produced in SfGalT cells by the ST recombinant virus bound to SNA, indicating that only this virus-cell combination was able to produce a galactosylated and sialylated end-product.
Figure 18B:
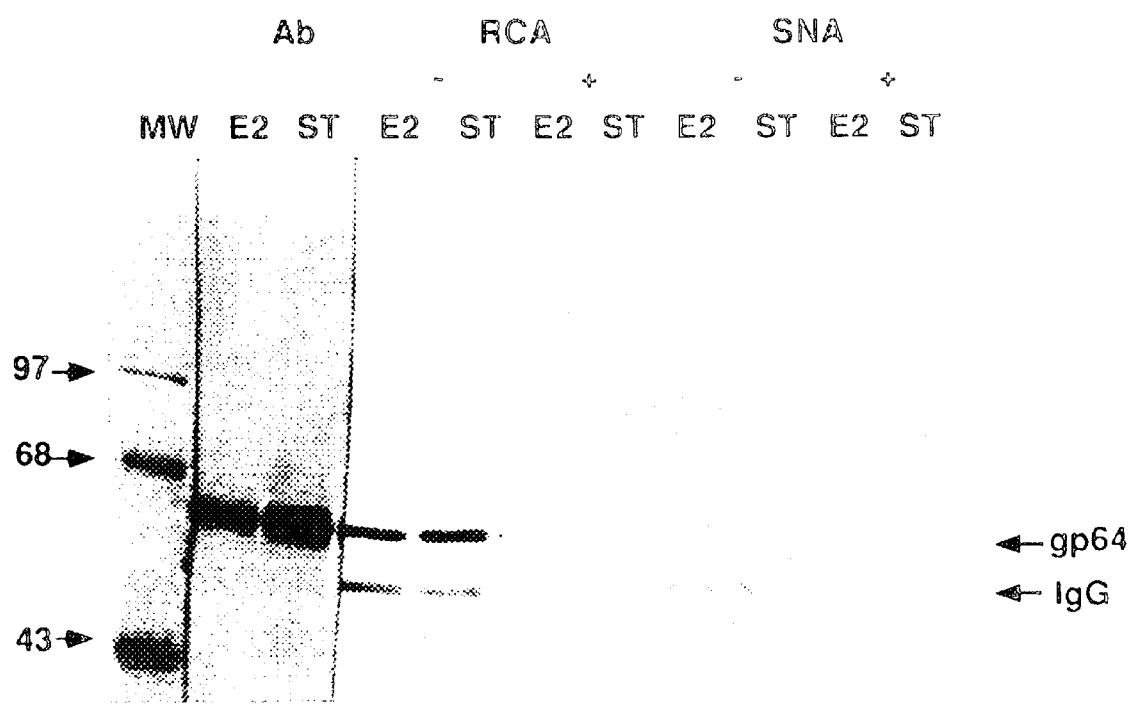
Figure 19:
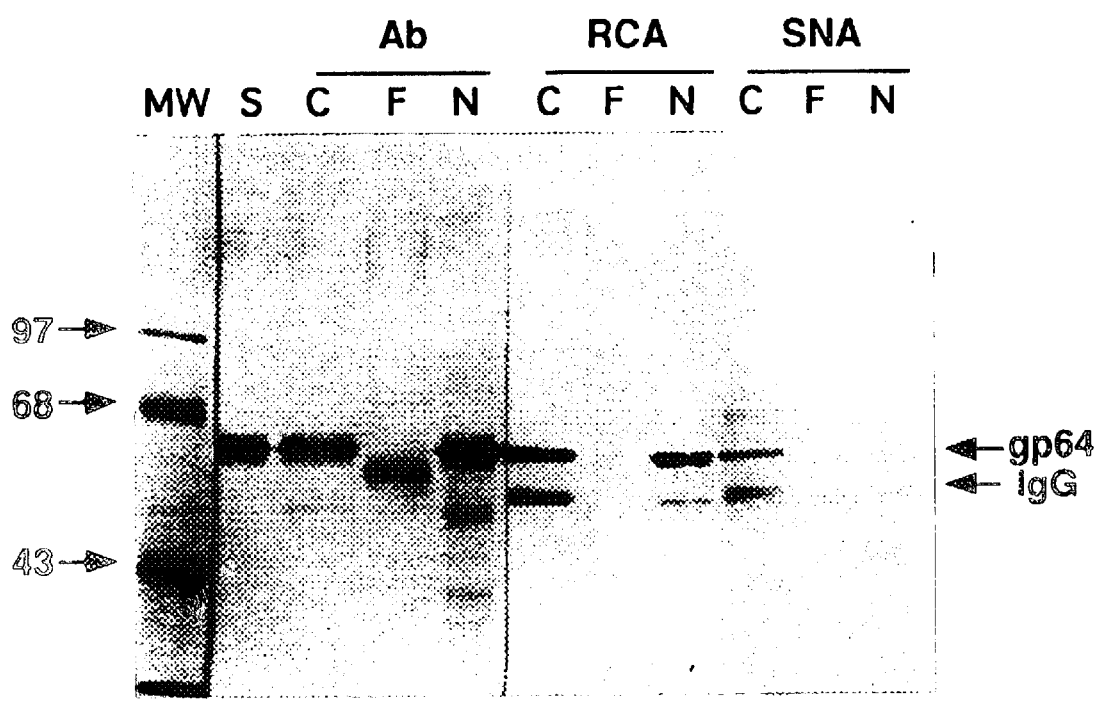
FIG. 19. Linkage analysis of sialylated oligosaccharides on gp64. gp64 was extracted and immunoprecipitated from the progeny virions produced by SfGalT cells infected with AcP(+)IE1ST. The immunoprecipitates were stored frozen without any treatment (Ab) or treated with buffer alone (C), peptide:N-glycosidase F (F), or neuraminidase (N). The reaction products were resolved by SDS-PAGE, transferred to immobilon filters, and analyzed by either immunoblotting with rabbit anti-gp64 (Ab) or lectin blotting with RCA (to detect galactose) or SNA (to detect sialic acid). The arrows on the right indicate the positions of gp64 and IgG heavy chain. The results showed clearly that SNA binding was precluded by either neuraminidase or peptide:N-glycosidase F treatment, whereas RCA binding was precluded only by peptide:N-glycosidase F treatment. Furthermore, there was a slight increase in the relative electrophoretic mobility of gp64 after neuraminidase treatment and a major increase after peptide:N-glycosidase F treatment. These results strongly support the conclusion that at least one N-linked oligosaccharide side-chain on gp64 was galactosylated and sialylated when SfGalT cells were infected with the AcP(+) IE1ST recombinant baculovirus.
Figure 21A:
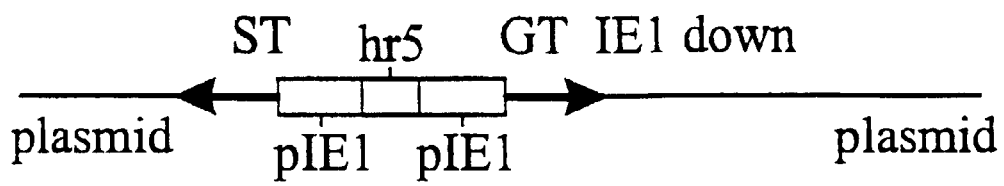
FIG. 21A, FIG. 21B, FIG. 21C and FIG. 21D. Expression plasmids for creation of stable insect cell lines expressing glycosylation enzymes, and selected stable insect cell lines.
Figure 21B:
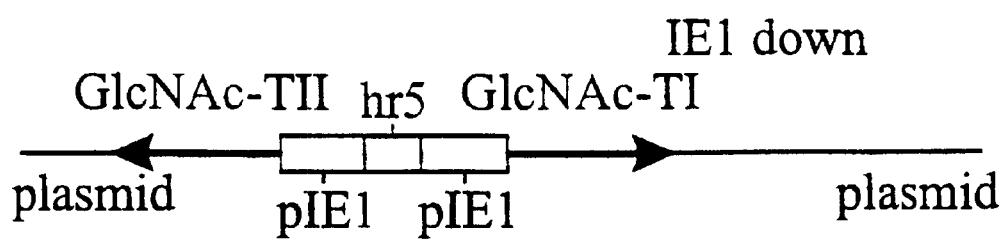
Figure 21C:
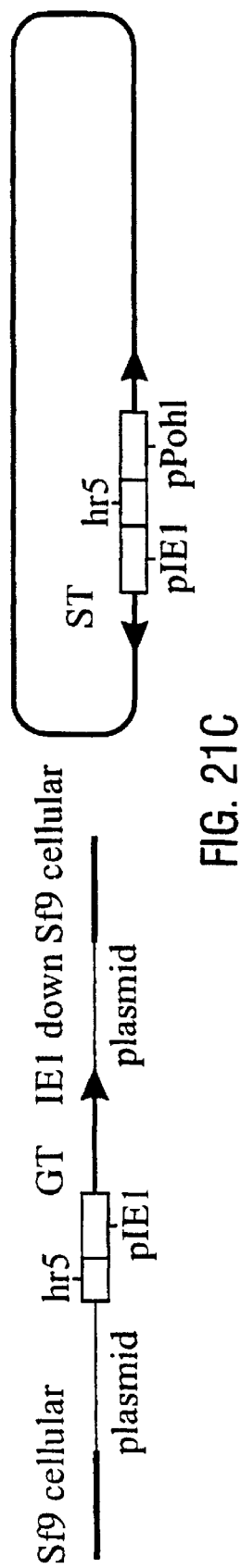

This is a combination of an Sf9 cell subclone that contains an early-promoted and hr-enhanced GT gene stably integrated into the genome of the cell, and a novel recombinant baculovirus that contains an early-promoted and enhanced ST gene (FIG. 21C). The SfGalT cells, which were isolated and characterized as described above in Example 20, contain stably-integrated copies of the expression plasmid, pIE1GT, and constitutively express GT activity. AcP(+)IE1ST contains an early-promoted and enhanced ST gene in the polyhedrin region of the baculovirus genome. The infection of SfGalT cells with AcP(+)IE1ST results in terminal sialylation of gp64 (FIG. 18A and FIG. 18B). This does not occur when SfGalT cells are infected with wild-type baculovirus, nor when Sf9 cells are infected with the AcP (+)IE1ST recombinant. The presence of terminal sialic acid residues was confirmed by linkage analysis of the oligosaccharides on gp64 (FIG. 19). Thus, the constitutive GT activity and the ST activity expressed by the virus early in infection collaborate to modify gp64, which is a natural virus-encoded product expressed predominantly during the late phase of infection.

As discussed above for the recombinant baculoviruses, any early viral or constitutive cellular promoter may be used to express the processing enzymes, and any enhancer may be used to increase expression of processing enzymes. Additionally, any promoter may be used to express the protein of interest. The ST gene may be inserted into other nonessential locations in viral genome. Further, any insect cell line may be used as the parent for stable transformation. Also, similar embodiments provide other types of protein processing, as discussed above.

2. SfGalT plus AcP(−)IE1ST

Figure 21D:
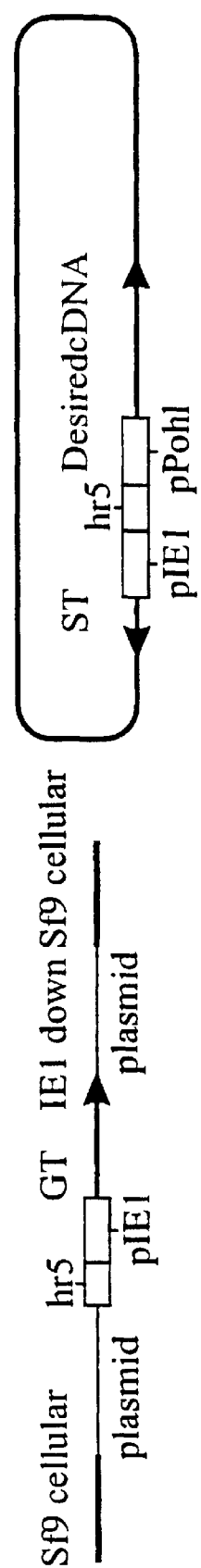

This is a combination of an Sf9 cell subclone that contains an early-promoted and hr-enhanced GT gene stably integrated into the genome of the cell, and a novel recombinant baculovirus that contains an early-promoted and enhanced ST gene and also encodes a late-promoted gene of interest (FIG. 21D). The SfGalT cells, which were isolated and characterized as described above, contain stably-integrated copies of the expression plasmid, pIE1GT, and constitutively express GT activity. AcP(−)IE1ST contains an early-promoted and enhanced ST gene and a late-promoted protein of interest in the polyhedrin region. Infection of SfGalT cells with AcP(+)IE1ST results in terminal sialylation of the protein of interest.

With this system, as described above, any early viral or constitutive cellular promoter may be used to express processing enzymes, and any enhancer may be used to increase expression of processing enzymes. The relative positions of the ST gene and the gene of interest are unimportant, and the ST gene may be inserted into other nonessential locations in the viral genome. Any promoter may be used to express the protein of interest, and any insect cell line may be used as the parent for stable transformation. As with all of these recombinant baculoviruses and cell lines, similar embodiments provide other types of protein processing.

3. SfSWT-1

SfSWT-1 (FIG. 21A) is an Sf9 cell subclone that contains early-promoted and hr-enhanced GT and ST genes. The cells were produced by cotransfecting Sf9 cells with pDIE-GTST plus pIE1Neo, followed by selection with G418 and limiting dilution. These cells contain stably-integrated copies of the expression plasmid and constitutively express GT and ST activities. Thus, these cells have a modified N-glycosylation pathway that can process a protein of interest more extensively. The protein of interest is expressed by infecting the cells with a conventional baculovirus expression vector, which contains the gene of interest under the control of any promoter.

As described above, any early viral or constitutive cellular promoter may be used to express processing enzymes, any enhancer may be used to increase expression of processing enzymes, and any promoter may be used to express the protein of interest. The relative positions of the GT and ST genes are unimportant. Again, any insect cell line may be used as the parent for stable transformation, and similar embodiments provide other types of protein processing.

4. SfSWT-2

SfSWT-2 (FIG. 21B) is an Sf9 cell subclone that contains early-promoted and hr-enhanced GT, ST, GlcNAc-TI, and GlcNAc-TII genes. These cells are produced by cotransfecting the SfSWT-1 cells from above with pDIE-GNTI-II plus pIE1Hygro, followed by selection with G418 plus hygromycin and limiting dilution. These cells contain stably-integrated copies of both expression plasmids (pDIE-GTST and pDIE-GNTI-II) and thus constitutively express not only GT and ST activities, as with the SfSWT-1 cells, but also express GlcNAc-TI and GlcNAc-TII, which are present only at very low levels in insect cells.

As described above for SfSWT-1, any early viral or constitutive cellular promoter may be used to express processing enzymes, any enhancer may be used to increase expression of processing enzymes, and any promoter may be used to express the protein of interest. Any insect cell line may be used as the parent for stable transformation, and the relative positions of the GT, ST, GlcNAc-TI and GlcNAc-TII genes are unimportant. Similar embodiments provide other types of protein processing.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ackermann et al., *Baculovirus and Insect Cell Gene Expr. Conf Abstr.*, ST13, 1995.
Adams and McClintock, In: *Atlas of Invertebrate Viruses*, Adams, J. R. and Bonami, J. R., eds., CRC Press, Inc., Boca Raton, Fla., 87–204, 1991.
Adang and Miller, *J. Virol.*, 44:782, 1982.
Adelman et al., *DNA* 2:183, 1983.
Aeed and Elhammer, *Biochemistry*, 33:8793, 1994.
Agarwal et al., *Oncogene*, 11:427, 1995.
Agbandje et al., *Virology*, 184:170, 1991.
Alnemri and Litwack, *Biochemistry*, 32:5387, 1993.
Alt et al., *J. Biol. Chem.*, 253:1357, 1978.
Altmann et al., *Glycobiology*, 3:619–625, 1993.
Altmann et al., *J. Biol. Chem.*, 270:17344–17349, 1995.
Andersons et al., *Biochem. J.*, 280:219, 1991.
Apte and Siebert, *Biotechniques*, 15:890–893, 1993.
Arp et al., *J. Gen. Virol.*, 74:211, 1993.
Aviv and Leder, *Proc. Nat. Acad. Sci. U.S.A.*, 69:1408–1412, 1972.
Ayres et al., *Virology*, 202:586, 1994.
Bailer et al., *Prot. Expr. Pur.*, 6:546, 1995.
Bakker et al., *J. Biol. Chem.*, 269(48):30326–33, 1994.
Bause et al., *Eau. J. Biochem*, 217:535–540, 1993.
Beames et al., *Biotechniques*, 11:378, 1991.
Becker et al., *Bio/Technology*, 12:69, 1994.
Belyaev and Roy, *Virology*, 190:840, 1992.
Belyaev et al., *Gene*, 156:229, 1995.
Bendiak et al., *Eur. J. Biochem.* 216(2):405–17, 1993.
Beniya et al., *Virology*, 216:12, 1996.
Benton and Davis, *Science*, 196:180–182, 1977.
Berger et al., *FEBS Letters*, 203:64–68, 1986.
Bischoff et al., *J. Biol. Chem.*, 165:17110–17117,1990.
Bishop et al., in *Novations*, 4:1, 1995.
Blake et al., *Anal. Biochem.*, 36:175–179, 1984.
Blissard and Rohrmann, *Virology*, 170:537–555,1989.
Blissard and Rohrmann, *Ann. Rev. Entomol.*, 35:127, 1990.
Blissard and Wenz, *J. Virol.*, 66:6829–6835, 1992.
Blobel and Dobberstein, *J. Cell Biol.*, 67:852–862, 1975.
Bonning et al., *J. Gen. Virol.*, 75:1551, 1994.
Boose et al., *Prot. Expr. Pur.*, 11:111, 1990.
Boublik et al., *Bio/Technology*, 13:1079, 1995.
Bozon et al., *J. Mol. Endocrinol.*, 14:277, 1995.
Broussard et al., *Virology*, 222:318, 1996.
Buss et al., *Mol. Cell. Biol.*, 11: 1523,1991.
Butters and Hughes, *Biochim. Biophys. Acta*, 640:655–671, 1981.
Camirand et al., *J. Biol. Chem.*, 266:15120–15127, 1991.
Capone, *Gene Anal. Tech.*, 6:62, 1989.
Carson et al., *Virology*, 182:279–286, 1991.
Cartier et al., *J. Virol.*, 68:7728–7737, 1994.
Cavener and Ray, *Nuc. Acids Res.*, 19:3185–3192, 1991.
Chalfie et al, *Science*, 263:802–805, 1994.
Chatterjee et al., *Int. J. Biochem. Cell Biol.* 27(3):329–36, 1995.
Chazenbalk and Rapoport, *J. Biol. Chem.*, 270:1543, 1995.
Chen et al., *J. Biol. Chem.*, 266:4081–4087, 1991.
Chirgwin et al., *Biochemistry*, 18:5294–5299, 1979.
Chisholm and Henner, *J. Virol.*, 62:3193, 1988.
Chou et al., *Proc. Natl. Acad. Sci. USA*, 92:4417, 1995.
Choudary et al., in: *Baculovirus Expression Protocols*, (C. D. Richardson ed.), Humana Press, Clifton, N.J, pp. 243–264, 1995.
Colberre-Garapin et al., *J. Mol. Biol.*, 150:1, 1981
Cooney et al., *Proc. Natl. Acad. Sci. USA*, 90:1882, 1993.
D'Agostaro et al., *J. Biol. Chem.* 270(25):15211–21, 1995.
Davidson and Castellino, *Biochemistry*, 30:6167–6174, 1991a.
Davidson et al., *Biochemistry*, 30:9811–9815, 1991.
Davidson et al., *Biochemistry*, 29:5584–5590, 1990.
Davies and Morgan, *Biochem. J*, 295:889, 1993.
Davis and Wood, *In Vitro Cellular & Developmental Biology, Animal* 31:659–663, 1995.
Davis et al., *In Vitro Cellular and Developmental Biology. Animal*, 29A:842–846, 1993.
Davrinche et al., *Biochem. Biophys. Res. Comm.*, 195:469, 1993.
Delchambre et al., *EMBO J.*, 8:2653, 1989.
Deutschmann and Jager, *Enz. Microb. Tech.*, 16:506, 1994.
Domingo and Trowbridge, *J. Biol. Chem.*, 263:13386, 1988.
Eichenlaub, *J. Bacteriol* 138:559–566, 1979.
Elbein, *FASEB J.*, 5:3055–3063, 1991.
Emery and Bishop, *Prot. Engr.*, 1:359, 1987.
Engelhard et al., *Proc. Natl. Acad. Sci. USA*, 91:3224, 1994.
Ernst et al., *Nuc. Acids Res.*, 22:2855, 1994.
Estes et al., *J. Virol.*, 61:1488, 1987.
Feinberg and Vogelstein, *Analyt. Biochem.*, 132:6–13, 1983.
Field and Wainwright, *Glycobiology*, 5:463–472, 1995.
Ford et al., *Prot. Expr. Pur.*, 2:95, 1991.
Forstova et al., *Human Gene Therapy*, 6:297, 1995.
Foster et al., *Gene*, 154:183–186, 1995.
Frohman et al., *Proc. Natl. Acad. Sci. USA*, 85:8998–9002, 1988.
Fuchs et al., *Eur. J. Biochem.*, 228:625, 1995.
Fuchs et al., *J. Virol.*, 48:641, 1983.

Fukada et al., *Biosci. Biotechnol. Biochem.* 58(1):200–1, 1994.
Furlong et al., *Biotech. Appl. Biochem.,* 10:454, 1988.
Garnier et al., *Bio/Technology,* 13:1101, 1995a.
Garnier el al., *J. Virol.,* 69:4060, 1995b.
Gething and Sambrook, *Nature,* 355:33–45, 1992.
Giese et al., *J. Virol.,* 63:3080, 1989.
Gluzman, *Cell,* 23:567–572,1981.
Godeau et al., *Nuc. Acids Res.,* 20:6239, 1992.
Grabenhorst et al., *Eur. J. Biochem.,* 215: 189–197, 1993.
Grabenhorst et al., *Eur. J. Biochem.,* 232:718–725, 1995.
Grace, *Nature* (London), 216:613, 1967.
Graham et al., The NIAID AIDS Vaccine Clinical Trials Network, *J. Inf. Dis.,* 167:533, 1993.
Granados and Naughton, *Intervirology,* 5:62–68, 1975.
Guarino and Dong, *Virology,* 200:328–335, 1994.
Guarino and Smith, *Virology,* 179:1–8, 1990.
Guarino and Summers, *J. Virol.,* 57:563–571, 1986.
Guarino and Summers, *J. Virol.,* 61:2091–2099, 1987.
Guarino et al., *J. Virol.,* 60:224–229, 1986.
Guarino et at., *J. Virol.,* 60:224–229, 1986.
Han et al., *Biochemistry,* 34:10835, 1995.
Harduin-Lepers et al., *J. Biol. Chem.,* 268:14348–14359, 1993.
Hart, *Curr. Op. Cell Biol.,* 4:1017, 1992.
Hartig et al., *Dev. Biol. Std.,* 76:313, 1992.
Hasemann and Capra, *Proc. Natl. Acad. Sci. USA,* 87:3942, 1990.
Hawtin et al., *Virology,* 212:673, 1995.
Hellers et al., *Eur. J. Biochem.,* 199:435, 1991.
Henderson et al., *FEBS Letters,* 371 (3):293–6, 1995.
Herscovics and Jelinek-Kelly, *Anal. Biochem.,* 166:85–89, 1987.
Herscovics et al., *J. Biol. Chem.,* 269:9864–9871, 1994.
Hill-Perkins and Possee, *J. Gen. Virol.,* 71:971, 1990.
Hills and Crane-Robinson, *Biochim. Biophys. Acta,* 1260:14, 1995.
Hink et al., *Biotech. Progr.,* 7:9, 1991.
Hooft van Iddekinge et al., *Virology,* 131:561–565, 1983.
Hopp, U.S. Pat. No. 4,554,101.
Hoss et al., *J. Virol.,* 64:4799, 1990.
Hsieh and Robbins, *J. Biol. Chem.,* 259:2375–2382, 1984.
Hsu et al., *Prot. Expr. Pur.,* 5:595, 1994.
Hu et al., *J. Virol.,* 61:3617, 1987.
Huh and Weaver, *J. Gen. Virol.,* 71:195–202, 1990.
Iatrou et al., *Proc. Natl. Acad. Sci. USA,* 86:9129, 1989.
Jarvis and Finn, *Virology,* 212:500–511, 1995.
Jarvis and Garcia, *BioTechniques,* 16:508–513, 1994.
Jarvis and Garcia, Jr., *Virology,* 205:300–313, 1994.
Jarvis and Guarino, *In: Methods in Molecular Biology*, C. D. Richardson (ed.), Baculovirus Expression Protocols., Humana Press, Clifton, N.J, 39:187–202, 1995.
Jarvis and Summers, *In: Recombinant DNA vaccines, rationale and strategies*, R. E. Isaacson (ed.), Marcel Dekker, Inc., New York, 265–291, 1992.
Jarvis and Summers, *Mol. Cell. Biol.,* 9:214–223, 1989.
Jarvis, *In: Insect cell culture engineering*, M. F. A Goosen, A. Daugulis, and P. Faulkner (eds.), Marcel Dekker, Inc., New York, 193–217, 1993a
Jarvis, *J. Virol.,* 67:2583–2591, 1993b.
Jarvis, *J. Virol.,* 67:2583, 1993.
Jarvis et al., *Virology,* 185:795–810, 1991.
Jarvis et al., *Bio/Technology,* 8:950–955, 1990.
Jarvis et al., *Biol. Control,* 7:228, 1996.
Jarvis et al., *J. Biol. Chem.,* 268:16754–16762, 1993.
Jeang et al., *J. Virol.,* 61:1761, 1987.
Johnson et al., *Virology,* 190:815–823, 1992.
Joyce et al., *FEBS Lett.,* 335:61–64, 1993.
Kalman et al., *J. Biol. Chem.,* 270:14835, 1995.
Kalsner et al., *Glycoconjugate J,* 12:360–370, 1995.
Kang et al., *J. Gen. Virol.,* 68:2607, 1987.
Kaufman, *Methods in Enzymology,* 185:537–566, 1990.
Keddie et al., *Science,* 243:1728, 1989.
Kerscher et al., *Dev. Biol.,* 168:613–626, 1995.
Kim and Weaver, *Virology,* 195:587, 1993.
King and Possee, "The baculovirus system: a laboratory guide," Chapman and Hall, London, 1992.
Kitts and Possee, *Biotechniques,* 14:810–817, 1993.
Kitts et al., *Nuc. Acids Res.,* 18:5667, 1990.
Kleymann et al., *Eur. J. Biochem.,* 213:797–804, 1993.
Knepper et al., *Biochemistry,* 31:11651–11659, 1992.
Kornfeld and Kornfeld, *Ann. Rev. Biochem.,* 54:631–664, 1985.
Kovacs et al., *Virology,* 185:633, 1991.
Kozak, Microbiol. Rev., 47:1–45, 1983.
Kozak, *J. Cell Biol.,* 108:229–241, 1986a.
Kozak, *Nuc. Acids Res.,* 12:857–872, 1984.
Kozak, *Cell,* 44:283–292, 1986b.
Kozma et al., *J. Biol. Chem.,* 268:7134, 1993.
Kretzschmar et al., *Biol. Chem. Hoppe-Seyler,* 375:23, 1994.
Ku and Omary, *Exp. Cell Res.,* 211:24, 1994.
Kubelka et al., *Arch. Bach. Biophys.,* 308:148–157, 1994.
Kuhn and Zipfel, *Gene,* 162:225, 1995.
Kumar et al., *Glycobiology* 2(4):383–93, 1992.
Kumar et al., *Proc. Natl. Acad Sci. U.S.A.,* 87:9948–9952, 1990.
Kunkel, *Proc. Natl. Acad Sci. U.S.A.,* 82:488–492, 1985.
Kuroda et al., *Virology,* 174:418–429, 1990.
Kuroda et al., *J. Virol.,* 63:1677, 1989.
Kuroda et al., *EMBO J.,* 5:1359, 1986.
Kuroda et al., *Virology,* 180:159, 1991.
Kuzio et al., *Virology,* 139:414–418, 1984.
Kyte and Doolittle, *J. Mol. Biol.,* 157:105–132, 1982.
Laemmli, Nature, 227:680–685, 1970.
Lal et al., *J. Biol. Chem.,* 269:9872–9881, 1994.
Lanford, *Virology,* 167:72, 1988.
Larsen et al., *Proc Natl Acad Sci USA* 87(17):6674–8, 1990.
Lawrie et al., *J. Biotech.,* 39:1, 1995.
Lebacq-Verheyden et al., *Mol. Cell. Biol.,* 8:3129, 1988.
Lee and Costlow, *Meth. Enzymol.,* 152:633–648, 1987.
Lee and Miller, *J. Virol.,* 27:754, 1978.
Lee et al., *J. Biol. Chem.,* 264:13848–13855, 1989.
Lerch and Friesen, *Nuc. Acids Res.,* 21:1753, 1993.
Leusch et al., *Gene,* 160:191, 1995.
Licari et al., *Biotech. Prog.,* 9:146–152, 1993.
Lowe, *Sem. Cell Biol.,* 2:289–307, 1991.
Lowe et al., *J. Biol. Chem.,* 266:1672, 1991.
Lowe et al., *Biochem. Soc. Trans.,* 20:484, 1992.
Lu and Miller, *J. Virol.,* 69:975–982, 1995.
Lu and Miller, *Biotechniques,* 21:63, 1996.
Luckow and Summers, *Virology* 170:31–39, 1989
Luckow and Summers, *Virology* 167:56–71, 1988
Luckow and Summers, *Bio/Technology,* 6:47, 1988.
Luckow, *In: Recombinant DNA technology and applications*, (A. Prokop, R. K. Bajpai and C. S. Ho, eds.), McGraw-Hill, Inc., New York, pp. 97–152, 1991.
Luckow et al., *J. Virol.,* 67:4566, 1993.
Maeda, *Ann. Rev. Entomol.,* 34:351, 1989.
Maeda et al., *Nature,* 315:592, 1985.
Maiorella et al., *Bio/Technology,* 6:1406, 1988.
Malitschek and Schartl, *Biotechniques,* 11:177, 1991.
Manneberg et al., *Protein Science,* 3:30–38, 1994.
Manns and Grosse, *Biotechniques,* 10:154, 1991.
Marsden et al., *Biochem. Cell Biol.,* 68:587–601, 1990.

Martens, et al., *J. Virol. Meth.*, 52:15, 1995.
Martin et al., *DNA*, 7:99, 1988.
Marz et al., *In: Glycoproteins*, Montreuil, J., Vliegenthart, J. F. G. and Schachter, H. (eds), Elsevier, Amsterdam, Vol. 29a, pp. 543–563, 1995.
Marz et al., *In: Glycoproteins*, (J. Montreuil, J. F. G. Vliegenthart and H. Schachter, eds.), Elsevier, Amsterdam, Vol. 29a, pp. 543–563, 1995.
Masri et al., *Biochem. Biophys. Res. Commun.* 157(2) :657–63, 1988.
Matsuura et al., *J. Gen. Virol.*, 68:1233, 1987.
McCutchen et al., *Bio/Technology*, 9:848, 1991.
McLachlin and Miller, *J. Virol.*, 68:7746–7756, 1994.
Melton et al., *Nuc. Acids Res.*, 12:7035–7055, 1984.
Merryweather et al., *J. Gen. Virol.*, 71:1535, 1990.
Messing et al., Third Cleveland Symposium on Macromoleculesand Recombinant DNA, Editor A. Walton, Elsevier, Amsterdam, 1981.
Miller, *Ann. Rev. Microbiol.*, 42:177–199, 1988.
Miller, *J. Virol.*, 39:973, 1981.
Min and Bishop, *J. Gen. Virol*, 72:2551, 1991.
Minch et al., *Biotechnol. Prog.*, 11:348–351, 1995.
Minetoki et al., *Biosci. Biotechnol. Biochem.* 59(8): 1516–21, 1995.
Misago et al., *Proc. Natl. Acad. Sci. U.S.A.*, 92:11766–11770,1995.
Montreuil et al., *In: New Comprehensive Biochemistry*, (A. Neuberger and L. L. M. Van Deenen, series eds.), Elsevier, Amsterdam, 1995.
Moremen and Robbins, *J. Cell Biol.*, 115:1521–1534, 1991.
Moremen, *Proc. Natl. Acad Sci. U.S.A.*, 86:5276–5280, 1989.
Moremen et al., *J. Biol. Chem.*, 266:16876–16885, 1991.
Moremen et al., *Glycobiology*, 4:113–125, 1994.
Morris and Miller, *J. Virol.*, 66:7397–7405, 1992.
Mouillac et al., *J. Biol. Chem.*, 267:21733, 1992.
Mroczkowski et al., *J. Biol. Chem.*, 269:13522, 1994.
Munro and Pelham, *Cell*, 46:291–300, 1986.
Murhammer and Goochee, *Bio/Technology*, 6:1411–1418, 1988.
Murphy et al., *Gen. Anal. Tech. Appl.*, 7:160–171, 1990.
Murphy et al., *Prot. Expr. Pur.*, 4:349, 1993.
Nagao et al., *Insect Biochem.*, 17:531–538, 1987.
Nakazawa et al., *J. Biochem* 104(2):165–8, 1988.
Nebes and Schmidt, *Biochem. Biophys. Res. Comm.*, 200:239–245, 1994.
Normington et al., *Cell*, 57:1223–1236, 1989.
Numata et al., *J. Clin. Micro.*, 32:121, 1994.
O'Reilly and Miller, *J. Virology*, 62:3109–3119, 1988.
O'Reilly et al., *In Baculovirus expression vectors*, W. H. Freeman and Company, N.Y, 1992.
Ogonah et al., *Bio/Technology*, 14:197–202, 1996.
Ohkawa et al., *J. Virol.*, 68:6619, 1994.
Oker-Blom et al., *Biochim. Biophys. Acta*, 1176:269, 1993.
Ooi and Miller, *Virology*, 166:515, 1988.
Ooi et al., *J. Mol. Biol.*, 210:721, 1989.
Page et al., *J. Biol. Chem.*, 264:19147, 1989.
Pajot-Augy et al., *J. Mol. EndocrinoL*, 14:51, 1995.
Parekh et al., *Prot. Expr. Pur.*, 6:537, 1995.
Park et al., *J. Virol. Meth.*, 45:303, 1993.
Passarelli and Miller, *J. Virol.*, 67:2149–2158, 1993.
Passarelli et al., *J. Virol.*, 68:4673, 1994.
Patel et al., *Nuc. Acids Res.*, 20:97, 1992.
Paulson and Colley, *J. Biol. Chem.*, 264:17615–17618, 1989.
Paulson et al., *J. Biol. Chem.*, 252(2356–2362), 1977.
Peakman et al., *Nuc. Acids Res.*, 20:6111, 1992a.
Peakman et al., *Nuc. Acids Res.*, 20:495, 1992b.
Pearson and Roy, *Immunol. Cell Biol.*, 71:381, 1993.
Pen et al., *Nuc. Acids Res.*, 17:451, 1989.
Peng et al., *Biotechniques*, 14:274, 1993.
Pennock et al., *Mol. Cell. Biol.*, 4:399, 1984.
Possee and Howard, *Nuc. Acids Res.*, 15:10233, 1987.
Pownall et al., *Genomics* 12(4):699–704, 1992.
Prasad et al., *J. Virol.*, 68:5117, 1994.
Pullen and Friesen, *J. Virol.*, 69:156–165, 1995.
Qin et al., *J. Gen. Virol.*, 70:1273, 1989.
Ranjan and Hasnain, *Virus Genes*, 9:149, 1995.
Rankin el al., *Gene*, 70:39, 1988.
Rankl et al., *Prot. Expr. Pur.*, 5:346, 1994.
Redfield et al., *New Engl. J. Med.*, 324:1677, 1991.
Reed and Mann, *Nuc. Acids Res.*, 13, 7207–7221, 1985.
Reed and Muench, *Am. J. Hyg.*, 27:493, 1938.
Ren et al., *Biochemistry*, 34:2489–2495, 1995.
Richardson, ed., "Baculovirus expression protocols," Vol 39 *In: Methods in Molecular Biology*, (J. M. Walker, series ed.), Humana Press, Totowa, N.J., 1995.
Risinger et al., *J. Biol. Chem.*, 267:5680, 1992.
Rodems and Friesen, *J. Virol.*, 67:5776–5785, 1993.
Roelvink, et al., *J. Gen. Virol.*, 73:1481, 1992.
Rohrmann, *J. Gen. Virol.*, 67:1499, 1986.
Roy, *Virology*, 216:1, 1996.
Rubin et al., *Gene*, 128:155–163, 1993.
Russo et al., *J. Biol. Chem.*, 267:9241–9247, 1992.
Ryan et at, *Arch. Biochem. Biophys.*, 243:115–124, 1985.
Saiki et al., *Science*, 230:1350–1354, 1985.
Saint Angelo et al., *J. Virology*, 61:361–365.
Sambrook et al., *In Molecular Cloning. A Laboratory Manual*, Second edition, Cold Spring Harbor Laboratory, Cold Spring Harbor, N.Y., 1989.
Sanger et al., *Proc. Natl. Acad. Sci. U.S.A.*, 74:5463–5467, 1977.
Santerre, et al., *Gene*, 30:147, 1984.
Sareneva et al., *J. Interf. Res.*, 13:267, 1993.
Sarkar et al., *Proc Natl Acad Sci USA*, 88(1):234–8, 1991.
Schatzle et al., *J. Biol. Chem.*, 267:4000–4007, 1992.
Shaper et al., *J. Biol. Chem.*, 263:10420–10428, 1988.
Short et al., *Nuc. Acids. Res.*, 16:7583–7600,1988.
Shuler et al., "Baculovirus expression systems and biopesticides," Wiley-Liss, Inc., New York, 1995.
Sisk et al., *Biotechniques*, 13:186, 1992.
Slightom and Sieu, *Biotechniques*, 13:94, 1992.
Smith et al., *J. Virol.*, 46:584–593, 1983a.
Smith et al., *Anal. Biochem.*, 150:76–85, 1985.
Smith et al., *J. Biol. Chem.*, 265:6225–6234, 1990.
Smith et al., *Mol. Cell. Biol.*, 3:2156, 1983b.
Smith et al., *J. Virol.*, 45:215, 1983c.
Southern, *J. Mol. Biol.*, 98:503–517, 1975.
Sridhar et al., *FEBS Lett.*, 3 15:282–286, 1993.
Sridhar et al, *FEBS Lett.*, 315:282, 1993.
St. Angelo et al., *J. Virol.*, 61:361, 1987.
Staden, *In: Nucleic acid and protein sequence analysis, a practical approach*, M. J. Bishop and C. J. Rawlings (eds.), IRL Press Limited, Eynsham, Oxford, England, 173–217, 1987.
Staudacher et al., *Eur. J. Biochem.*, 207:987–993, 1992.
Stewart et al., *Nature*, 352:85, 1991.
Stoltz et al., *J. Gen. Virol.*, 19:145, 1973.
Summers and Smith, *Texas Agricultural Experiment Station Bulletin No.* 1555, 1987.
Suzuki et al., *EMBO J.*, 9:4259, 1990.
Takagi et al., *Biochem. Biophys. Res. Comm.*, 184:471, 1992.
Tan et al., *Eur J Biochem*, 231 (2):317–28, 1995.

Taticek et al., *Curr. Op. Biotech.*, 5:165, 1994.
Tessier et al., *Gene*, 98:177, 1991.
Thiem and Miller, *J. Virology*, 63:2008–18, 1989.
Thiem and Miller, et al., *Gene*, 91:87, 1990.
Thompsen et al., *J. Cell. Biochem.*, 43:67, 1990.
Ting et al., *Gene*, 55:147–152, 1987.
Todd et al., *J. Virol.*, 69:968–974, 1995.
Tomita et al., *Cytotechnology*, 17:65, 1995.
Towbin et al., *Proc. Natl. Acad. Sci. U.S.A.* 76:4350–4353, 1979.
Tramper et al., *Bioproc. Tech.*, 17:139, 1993.
Troutt et al., *Proc. Natl. Acad Sci. U.S.A.*, 89:9823–9825, 1992.
Tsao et al., *J. Biol. Chem.*, 265:5188, 1990.
Urakawa and Roy, *J. Virol.*, 62:3919, 1988.
Urakawa et al., *J. Gen. Virol.*, 70:1453, 1989.
Urbancikova and Hitchcock-DeGregori, *J. Biol. Chem.*, 269:24310, 1994.
Vail et al., *J. Invert. Path.*, 17:383, 1971.
Vakharia et al., *Insect Biochem. Mol. Biol.*, 25:583, 1995.
van Lier et al., *Biotech. Progr.*, 10:60, 1994.
Vaughn el al., *In Vitro*, 13:213–217, 1977,
Veit el al., *FEBS Lett.*, 339:160, 1994.
Velardo et al., *J. Biol. Chem.* 268:17902–7, 1993.
Vialard and Richardson, *J. Virol.*, 67:5859, 1993.
Vialard et al., *J. Virol.*, 64:37, 1990.
Vieira and Messing, *Gene*, 19:259–268, 1982.
Vihko et al., *Proc. Natl. Acad. Sci. USA*, 90:799, 1993.
Vlak et al., *Virology*, 179:312–320, 1990.
Vlak et al., *J. Virol.*, 40:762, 1981.
Volkman and Goldsmith, *Virology*, 143:185–195, 1985.
Volkman and Goldsmith, *Virology*, 143:185–195,1985.
Volkman and Summers, *J. Invert. Path.*, 30:102, 1977.
Volkman, *Curr. Top. Microbiol. Immunol.*, 131:103–118, 1986.
Volkman et al., "Virus Taxonomy, in: Sixth Report of the International Committee on Taxonomy of Viruses, (F. A. Murphy, C. M. Fauquet, D. H. L. Bishop, S. A. Ghabrial, A. W. Jarvis, G. P. Martelli, M. A. Mayo and M. D. Summers, eds.), Springer-Verlag, Wien, pp. 104, 1995.
Volkman et al., *Virology*, 133:354–362, 1984.
Volkman et al., *J. Virol.*, 19:820, 1976.
Vulsteke et al., *Insect Mol. Biol.*, 2:195–204, 1993.
Wagner et al., *J. Virol.*, 70:4103–4109, 1996a.
Wagner et al., *Glycobiology*, 6:165–175, 1996b.
Wang and Fraser, *J. Virol. Meth.*, 31:113, 1991.
Wang et al., *J Biol Chem*, 268(6):4355–61, 1993.
Wang et al., *Gene*, 100:131, 1991.
Wathen et al., *Biochemistry*, 30:2863–2868, 1991.
Webb and Summers, *Technique*, 2:173–188, 1990.
Webb et al., *Biotechniques*, 11:512, 1991.
Weinstein et al., *J. Biol. Chem.*, 262:17735–17743, 1987.
Weiss et al., *In: Baculovirus Expression Protocols*, (C. D. Richardson ed.), Humana Press, Clifton, N.J.79, pp. 79–95, 1995a.
Weiss et al., *In: Baculovirus Expression Protocols*, (C. D. Richardson ed.), Humana Press, Clifton, N.J., pp. 65–78, 1995b.
Welply, *Bio/Technology*, 17:59, 1991.
Westwood et al., *Virology*, 195:90, 1993.
Weyer and Possee, *J. Gen. Virol.*, 72:2967, 1991.
Weyer and Possee, *J. Gen. Virol.*, 70:203, 1989.
Weyer et al., *J. Gen. Virol.*, 71:1525, 1990.
Whiteheart et al., *Meth. Enzymol.*, 179:82–95, 1989.
Whitford et al., *J. Virology*, 63:1393–1399, 1989.
Wickham et al., *Biotechnology Progress* 8:391–396, 1992.
Williams et al, *Biochim. Biophys. Acta*, 1075:146–153, 1991.
Wilson et al., *J. Virol.* 61:661–666, 1987.
Wilson et al., *J. Virol.*, 61:661, 1987.
Winter et al., *Ann. Rev. Immunol.*, 12:433, 1994.
Wong et al., *Cytotechnology*, 15:157, 1994.
Xia et al., *Virology*, 196:817, 1993.
Xie et al., *J. Biol. Chem.*, 267:4939, 1992.
Xu et al., *J. Virol.*, 69, 2912–2917, 1995.
Yamshchikov et al., *Virology*, 214:50, 1995.
Yanisch-Perron et al., *Gene*, 33, 103–119, 1985.
Yeh et al., *Biochemistry*, 32:11087–11099, 1993.
Yoshihisa and Anraku, *Biochem. Biophys. Res. Comm.*, 163, 908–915, 1989.
Zilberstein et al., *Cell*, 21, 417–427, 1980.
Zuidema et al., *J. Gen. Virology*, 71:2201–2209, 1990.

What is claimed is:

1. A baculovirus expression vector comprising at least a first glycosylation enzyme transcriptional unit and a second glycosylation enzyme transcriptional unit, the first glycosylation enzyme transcriptional unit comprising a nucleic acid encoding a galactosyltransferase under the control of a first baculovirus early promoter, and the second glycosylation enzyme transcriptional unit comprising a nucleic acid encoding a sialyltransferase operatively positioned under the control of a second baculovirus early promoter.

2. The vector of claim 1, further comprising a third glycosylation enzyme transcriptional unit comprising a nucleic acid encoding a third oligosaccharide processing enzyme operatively positioned under the control of a promoter.

3. The vector of claim 2, further comprising a fourth glycosylation enzyme transcriptional unit comprising a nucleic acid encoding a fourth oligosaccharide processing enzyme operatively positioned under the control of a promoter.

4. The vector of claim 3, further comprising a fifth glycosylation enzyme transcriptional unit comprising a nucleic acid encoding a fifth oligosaccharide processing enzyme operatively positioned under the control of a promoter.

5. The vector of claim 4, further comprising a sixth glycosylation enzyme transcriptional unit comprising a nucleic acid encoding a sixth oligosaccharide processing enzyme operatively positioned under the control of a promoter.

6. The vector of claim 3, further comprising a seventh glycosylation enzyme transcriptional unit comprising a nucleic acid encoding a seventh oligosaccharide processing enzyme operatively positioned under the control of a promoter.

7. The vector of claim 6, further comprising a eighth glycosylation enzyme transcriptional unit comprising a nucleic acid encoding a eighth oligosaccharide processing enzyme operatively positioned under the control of a promoter.

8. The vector of claim 7, further comprising a ninth glycosylation enzyme transcriptional unit comprising a nucleic acid encoding a ninth oligosaccharide processing enzyme operatively positioned under the control of a promoter.

9. The vector of claim 2, wherein said third oligosaccharide processing enzyme is an α-glucosidase, an α-mannosidase, an N-acetylglucosaminyltransferase, or a fucosyltransferase.

10. The vector of claim 1, wherein at least one of said first and said second promoter is a baculovirus immediate early promoter.

11. The vector of claim 1, wherein at least one of said first and said second promoter is a baculovirus delayed early promoter.

12. The vector of claim 1, wherein at least one of said first and said second promoter is an IE1, IEN (IE2), or IE10 promoter.

13. The vector of claim 1, wherein said first or second promoter is an *Autographa californica* NPV, *Trichoplusia ni* NPV, *Rachipulsia ou* NPV, *Orgyia pseudosugata* NPV, *Bombyx mori* NPV, *Heliothis zea* NPV, *Spodoptera exigua* NPV or *Galleria mellonella* NPV promoter.

14. The vector of claim 1, further comprising an enhancer operatively positioned to enhance expression of said transcriptional unit or units.

15. The vector of any preceding claim, further comprising a structural gene encoding a protein disulphide isomerase operatively positioned under the control of a promoter.

16. The vector of any preceding claim, further comprising a structural gene encoding a peptidyl prolyl cis-trans isomerase operatively positioned under the control of a promoter.

17. The vector of claim 1, further comprising a nucleic acid encoding a protein disulphide isomerase operatively positioned under the control of a promoter.

18. The vector of claim 1, further comprising a nucleic acid encoding a peptidyl prolyl cis-trans isomerase operatively positioned under the control of a promoter.

19. The vector of claim 1, further comprising a nucleic acid encoding a chaperone protein operatively positioned under the control of a promoter.

20. The vector of claim 19, wherein said nucleic acid is a BiP/GRP78 encoding nucleic acid.

21. The vector of claim 20, wherein said structural gene is an antibiotic or toxin resistance gene.

22. The vector of claim 1, further comprising a nucleic acid encoding a selectable marker protein operatively positioned under the control of a promoter.

23. The vector of claim 22, wherein said nucleic acid encodes an antibiotic or toxin resistance conferring protein.

24. The vector of claim 1, further comprising a nucleic acid encoding a protein kinase operatively positioned under the control of a promoter.

25. The vector of claim 1, further comprising a baculovirus nucleic acid.

26. The vector of claim 25, wherein said baculovirus nucleic acid is gp64, p10 or polyhedrin.

27. The vector of claim 1, further comprising a DNA insert comprising a multiple cloning cassette.

28. The vector of claim 1, further comprising at least one heterologous nucleic acid encoding a selected protein, said nucleic acid operatively positioned under the control of a promoter.

29. The vector of claim 28, wherein said very late promoter is a polyhedrin or p10 promoter.

30. The vector of claim 27, wherein said baculoviral promoter is a very late promoter.

31. The vector of claim 29, wherein said very late promoter is a p10 promoter.

32. The vector of claim 29, wherein said baculoviral promoter is a late promoter.

33. The vector of claim 32, wherein said late promoter is a p6.9 or capsid promoter.

34. The vector of claim 28, wherein said promoter is a promoter naturally associated with said heterologous nucleic acid.

35. The vector of claim 28, wherein said vector comprises at least one nucleic acid encoding an insecticidal protein.

36. The vector of claim 35, wherein said vector comprises at least one nucleic acid encoding a *Bacillus thuringiensis* crystal toxin, a protease inhibitor, a lectin, a chitinase, a juvenile hormone esterase, a toxin or a trypsin inhibitor insecticidal protein.

37. The vector of claim 36, wherein said vector comprises at least one nucleic acid encoding a juvenile hormone esterase.

38. The vector of claim 36, wherein said toxin is AaIt or LqhIT2.

39. The vector of claim 1, wherein said transcriptional unit replaces a gp64 encoding locus, a p10 encoding locus, or a polyhedrin encoding locus.

40. The vector of claim 1, encapsulated within a baculovirus.

41. The vector of claim 1, further defined as being comprised in a baculovirus expression vehicle.

42. A population of baculovirus expression vehicles comprising a baculovirus expression vector characterized as comprising at least a first glycosylation enzyme transcriptional unit and a second glycosylation enzyme transcriptional unit, the first glycosylation enzyme transcriptional unit comprising a nucleic acid encoding a galactosyltransferase under the control of a first baculovirus early promoter, and the second glycosylation enzyme transcriptional unit comprising a nucleic acid encoding a sialyltransferase operatively positioned under the control of a second baculovirus early promoter.

43. An insect cell comprising a baculovirus expression vector characterized as comprising at least a first glycosylation enzyme transcriptional unit and a second glycosylation enzyme transcriptional unit, the first glycosylation enzyme transcriptional unit comprising a nucleic acid encoding a galactosyltransferase under the control of a first baculovirus early promoter, and the second glycosylation enzyme transcriptional unit comprising a nucleic acid encoding a sialyltransferase operatively positioned under the control of a second baculovirus early promoter.

44. The insect cell of claim 43, wherein said insect cell is a stably transformed insect cell clone.

45. The insect cell of claim 44, wherein said insect cell is a Lepidopteran insect cell.

46. The insect cell of claim 45, wherein said insect cell is a *Spodoptera frugiperda, Bombyx mori, Heliothis virescens, Heliothis zea, Mamestra brassicas, Estigmene acrea* or *Trichoplusia ni* insect cell.

* * * * *

UNITED STATES PATENT AND TRADEMARK OFFICE
CERTIFICATE OF CORRECTION

PATENT NO.   : 6,461,863 B1
DATED        : October 8, 2002
INVENTOR(S)  : Donald L. Jarvis It is certified that error appears in the above-identified patent and that said Letters Patent is hereby corrected as shown below:

<u>Title page,</u>
Item [54], Title, please delete "GYLCOSYLATION" and insert
-- GLYCOSYLATION -- therefor.

<u>Column 139,</u>
Line 1, please delete "3" and insert -- 5 -- therefor.
Line 26, please delete "IE10" and insert -- IE0 -- therefor.

<u>Column 140,</u>
Line 28, please delete "AaIt" and insert -- AaIT -- therefor.

Signed and Sealed this

Twenty-fourth Day of December, 2002

JAMES E. ROGAN
*Director of the United States Patent and Trademark Office*